United States Patent
Dube et al.

(10) Patent No.: US 6,919,353 B2
(45) Date of Patent: Jul. 19, 2005

(54) SUBSTITUTED 8-ARYLQUINOLUNE PDE4 INHIBITORS

(75) Inventors: Daniel Dube, St-Lazare (CA); Yves Girard, L'lle-Bizard (CA); Dwight MacDonald, L'lle-Bizard (CA); Anthony Mastracchio, Linden, NJ (US); Michel Gallant, Montreal (CA); Patrick Lacombe, Montreal (CA); Denis Deschenes, Carson Dorval (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 10/478,791

(22) PCT Filed: Jun. 26, 2002

(86) PCT No.: PCT/CA02/00953

§ 371 (c)(1),
(2), (4) Date: Nov. 25, 2003

(87) PCT Pub. No.: WO03/002118

PCT Pub. Date: Jan. 9, 2003

(65) Prior Publication Data

US 2004/0162314 A1 Aug. 19, 2004

Related U.S. Application Data

(60) Provisional application No. 60/301,220, filed on Jun. 27, 2001, and provisional application No. 60/303,472, filed on Jul. 6, 2001.

(51) Int. Cl.[7] .................. A61K 31/47; C07D 215/14
(52) U.S. Cl. .................. 514/314; 514/311; 546/173
(58) Field of Search .................. 546/173; 514/314, 514/311

(56) References Cited

U.S. PATENT DOCUMENTS 5,455,252 A   10/1995   Wilhelm et al.

FOREIGN PATENT DOCUMENTS

WO          WO 01/46151 A1        6/2001

*Primary Examiner*—D. Margaret Seaman
(74) *Attorney, Agent, or Firm*—Curtis C. Panzer; David L. Rose

(57) ABSTRACT

8-arylquinolines of formula (I) wherein the aryl group at the 8-position contains a meta two atom bridge to an optionally substituted phenyl or pyridyl group, are PDE4 inhibitors useful to treat asthma, chronic bronchitis, chronic obstructive pulmonary disease, arthritis, respiratory distress syndrome, allergic rhinitis, neurogenic inflammation, pain, rheumatoid arthritis, and other diseases. $R^1$–$R^7$ and Ar are as in claim 1.

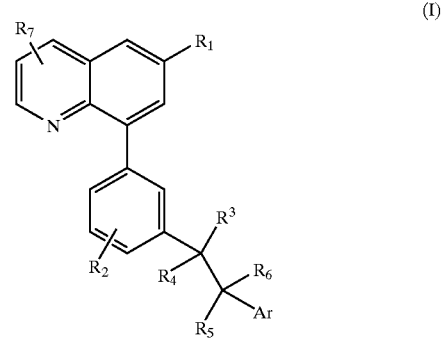

23 Claims, No Drawings

SUBSTITUTED 8-ARYLQUINOLINE PDE4 INHIBITORS

CROSS REFERENCE TO RELATED APPLICATIONS

This application is a U.S. National Phase application under 35 U.S.C. §371 of PCT Application No. PCT/CA02/00953, filed Jun. 26, 2002, which claims priority from U.S. Ser. No. 60/301,220, filed Jun. 27, 2001 and 60/303,472, filed Jul. 6, 2001.

BACKGROUND OF THE INVENTION

1. Field of the Invention

The present invention is directed to compounds that are substituted 8-arylquinolines. In particular, this invention is directed to substituted 8-arylquinolines which are phosphodiesterase-4 inhibitors wherein the aryl group at the 8-position contains a meta two carbon atom bridge to an optionally substituted phenyl or pyridyl group.

2. Related Background

Hormones are compounds that variously affect cellular activity. In many respects, hormones act as messengers to trigger specific cellular responses and activities. Many effects produced by hormones, however, are not caused by the singular effect of just the hormone. Instead, the hormone first binds to a receptor, thereby triggering the release of a second compound that goes on to affect the cellular activity. In this scenario, the hormone is known as the first messenger while the second compound is called the second messenger. Cyclic adenosine monophosphate (adenosine 3',5'-cyclic monophosphate, "cAMP" or "cyclic AMP") is known as a second messenger for hormones including epinephrine, glucagon, calcitonin, corticotrophin, lipotropin, luteinizing hormone, norepinephrine, parathyroid hormone, thyroid-stimulating hormone, and vasopressin. Thus, cAMP mediates cellular responses to hormones. Cyclic AMP also mediates cellular responses to various neurotransmitters.

Phosphodiesterases ("PDE") are a family of enzymes that metabolize 3',5' cyclic nucleotides to 5' nucleoside monophosphates, thereby terminating cAMP second messenger activity. A particular phosphodiesterase, phosphodiesterase-4 ("PDE4", also known as "PDE-IV"), which is a high affinity, cAMP specific, type IV PDE, has generated interest as potential targets for the development of novel anti-asthmatic and anti-inflammatory compounds. PDE4 is known to exist as at lease four isoenzymes, each of which is encoded by a distinct gene. Each of the four known PDE4 gene products is believed to play varying roles in allergic and/or inflammatory responses. Thus, it is believed that inhibition of PDE4, particularly the specific PDE4 isoforms that produce detrimental responses, can beneficially affect allergy and inflammation symptoms. It would be desirable to provide novel compounds and compositions that inhibit PDE4 activity.

Inhibition of PDE4 activity is believed effective for the treatment of osteoporosis by reducing bone loss. For example, Ken-ici Miyamoto et al., Biochem. Pharmacology, 54:613–617(1997) describes the effect of a PDE4 on bone loss. Therefore, it would be desirable to provide novel compounds and compositions that inhibit PDE4 activity.

A major concern with the use of PDE4 inhibitors is the side effect of emesis which has been observed for several candidate compounds as described in C. Burnouf et al. Ann. Rep. In Med. Chem., 33:91–109(1998). B. Hughes et al., Br. J. Pharmacol., 118:1183–1191(1996); M. J. Perry et al., Cell Biochem. Biophys., 29:113–132(1998); S. B. Christensen et al., J. Med. Chem., 41:821–835(1998); and Burnouf (Ibid.) describe the wide variation of the severity of the undesirable side effects exhibited by various compounds. As described in M. D. Houslay et al., Adv. In Pharmacol., 44:225–342(1998) and D. Spina et al., Adv. In Pharmacol., 44:33–89(1998), there is great interest and research of therapeutic PDE4 inhibitors.

International Patent Publication WO9422852 describes quinolines as PDE4 inhibitors.

A. H. Cook, et al., J. Chem. Soc., 413–417(1943) describes gamma-pyridylquinolines. Other quinoline compounds are described in Kei Manabe et al., J. Org. Chem., 58(24):6692–6700(1993); Kei Manabe et al., J. Am. Chem. Soc., 115(12):5324–5325(1993); and Kei Manabe et al., J. Am. Chem. Soc., 114(17):6940–6941(1992).

Compounds that include ringed systems are described by various investigators as effective for a variety of therapies and utilities. For example, International Patent Publication No. WO 98/25883 describes ketobenzamides as calpain inhibitors, European Patent Publication No. EP 811610 and U.S. Pat. Nos. 5,679,712, 5,693,672 and 5,747,541 describe substituted benzoylguanidine sodium channel blockers, U.S. Pat. No. 5,736,297 describes ring systems useful as a photosensitive composition.

U.S. Pat. Nos. 5,491,147, 5,608,070, 5,622,977, 5,739,144, 5,776,958, 5,780,477, 5,786,354, 5,798,373, 5,849,770, 5,859,034, 5,866,593, 5,891,896, and International Patent Publication WO 95/35283 describe PDE4 inhibitors that are tri-substituted aryl or heteroaryl phenyl derivatives. U.S. Pat. No. 5,580,888 describes PDE4 inhibitors that are styryl derivatives. U.S. Pat. No. 5,550,137 describes PDE4 inhibitors that are phenylaminocarbonyl derivatives. U.S. Pat. No. 5,340,827 describes PDE4 inhibitors that are phenylcarboxamide compounds. U.S. Pat. No. 5,780,478 describes PDE4 inhibitors that are tetra-substituted phenyl derivatives. International Patent Publication WO 96/00215 describes substituted oxime derivatives useful as PDE4 inhibitors. U.S. Pat. No. 5,633,257 describes PDE4 inhibitors that are cyclo(alkyl and alkenyl)phenyl-alkenyl (aryl and heteroaryl) compounds.

However, there remains a need for novel compounds and compositions that therapeutically inhibit PDE4 with minimal side effects.

SUMMARY OF THE INVENTION

The present invention is directed to novel substituted 8-arylquinolines that are PDE4 inhibitors, wherein the aryl group at the 8-position contains a meta two carbon atom bridge to an optionally substituted phenyl or pyridyl group. This invention also provides a pharmaceutical composition which includes an effective amount of the novel substituted 8-arylquinoline and a pharmaceutically acceptable carrier.

This invention further provides a method of treatment in mammals of, for example, asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, osteoporosis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, monopolar depression, acute and chronic neurodegenerative disorders with inflammatory components, Parkinson disease, Alzheimer's disease, spinal cord trauma, head injury, multiple sclerosis, tumour growth and cancerous invasion of normal tissues by the administration of an effective amount of the novel substituted 8-arylquinoline or a precursor compound which forms in vivo the novel substituted 8-arylquinoline.

DETAILED DESCRIPTION OF THE INVENTION

A compound of this invention is represented by Formula (I):

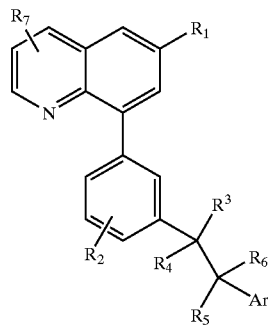

(I)

or a pharmaceutically acceptable salt thereof, wherein

Ar is phenyl, pyridinone, pyridyl, or pyridyl N-oxide, optionally substituted with 1–5 independent —$C_{1-6}$alkyl, —OH, —CN, halogen, —$CF_3$, —($C_{0-6}$alkyl)-$SO_n$—($C_{1-6}$alkyl), —($C_{0-6}$alkyl)-$SO_n$—NH—($C_{1-6}$alkyl) or 5-membered heteroaryl ring containing 1–4 heteroatoms independently selected from O, S or N, wherein the 5-membered-ring is optionally substituted with $C_{1-6}$alkyl, and the alkyl group- is optionally substituted with 1–3 independent —OH, —CN, halogen, or —$CF_3$;

$R_1$ is hydrogen, halogen; or a —$C_{1-6}$alkyl, -cyclo$C_{3-6}$alkyl, —$C_{1-6}$alkenyl, —$C_{0-4}$alkyl-C(O)—$C_{0-4}$alkyl, —$C_{1-6}$alkoxy, aryl, heteroaryl, —CN, -heterocyclo$C_{3-6}$alkyl, -amino, —$C_{1-6}$alkylamino, —$C_{1-6}$alkyl)($C_{1-6}$alkyl)amino, —$C_{1-6}$alkyl(oxy)$C_{1-6}$alkyl, —C(O)NH(aryl), —C(O)NH(heteroaryl), —$SO_n$NH(aryl), —$SO_n$NH(heteroaryl), —$SO_n$NH($C_{1-6}$alkyl), —C(O)N($C_{0-6}$alkyl)($C_{0-6}$alkyl), —NH—$SO_n$—($C_{1-6}$alkyl), -carbamoyl, —($C_{1-6}$alkyl)-O—C(CN)-dialkylamino, or —($C_{0-6}$alkyl)-$SO_n$—($C_{1-6}$alkyl) group, wherein any of the groups is optionally substituted with 1–5 substituents; wherein each substituent is independently a halogen, —OH, —CN, —$C_1$–$C_6$alkyl, —C(O)(heterocyclo$C_{3-6}$alkyl), —C(O)—O—($C_{0-6}$alkyl), —C(O)—O-aryl, alkoxy, cycloalkyloxy, acyl, acyloxy, -cyclo$C_{3-6}$alkyl, heterocyclo$C_{3-6}$alkyl, aryl, heteroaryl, pyridyl N-oxide, carbonyl, carbamoyl, or —$SO_n$—($C_{1-6}$alkyl);

$R_2$, $R_3$, $R_6$, and $R_7$ are each independently hydrogen, halogen, hydroxyl, —$C_{1-6}$alkyl, or —$C_{1-6}$alkoxy, wherein the alkyl and alkoxy are optionally substituted with 1–3 independently halogen or OH;

$R_4$ is hydrogen, halogen, —CN, phenyl, oxadiazolyl, or —C(O)—O—$C_{0-6}$alkyl, wherein the phenyl, oxadiazolyl, or —C(O)—O—$C_{0-6}$alkyl is optionally substituted with 1–3 independent halogen, CN, CF3, —$SO_n$—$C_{1-6}$alkyl, or $C_{1-6}$alkyl substituents, and the alkyl group is optionally substituted with OH R5 is hydrogen, hydroxyl, —CN; or a —$C_{1-6}$alkyl, —C(O)$C_{1-6}$alkyl, —C(O)-aryl, —C(O)-pyridyl, —C(O)—O—$C_{3-6}$alkyl, —C(O)—$C_{3-7}$cycloalkyl, —$C_{1-6}$alkyl-$C_{3-7}$cycloalkyl, —$C_{1-6}$alkyl($C_{3-7}$cycloalkyl)$_2$, —$C_{1-6}$alkyl-aryl, —C(O)—N($C_{0-6}$alkyl)$_2$, —$SO_n$aryl, —$SO_n$—$C_{1-6}$alkyl, —$SO_n$—$C_{3-7}$cycloalkyl, —$SO_n$—N($C_{0-6}$alkyl)$_2$, —P(O)($C_{1-6}$alkyl)$_2$, —P(O)($C_{1-6}$alkoxy)$_2$, phenyl, pyridyl, —$SO_n$imidazolyl, —$SO_n$thiazolyl, 5-membered heteroaryl ring containing 1–4 heteroatoms independently selected from O, S or N or oxoisoxaphosphinanyl group, any of which group optionally substituted with 1–6 independent halogen, hydroxyl, —CN, —$CF_3$, —$C_{1-6}$alkyl, —$SO_n$—$C_{1-6}$alkyl, —C(O)—O—$C_{0-6}$alkyl, or hydroxy$C_{1-6}$alkyl substituents;

or $R_5$ and $R_6$ form =O;

or $R_6$ and $R_3$ form —$CH_2$— or —O—; and n is 0, 1, or 2.

In one aspect, the compound of this invention is represented by Formula (I) or a pharmaceutically acceptable salt thereof, wherein Ar is phenyl, optionally substituted with 1–3 independent —$C_{1-6}$alkyl, —OH, —CN, halogen, —$CF_3$, —($C_{0-6}$alkyl)-$SO_n$—($C_{1-6}$alkyl), —($C_{0-6}$alkyl)-$SO_n$—NH—($C_{1-6}$alkyl) or 5-membered heteroaryl ring containing 1–4 heteroatoms independently selected from O, S or N, wherein the 5-membered-ring is optionally substituted with $C_{1-6}$alkyl, and the alkyl group- is optionally substituted with 1–3 independent —OH, —CN, halogen, or —$CF_3$;

$R_1$ is hydrogen, halogen; or a —$C_{1-6}$alkyl, -cyclo$C_{3-6}$alkyl, —$C_{1-6}$alkenyl, —$C_{0-4}$alkyl-C(O)—$C_{0-4}$alkyl, —$C_{1-6}$alkoxy, aryl, heteroaryl, —CN, -heterocyclo$C_{3-6}$alkyl, -amino, —$C_{1-6}$alkylamino, —$C_{1-6}$alkyl)($C_{1-6}$alkyl)amino, —$C_{1-6}$alkyl(oxy)$C_{1-6}$alkyl, —C(O)NH(aryl), —C(O)NH(heteroaryl), —$SO_n$NH(aryl), —$SO_n$NH(heteroaryl), —$SO_n$NH($C_{1-6}$alkyl), —C(O)N($C_{0-6}$alkyl)($C_{0-6}$alkyl), —NH—$SO_n$—($C_{1-6}$alkyl), -carbamoyl, —($C_{1-6}$alkyl)-O—C(CN)-dialkylamino, or —($C_{0-6}$alkyl)-$SO_n$—($C_{1-6}$alkyl) group, wherein any of the groups is optionally substituted with 1–5 substituents; wherein each substituent is independently a halogen, —OH, —CN, —$C_1$–$C_6$alkyl, —C(O)(heterocyclo$C_{3-6}$alkyl), —C(O)—O—($C_{0-6}$alkyl), —C(O)—O-aryl, alkoxy, cycloalkyloxy, acyl, acyloxy, -cyclo$C_{3-6}$alkyl, heterocyclo$C_{3-6}$alkyl, aryl, heteroaryl, pyridyl N-oxide, carbonyl, carbamoyl, or —$SO_n$—$C_{1-6}$alkyl);

$R_2$, $R_3$, $R_6$, and $R_7$ are each independently hydrogen, halogen, hydroxyl, —$C_{1-6}$alkyl, or —$C_{1-6}$alkoxy, wherein the alkyl and alkoxy are optionally substituted with 1–3 independently halogen or hydroxyl;

$R_4$ is hydrogen, halogen, —CN, phenyl, oxadiazolyl, or —C(O)—O—$C_{0-6}$alkyl, wherein the phenyl, oxadiazolyl, or —C(O)—O—$C_{0-6}$alkyl is optionally substituted with 1–3 independent halogen, CN, CF3, —$SO_n$—$C_{1-6}$alkyl, or $C_{1-6}$alkyl substituents, and the alkyl group is optionally substituted with OH;

R5 is hydrogen, hydroxyl, —CN; or a —$C_{1-6}$alkyl, —C(O)$C_{1-6}$alkyl, —C(O)-aryl, —C(O)-pyridyl, —C(O)—O—$C_{0-6}$alkyl, —C(O)—$C_{3-7}$cycloalkyl, —$C_{1-6}$alkyl-$C_{3-7}$cycloalkyl, —$C_{1-6}$alkyl($C_{3-7}$cycloalkyl)$_2$, —$C_{1-6}$alkyl-aryl, —C(O)—N($C_{0-6}$alkyl)$_2$, —$SO_n$aryl, —$SO_n$—$C_{1-6}$alkyl, —$SO_n$—$C_{3-7}$cycloalkyl, —$SO_n$—N($C_{0-6}$alkyl)$_2$, —P(O)($C_{1-6}$alkyl)$_2$, —P(O)($C_{1-6}$alkoxy)$_2$, phenyl, pyridyl, —$SO_n$imidazolyl, —$SO_n$thiazolyl, 5-membered heteroaryl ring containing 1–4 heteroatoms independently selected from O, S or N or oxoisoxaphosphinanyl group, any of which group optionally substituted with 1–6 independent halogen, hydroxyl, —CN, —CF$_3$, —C$_{1-6}$alkyl, —SO$_n$—C$_{1-6}$alkyl, —C(O)—O—C$_{0-6}$alkyl, or hydroxyC$_{1-6}$alkyl substituents;

or R$_5$ and R$_6$ form =O;
or R$_6$ and R$_3$ form —CH$_2$— or —O—; and
n is 0, 1, or 2.

In an embodiment of this one aspect, the compound of this invention is represented by Formula (I) or a pharmaceutically acceptable salt thereof, wherein Ar is phenyl, optionally substituted with 1–3 independent —C$_{1-6}$alkyl, —OH, —CN, halogen, —CF$_3$, —(C$_{0-6}$alkyl)-SO$_n$—(C$_{1-6}$alkyl), —(C$_{0-6}$alkyl)-SO$_n$—NH—(C$_{1-6}$alkyl) or 5-membered heteroaryl ring containing 1–4 heteroatoms independently selected from O, S or N, wherein the 5-membered-ring is optionally substituted with C$_{1-6}$alkyl, and the alkyl group- is optionally substituted with 1–3 independent —OH, —CN, halogen, or —CF$_3$;

R$_1$ is hydrogen, halogen; or a —C$_{1-6}$alkyl, -cycloC$_{3-6}$alkyl, —C$_{1-6}$alkenyl, —C$_{0-4}$alkyl-C(O)—C$_{0-4}$alkyl, —C$_{1-6}$alkoxy, aryl, heteroaryl, —CN, -heterocycloC$_{3-6}$alkyl, -amino, —C$_{1-6}$alkylamino, —(C$_{1-6}$alkyl)(C$_{1-6}$alkyl)amino, —C$_{1-6}$alkyl(oxy)C$_{1-6}$alkyl, —C(O)NH(aryl), —C(O)NH(heteroaryl), —SO$_n$NH(aryl), —SO$_n$NH(heteroaryl), —SO$_n$NH(C$_{1-6}$alkyl), —C(O)N(C$_{0-6}$alkyl)(C$_{0-6}$alkyl), —NH—SO$_n$—(C$_{1-6}$alkyl), -carbamoyl, —(C$_{1-6}$alkyl)-O—C(CN)-dialkylamino, or —(C$_{0-6}$alkyl)-SO$_n$—(C$_{1-6}$alkyl) group, wherein any of the groups is optionally substituted with 1–5 substituents; wherein each substituent is independently a halogen, —OH, —CN, —C$_1$-C$_6$alkyl, —C(O)(heterocycloC$_{3-6}$alkyl), —C(O)—O—(C$_{0-6}$alkyl), —C(O)—O-aryl, alkoxy, cycloalkyloxy, acyl, acyloxy, -cycloC$_{3-6}$alkyl, heterocycloC$_{3-6}$alkyl, aryl, heteroaryl, pyridyl N-oxide, carbonyl, carbamoyl, or —SO$_n$—(C$_{1-6}$alkyl);

R$_2$, R$_3$, R$_6$, and R$_7$ are each independently hydrogen, halogen, hydroxyl, —C$_{1-6}$alkyl, or —C$_{1-6}$alkoxy, wherein the alkyl and alkoxy are optionally substituted with 1–3 independently halogen or hydroxyl;

R$_4$ is hydrogen, halogen, —CN, or —C(O)—O—C$_{0-6}$alkyl, wherein the —C(O)—O—C$_{0-6}$alkyl is optionally substituted with 1–3 independent halogen, CN, CF3, —SO$_n$—C$_{1-6}$alkyl, or C$_{1-6}$alkyl substituents, and the alkyl group is optionally substituted with OH;

R5 is hydrogen, hydroxyl, —CN; or a —C$_{1-6}$alkyl, —C(O)C$_{1-6}$alkyl, —C(O)-aryl, —C(O)-pyridyl, —C(O)—O—C$_{0-6}$alkyl, —C(O)—C$_{3-7}$cycloalkyl, —C$_{1-6}$alkyl-C$_{3-7}$cycloalkyl, C$_{1-6}$alkyl(C$_{3-7}$cycloalkyl)$_2$, —C$_{1-6}$alkyl-aryl, C(O)—N(C$_{0-6}$alkyl)$_2$, —SO$_n$aryl, —SO$_n$—C$_{1-6}$alkyl, —SO$_n$—C$_{3-7}$cycloalkyl, —SO$_n$—N(C$_{0-6}$alkyl)$_2$, —P(O)(C$_{1-6}$alkyl)$_2$, —P(O)(C$_{1-6}$alkoxy)$_2$, phenyl, pyridyl, —SO$_n$imidazolyl, —SO$_n$thiazolyl, 5-membered heteroaryl ring containing 1–4 heteroatoms independently selected from O, S or N or oxoisoxaphosphinanyl group, any of which group optionally substituted with 1–6 independent halogen, hydroxyl, —CN, —CF$_3$, —C$_{1-6}$alkyl, —SO$_n$—C$_{1-6}$alkyl, —C(O)—O—C$_{0-6}$alkyl, or hydroxyC$_{1-6}$alkyl substituents;

or R$_5$ and R$_6$ form =O;
or R$_6$ and R$_3$ form —CH$_2$— or —O—; and
n is 0, 1, or 2.

In another embodiment of this one aspect, the compound of this invention is represented by Formula (I) or a pharmaceutically acceptable salt thereof, wherein Ar is phenyl, optionally substituted with 1–3 independent —C$_{1-6}$alkyl, —OH, —CN, halogen, —CF$_3$, —(C$_{0-6}$alkyl)-SO$_n$—(C$_{1-6}$alkyl), —(C$_{0-6}$alkyl)-SO$_n$—NH—(C$_{1-6}$alkyl) or 5-membered heteroaryl ring containing 1–4 heteroatoms independently selected from O, S or N, wherein the 5-membered-ring is optionally substituted with C$_{1-6}$alkyl, and the alkyl group- is optionally substituted with 1–3 independent —OH, —CN, halogen, or —CF$_3$;

R$_1$ is hydrogen, halogen; or a —C$_{1-6}$alkyl, -cycloC$_{3-6}$alkyl, —C$_{1-6}$alkenyl, —C$_{0-4}$alkyl-C(O)—C$_{0-4}$alkyl, —C$_{1-6}$alkoxy, aryl, heteroaryl, —CN, -heterocycloC$_{3-6}$alkyl, -amino, —C$_{1-6}$alkylamino, —(C$_{1-6}$alkyl)(C$_{1-6}$alkyl)amino, —C$_{1-6}$alkyl(oxy)C$_{1-6}$alkyl, —C(O)NH(aryl), —C(O)NH(heteroaryl), —SO$_n$NH(aryl), —SO$_n$NH(heteroaryl), —SO$_n$NH(C$_{1-6}$alkyl), —C(O)N(C$_{0-6}$alkyl)(C$_{0-6}$alkyl), —NH—SO$_n$—(C$_{1-6}$alkyl), -carbamoyl, —(C$_{1-6}$alkyl)-O—C(CN)-dialkylamino, or —(C$_{0-6}$alkyl)-SO$_n$—(C$_{1-6}$alkyl) group, wherein any of the groups is optionally substituted with 1–5 substituents; wherein each substituent is independently a halogen, —OH, —CN, —C$_1$-C$_6$alkyl, —C(O)(heterocycloC$_{3-6}$alkyl), —C(O)—O—(C$_{0-6}$alkyl), —C(O)—O-aryl, alkoxy, cycloalkyloxy, acyl, acyloxy, -cycloC$_{3-6}$alkyl, heterocycloC$_{3-6}$alkyl, aryl, heteroaryl, pyridyl N-oxide, carbonyl, carbamoyl, or —SO$_n$—C$_{1-6}$alkyl);

R$_2$, R$_3$, R$_6$, and R$_7$ are each independently hydrogen, halogen, hydroxyl, —C$_{1-6}$alkyl, or —C$_{1-6}$alkoxy, wherein the alkyl and alkoxy are optionally substituted with 1–3 independently halogen or hydroxyl;

R$_4$ is oxadiazolyl optionally substituted with 1–3 independent halogen, CN, CF3, —SO$_n$—C$_{1-6}$alkyl, or C$_{1-6}$alkyl substituents, and the alkyl group is optionally substituted with OH;

R5 is hydrogen, hydroxyl, —CN; or a —C$_{1-6}$alkyl, —C(O)C$_{1-6}$alkyl, —C(O)-aryl, —C(O)-pyridyl, —C(O)—O—C$_{0-6}$alkyl, —(O)C$_{3-7}$cycloalkyl, —C$_{1-6}$alkyl-C$_{3-7}$cycloalkyl, C$_{1-6}$alkyl(C$_{3-7}$cycloalkyl)$_2$, —C$_{1-6}$alkyl-aryl, —C(O)—N(C$_{0-6}$alkyl)$_2$, —SO$_n$aryl, —SO$_n$—C$_{1-6}$alkyl, —SO$_n$—C$_{3-7}$cycloalkyl, —SO$_n$—N(C$_{0-6}$alkyl)$_2$, —P(O)(C$_{1-6}$alkyl)$_2$, —P(O)(C$_{1-6}$alkoxy)$_2$, phenyl, pyridyl, —SO$_n$imidazolyl, —SO$_n$thiazolyl, 5-membered heteroaryl ring containing 1–4 heteroatoms independently selected from O, S or N or oxoisoxaphosphinanyl group, any of which group optionally substituted with 1–6 independent halogen, hydroxyl, —CN, —CF$_3$, —C$_{1-6}$alkyl, —SO$_n$—C$_{1-6}$ alkyl, —C(O)—O—C$_{0-6}$alkyl, or hydroxy C$_{1-6}$alkyl substituents;

or R$_5$ and R$_6$ form =O;
or R$_6$ and R$_3$ form —CH$_2$— or —O—; and
n is 0, 1, or 2.

In still another embodiment of this one aspect, the compound of this invention is represented by Formula (I) or a pharmaceutically acceptable salt thereof, wherein Ar is phenyl, optionally substituted with 1–3 independent —C$_{1-6}$alkyl, —OH, —CN, halogen, —CF$_3$, —(C$_{1-6}$alkyl)-SO$_n$—(C$_{1-6}$alkyl), —(C$_{0-6}$alkyl)-SO$_n$—NH—(C$_{1-6}$alkyl) or 5-membered heteroaryl ring containing 1–4 heteroatoms independently selected from O, S or N, wherein the 5-membered-ring is optionally substituted with C$_{1-6}$alkyl, and the alkyl group- is optionally substituted with 1–3 independent —OH, —CN, halogen, or —CF$_3$;

R$_1$ is hydrogen, halogen; or a —C$_{1-6}$alkyl, -cycloC$_{3-6}$alkyl, —C$_{1-6}$alkenyl, —C$_{0-4}$alkyl-C(O)—C$_{0-4}$alkyl, —C$_{1-6}$alkoxy, aryl, heteroaryl, —CN, -heterocycloC$_{3-6}$alkyl, -amino, —C$_{1-6}$alkylamino, —(C$_{1-6}$alkyl)(C$_{1-6}$alkyl)amino, —C$_{1-6}$alkyl(oxy)C$_{1-6}$alkyl, —C(O)NH(aryl), —C(O)NH(heteroaryl), —SO$_n$NH(aryl), —SO$_n$NH(heteroaryl), —SO$_n$NH(C$_{1-6}$alkyl), —C(O)N(C$_{0-6}$alkyl)(C$_{0-6}$alkyl), —NH—SO$_n$—(C$_{1-6}$alkyl), -carbamoyl, —(C$_{1-6}$alkyl)-O—

C(CN)-dialkylamino, or —($C_{0-6}$alkyl)-$SO_n$—($C_{1-6}$alkyl) group, wherein any of the groups is optionally substituted with 1–5 substituents; wherein each substituent is independently a halogen, —OH, —CN, —$C_1$-$C_6$alkyl, —C(O)(heterocyclo$C_{3-6}$alkyl), —C(O)—O—($C_{0-6}$alkyl), —C(O)—O-aryl, alkoxy, cycloalkyloxy, acyl, acyloxy, -cyclo$C_{3-6}$alkyl, heterocyclo$C_{3-6}$alkyl, aryl, heteroaryl, pyridyl N-oxide, carbonyl, carbamoyl, or —$SO_n$($C_{1-6}$alkyl);

$R_2$ and $R_7$ are each independently hydrogen, halogen, hydroxyl, —$C_{1-6}$alkyl, or —$C_{1-6}$alkoxy, wherein the alkyl and alkoxy are optionally substituted with 1–3 independently halogen or hydroxyl;

$R_4$ is hydrogen, halogen, —CN, phenyl, oxadiazolyl, or —C(O)—O—$C_{0-6}$alkyl, wherein the phenyl, oxadiazolyl, or —C(O)—$C_{0-6}$alkyl is optionally substituted with 1–3 independent halogen, CN, CF3, —$SO_n$—$C_{1-6}$alkyl, or $C_{1-6}$alkyl substituents, and the alkyl group is optionally substituted with OH;

R5 is hydrogen, hydroxyl, —CN; or a —$C_6$alkyl, —C(O)$C_{1-6}$alkyl, —C(O)-aryl, —C(O)-pyridyl, —C(O)—O—$C_{0-6}$alkyl, —C(O)—$C_{3-7}$cycloalkyl, —$C_{1-6}$alkyl-$C_{3-7}$cycloalkyl, —$C_{1-6}$alkyl($C_{3-7}$cycloalkyl)$_2$, —$C_{1-6}$alkyl-aryl, —C(O)—N($C_{0-6}$alkyl)$_2$, —$SO_n$aryl, —$SO_n$—$C_{1-6}$alkyl, $SO_n$—$C_{3-7}$cycloalkyl, —$SO_n$—N($C_{0-6}$alkyl)$_2$, —P(O)($C_{1-6}$alkyl)$_2$, —P(O)($C_{1-6}$alkoxy)$_2$, phenyl, pyridyl, —$SO_n$imidazolyl, —$SO_n$thiazolyl, 5-membered heteroaryl ring containing 1–4 heteroatoms independently selected from O, S or N or oxoisoxaphosphinanyl group, any of which group optionally substituted with 1–6 independent halogen, hydroxyl, —CN, —$CF_3$, —$C_{1-6}$alkyl, —$SO_n$—$C_{1-6}$ alkyl, —C(O)—O—$C_{0-6}$alkyl, or hydroxy$C_{1-6}$alkyl substituents;

$R_6$ and $R_3$ form —$CH_2$—; and n is 0, 1, or 2.

In still another embodiment of this one aspect, the compound of this invention is represented by Formula (I) or a pharmaceutically acceptable salt thereof, wherein Ar is phenyl, optionally substituted with 1–3 independent —$C_{1-6}$alkyl, —OH, —CN, halogen, —$CF_3$, —($C_{0-6}$alkyl)-$SO_n$—($C_{1-6}$alkyl), —($C_{0-6}$alkyl)-$SO_n$—NH—($C_{1-6}$alkyl) or 5-membered heteroaryl ring containing 1–4 heteroatoms independently selected from O, S or N, wherein the 5-membered-ring is optionally substituted with $C_{1-6}$alkyl, and the alkyl group- is optionally substituted with 1–3 independent —OH, —CN, halogen, or —$CF_3$;

$R_1$ is —$C_{1-6}$alkyl, optionally substituted with 1–5 substituents; wherein each substituent is independently a halogen, —H, —CN, —$C_1$-$C_6$alkyl, —C(O)(heterocyclo$C_{3-6}$alkyl), —C(O)O—($C_{0-6}$alkyl), —(O)—O-aryl, alkoxy, cycloalkyloxy, acyl, acyloxy, -cyclo$C_{3-6}$alkyl, heterocyclo$C_{3-6}$alkyl, aryl, heteroaryl, pyridyl N-oxide, carbonyl, carbamoyl, or —$SO_n$—($C_{1-6}$alkyl);

$R_2$, $R_3$, $R_6$, and $R_7$ are each independently hydrogen, halogen, hydroxyl, —$C_{1-6}$alkyl, or —$C_{1-6}$alkoxy, wherein the alkyl and alkoxy are optionally substituted with 1–3 independently halogen or hydroxyl;

$R_4$ is hydrogen, halogen, CN, phenyl, oxadiazolyl, or —C(O)—O—$C_{0-6}$alkyl, wherein the phenyl, oxadiazolyl, or —C(O)—O—$C_{0-6}$alkyl is optionally substituted with 1–3 independent halogen, CN, CF3, —$SO_n$—$C_{1-6}$alkyl, or $C_{1-6}$alkyl substituents, and the alkyl group is optionally substituted with OH R5 is hydrogen, hydroxyl, —CN; or a —$C_{1-6}$alkyl, —C(O)$C_{1-6}$alkyl, —C(O)-aryl, —C(O)-pyridyl, —C(O)—O—$C_{0-6}$alkyl, —C(O)—$C_{3-7}$cycloalkyl, —$C_{1-6}$alkyl-$C_{3-7}$cycloalkyl, —$C_{1-6}$alkyl($C_{3-7}$cycloalkyl)$_2$, —$C_{1-6}$alkyl-aryl, —C(O)—N($C_{0-6}$alkyl)$_2$, —$SO_n$aryl, —$SO_n$—$C_{1-6}$alkyl, —$SO_n$—$C_{3-7}$cycloalkyl, —$SO_n$—N($C_{0-6}$alkyl)$_2$, —P(O)($C_{1-6}$alkyl)$_2$, —P(O)($C_{1-6}$alkoxy)$_2$, phenyl, pyridyl, —$SO_n$imidazolyl, —$SO_n$thiazolyl, 5-membered heteroaryl ring containing 1–4 heteroatoms independently selected from O, S or N group or oxoisoxaphosphinanyl group, any of which group optionally substituted with 1–6 independent halogen, hydroxyl, —CN, —$CF_3$, —$C_{1-6}$alkyl, —SO—$C_{1-6}$ alkyl, —C(O)—O—$C_{0-6}$alkyl, or hydroxy$C_{1-6}$alkyl substituents;

or $R_5$ and $R_6$ form =O;

or $R_6$ and $R_3$ form —$CH_2$— or —O—; and n is 0, 1, or 2.

In still another embodiment of this one aspect, the compound of this invention is represented by Formula (I) or a pharmaceutically acceptable salt thereof, wherein Ar is phenyl, optionally substituted with 1–3 independent —$C_{1-6}$alkyl, —OH, —CN, halogen, —$CF_3$, —($C_{0-6}$alkyl)-$SO_n$—($C_{1-6}$alkyl), —($C_{0-6}$alkyl)-$SO_n$—NH—($C_{1-6}$alkyl) or 5-membered heteroaryl ring containing 1–4 heteroatoms independently selected from O, S or N, wherein the 5-membered-ring is optionally substituted with $C_{1-6}$alkyl, and the alkyl group- is optionally substituted with 1–3 independent —OH, —CN, halogen, or —$CF_3$;

$R_1$ is —$C_{1-6}$alkyl, optionally substituted with 1–5 substituents; wherein each substituent is independently a halogen, —OH, —CN, —$C_1$-$C_6$alkyl, —C(O)(heterocyclo$C_{3-6}$alkyl), —C(O)—O—($C_{0-6}$alkyl), —C(O)—O-aryl, alkoxy, cycloalkyloxy, acyl, acyloxy, -cyclo$C_{3-6}$alkyl, heterocyclo$C_{3-6}$alkyl, aryl, heteroaryl, pyridyl N-oxide, carbonyl, carbamoyl, or —$SO_n$—($C_{1-6}$alkyl);

$R_2$, and $R_3$ are each hydrogen;

$R_4$ is hydrogen;

R5 is hydrogen, hydroxyl, —CN; or a —$C_{1-6}$alkyl, —C(O)$C_{1-6}$alkyl, —C(O)-aryl, —C(O)-pyridyl, —C(O)—O—$C_{0-6}$alkyl, —C(O)—$C_{3-7}$cycloalkyl, —$C_{1-6}$alkyl-$C_{3-7}$cycloalkyl, —$C_{1-6}$alkyl($C_{3-7}$cycloalkyl)$_2$, —$C_{1-6}$alkyl-aryl, —C(O)—N($C_{0-6}$alkyl)$_2$, —$SO_n$aryl, —$SO_n$—$C_{1-6}$alkyl, —$SO_n$—$C_{3-7}$cycloalkyl, —$SO_n$—N($C_{0-6}$alkyl)$_2$, —P(O)($C_{1-6}$alkyl)$_2$, —P(O)($C_{1-6}$alkoxy)$_2$, phenyl, pyridyl, —$SO_n$imidazolyl, —$SO_n$thiazolyl, 5-membered heteroaryl ring containing 1–4 heteroatoms independently selected from O, S or N group or oxoisoxaphosphinanyl group, any of which group optionally substituted with 1–6 independent halogen, hydroxyl, —CN, —$CF_3$, —$C_{1-6}$alkyl, —$SO_n$—$C_{1-6}$ alkyl, C(O)—O—$C_{0-6}$alkyl, or hydroxy$C_{1-6}$alkyl substituents;

$R_6$, and $R_7$ are each independently hydrogen, halogen, hydroxyl, —$C_{1-6}$alkyl, or —$C_{1-6}$alkoxy, wherein the alkyl and alkoxy are optionally substituted with 1–3 independently halogen or hydroxyl;

or $R_5$ and $R_6$ form =O;

or $R_6$ and $R_3$ form —$CH_2$— or —O—; and n is 0, 1, or 2.

In still another embodiment of this one aspect, the compound of this invention is represented by Formula (I) or a pharmaceutically acceptable salt thereof, wherein Ar is phenyl substituted with —($C_{0-6}$alkyl)-$SO_n$—($C_{1-6}$alkyl), and the alkyl group is optionally substituted with 1–3 independent —OH, —CN, halogen, or —$CF_3$;

$R_1$ is —$C_{1-6}$alkyl, optionally substituted with 1–5 substituents; wherein each substituent is independently a halogen, —OH, —CN, —$C_1$-$C_6$alkyl, —C(O)(heterocyclo$C_{3-6}$alkyl), —C(O)—O—($C_{0-6}$alkyl), —C(O)—O-aryl, alkoxy, cycloalkyloxy, acyl, acyloxy, -cyclo$C_{3-6}$alkyl, heterocyclo$C_{3-6}$alkyl, aryl, heteroaryl, pyridyl N-oxide, carbonyl, carbamoyl, or —$SO_n$—($C_{1-6}$alkyl);

$R_2$, $R_3$, $R_6$, and $R_7$ are each independently hydrogen, halogen, hydroxyl, —$C_{1-6}$alkyl, or —$C_{1-6}$alkoxy, wherein the alkyl and alkoxy are optionally substituted with 1–3 independently halogen or hydroxyl;

$R_4$ is hydrogen, halogen, —CN, phenyl, oxadiazolyl, or —C(O)—O—$C_{0-6}$alkyl, wherein the phenyl, oxadiazolyl, or —C(O)—O—$C_{0-6}$alkyl is optionally substituted with 1–3 independent halogen, CN, CF3, —$SO_{n-1}C_{1-6}$alkyl, or $C_{1-6}$alkyl substituents, and the alkyl group is optionally substituted with OH R5 is hydrogen, hydroxyl, —CN; or a —$C_{1-6}$alkyl, —$C(O)C_{1-6}$alkyl, —C(O)-aryl, —C(O)-pyridyl, —C(O)—O—$C_{0-6}$alkyl, —C(O)—$C_{3-7}$cycloalkyl, —$C_{1-6}$alkyl-$C_{3-7}$cycloalkyl, —$C_{1-6}$alkyl($C_{3-7}$cycloalkyl)$_2$, —$C_{1-6}$alkyl-aryl, —C(O)—N($C_{0-6}$alkyl)$_2$, —$SO_n$aryl, —$SO_n$—$C_{1-6}$alkyl, —$SO_n$—$C_{3-7}$cycloalkyl, —$SO_n$—N($C_{0-6}$alkyl)$_2$, —P(O)($C_{1-6}$alkyl)$_2$, —P(O)($C_{1-6}$alkoxy)$_2$, phenyl, pyridyl, —$SO_n$imidazolyl, —$SO_n$thiazolyl, 5-membered heteroaryl ring containing 1–4 heteroatoms independently selected from O, S or N group or oxoisoxaphosphinanyl group, any of which group optionally substituted with 1–6 independent halogen, hydroxyl, —CN, —$CF_3$, —$C_{1-6}$alkyl, —$SO_n$—$C_{1-6}$ alkyl, —C(O)—O—$C_{0-6}$alkyl, or hydroxy$C_{1-6}$alkyl substituents;

or $R_5$ and $R_6$ form =O;
or $R_6$ and $R_3$ form —$CH_2$— or —O—; and
n is 0, 1, or 2.

In still another embodiment of this one aspect, the compound of this invention is represented by Formula (I) or a pharmaceutically acceptable salt thereof, wherein Ar is phenyl substituted with —($C_{0-6}$alkyl)-$SO_n$—($C_{1-6}$alkyl), and the alkyl group- is optionally substituted with 1–3 independent —OH, —CN, halogen, or —$CF_3$;

$R_1$ is —$C_{1-6}$alkyl, optionally substituted with 1–5 substituents; wherein each substituent is independently a halogen, —OH, —CN, —$C_1$-$C_6$alkyl, —C(O)(heterocyclo$C_{3-6}$alkyl), —C(O)—O—($C_{0-6}$alkyl), —C(O)—O-aryl, alkoxy, cycloalkyloxy, acyl, acyloxy, -cyclo$C_{3-6}$alkyl, heterocyclo$C_{3-6}$alkyl, aryl, heteroaryl, pyridyl N-oxide, carbonyl, carbamoyl, or —$SO_n$—($C_{1-6}$alkyl);

$R_2$ and $R_3$ are each hydrogen;
$R_4$ is hydrogen;

R5 is hydrogen, hydroxyl, —CN; or a $C_{1-6}$alkyl, —C(O)$C_{1-6}$alkyl, —C(O)-aryl, —C(O)-pyridyl, —C(O)—O—$C_{0-6}$alkyl, —C(O)—$C_{3-7}$cycloalkyl, —$C_{1-6}$alkyl-$C_{3-7}$cycloalkyl, —$C_{1-6}$alkyl($C_{3-7}$cycloalkyl)$_2$, —$C_{1-6}$alkyl-aryl, —C(O)—N($C_{0-6}$alkyl)$_2$, —$SO_n$aryl, —$SO_n$—$C_{1-6}$alkyl, —$SO_n$—$C_{3-7}$cycloalkyl, —$SO_n$—N($C_{0-6}$alkyl)$_2$, —P(O)($C_{1-6}$alkyl)$_2$, —P(O)($C_{1-6}$alkoxy)$_2$, phenyl, pyridyl, —$SO_n$imidazolyl, —$SO_n$thiazolyl, 5-membered heteroaryl ring containing 1–4 heteroatoms independently selected from O, S or N group or oxoisoxaphosphinanyl group, any of which group optionally substituted with 1–6 independent halogen, hydroxyl, —CN, —$CF_3$, —$C_{1-6}$alkyl, —$SO_n$—$C_{1-6}$alkyl, —C(O)—O—$C_{0-6}$alkyl, or hydroxy$C_{1-6}$alkyl substituents;

$R_6$, and $R_7$ are each independently hydrogen, halogen, hydroxyl, —$C_{1-6}$alkyl, or —$C_{1-6}$alkoxy, wherein the alkyl and alkoxy are optionally substituted with 1–3 independently halogen or hydroxyl;

or $R_5$ and $R_6$ form =O;
or $R_6$ and $R_3$ form $CH_2$— or —O—; and
n is 0, 1, or 2.

In a second aspect of the invention, the compound of this invention is represented by Formula (1) or a pharmaceutically acceptable salt thereof, wherein Ar is pyridyl, or pyridyl N-oxide, optionally substituted with 1–3 independent —$C_{1-6}$alkyl, —OH, —CN, halogen, —$CF_3$, —($C_{0-6}$alkyl)-$SO_n$—($C_{1-6}$alkyl), —($C_{0-6}$alkyl)-$SO_n$—NH—($C_{1-6}$alkyl) or 5-membered heteroaryl ring containing 1–4 heteroatoms independently selected from O, S or N, wherein the 5-membered-ring is optionally substituted with $C_{1-6}$alkyl, and the alkyl group- is optionally substituted with 1–3 independent —OH, —CN, halogen, or —$CF_3$;

$R_1$ is hydrogen, halogen; or a —$C_{1-6}$alkyl, -cyclo$C_{3-6}$alkyl, —$C_{1-6}$alkenyl, —$C_{0-4}$alkyl-C(O)—$C_{0-4}$alkyl, —$C_{1-6}$alkoxy, aryl, heteroaryl, —CN, -heterocyclo$C_{3-6}$alkyl, -amino, —$C_{1-6}$alkylamino, —($C_{1-6}$alkyl)($C_{1-6}$alkyl)amino, —$C_{1-6}$alkyl(oxy)$C_{1-6}$alkyl, —C(O)NH(aryl), —C(O)NH(heteroaryl), —$SO_n$NH(aryl), —$SO_n$NH(heteroaryl), —$SO_n$NH($C_{1-6}$alkyl), —C(O)N($C_{0-6}$alkyl)($C_{0-6}$alkyl), —NH—$SO_n$—($C_{1-6}$alkyl), -carbamoyl, —($C_{1-6}$alkyl)-O—C(CN)-dialkylamino, or —($C_{0-6}$alkyl)-$SO_n$—($C_{1-6}$alkyl) group, wherein any of the groups is optionally substituted with 1–5 substituents; wherein each substituent is independently a halogen, —OH, —CN, —$C_1$-$C_6$alkyl, —C(O)(heterocyclo$C_{3-6}$alkyl), —C(O)—O—($C_{0-6}$alkyl), —C(O)—O-aryl, alkoxy, cycloalkyloxy, acyl, acyloxy, -cyclo$C_{3-6}$alkyl, heterocyclo$C_{3-6}$alkyl, aryl, heteroaryl, pyridyl N-oxide, carbonyl, carbamoyl, or —$SO_n$—($C_{1-6}$alkyl);

$R_2$, $R_3$, $R_6$, and $R_7$ are each independently hydrogen, halogen, hydroxyl, —$C_{1-6}$alkyl, or —$C_{1-6}$alkoxy, wherein the alkyl and alkoxy are optionally substituted with 1–3 independently halogen or hydroxyl;

$R_4$ is hydrogen, halogen, —CN, phenyl, oxadiazolyl, or —C(O)—O—$C_{0-6}$alkyl, wherein the phenyl, oxadiazolyl, or —C(O)—O—$C_{0-6}$alkyl is optionally substituted with 1–3 independent halogen, CN, CF3, —$SO_n$—$C_{1-6}$alkyl, or $C_{1-6}$alkyl substituents, and the alkyl group is optionally substituted with OH;

R5 is hydrogen, hydroxyl, —CN; or a —$C_{1-6}$alkyl, —C(O)$C_{1-6}$alkyl, —C(O)-aryl, —C(O)-pyridyl, —C(O)—O—$C_{0-6}$alkyl, —C(O)—$C_{3-7}$cycloalkyl, —$C_{1-6}$alkyl-$C_{3-7}$cycloalkyl, —$C_{1-6}$alkyl($C_{3-7}$cycloalkyl)$_2$, —$C_{1-6}$alkyl-aryl, —C(O)—N($C_{0-6}$alkyl)$_2$, —$SO_n$aryl, —$SO_n$—$C_{1-6}$alkyl, —$SO_n$—$C_{3-7}$cycloalkyl, —$SO_n$—N($C_{0-6}$alkyl)$_2$, —P(O)($C_{1-6}$alkyl)$_2$, —P(O)($C_{1-6}$alkoxy)$_2$, phenyl, pyridyl, —$SO_n$imidazolyl, —$SO_n$thiazolyl, 5-membered heteroaryl ring containing 1–4 heteroatoms independently selected from O, S or N or oxoisoxaphosphinanyl group, any of which group optionally substituted with 1–6 independent halogen, hydroxyl, —CN, —$CF_3$, —$C_{1-6}$alkyl, —$SO_n$—$C_{1-6}$ alkyl, —C(O)—O—$C_{0-6}$alkyl, or hydroxy$C_{1-6}$alkyl substituents;

or $R_5$ and $R_6$ form =O;
or $R_6$ and $R_3$ form —$CH_2$— or —O—; and
n is 0, 1, or 2.

In an embodiment of this one aspect, the compound of this invention is represented by Formula (I) or a pharmaceutically acceptable salt thereof, wherein Ar is pyridyl, or pyridyl N-oxide, optionally substituted with 1–3 independent —$C_{1-6}$alkyl, —OH, —CN, halogen, —$CF_3$, —($C_{0-6}$alkyl)-$SO_n$—($C_{1-6}$alkyl), —($C_{0-6}$alkyl)-$SO_n$—NH—($C_{1-6}$alkyl) or 5-membered heteroaryl ring containing 1–4 heteroatoms independently selected from O, S or N, wherein the 5-membered-ring is optionally substituted with $C_{1-6}$alkyl, and the alkyl group- is optionally substituted with 1–3 independent —OH, —CN, halogen, or —$CF_3$;

$R_1$ is hydrogen, halogen; or a —$C_{1-6}$alkyl, -cyclo$C_{3-6}$alkyl, —$C_{1-6}$alkenyl, —$C_{0-4}$alkyl-C(O)—$C_{0-4}$alkyl, —$C_{1-6}$alkoxy, aryl, heteroaryl, —CN, -heterocyclo$C_{3-6}$alkyl, -amino, —$C_{1-6}$alkylamino, —($C_{1-6}$alkyl)($C_{1-6}$alkyl)amino, —$C_{1-6}$alkyl(oxy)$C_{1-6}$alkyl, —C(O)NH(aryl), —C(O)NH(heteroaryl), —SO$_n$NH(aryl), —SO$_n$NH(heteroaryl), —SO$_n$NH($C_{1-6}$alkyl), —C(O)N($C_{0-6}$alkyl)($C_{0-6}$alkyl), —NH—SO$_n$—($C_{1-6}$alkyl), -carbamoyl, —($C_{1-6}$alkyl)-O—C(CN)-dialkylamino, or —($C_{0-6}$alkyl)-SO$_n$—($C_{1-6}$alkyl) group, wherein any of the groups is optionally substituted with 1–5 substituents; wherein each substituent is independently a halogen, —OH, —CN, —$C_1$–$C_{1-6}$alkyl, —C(O)(heterocyclo$C_{3-6}$alkyl), —C(O)—O—($C_{0-6}$alkyl), —C(O)—O-aryl, alkoxy, cycloalkyloxy, acyl, acyloxy, -cyclo$C_{3-6}$alkyl, heterocyclo$C_{3-6}$alkyl, aryl, heteroaryl, pyridyl N-oxide, carbonyl, carbamoyl, or —SO$_n$—($C_{1-6}$alkyl);

$R_2$, $R_3$, $R_6$, and $R_7$ are each independently hydrogen, halogen, hydroxyl, —$C_{1-6}$alkyl, or —$C_{1-6}$alkoxy, wherein the alkyl and alkoxy are optionally substituted with 1–3 independently halogen or hydroxyl;

$R_4$ is phenyl optionally substituted with 1–3 independent halogen, CN, CF$_3$, —SO$_n$—$C_{1-6}$alkyl, or $C_{1-6}$alkyl substituents, and the alkyl group is optionally substituted with OH;

R5 is hydrogen, hydroxyl, —CN; or a —$C_{1-6}$alkyl, —C(O)$C_{1-6}$alkyl, —C(O)-aryl, —C(O)-pyridyl, —C(O)—O—$C_{0-6}$alkyl, —C(O)—$C_{3-7}$cycloalkyl, —$C_{1-6}$alkyl-$C_{3-7}$cycloalkyl, —$C_{1-6}$alkyl($C_{3-7}$cycloalkyl)$_2$, —$C_{1-6}$alkyl-aryl, —C(O)—N($C_{0-6}$alkyl)$_2$, —SO$_n$aryl, —SO$_n$—$C_{1-6}$alkyl, —SO$_n$—$C_{3-7}$cycloalkyl, —SO$_n$—N($C_{0-6}$alkyl)$_2$, —P(O)($C_{1-6}$alkyl)$_2$, —P(O)($C_{1-6}$alkoxy)$_2$, phenyl, pyridyl, —SO$_n$imidazolyl, —SO$_n$thiazolyl, 5-membered heteroaryl ring containing 1–4 heteroatoms independently selected from O, S or N or oxoisoxaphosphinanyl group, any of which group optionally substituted with 1–6 independent halogen, hydroxyl, —CN, —CF$_3$, —$C_{1-6}$alkyl, —SO$_n$—$C_{1-6}$alkyl, —C(O)—O—$C_{0-6}$alkyl, or hydroxy$C_{1-6}$alkyl substituents;

or $R_5$ and $R_6$ form =O;

or $R_6$ and $R_3$ form —CH$_2$— or —O—; and n is 0, 1, or 2.

In another embodiment of this one aspect, the compound of this invention is represented by Formula (I) or a pharmaceutically acceptable salt thereof, wherein Ar is pyridyl, or pyridyl N-oxide, optionally substituted with 1–3 independent —$C_{1-6}$alkyl, —OH, —CN, halogen, —CF$_3$, —($C_{0-6}$alkyl)-SO$_n$—($C_{1-6}$alkyl), —($C_{0-6}$alkyl)-SO$_n$—NH—($C_{1-6}$alkyl) or 5-membered heteroaryl ring containing 1–4 heteroatoms independently selected from O, S or N, wherein the 5-membered-ring is optionally substituted with $C_{1-6}$alkyl, and the alkyl group- is optionally substituted with 1–3 independent —OH, —CN, halogen, or —CF$_3$;

$R_1$ is hydrogen, halogen; or a —$C_{1-6}$alkyl, -cyclo$C_{3-6}$alkyl, —$C_{1-6}$alkenyl, —$C_{0-4}$alkyl-C(O)—$C_{0-4}$alkyl, —$C_{1-6}$alkoxy, aryl, heteroaryl, —CN, -heterocyclo$C_{3-6}$alkyl, -amino, —$C_{1-6}$alkylamino, —($C_{1-6}$alkyl)($C_{1-6}$alkyl)amino, —$C_{1-6}$alkyl(oxy)$C_{1-6}$alkyl, —C(O)NH(aryl), —C(O)NH(heteroaryl), —SO$_n$NH(aryl), —SO$_n$NH(heteroaryl), —SO$_n$NH($C_{1-6}$alkyl), —C(O)N($C_{0-6}$alkyl)($C_{0-6}$alkyl), —NH—SO$_n$—($C_{1-6}$alkyl), -carbamoyl, —($C_{1-6}$alkyl)-O—C(CN)-dialkylamino, or —($C_{0-6}$alkyl)-SO$_n$—($C_{1-6}$alkyl) group, wherein any of the groups is optionally substituted with 1–5 substituents; wherein each substituent is independently a halogen, —H, —CN, —$C_1$–$C_6$alkyl, —C(O)(heterocyclo$C_{3-6}$alkyl), —C(O)—O—($C_{0-6}$alkyl), —C(O)—O-aryl, alkoxy, cycloalkyloxy, acyl, acyloxy, -cyclo$C_{3-6}$alkyl, heterocyclo$C_{3-6}$alkyl, aryl, heteroaryl, pyridyl N-oxide, carbonyl, carbamoyl, or —SO$_n$—($C_{1-6}$alkyl);

$R_2$, $R_3$, $R_6$, and $R_7$ are each independently hydrogen, halogen, hydroxyl, —$C_{1-6}$alkyl, or —$C_{1-6}$alkoxy, wherein the alkyl and alkoxy are optionally substituted with 1–3 independently halogen or hydroxyl;

$R_4$ is hydrogen, halogen, —CN, or —C(O)—O—$C_{0-6}$alkyl, wherein the phenyl, oxadiazolyl, or —C(O)—O—$C_{0-6}$alkyl is optionally substituted with 1–3 independent halogen, CN, CF3, —SO$_n$—$C_{1-6}$alkyl, or $C_{1-6}$alkyl substituents, and the alkyl group is optionally substituted with OH;

R5 is hydrogen, hydroxyl, —CN; or a —$C_{1-6}$alkyl, —C(O)$C_{1-6}$alkyl, —C(O)-aryl, —C(O)-pyridyl, —C(O)—O—$C_{0-6}$alkyl, —C(O)—$C_{3-7}$cycloalkyl, —$C_{1-6}$alkyl-$C_{3-7}$cycloalkyl, —$C_{1-6}$alkyl($C_{3-7}$cycloalkyl)$_2$, —$C_{1-6}$alkyl-aryl, —C(O)—N($C_{0-6}$alkyl)$_2$, —SO$_n$aryl, —SO$_n$—$C_{1-6}$alkyl, —SO$_n$—$C_{3-7}$cycloalkyl, —SO$_n$—N($C_{0-6}$alkyl)$_2$, —P(O)($C_{1-6}$alkyl)$_2$, —P(O)($C_{1-6}$alkoxy)$_2$, phenyl, pyridyl, —SO$_n$imidazolyl, —SO$_n$thiazolyl, 5-membered heteroaryl ring containing 1–4 heteroatoms independently selected from O, S or N or oxoisoxaphosphinanyl group, any of which group optionally substituted with 1–6 independent halogen, hydroxyl, —CN, —CF$_3$, —$C_{1-6}$alkyl, —SO$_n$—$C_{1-6}$ alkyl, —C(O)—O—$C_{0-6}$alkyl, or hydroxy$C_{1-6}$alkyl substituents;

or $R_5$ and $R_6$ form =O;

or $R_6$ and $R_3$ form CH$_2$— or —O—; and n is 0, 1, or 2.

In another embodiment of this one aspect, the compound of this invention is represented by Formula (I) or a pharmaceutically acceptable salt thereof, wherein Ar is pyridyl, or pyridyl N-oxide, optionally substituted with 1–3 independent —$C_{1-6}$alkyl, —OH, —CN, halogen, —CF$_3$, —($C_{0-6}$alkyl)-SO$_n$—($C_{1-6}$alkyl), —($C_{0-6}$alkyl)-SO$_n$—NH—($C_{1-6}$alkyl) or 5-membered heteroaryl ring containing 1–4 heteroatoms independently selected from O, S or N, wherein the 5-membered-ring is optionally substituted with $C_{1-6}$alkyl, and the alkyl group- is optionally substituted with 1–3 independent —OH, —CN, halogen, or —CF$_3$;

$R_1$ is hydrogen, halogen; or a —$C_{1-6}$alkyl, -cyclo$C_{3-6}$alkyl, —$C_{1-6}$alkenyl, —$C_{0-4}$alkyl-C(O)—$C_{0-4}$alkyl, —$C_{1-6}$alkoxy, aryl, heteroaryl, —CN, -heterocyclo$C_{3-6}$alkyl, -amino, —$C_{1-6}$alkylamino, —($C_{1-6}$alkyl)($C_{1-6}$alkyl)amino, —$C_{1-6}$alkyl(oxy)$C_{1-6}$alkyl, —C(O)NH(aryl), —C(O)NH(heteroaryl), —SO$_n$NH(aryl), —SO$_n$NH(heteroaryl), —SO$_n$NH($C_{1-6}$alkyl), —C(O)N($C_{0-6}$alkyl)($C_{0-6}$alkyl), —NH—SO$_n$—($C_{1-6}$alkyl), -carbamoyl, —($C_{1-6}$alkyl)-O—C(CN)-dialkylamino, or —($C_{0-6}$alkyl)-SO$_n$—($C_{1-6}$alkyl) group, wherein any of the groups is optionally substituted with 1–5 substituents; wherein each substituent is independently a halogen, —OH, —CN, —$C_1$–$C_6$alkyl, —C(O)(heterocyclo$C_{3-6}$alkyl), —C(O)—O—($C_{0-6}$alkyl), —C(O)—O-aryl, alkoxy, cycloalkyloxy, acyl, acyloxy, -cyclo$C_{3-6}$alkyl, heterocyclo$C_{3-6}$alkyl, aryl, heteroaryl, pyridyl N-oxide, carbonyl, carbamoyl, or —SO$_n$—($C_{1-6}$alkyl);

$R_2$, $R_3$, $R_6$, and $R_7$ are each independently hydrogen, halogen, hydroxyl, —$C_{1-6}$alkyl, or —$C_{1-6}$alkoxy, wherein the alkyl and alkoxy are optionally substituted with 1–3 independently halogen or hydroxyl;

$R_4$ is hydrogen, halogen, —CN, phenyl, oxadiazolyl, or —C(O)—O—$C_{0-6}$alkyl, wherein the phenyl, oxadiazolyl, or —C(O)—O—$C_{0-6}$alkyl is optionally substituted with 1–3 independent halogen, CN, CF3, —SO$_n$—$C_{1-6}$alkyl, or $C_{1-6}$alkyl substituents, and the alkyl group is optionally substituted with OH;

R5 is hydrogen, hydroxyl, —CN; or a —$C_{1-6}$alkyl, —C(O)$C_{1-6}$alkyl, —C(O)-aryl, —C(O)-pyridyl, —C(O)—O—$C_{0-6}$alkyl, —C(O)—$C_{3-7}$cycloalkyl, —$C_{1-6}$alkyl-$C_{3-7}$cycloalkyl, —$C_{1-6}$alkyl($C_{3-7}$cycloalkyl)$_2$, —$C_{1-6}$alkyl-aryl, —C(O)—N($C_{0-6}$alkyl)$_2$, —SO$_n$aryl, —SO$_n$—$C_{1-6}$alkyl, —SO$_n$—$C_{3-7}$cycloalkyl, —SO$_n$—N($C_{0-6}$alkyl)$_2$, —P(O)($C_{1-6}$alkyl)$_2$, —P(O)($C_{1-6}$alkoxy)$_2$, phenyl, pyridyl, —SO$_n$imidazolyl, —SO$_n$thiazolyl, 5-membered heteroaryl ring containing 1–4 heteroatoms independently selected from O, S or N or oxoisoxaphosphinanyl group, any of which group optionally substituted with 1–6 independent halogen, hydroxyl, —CN, —CF$_3$, —$C_{1-6}$alkyl, —SO$_n$—$C_{1-6}$alkyl, —C(O)—O—$C_{0-6}$alkyl, or hydroxy$C_{1-6}$alkyl substituents;

or R$_5$ and R$_6$ form =O;
or R$_6$ and R$_3$ form —O—; and
n is 0, 1, or 2.

In another embodiment of this one aspect, the compound of this invention is represented by Formula (I) or a pharmaceutically acceptable salt thereof, wherein Ar is pyridyl, or pyridyl N-oxide, optionally substituted with 1–3 independent —$C_{1-6}$alkyl, —OH, —CN, halogen, —CF$_3$, —($C_{0-6}$alkyl)-SO$_n$—($C_{1-6}$alkyl), —($C_{0-6}$alkyl)-SO$_n$—NH—($C_{1-6}$alkyl) or 5-membered heteroaryl ring containing 1–4 heteroatoms independently selected from O, S or N, wherein the 5-membered-ring is optionally substituted with $C_{1-6}$alkyl, and the alkyl group- is optionally substituted with 1–3 independent —OH, —CN, halogen, or —CF$_3$;

R$_1$ is —$C_{1-6}$alkyl or -cyclo$C_{3-6}$alkyl, wherein any of the groups is optionally substituted with 1–5 substituents; wherein each substituent is independently a halogen, —OH, —CN, —$C_1$-C$_6$alkyl, —C(O)(heterocyclo$C_{3-6}$alkyl), —C(O)—O—($C_{0-6}$alkyl), —C(O)—O-aryl, alkoxy, cycloalkyloxy, acyl, acyloxy, -cyclo$C_{3-6}$alkyl, heterocyclo$C_{3-6}$alkyl, aryl, heteroaryl, pyridyl N-oxide, carbonyl, carbamoyl, or —SO$_n$—($C_{1-6}$alkyl);

R$_2$, R$_3$, R$_6$, and R$_7$ are each independently hydrogen, halogen, hydroxyl, —$C_{1-6}$alkyl, or —$C_{1-6}$alkoxy, wherein the alkyl and alkoxy are optionally substituted with 1–3 independently halogen or hydroxyl;

R$_4$ is hydrogen, halogen, —CN, phenyl, oxadiazolyl, or —C(O)—O—$C_{0-6}$alkyl, wherein the phenyl, oxadiazolyl, or —C(O)—O—$C_{0-6}$alkyl is optionally substituted with 1–3 independent halogen, CN, CF3, —SO$_n$—$C_{1-6}$alkyl, or $C_{1-6}$alkyl substituents, and the alkyl group is optionally substituted with OH;

R5 is hydrogen, hydroxyl, —CN; or a —$C_{1-6}$alkyl, —C(O)$C_{1-6}$alkyl, —C(O)-aryl, —C(O)-pyridyl, —C(O)—O—$C_{0-6}$alkyl, —C(O)—$C_{3-7}$cycloalkyl, —$C_{1-6}$alkyl-$C_{3-7}$cycloalkyl, —$C_{1-6}$alkyl($C_{3-7}$cycloalkyl)$_2$, —$C_{1-6}$alkyl-aryl, —C(O)—N($C_{0-6}$alkyl)$_2$, —SO$_n$aryl, —SO$_n$—$C_{1-6}$alkyl, —SO$_n$—$C_{3-7}$cycloalkyl, —SO$_n$—N($C_{0-6}$alkyl)$_2$, —P(O)($C_{1-6}$alkyl)$_2$, —P(O)($C_{1-6}$alkoxy)$_2$, phenyl, pyridyl, —SO$_n$imidazolyl, —SO$_n$thiazolyl, 5-membered heteroaryl ring containing 1–4 heteroatoms independently selected from O, S or N or oxoisoxaphosphinanyl group, any of which group optionally substituted with 1–6 independent halogen, hydroxyl, —CN, —CF$_3$, —$C_{1-6}$alkyl, —SO$_n$—$C_{1-6}$ alkyl, —C(O)—O—$C_{0-6}$alkyl, or hydroxy$C_{1-6}$alkyl substituents;

or R$_5$ and R$_6$ form =O;
or R$_6$ and R$_3$ form —CH$_2$— or —O—; and
n is 0, 1, or 2.

In another embodiment of this one aspect, the compound of this invention is represented by Formula (I) or a pharmaceutically acceptable salt thereof, wherein Ar is pyridyl, or pyridyl N-oxide, optionally substituted with 1–3 independent —$C_{1-6}$alkyl, —OH, —CN, halogen, —CF$_3$, —($C_{0-6}$alkyl)-SO$_n$—($C_{1-6}$alkyl), —($C_{0-6}$alkyl)-SO$_n$—NH—($C_{1-6}$alkyl) or 5-membered heteroaryl ring containing 1–4 heteroatoms independently selected from O, S or N, wherein the 5-membered-ring is optionally substituted with $C_{1-6}$alkyl, and the alkyl group- is optionally substituted with 1–3 independent —OH, —CN, halogen, or —CF$_3$;

R$_1$ is —$C_{1-6}$alkyl, -cyclo$C_{3-6}$alkyl, wherein any of the groups is optionally substituted with 1–5 substituents; wherein each substituent is independently a halogen, —OH, —CN, —$C_1$-C$_6$alkyl, —C(O)(heterocyclo$C_{3-6}$alkyl), —C(O)—O—($C_{0-6}$alkyl), —C(O)—O-aryl, alkoxy, cycloalkyloxy, acyl, acyloxy, -cyclo$C_{3-6}$alkyl, heterocyclo$C_{3-6}$alkyl, aryl, heteroaryl, pyridyl N-oxide, carbonyl, carbamoyl, or —SO$_n$—($C_{1-6}$alkyl);

R$_2$, R$_3$, R$_6$, and R$_7$ are each independently hydrogen, halogen, hydroxyl, —$C_{1-6}$alkyl, or —$C_{1-6}$alkoxy, wherein the alkyl and alkoxy are optionally substituted with 1–3 independently halogen or hydroxyl;

R$_4$ is hydrogen, halogen, —CN, or —C(O)—O—$C_{0-6}$alkyl, wherein the —C(O)—O—$C_{0-6}$alkyl is optionally substituted with 1–3 independent halogen, CN, CF$_3$, —SO$_n$—$C_{1-6}$alkyl, or $C_{1-6}$alkyl substituents, and the alkyl group is optionally substituted with OH R5 is hydrogen, hydroxyl, —CN; or a —$C_{1-6}$alkyl, —C(O)$C_{1-6}$alkyl, —C(O)-aryl, —C(O)-pyridyl, —C(O)—O—$C_{0-6}$alkyl, —C(O)—$C_{3-7}$cycloalkyl, —$C_{1-6}$alkyl-$C_{3-7}$cycloalkyl, —$C_{1-6}$alkyl($C_{3-7}$cycloalkyl)$_2$, —$C_{1-6}$alkyl-aryl, —C(O)—N($C_{0-6}$alkyl)$_2$, —SO$_n$aryl, —SO$_n$—$C_{1-6}$alkyl, —SO$_n$—$C_{3-7}$cycloalkyl, —SO$_n$—N($C_{0-6}$alkyl)$_2$, —P(O)($C_{1-6}$alkyl)$_2$, —P(O)($C_{1-6}$alkoxy)$_2$, phenyl, pyridyl, —SO$_n$imidazolyl, —SO$_n$thiazolyl, 5-membered heteroaryl ring containing 1–4 heteroatoms independently selected from O, S or N or oxoisoxaphosphinanyl group, any of which group optionally substituted with 1–6 independent halogen, hydroxyl, —CN, —CF3, —$C_{1-6}$alkyl, —SO$_n$—$C_{1-6}$ alkyl, —C(O)—O—$C_{0-6}$alkyl, or hydroxy$C_{1-6}$alkyl substituents;

or R$_5$ and R$_6$ form =O;
or R$_6$ and R$_3$ form —CH$_2$— or —O—; and
n is 0, 1, or 2.

In another embodiment of this one aspect, the compound of this invention is represented by Formula (I) or a pharmaceutically acceptable salt thereof, wherein Ar is pyridyl, or pyridyl N-oxide, optionally substituted with 1–3 independent —$C_{1-6}$alkyl, —OH, —CN, halogen, —CF$_3$, —($C_{0-6}$alkyl)-SO$_n$—($C_{1-6}$alkyl), —($C_{0-6}$alkyl)-SO$_n$—NH—($C_{1-6}$alkyl) or 5-membered heteroaryl ring containing 1–4 heteroatoms independently selected from O, S or N, wherein the 5-membered-ring is optionally substituted with $C_{1-6}$alkyl, and the alkyl group- is optionally substituted with 1–3 independent —OH, —CN, halogen, or —CF$_3$;

R$_1$ is —$C_{1-6}$alkyl, -cyclo$C_{3-6}$alkyl, wherein any of the groups is optionally substituted with 1–5 substituents; wherein each substituent is independently a halogen, —OH, —CN, —$C_1$-C$_6$alkyl, —C(O)(heterocyclo$C_{3-6}$alkyl), —C(O)—O—($C_{0-6}$alkyl), —C(O)—O-aryl, alkoxy, cycloalkyloxy, acyl, acyloxy, -cyclo$C_{3-6}$alkyl, heterocyclo$C_{3-6}$alkyl, aryl, heteroaryl, pyridyl N-oxide, carbonyl, carbamoyl, or —SO$_n$($C_{1-6}$alkyl);

R$_2$, R$_3$, R$_6$, and R$_7$ are each independently hydrogen, halogen, hydroxyl, —$C_{1-6}$alkyl, or —$C_6$alkoxy, wherein the alkyl and alkoxy are optionally substituted with 1–3 independently halogen or hydroxyl;

R$_4$ is hydrogen, halogen, —CN, phenyl, oxadiazolyl, or —C(O)—O—$C_{0-6}$alkyl, wherein the phenyl, oxadiazolyl, or —C(O)—O—$C_{0-6}$alkyl is optionally substituted with 1–3 independent halogen, CN, CF3, —SO$_n$—$C_{1-6}$alkyl, or $C_{1-6}$alkyl substituents, and the alkyl group is optionally substituted with OH R5 is phenyl, pyridyl, or a 5-membered heteroaryl ring containing 1–4 heteroatoms independently selected from O, S or N, any of which group optionally substituted with 1–6 independent halogen, hydroxyl, —CN, —CF3, —$C_{1-6}$alkyl, —$SO_n$—$C_{1-6}$alkyl, —C(O)—O—$C_{0-6}$alkyl, or hydroxy$C_{1-6}$alkyl substituents;

or $R_5$ and $R_6$ form =O;

or $R_6$ and $R_3$ form —$CH_2$— or —O—; and n is 0, 1, or 2.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "aryl" means an aromatic subsituent which is a single ring or multiple rings fused together. When formed of multiple rings, at least one of the constituent rings is aromatic. The preferred aryl substituents are phenyl and napthyl groups.

The term "cycloalkyloxy" unless specifically stated otherwise includes a cycloalkyl group connected by a short $C_{1-2}$alkyl length to the oxy connecting atom.

The term "$C_{0-6}$alkyl" includes alkyls containing 6, 5, 4, 3, 2, 1, or no carbon atoms. An alkyl with no carbon atoms is a hydrogen atom substituent when the alkyl is a terminal group and is a direct bond when the alkyl is a bridging group.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocyclo$C_5$alkyl is a five member ring containing from 5 to no carbon atoms. Examples of heteroaryls include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, and tetrazolyl. Examples of heterocycloalkyls include azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

The term "amine" unless specifically stated otherwise includes primary, secondary and tertiary amines.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, optionally substituted multiple moieties such as, for example, alkylaryl are intended to mean that the aryl and the aryl groups are optionally substituted. If only one of the multiple moieties is optionally substituted then it will be specifically recited such as "an alkylaryl, the aryl optionally substituted with halogen or hydroxyl."

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) Leukotriene receptor antagonists, ii) Leukotriene biosynthesis inhibitors, iii) corticosteroids, iv) H1 receptor antagonists, v) beta 2 adrenoceptor agonists, vi) COX-2 selective inhibitors, vii) statins, viii) non-steroidal anti-inflammatory drugs ("NSAID"), and ix) M2/M3 antagonists. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Creams, ointments, jellies, solutions, or suspensions containing the compound of Formula I can be employed for topical use. Mouth washes and gargles are included within the scope of topical use for the purposes of this invention.

Dosage levels from about 0.01 mg/kg to about 140 mg/kg of body weight per day are useful in the treatment of conditions such as asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, chronic glomerulonephritis, atopic dermatitis, urticaria, adult respiratory distress syndrome, chronic obstructive pulmonary disease in animals, diabetes insipidus, allergic rhinitis, allergic conjunctivitis, vernal conjunctivitis, arterial restenosis, ortheroschlerosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, tumour growth and cancerous invasion of normal tissues which are responsive to PDE4 inhibition, or alternatively about 0.5 mg to about 7 g per patient per day. For example, inflammation may be effectively treated by the administration of from about 0.01 mg to 50 mg of the compound per kilogram of body weight per day, or alternatively about 0.5 mg to about 3.5 g per patient per day. Further, it is understood that the PDE4 inhibiting compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 1000 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient. Thus, a tablet, cachet, or capsule conveniently contains 0.1 mg, 1 mg, 5 mg, 25 mg, 50 mg, 100 mg, 200 mg, 300 mg, 400 mg, or 500 mg of the active ingredient taken one or two tablets, cachets, or capsules, once, twice, or three times daily.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability.

The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The compounds and pharmaceutical compositions of this invention have been found to exhibit biological activity as PDE4 inhibitors. Accordingly, another aspect of the invention is the treatment in mammals of, for example, asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, chronic glomerulonephritis, atopic dermatitis, urticaria, adult respiratory distress syndrome, chronic obstructive pulmonary disease in animals, diabetes insipidus, allergic rhinitis, allergic conjunctivitis, vernal conjunctivitis, arterial restenosis, ortherosclerosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, tumour growth and cancerous invasion of normal tissues—maladies that are amenable to amelioration through inhibition of the PDE4 isoenzyme and the resulting elevated cCAMP levels—by the administration of an effective amount of the compounds of this invention. The term "mammals" includes humans, as well as other animals such as, for example, dogs, cats, horses, pigs, and cattle. Accordingly, it is understood that the treatment of mammals other than humans is the treatment of clinical correlating afflictions to those above recited examples that are human afflictions.

Further, as described above, the compound of this invention can be utilized in combination with other therapeutic compounds. In particular, the combinations of the PDE4 inhibiting compound of this invention can be advantageously used in combination with i) Leukotriene receptor antagonists, ii) Leukotriene biosynthesis inhibitors, or iii) M2/M3 antagonists.

The abbreviations used herein have the following tabulated meanings. Abbreviations not tabulated below have their meanings as commonly used unless specifically stated otherwise.

| | |
|---|---|
| Ac | acetyl |
| AIBN | 2,2'-azobis(isobutyronitrile) |
| BINAP | 1,1'-bi-2-naphthol |
| Bn | benzyl |
| CAMP | cyclic adenosine-3',5'-monophosphate |
| DAST | (diethylamino)sulfur trifluoride |
| DEAD | diethyl azodicarboxylate |
| DBU | 1,8-diazabicyclo[5.4.0]undec-7-ene |
| DIBAL | diisobutylaluminum hydride |
| DMAP | 4-(dimethylamino)pyridine |
| DMF | N,N-dimethylformamide |
| dppf | 1,1'-bis(diphenylphosphino)-ferrocene |
| EDCI | 1-(3-dimethylaminopropyl)-3-ethylcarbodiimide hydrochloride |
| $Et_3N$ | triethylamine |
| GST | glutathione transferase |
| HMDS | hexamethyldisilazide |
| LDA | lithium diisopropylamide |
| m-CPBA | metachloroperbenzoic acid |
| MMPP | monoperoxyphthalic acid |
| MPPM | monoperoxyphthalic acid, magnesium salt $6H_2O$ |
| Ms | methanesulfonyl = mesyl = $SO_2Me$ |
| MsO | methanesulfonate = mesylate |
| NBS | N-bromo succinimide |
| NSAID | non-steroidal anti-inflammatory drug |
| o-Tol | ortho-tolyl |
| OXONE ® | $2KHSO_5 \cdot KHSO_4 \cdot K_2SO_4$ |

-continued

| | |
|---|---|
| PCC | pyridinium chlorochromate |
| Pd$_2$(dba)$_3$ | Bis(dibenzylideneacetone)palladium(0) |
| PDC | pyridinium dichromate |
| PDE | Phosphodiesterase |
| Ph | Phenyl |
| Phe | Benzenediyl |
| PMB | para-methoxybenzyl |
| Pye | Pyridinediyl |
| r.t. | room temperature |
| Rac. | Racemic |
| SAM | aminosulfonyl or sulfonamide or SO$_2$NH$_2$ |
| SEM | 2-(trimethylsilyl)ethoxymethoxy |
| SPA | scintillation proximity assay |
| TBAF | tetra-n-butylammonium fluoride |
| Th | 2- or 3-thienyl |
| TFA | trifluoroacetic acid |
| TFAA | trifluoroacetic acid anhydride |
| THF | Tetrahydrofuran |
| Thi | Thiophenediyl |
| TLC | thin layer chromatography |
| TMS-CN | trimethylsilyl cyanide |
| TMSI | trimethylsilyl iodide |
| Tz | 1H (or 2H)-tetrazol-5-yl |
| XANTPHOS | 4,5-Bis-diphenylphosphanyl-9,9-dimethyl-9H-xanthene |
| C$_3$H$_5$ | Allyl |

Alkyl Group Abbreviations

| | |
|---|---|
| Me = | Methyl |
| Et = | ethyl |
| n-Pr = | normal propyl |
| i-Pr = | isopropyl |
| n-Bu = | normal butyl |
| i-Bu = | isobutyl |
| s-Eu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

Assays Demonstrating Biological Activity

LPS and FMLP-Induced TNF-α and LTB$_4$ Assays in Human Whole Blood

Whole blood provides a protein and cell-rich milieu appropriate for the study of biochemical efficacy of anti-inflammatory compounds such as PDE4-selective inhibitors. Normal non-stimulated human blood does not contain detectable levels of TNF-α and LTB$_4$. Upon stimulation with LPS, activated monocytes express and secrete TNF-α up to 8 hours and plasma levels remain stable for 24 hours. Published studies have shown that inhibition of TNF-α by increasing intracellular cAMP via PDE4 inhibition and/or enhanced adenylyl cyclase activity occurs at the transcriptional level. LTB$_4$ synthesis is also sensitive to levels of intracellular cAMP and can be completely inhibited by PDE4-selective inhibitors. As there is little LTB$_4$ produced during a 24 hour LPS stimulation of whole blood, an additional LPS stimulation followed by tMTP challenge of human whole blood is necessary for LTB$_4$ synthesis by activated neutrophils. Thus, by using the same blood sample, it is possible to evaluate the potency of a compound on two surrogate markers of PDE4 activity in the whole blood by the following procedure.

Fresh blood was collected in heparinized tubes by venipuncture from healthy human volunteers (male and female). These subjects had no apparent inflammatory conditions and had not taken any NSAIDs for at least 4 days prior to blood collection. 500 μL aliquots of blood were pre-incubated with either 2 μL of vehicle (DMSO) or 2 μL of test compound at varying concentrations for 15 minutes at 37° C. This was followed by the addition of either 10 μL vehicle (PBS) as blanks or 10 μL LPS (1 μg/mL final concentration, #L-2630 (Sigma Chemical Co., St. Louis, Mo.) from E. coli, serotype 0111:B4; diluted in 0.1% w/v BSA (in PBS)). After 24 hours of incubation at 37° C., another 10 μL of PBS (blank) or 10 μL of LPS (1 μg/mL final concentration) was added to blood and incubated for 30 minutes at 37° C. The blood was then challenged with either 10 μL of PBS (blank) or 10 μL of fMLP (1 μM final concentration, #F-3506 (Sigma); diluted in 1% w/v BSA (in PBS)) for 15 minutes at 37° C. The blood samples were centrifuged at 1500×g for 10 minutes at 4° C. to obtain plasma. A 50 μL aliquot of plasma was mixed with 200 μL methanol for protein precipitation and centrifuged as above. The supernatant was assayed for LTB$_4$ using an enzyme immunoassay kit (#520111 from Cayman Chemical Co., Ann Arbor, Mich.) according to the manufacturer's procedure. TNF-α was assayed in diluted plasma (in PBS) using an ELISA kit (Cistron Biotechnology, Pine Brook, N.J.) according to manufacturer's procedure. The IC$_{50}$ values of Examples 1–113 generally ranged from 0.02 μM to 26 μM.

Anti-allergic Activity In Vivo

Compounds of the invention have been tested for effects on an IgE-mediated allergic pulmonary inflammation induced by inhalation of antigen by sensitized guinea pigs. Guinea pigs were initially sensitized to ovalbumin under mild cyclophosphamide-induced immunosuppression, by intraperitoneal injection of antigen in combinations with aluminum hydroxide and pertussis vaccine. Booster doses of antigen were given two and four weeks later. At six weeks, animals were challenged with aerosolized ovalbumin while under cover of an intraperitoneally administered antihistamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the Examples (0.001–10 mg/kg i.p. or p.o.), up to three times during the 48 h following antigen challenge, lead to a significant reduction in the eosinophilia and the accumulation of other inflammatory leukocytes. There was also less inflammatory damage in the lungs of animals treated with compounds of the Examples.

SPA Based PDE Activity Assay Protocol

Compounds which inhibit the hydrolysis of cAMP to AMP by the type-IV cAMP-specific phosphodiesterases were screened in a 96-well plate format as follows:

In a 96 well-plate at 30° C. was added the test compound (dissolved in 2 μL DMSO), 188 mL of substrate buffer containing [2,8-$^3$H] adenosine 3',5'-cyclic phosphate (cAMP, 100 nM to 50 μM), 10 mMmgCl$_2$, 1 mM EDTA, 50 mM Tris, pH 7.5. The reaction was initiated by the addition of 10 mL of human recombinant PDE4 (the amount was controlled so that ~10% product was formed in 10 min.). The reaction was stopped after 10 min. by the addition of 1 mg of PDE-SPA beads (Amersham Pharmacia Biotech, Inc., Piscataway, N.J.). The product AMP generated was quantified on a Wallac Microbeta® 96-well plate counter (EG&G Wallac Co., Gaithersburg, Md.). The signal in the absence of enzyme was defined as the background. 100% activity was defined as the signal detected in the presence of enzyme and DMSO with the background subtracted. Percentage of inhibition was calculated accordingly. IC$_{50}$ value was approximated with a non-linear regression fit using the standard 4-parameter/multiple binding sites equation from a ten point titration.

The IC$_{50}$ values of Examples 1–113 were determined with 100 nM cAMP using the purified GST fusion protein of the human recombinant phosphodiesterase IVa (met-248) produced from a baculovirus/Sf-9 expression system. The IC$_{50}$ values of Examples 1–113 generally ranged from 0.1 nM to 25 nM.

The examples that follow are intended as an illustration of certain preferred embodiments of the invention and no limitation of the invention is implied.

Unless specifically stated otherwise, the experimental procedures were performed under the following conditions. All operations were carried out at room or ambient temperature—that is, at a temperature in the range of 18–25° C. Evaporation of solvent was carried out using a rotary evaporator under reduced pressure (600–4000 pascals: 4.5–30 mm. Hg) with a bath temperature of up to 60° C. The course of reactions was followed by thin layer chromatography (TLC) and reaction times are given for illustration only. Melting points are uncorrected and 'd' indicates decomposition. The melting points given are those obtained for the materials prepared as described. Polymorphism may result in isolation of materials with different melting points in some preparations. The structure and purity of all final products were assured by at least one of the following techniques: TLC, mass spectrometry, nuclear magnetic resonance (NMR) spectrometry or microanalytical data. Yields are given for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. broad; etc. In addition, "Ar" signifies an aromatic signal. Chemical symbols have their usual meanings; the following abbreviations have also been used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

Methods of Synthesis

Compounds of the present invention can be prepared according to the following methods. The substituents are the same as in Formula I except where defined otherwise.

Scheme 1:
Preparation of 8-bromo-quinolines

The quinolines of formula IV may be obtained from literature procedure (R. H. F. Manske and M. Kulka, "The Skraup Synthesis of Quinolines"; Org. Reaction, vol. 7, p. 59–98, 1953 or in International Patent Publication WO 94/22852) or prepared in a multi-step sequence from the requisite 8-bromo-6-methyl-quinoline II. Treatment of 8-bromo-6-methyl-quinoline (from references cited in text) with brominating agents such as NBS in solvents such as chlorobenzene in presence of radical initiator such as AIBN or benzoyl peroxide provide the 8-bromo-6-bromomethyl-quinoline II. The primary bromide can be displace by nucleophiles such as sodium methanesulfinate or potassium cyanide in a solvent such as DMF. Two sequential alkylation using alkylating agents such as iodomethane and a base such as potassium t-butoxide in a solvent such as THF can yields 8-bromo-quinolines of such as IV.

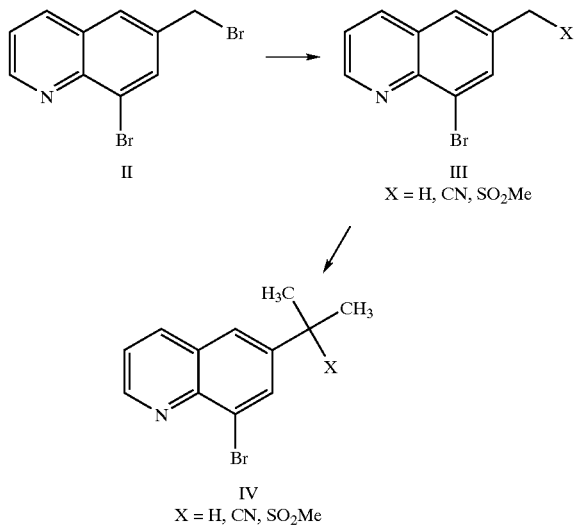

Scheme 2:
Preparation of 8-Aryl-quinolines

The 8-aryl-quinolines of the formula VIII may be prepared by coupling the 8-bromo-quinoline such as V with appropriately substituted phenyl-boronic acids or esters such as VII with heating in the presence of various palladium catalyst such as Pd(Ph$_3$P)$_4$ and a base such as sodium carbonate in a mixture of solvent such as DME-H$_2$O. The alcohol VIII X=CH$_2$OH) may be converted to the bromide by treatment with HBr (aq.) in a solvent such as acetic acid or to the mesylate and then to the cyanide derivatives using standard organic chemistry protocols.

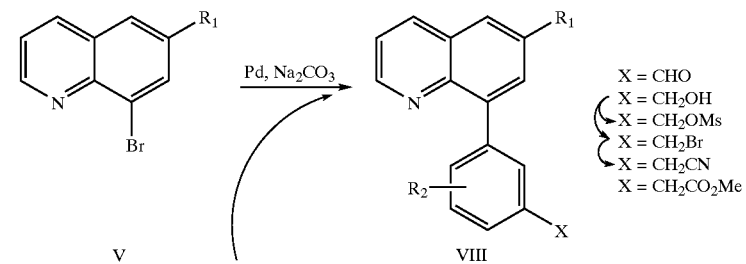

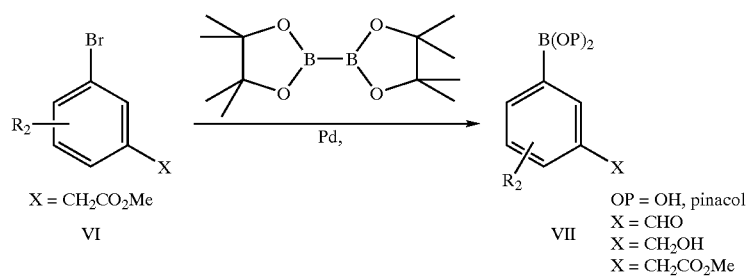

X = CH₂CO₂Me
VI

OP = OH, pinacol
X = CHO
X = CH₂OH
X = CH₂CO₂Me
VII

Scheme 3:
Preparation of Phenyl Acetic Acid Derivatives

The phenyl acetic acid derivatives XI may be prepared from esterification of commercial product such as X using diazomethane for example or by reduction of alpha-keto analog IX (*J. Med. Chem.*, 24:399(1981)) using hydride such as NaBH₄ in a solvent such as ethanol. The alcohol XI (X=OH) can be transformed into XI (X=F) using DAST (*J. Org. Chem.*, 40:574(1975)) or other commercial equivalents. Sulfur atom may also be oxidized to sulfone by oxidizing agent such as oxone in a mixture of solvents such as THF/MeOH/H₂O.

Scheme 3
Ester 01–04

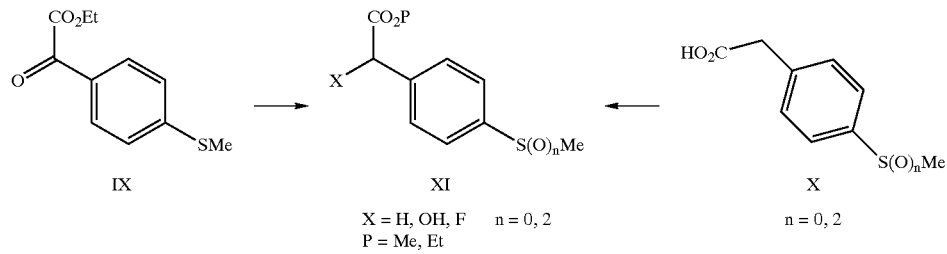

IX

XI
X = H, OH, F   n = 0, 2
P = Me, Et

X
n = 0, 2

Scheme 4:

Preparation of Phenyl Ethanone Derivatives

Phenyl-ethanone intermediate like XX or XV may be prepared from appropriately substituted aryl bromide and a methylketone using as a catalysis such as Pd₂(dba)₃ with ligands such as xanphos or binap in a solvent like THF with a base such sodium tert-butoxide. Methyl ketone such as XIV can be obtained from commercial sources or prepared from condensation of ethyl vinyl ether lithium salt onto ketone such as 3-pentanone followed by hydrolysis in acidic media. Aryl bromide such as XIII or XVIX can be prepared using standard organic chemistry protocols. Further modifications of phenyl-ethanone such as XV will lead to substituted ethanone XVI and XVII by alkylation with alkyl idodide such as methyl iodide or a fluoride source such as N-fluorobenzenesulfonimide (*Synlett*, 187, (1991)) and a base such as potassium tert-butoxide.

Scheme 4

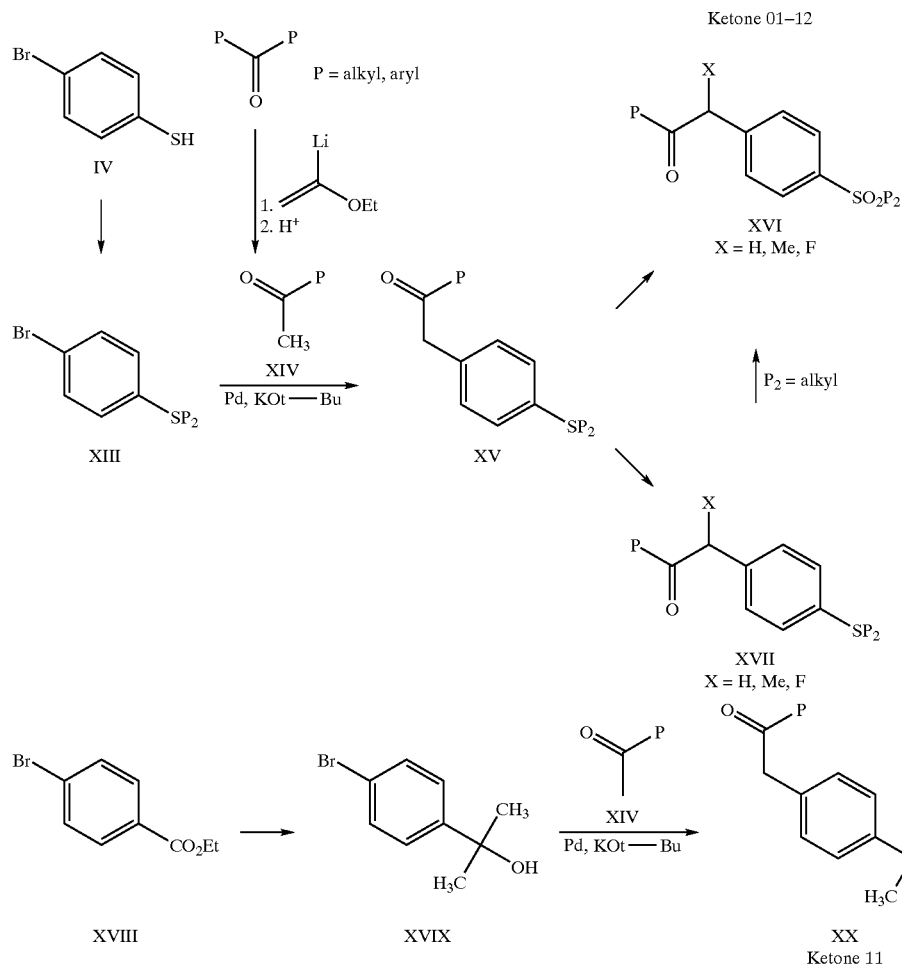

Scheme 5:
Preparation of Sulfonylmethyl-phenyl Derivatives

Sulfonylmethyl phenyl intermediate like XXIV to XXX may be prepared from appropriately substituted benzyl halide by displacement of halide by nucleophiles such as methanesulfinic acid sodium salt in a solvent such as DMF. Alternatively, alkyl and aryl thiols can displace the benzylic halide with a base such as cesium carbonate in a solvent such as DMP. Oxidation of sulfide such as XXX with oxidizing agents such as oxone will lead to sulfone derivatives such as XXVIII. Displacement of the benzylic halide with sulfur followed by oxidation with $Cl_2$ for example will afford the corresponding sulfonyl chloride such as XXVI. Further condensation with nucleophiles such as amines in a solvent like dichloromethane will give sulfonimides such as XVII. Those methylsulfone XV to XVIII can also be alkylated with a fluoride source such as N-fluorobenzenesulfonimide (*Synlett*, 187, (1991)) and a base such as potassium tert-butoxide to give alpha fluoro analogs such as XXIX.

Scheme 5

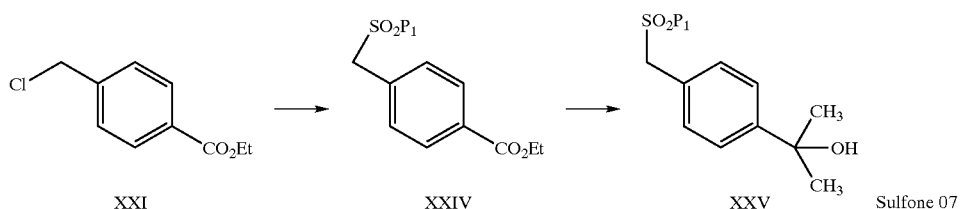

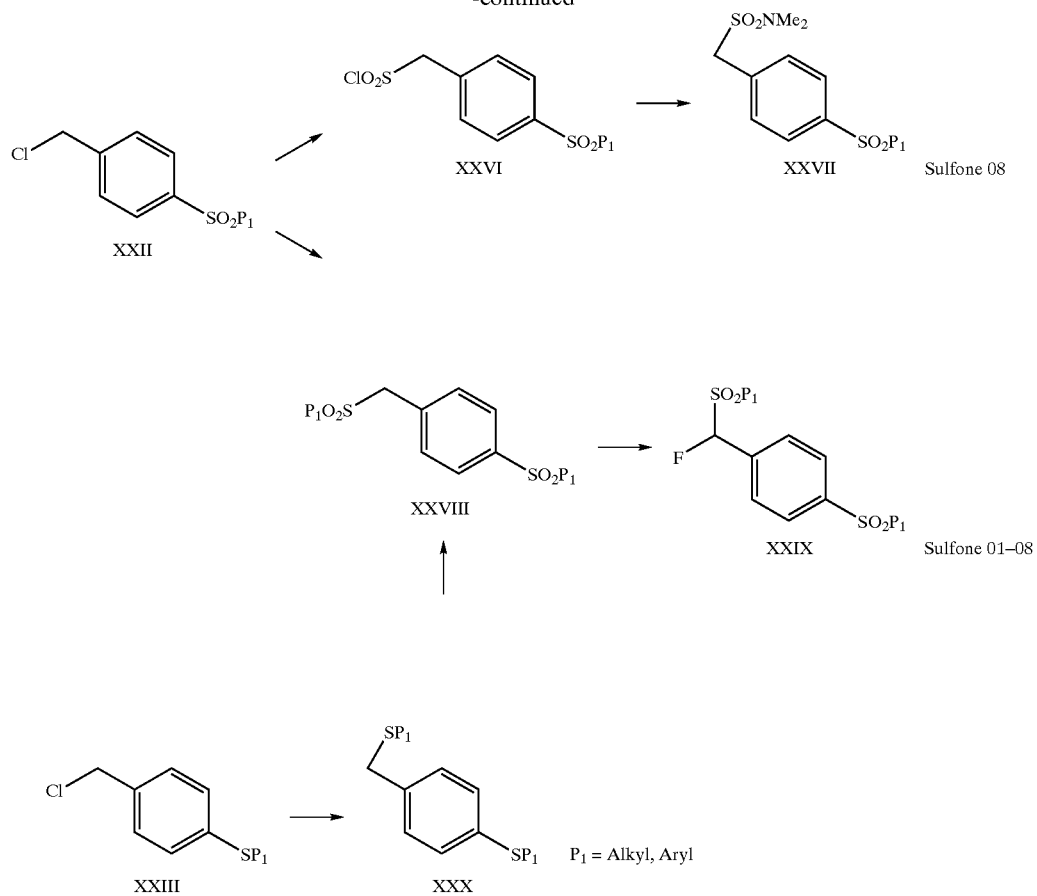

Scheme 6:

Preparation of Phosphonylmethyl-phenyl Derivatives

Phosphonylmethyl phenyl intermediate like XXXI to XXXIV may be prepared from appropriately substituted benzyl halide by displacement of halide by nucleophiles such as trimethylphosphite. Hydrolysis to phosphonic acid may be accomplished using TMSBr in a solvent such as chloroform. Conversion to the acid chloride using oxalyl chloride for example in a solvent such as dichloromethane will provide the starting material for further condensation with nucleophiles such as alcohol in a solvent like dichloromethane and with a base such as triethylamine to give various phosphonate esters such as XXXIV. The latter can also be alkylated with a fluoride source such as N-fluorobenzenesulfonimide (*Synlett*, 187, (1991)) and a base such as potassium tert-butoxide to give alpha fluoro analogs such as XXXII.

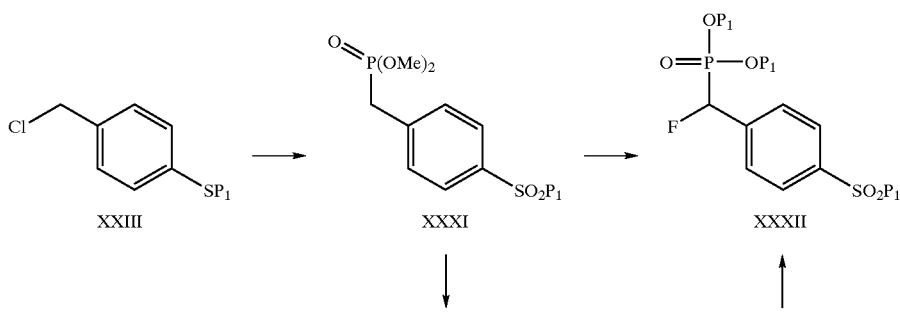

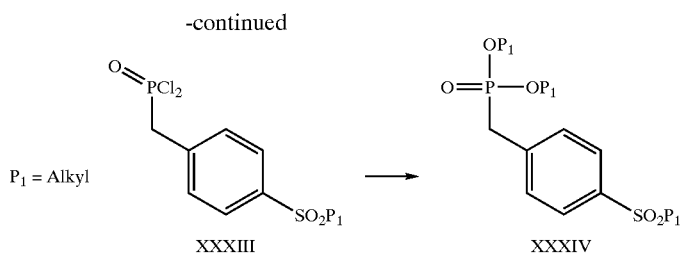

P₁ = Alkyl

XXXIII → XXXIV

Scheme 7:

Preparation of Quinoline of Formula I

The quinolines of formula I may be obtained from alkylation of various carbonyl containing intermediates from Schemes 3 to 6 (esters, ketones, aldehydes, sulfonyl or phosphonates) with appropriate electrophile derivatives (Scheme 2). For example, the treatment of an intermediate (containing an acidic proton like a ketone etc.) with a base such as potassium t-butoxide in a organic solvent such THF, followed by quenching with an electrophile such as bromomethyl quinoline VIII, (X=CH₂Br) will give desired product of formula I. Alternatively, the quinoline/electrophile can be reverse to a quinoline/nucleophile and coupling with aryl halide will afford compounds with a different substitution pattern as described in Scheme 7.

Scheme 7

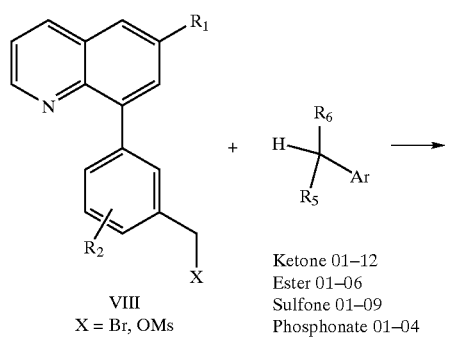

VIII
X = Br, OMs

Ketone 01–12
Ester 01–06
Sulfone 01–09
Phosphonate 01–04

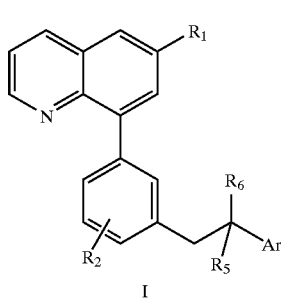

I

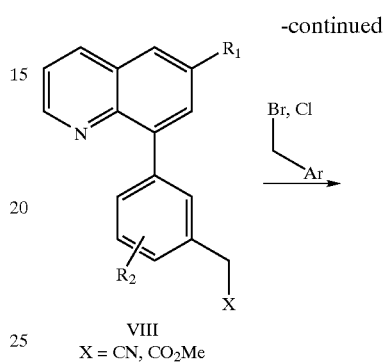

VIII
X = CN, CO₂Me

Scheme 8:

Preparation of Carboxylic Acid Derived Analogs

Quinoline of formula I containing a carboxylic acid derivative such as XXXV can serve as a starting material for various other analogs as exemplified in Scheme 8. Formation of oxadiazole XXXVII may be achieved by activation of acetic acid XXXVI with EDCI in a solvent such as diglyme followed by the addition of N-hydroxy-acetamidine and subsequent heating of the reaction mixture. Formation of the acid chloride or activation of acid by using standard procedures followed by addition of amines produces amide XXXVIII. Tetrazole like XXXXVI can be obtained from nitrile XXXXV by heating with tributyltin azide in a solvent such as xylene. All other derivatives described in scheme 8 can be obtained using standard organic synthesis procedures related to reduction and addition of nucleophiles such as lithium or magnesium salts to the carbonyl functional group. Those standards procedure also includes oxidation of alcohol to ketone and transformation of ester to Weinred type amide. All analogs containing a acidic proton at the benzilic position, can also be alkylated with a fluoride source such as N-fluorobenzenesulfonimide (*Synlett*, 187, (1991)) or alkyl halide such as methyl iodide and a base such as potassium tert-butoxide to give alpha fluoro analogs such as I ($R_6$=F or Me).

Scheme 8

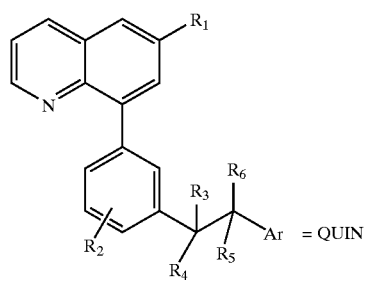

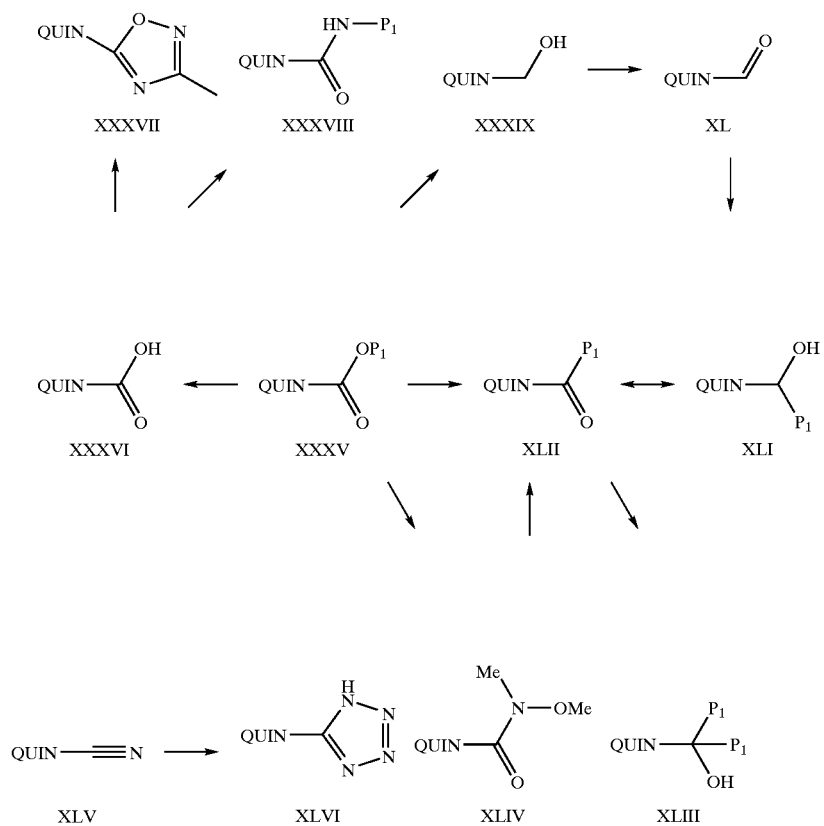

$P_1$ = Alkyl, Aryl

Scheme 9:

Preparation of Derivatives of Quinoline of Formula I

Alternatively, derivatives of formula I containing a masked carbonyl function in the form of a cyanohydrin of type XLVIII can be treated with tetra-butyl-ammonium fluoride in a solvent such as THF to give the ketone XLIX. Reduction of the carbonyl function with an hydride source such as sodium borohydride in a solvent such as methanol provides the secondary alcohol L. Mitsunubo type displacement of the benzylic alcohol with appropriate nucleophiles such as a substituted thiophenol will give the corresponding thio ether LI. Further manipulation of ester function to the tertiary alcohol and oxidation of sulfur to sulfone with an oxidizing agent such as oxone in a solvent such a mixture of THF/MeOH/H$_2$O gives LIII. 1,2-Diols like XLVI can be cyclized to carbonate XLVII using, for example, carbonyl diimidazole and heating.

Scheme 9

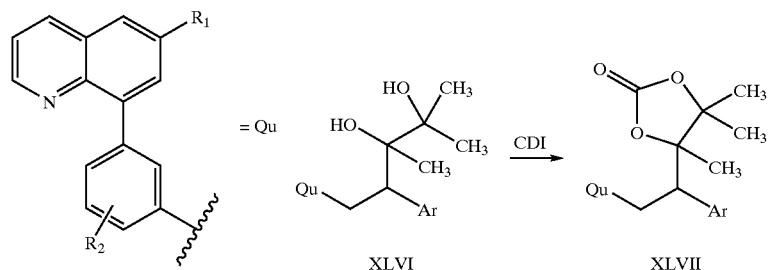

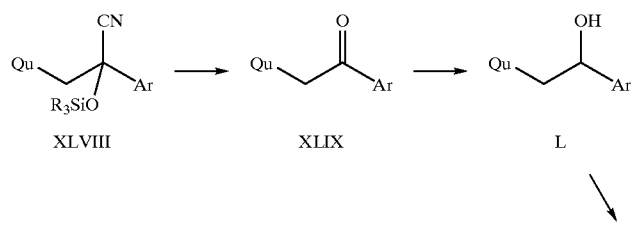

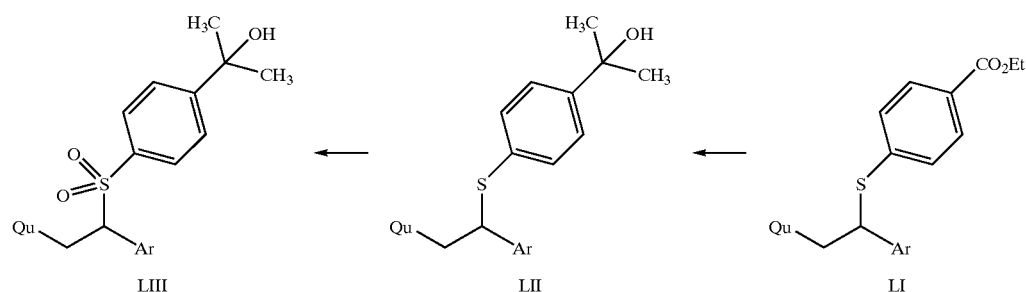

Scheme 10:

Preparation of 4-Pyridinyl Derivatives of Quinoline of Formula I

Another synthetic approaches to quinoline of formula I is derived from custom made or commercial 3-bromobenzyl halides like LV. The latter can be derived from appropriately substituted benzaldehyde by addition of alkyl or arylmagnesium or lithium salts followed by conversion of the corresponding alcohol to the halide by using thionyl chloride, for example, in a solvent such as benzene. 4-Pyridinyl acetate or 4-pyridinyl acetonitrile can be deprotonated using a base such as NaHMDS and then alkylated with the benzylic halide LV or benzyl halide derived from quinoline VIII (Scheme 2). The derivatives of type LVII, with an ester functional group, can be hydrolyzed and decarboxylated to LVIII using an aqueous base such as NaOH followed by an acidic work-up. Alternatively, treatment of LVII with a nucleophiles like methylmagnesium bromide for example, can produce tertiary alcohol like LIX. Other functional group manipulation from an ester was described in Scheme 8. The pyridinyl can be oxidized to the pyridinyl N-oxide with an oxidizing agent such as MMPP in a solvent such a mixture of $CH_2Cl_2$/MeOH to gives LX or LXI.

Scheme 10

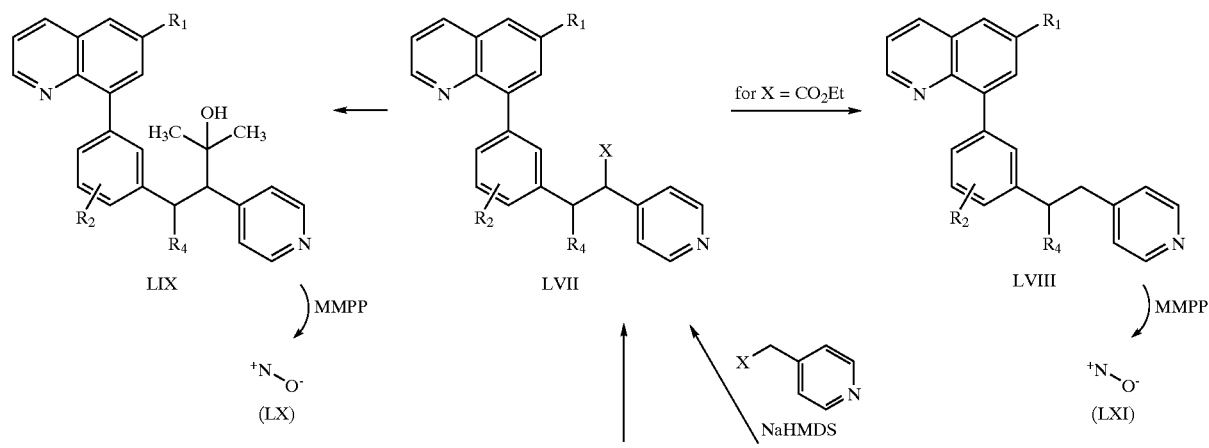

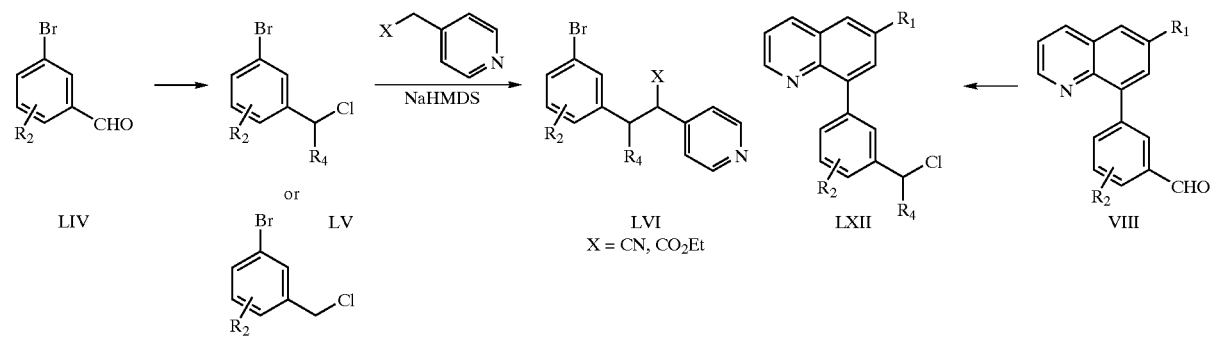

Scheme 11:

Preparation of Stilbene Derivatives of Quinoline of Formula I

Intermediate such as LXII-containing a double bond can serve as a precursor to compound of formula I. Condensation of aldehydes VIII with substituted acetic acid or acetonitrile and a base such as piperidine and heating will provide LXII. Alternatively, phosphonium salts LXV with a base such as potassium tert-butoxide in a solvent such as THF can react with aldehyde of formula VIII. Reduction of the olefin using catalyst such as palladium on carbon in a solvent such as THF/MeOH under hydrogen atmosphere or polymer supported phenylhydrazide in a solvent such as toluene with heating will provide compound like LXIII. Cyclopropanation of the double bond using trimethyl-sulfoxonium iodide and a base such as NaH in a solvent such as DMSO will give derivatives of formula LXIV.

Scheme 11

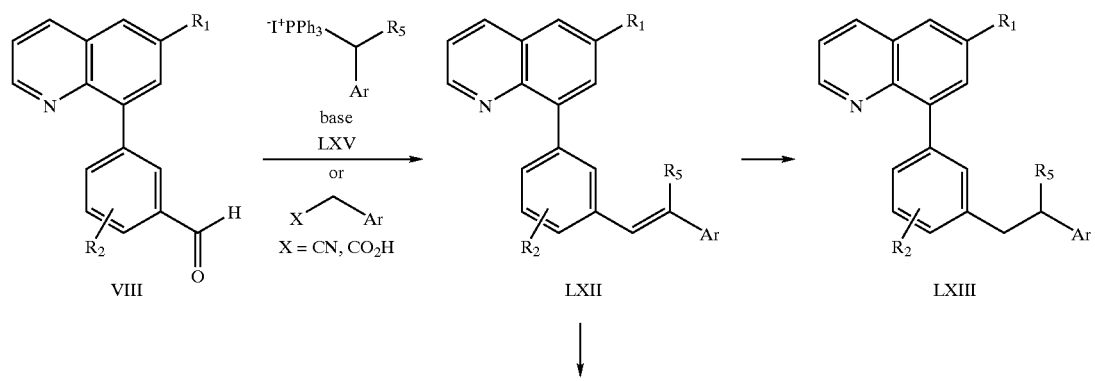

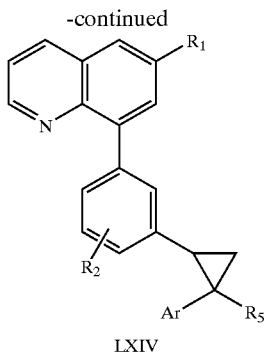

LXIV

Preparation of Intermediates
Preparation of Quinolines
Quinoline 01

8-(3-Bromomethyl-phenyl)-6-(1-methanesulfonyl-1-methyl-ethyl)-quinoline

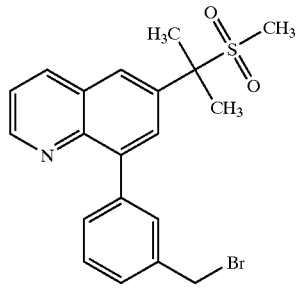

Step 1: 8-Bromo-6-methanesulfonylmethyl-quinoline

To a solution of 6-bromomethyl-8-bromoquinoline (60 g, 200 mmol, described in International Patent Publication WO 94/22852) in DMF (500 mL) was added sodium methanesulfinate (27.6 g, 270 mmol). After stirring overnight at 21° C., the mixture was quenched with $H_2O$ (2L), stirred for 1 h, isolated by filtration, and washed with $Et_2O$ to yield the 8-Bromo-6-methanesulfonylmethyl-quinoline as a white solid.

Step 2: 8-Bromo-6-(1-methanesulfonyl-1-methyl-ethyl)-quinoline

To a solution of the 8-Bromo-6-methanesulfonylmethyl-quinoline from Step 1 above (60 g, 200 mmol) in THF (2L) at 0° C. (internal), was added potassium t-butoxide (260 mL, 1M, THF) over 30 min. After 0.5 h at 0° C., MeI (20 mL, 320 mmol) was added and the resulting reaction mixture stirred at 0° C. for 2 h. More potassium t-butoxide (200 mL, 1M, THF) was then added over 30 min, followed by MeI (20 mL, 320 mmol), and the mixture stirred at rt for 2 h. The mixture was neutralised with saturated $NH_4Cl$ solution and extracted with EtOAc. The organic extracts were washed ($H_2O$), (brine), dried ($MgSO_4$), filtered and concentrated. Stirring the solid in ether, followed by filtration gave the 8-Bromo-6-(1-methanesulfonyl-1-methyl-ethyl)-quinoline as a pale yellow solid.

Step 3: {3-[6-(1-Methanesulfonyl-1-methyl-ethyl)-quinolin-8-yl]-phenyl}-methanol A mixture of the 8-Bromo-6-(1-methanesulfonyl-1-methyl-ethyl)-quinoline from Step 2 above (26 g, 79 mmol), 3-(hydroxymethyl)phenyl-boronic acid (14 g, 92 mmol), sodium carbonate (120 mL, 2M, $H_2O$), $PdCl_2(Ph_3P)_2$ (2 g) in DME (300 mL) was heated at 90–100° C. for 8 h. The resulting reaction mixture was filtered on a large plug/column of silica gel and the eluted with EtOAc. The organic extracts were concentrated and the resulting suspension diluted with $Et_2O$ and stirred vigorously for 3 h. The desired {3-[6-(1-Methanesulfonyl-1-methyl-ethyl)-quinolin-8-yl]-phenyl}-methanol was isolated as a white solid by filtration.

Step 4: 8-(3-Bromomethyl-phenyl)-6-(1-methanesulfonyl-1-methyl-ethyl)-quinoline A suspension of the {3-[6-(1-Methanesulfonyl-1-methyl-ethyl)-quinolin-8-yl]-phenyl}-methanol compound from Step 3 above (30 g, 85 mmol) in AcOH (140 mL) and HBr (48 mL, 48% aq) was stirred for 18 h at 80° C. The resulting mixture was cooled to 0° C. and poured into 2L of cold NaOH (0.3N). The pH of the resulting solution was adjusted to 5 and filtered. The resulting solid was dissolved in EtOAc, washed with saturated $NaHCO_3$ solution, brine, dried ($MgSO_4$), filtered and concentrated. Stirring the solid in ether/EtOAc, followed by filtration gave desired 8-(3-Bromomethyl-phenyl)-6-(1-methanesulfonyl-1-methyl-ethyl)-quinoline as a pale brown solid.

Quinoline 02

{3-[6-(1-Methanesulfonyl-1-methyl-ethyl)-quinolin-8-yl]-phenyl}-methanol O-methanesulfonate

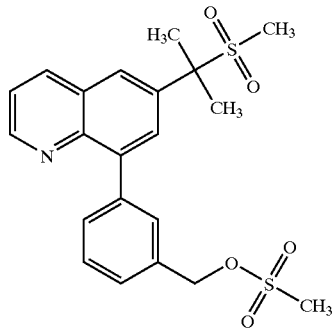

To a solution of the alcohol from Quinoline 01, Step 3 (5.15 g, 17 mmol) in $CH_2Cl_2$ (150 mL) at −78° C. was added $Et_3N$ (3.6 mL, 26 mmol) and methanesulfonyl chloride (1.6 mL, 21 mmol). After 0.5 h at −78° C., the mixture was neutralized with saturated $NH_4Cl$ solution, diluted with water, and extracted with ether. The organic extracts were washed ($H_2O$, brine), dried ($MgSO_4$), filtered, and concentrated to yield the title compound as a white foam.

Quinoline 03

3-[6-(1-Methanesulfonyl-1-methyl-ethyl)-quinolin-8-yl]-benzaldehyde

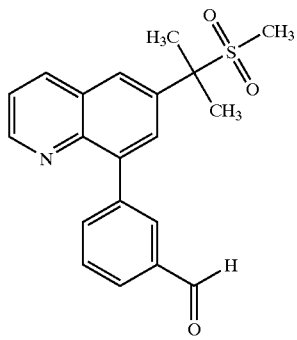

Following the procedures described in Quinoline 01, Steps 1–3, but substituting 3-formylphenyl-boronic acid for 3-(hydroxymethyl)-phenyl-boronic acid in Step 3, the title compound was obtained as pale yellow solid.

Quinoline 04

3-(6-Isopropyl-quinolin-8-yl)-benzaldehyde

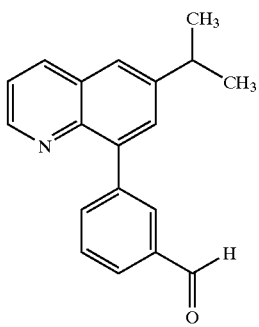

A mixture of 8-bromo-6-isopropyl-quinoline (9.79 g, 39 mmol, described in International Patent Publication WO 94/22852), 3-(formyl)-phenyl-boronic acid (11.7 g, 78 mmol), sodium carbonate (78 mL, 2M, $H_2O$), $Pd(Ph_3P)_4$ (2.7 g, 2.3 mmol) in DME (200 mL) was heated at 70° C. for 18 h. The reaction mixture was cooled to 21° C. then diluted with water and ethyl acetate. The organic extracts were washed ($H_2O$, brine), dried ($MgSO_4$), filtered and concentrated. Purification by flash chromatography (eluting with hexane/ethyl acetate, 80:20) provided the title compound.

Quinoline 05

[3-(6-Isopropyl-quinolin-8-yl)-phenyl]-acetic acid methyl ester

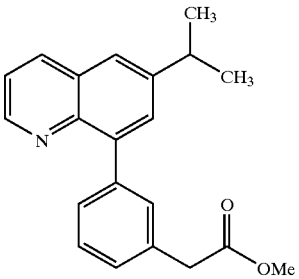

Step 1: (3-Bromo-phenyl)-acetic acid methyl ester

To a solution of 3-bromophenylacetic acid (10 g, 46 mmol) in $CH_2Cl_2$ (20 mL) was added $CH_2N_2$ ($Et_2O$) until yellow coloration persisted. The resulting reaction mixture was quenched with AcOH, and diluted with a $NaHCO_3$ solution and ethyl acetate. The organic extracts were washed ($H_2O$, brine), dried ($MgSO_4$), filtered and concentrated to provided the (3-Bromo-phenyl)-acetic acid methyl ester compound.

Step 2: [3-(4,4,5,5-Tetramethyl-[1,3,2]dioxaborolan-2-yl)-phenyl]-acetic acid methyl ester A solution of (3-Bromo-phenyl)-acetic acid methyl ester from Step 1 (10.9 mg, 48 mmol), diboron pinacol ester (14.5 g, 57 mmol), KOAc (16.33 g, 166 mmol) and $PdCl_2(dppf)$ (1.94 g, 2.38 mmol) in DMF (250 mL) was heated at 80° C. under $N_2$ for 3 h. The resulting reaction mixture was cooled to 21° C. and diluted with water and ethyl acetate. The organic extracts were washed ($H_2O$, brine), dried ($MgSO_4$), filtered and concentrated. Purification by flash chromatography (eluting with hexane/ethyl acetate, 65:35) provided the [3-(4,4,5,5-Tetramethyl-[1,3,2]dioxaborolan-2-yl)-phenyl]-acetic acid methyl ester compound.

Step 3: [3-(6-Isopropyl-quinolin-8-yl)-phenyl]-acetic acid methyl ester

A solution of [3-(4,4,5,5-Tetramethyl-[1,3,2]dioxaborolan-2-yl)-phenyl]-acetic acid methyl ester from Step 2 (4 g, 14 mmol), 8-bromo-6-isopropylquinoline (3 g, 12 mmol), $Na_2CO_3$ (2M, 18 mL, 36 mmol) and $Pd(PPh_3)_4$ (692 mg, 0.6 mmol) in DMF (250 mL) was heated at 80° C. under $N_2$ for 18 h. The resulting reaction mixture was cooled to 21° C. and diluted with water and ethyl acetate. The organic extracts were washed ($H_2O$, brine), dried ($MgSO_4$), filtered and concentrated. Purification by flash chromatography (eluting with hexane/ethyl acetate, 80:20) provided the [3-(6-Isopropyl-quinolin-8-yl)-phenyl]-acetic acid methyl ester compound.

Quinoline 06

8-(3-Bromomethyl-phenyl)-6-isopropyl-quinoline

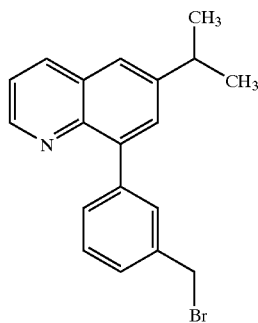

Quinoline 06 was prepared according to the procedure described in Quinoline 01, Steps 3 and 4, but 6-isopropyl-8-bromo-quinoline was used as the starting material. Flash chromatography (hexane/EtOAc) afforded the title compound as a yellow solid.

Quinoline 07

[3-(6-Isopropyl-quinolin-8-yl)-phenyl]-acetonitrile

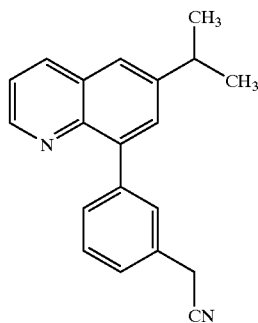

To a solution of Quinoline 06 (1.0 g, 2.94 mmol) in $CH_3CN$ (15 mL) was added KCN (244 mg, 3.74 mmol) and 18-crown-6 (100 mg, 0.37 mmol). The resulting reaction mixture was stirred 18 h at 80° C., then diluted with a sodium bicarbonate solution and ethyl acetate. The organic extracts were washed ($H_2O$, brine), dried ($MgSO_4$), filtered and concentrated. Purification by flash chromatography (eluting with hexane/ethyl acetate, 75:25) provided the title compound.

Quinoline 08

2-(8-Bromo-quinolin-6-yl)-2-methyl-propionitrile

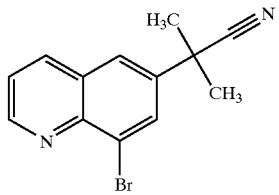

Step 1: (8-Bromo-quinolin-6-yl)-acetonitrile

DMP (10 mL) and $H_2O$ (5 mL) were added to 6-bromomethyl-8-bromoquinoline (3 g) (described in International Patent Publication WO 94/22852) and potassium cyanide (1.6 g). After heating at 100° C. for 1 hour, the resulting mixture was quenched with $H_2O$ (100 mL) and extracted with EtOAc. The combined organic extracts were washed with water (3×), brine, dried over $MgSO_4$, filtered and concentrated. Flash chromatography (hexane:EtOAc, 3:1) yielded the (8-Bromo-quinolin-6-yl)-acetonitrile compound as a white solid.

Step 2: 2-(8-Bromoquinolin-6-yl)-2-methyl-propionitrile

To a solution of (8-Bromo-quinolin-6-yl)-acetonitrile from Step 1 (3 g, 12.1 mmol) in THF (100 mL) at −78° C., was added MeI (1.7 mL, 27 mmol) followed by potassium t-butoxide (27 mL, 27 mmol). After 2 h at −78° C., the resulting mixture was warmed to 0° C., was poured in saturated aqueous $NH_4Cl$, then extracted with EtOAc (2×). The combined organic extracts were washed with brine, dried over $MgSO_4$, filtered and concentrated. Flash chromatography (hexane:EtOAc, 3:1) afforded the 2-(8-Bromoquinolin-6-yl)-2-methyl-propionitrile as a white solid.

Quinoline 09

2-[8-(3-Bromomethyl-phenyl)-quinolin-6-yl]-2-methyl-propionitrile

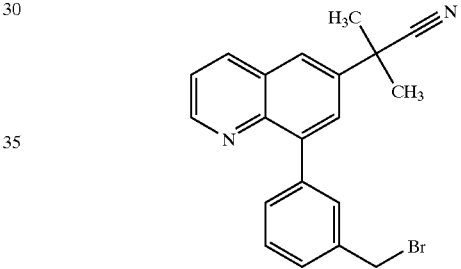

Quinoline 09 was prepared according to the procedure described above in Quinoline 01, Steps 3 and 4 but used Quinoline 08 as the starting material. Flash chromatography (hexane/EtOAc) afforded the title compound as a yellow solid.

Preparations of Esters

Ester 01

(4-Methanesulfonyl-phenyl)-acetic acid methyl ester

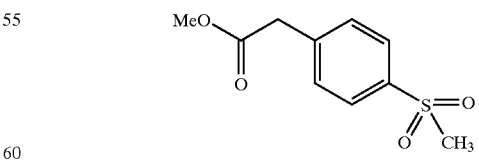

(4-Methanesulfonyl-phenyl)-acetic acid was treated with an etheral solution of diazomethane until completion of esterification by TLC. The solvent was evaporated, the residue triturated in hexane/ether and filtered to afford the title compound as a white solid.

Ester 02

Hydroxy-(4-methylsulfanyl-phenyl)-acetic acid ethyl ester

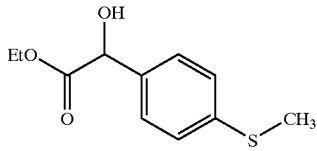

To a solution of ethyl α-oxo 4-methylthiophenylacetate (obtained from thioanisole and ethyl oxalyl chloride using procedure described in *J. Med. Chem.,* p.403(1981) (30 g, 134 mmol) in EtOH at −78° C., was added NaBH$_4$ (2.5 g, 66 mmol) portionwise. After 40 min at −78° C., the resulting reaction mixture was quenched by slow addition of a saturated ammonium chloride solution, allowed to warm to 21° C., poured into water (0.5L) and stirred for 2 h. The suspension was filtered to provide the title compound as a white solid.

Ester 03

Fluoro-(4-methylsulfanyl-phenyl)-acetic acid ethyl ester

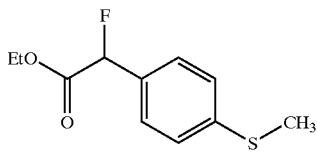

To a solution of Ester 02 (10.9 g, 48 mmol) in CH$_2$Cl$_2$ (300 mL) at −78° C. was added [bis(2-methoxyethyl)amino] sulfur trifluoride (10 mL, 54 mmol) dropwise. The resulting reaction mixture was warmed slowly to 10° C., then poured into an ether/NaHCO$_3$ solution. The organic extracts were washed (H$_2$O), (brine), dried (MgSO$_4$), filtered, and concentrated. Purification by flash chromatography (eluting with hexane/ethyl acetate, 95:5) provided the title compound as an oil.

Ester 04

(4-Methylsulfanyl-phenyl)-acetic acid methyl ester

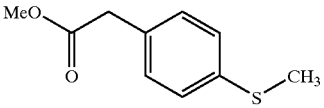

(4-Methylsulfanyl-phenyl)-acetic acid was treated with an etheral solution of diazomethane until completion of esterification. The solvent was evaporated, the residue triturated in hexane/ether, and filtered to afford the title compound as a white solid.

Ester 05

N-Isopropyl-2-(4-methanesulfonyl-phenyl)-acetamide

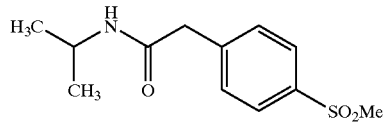

To a solution of (4-methanesulfonyl-phenyl)-acetic acid (2.5 g, 11.7 mmol) in CH$_2$Cl$_2$ (20 mL) was added EDCI (2.46 g, 12.9 mmol) followed by diisopropyl amine (1.2 mL) and DMAP (140 mg, 1.2 mmol). After 18 h at 21° C., the resulting reaction mixture was diluted with a saturated ammonium chloride solution and ethyl acetate. The organic extracts were washed (H$_2$O, brine), dried (MgSO$_4$), filtered and concentrated. Purification by flash chromatography (eluting with hexane/ethyl acetate/THF, 35:60:5) provided the title compound as a white solid.

Ester 06

5-(4-Methanesulfonyl-benzyl)-3-methyl-[1,2,4] oxadiazole

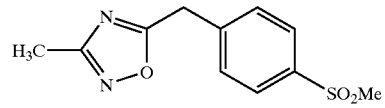

Ester 06 prepared according to the procedure described in Example 83 but using (4-methanesulfonyl-phenyl)-acetic acid as the starting material. Flash chromatography (hexane/EtOAc) afforded the title compound as a yellow solid.

Preparation of Ketones

Ketone 01

3-Hydroxy-3-methyl-1-(4-methylsulfanyl-phenyl)-butan-2-one

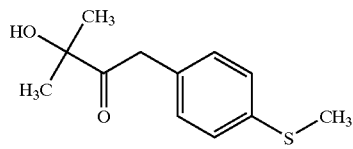

To a solution of sodium tert-butoxide (12 g, 125 mmol), XANTPHOS (2.05 g, 3.5 mmol) and Pd$_2$(dba)$_3$ (1.35 g, 1.5 mmol) in THF (600 mL) was added 4-bromothioanisole (20 g, 98 mmol) and 3-hydroxy-3-methyl-butan-2-one (12 g, 117 mmol). The resulting reaction mixture was heated to 75° C. for 2 h then cooled to r.t. and diluted with water. The organic extracts were washed (H$_2$O), (brine), dried (MgSO$_4$), filtered and concentrated. Purification by flash chromatography (eluting with hexane/ethyl acetate, 85:15–80:20) provided the title compound as a pale brown solid.

Ketone 02

3-Hydroxy-1-(4-methanesulfonyl-phenyl)-3-methyl-butan-2-one

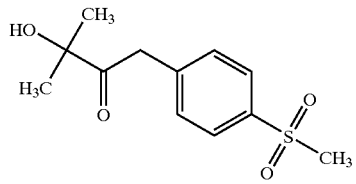

To a solution of Ketone 91 (10.7 g, 48 mmol) in THF/MeOH (2:1, 375 mL) was added OXONE® (60 g, 98 mmol) followed by water (slowly, 125 mL). After 2 h, the reaction mixture was diluted with ether and a saturated $NaHCO_3$ solution. The organic extracts were washed ($H_2O$), (brine), dried ($MgSO_4$), filtered and concentrated. Purification by stirring vigorously in hexane/ether and isolation by filtration gave the desired product as a pale yellow solid (8.3 g).

Ketone 03

1-(4-Fluoro-phenyl)-2-(4-methanesulfonyl-phenyl)-ethanone

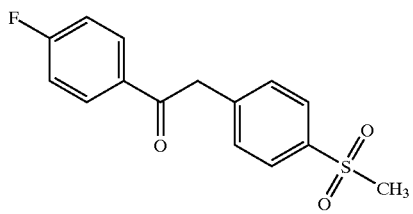

Step 1: 1-(4-Fluoro-phenyl)-2-(4-methylsulfanyl-phenyl)-ethanone

To a solution of sodium tert-butoxide (480 mg, 5 mmol), BINAP (racemic, 112 mg, 0.18 mmol) and $Pd_2(dba)_3$ (68 mg, 0.075 mmol) in THF (10 mL) was added 4-bromo-thioanisole (914 mg, 4.5 mmol) and 4-fluoro-acetophenone (690 mg, 5 mmol). The resulting reaction mixture was heated to 80° C. for 3 h then cooled to 21° C. and diluted with water. The organic extracts were washed ($H_2O$), (brine), dried ($MgSO_4$), filtered and concentrated. Purification by flash chromatography (eluting with hexane/ethyl acetate, 8:2) provided the 1-(4-Fluoro-phenyl)-2-(4-methylsulfanyl-phenyl)-ethanone compound as a solid after precipitation in ether/ethyl acetate.

Step 2: 1-(4-Fluoro-phenyl)-2-(4-methanesulfonyl-phenyl)-ethanone

Following the procedures described in Ketone 02 but substituting 1-(4-fluoro-phenyl)-2-(4-methylsulfanyl-phenyl)-ethanone for Ketone 01, the 1-(4-fluoro-phenyl)-2-(4-methanesulfonyl-phenyl)-ethanone compound was obtained as a white solid.

Ketone 04

2-(4-Methanesulfonyl-phenyl)-1-p-tolyl-ethanone

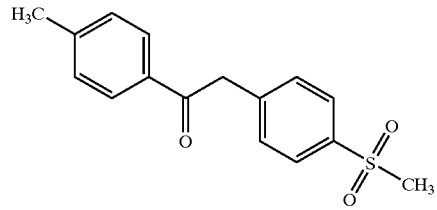

Following the procedures described in Ketone 03, but substituting 4-methyl-acetophenone for 4-fluoro-acetophenone, the title compound was obtained as a white solid.

Ketone 05

2-(4-Methanesulfonyl-phenyl)-1-pyridin-2-yl-ethanone

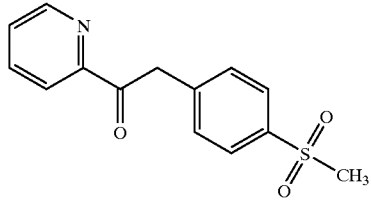

Following the procedures described in Ketone 03, but substituting 2-acetylpyridine for 4-fluoroacetophenone, the title compound was obtained as a beige solid.

Ketone 06

2-(4-Methanesulfonyl-phenyl)-1-pyridin-3-yl-ethanone

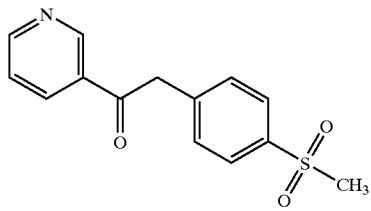

Following the procedures described in Ketone 03, but substituting 3-acetyl-pyridine for 4-fluoro-acetophenone, the title compound was obtained.

Ketone 07

1-(4-Methanesulfonyl-phenyl)-3,3-dimethyl-butan-2-one

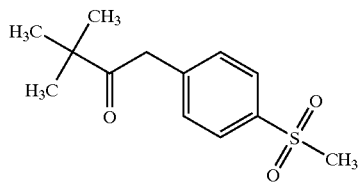

Following the procedures described in Ketone 03, but substituting pinacolone for 4-fluoroacetophenone, the title compound was obtained as a white solid.

Ketone 08

1-Cyclopropyl-2-(4-methanesulfonyl-phenyl)-ethanone

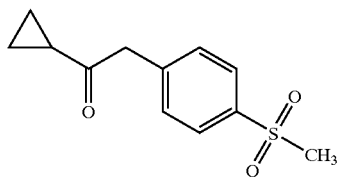

Following the procedures described in Ketone 01 and Ketone 02, but substituting 1-cyclopropyl-ethanone for 3-hydroxy-3-methyl-butan-2-one, the title compound was obtained.

Ketone 09

1-(4-Fluoro-phenyl)-2-(4-methanesulfonyl-phenyl)-propan-1-one

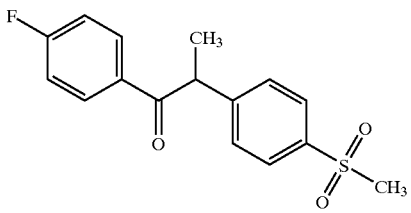

To a solution of Ketone 03 (240 mg, 0.822 mmol) in THF (8 mL) at −30° C. was added potassium tert-butoxide (1M, THF, 0.9 mL, 0.9 mmol) dropwise. After 20 min, iodomethane (0.076 mL, 1.22 mmol) was added and the resulting reaction mixture was stirred for 2 h at −20° C., and then diluted with a saturated ammonium chloride solution and ethyl acetate. The organic extracts were washed ($H_2O$), (brine), dried ($MgSO_4$), filtered and concentrated. Purification by flash chromatography (eluting with toluene/acetone, 95:5) provided the title compound.

Ketone 10

4-(4-Methanesulfonyl-phenyl)-2,2-dimethyl-pentan-3-one

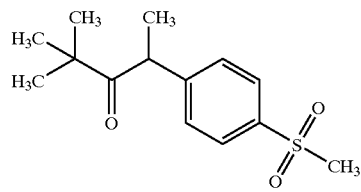

Following the procedures described in Ketone 01, but substituting pinacolone for 3-hydroxy-3-methyl-butan-2-one, followed by the procedures described in Ketone 09 and finally using procedures described in Ketone 02, the title compound was obtained.

Ketone 11

3-Hydroxy-1-[4-(1-hydroxy-1-methyl-ethyl)-phenyl]-3-methyl-butan-2-one

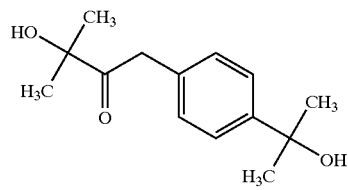

Step 1: 2-(4-Bromo-phenyl)-propan-2-ol

Following the procedures described in Example 24, but substituting ethyl 4-bromobenzoate for Example 07, the 2-(4-bromo-phenyl)-propan-2-ol compound was obtained as a white solid.

Step 2: 3-Hydroxy-1-[4-(1-hydroxy-1-methyl-ethyl)-phenyl]-3-methyl-butan-2-one

Following the procedures described in Ketone 01, but substituting 2-(4-bromophenyl)-2-propanol for 4-bromothioanisole, the 3-hydroxy-1-[4-(1-hydroxy-1-methyl-ethyl)-phenyl]-3-methyl-butan-2-one compound was obtained as an oil.

Ketone 12

3-Ethyl-3-hydroxy-1-(4-methanesulfonyl-phenyl)-pentan-2-one

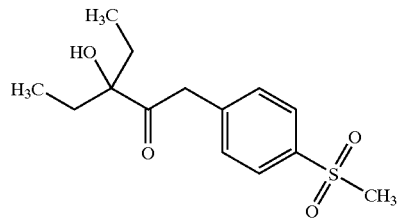

Step 1: 3-Ethyl-3-hydroxy-pentan-2-one

To a solution of ethyl vinylether (10 mL, 104 mmol) in THF (50 mL) at −78° C. was added tert-BuLi (1.7M, pentane, 45 mL, 76 mmol) dropwise. The mixture was stirred at −10° C. for 15 min then cooled to −78° C. and 3-pentanone (5.0 g, 58 mmol, in 5 mL of THF) was added dropwise. The resulting reaction mixture was allowed to warm slowly to 21° C., then diluted with a saturated ammonium chloride solution and ethyl acetate. The organic extract was stirred with 6 mL of HCl 2% for 18 h then washed (H₂O, brine), dried (MgSO₄), filtered and concentrated. The residue was purified by flash chromatography (eluting with hexane/ethyl acetate, 95:5) to provide the 3-ethyl-3-hydroxy-pentan-2-one compound as an oil.

Step 2: 3-Ethyl-3-hydroxy-1-(4-methanesulfonyl-phenyl)-pentan-2-one

Following the procedures described in Ketone 01 then in Ketone 02, but substituting 3-ethyl-3-hydroxy-pentan-2-one for 3-hydroxy-3-methyl-butan-2-one. Purification by flash chromatography (eluting with ethyl acetate/hexane, 3:2) afforded the 3-ethyl-3-hydroxy-1-(4-methanesulfonyl-phenyl)-pentan-2-one compound as a white foam.

Preparation of Sulfones

Sulfone 01

1-Methanesulfonyl-4-methanesulfonylmethyl-benzene

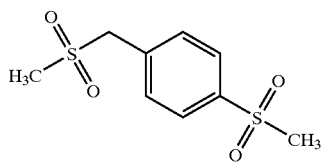

To a solution of 4-methanesulfonylbenzyl chloride (2 g, 10 mmol) in DMF (20 mL) at 21° C. was added sodium methanesulfinate (1.5 g, 15 mmol). After 18 h, the mixture is poured into cold water (100 mL), stirred for 30 min then filtered off to afford the title compound as a white solid.

Sulfone 02

1-(Fluoro-methanesulfonyl-methyl)-4-methanesulfonyl-benzene

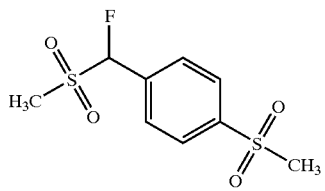

To a solution of Sulfone 01 (275 mg, 1.1 mmol) in DMF (6 mL) at 0° C. was added potassium tert-butoxide (1M THF, 1.5 mL, 1.5 mmol) followed, after 10 min, by N-fluorobenzenesulfonimide (419 mg, 1.3 mmol). The reaction mixture was diluted with a saturated sodium bicarbonate solution and ethyl acetate. The organic extracts were washed (H₂O), (brine), dried (MgSO₄), filtered and concentrated. Purification by flash chromatography (eluting with CH₂Cl₂/acetone, 97:3) provided the title compound.

Sulfone 03

1-Cyclopropanesulfonylmethyl-4-methanesulfonyl-benzene

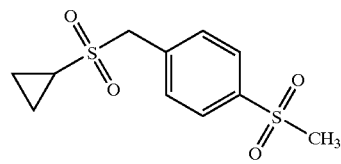

Step 1: (4-Methylsulfanyl-phenyl)-methanethiol disulfide

A solution of sulfur (1 g, 29 mmol) in benzene (60 mL), PEG 400 (1 drop) and NaOH (5N, 46 mL, 232 mmol) was heated at 65° C. for 3 h. 4-methylthiobenzyl chloride (4 g, 23 mmol) and a catalytic amount of tetrabutylammonium iodide was added and the mixture stirred at 65° C. for 2 h. The reaction was cooled at 21° C. and diluted with a saturated ammonium chloride solution and ethyl acetate. The organic extracts were washed (H₂O), (brine), dried (MgSO₄), filtered and concentrated. The residue was stirred vigorously in ethanol/ether for 1 h then filtered to afford the (4-methylsulfanyl-phenyl)-methanethiol disulfide compound as a pale rose powder.

Step 2: 1-Cyclopropylsulfanylmethyl-4-methylsulfanyl-benzene

To a solution of (4-methylsulfanyl-phenyl)-methanethiol disulfide from Step 1 in THF (50 mL) at 21° C. was added cyclopropylmagnesium bromide (excess) dropwise. The reaction mixture was stirred 18 h at 21° C., then diluted with a saturated ammonium chloride solution and ethyl acetate. The organic extracts were washed (H₂O), (brine), dried (MgSO₄), filtered and concentrated. Purification by flash chromatography (eluting with hexane/ethyl acetate, 98:2) provided the 1-cyclopropylsulfanylmethyl-4-methylsulfanyl-benzene compound as an oil.

Step 3: 1-Cyclopropanesulfonylmethyl-4-methanesulfonyl-benzene

Following the procedures described in Example 16, but substituting 1-cyclopropylsulfanylmethyl-4-methylsulfanyl-benzene thioether from Step 2 for Example 15 and purification by flash chromatography (eluting with hexane/ethyl acetate, 50:50 to 0:100) provided the 1-cyclopropanesulfonylmethyl-4-methanesulfonyl-benzene compound as a solid.

Sulfone 04

1-Ethanesulfonylmethyl-4-methanesulfonyl-benzene

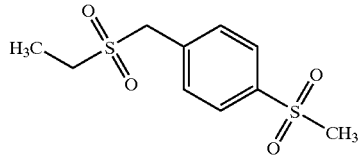

Step 1: 1-Ethylsulfanylmethyl-4-methanesulfonyl-benzene

To a solution of ethanethiol (0.3 mL, 4.9 mmol) and 4-methanesulfonylbenzyl chloride (1 g, 4,9 mmol) in DMF (10 mL) at 21° C. was added cesium carbonate (0.8 g, 2.5 mmol). After 18 h, the reaction mixture was poured into water and then filtered off to provide the 1-ethylsulfanylmethyl-4-methanesulfonyl-benzene compound as a white solid.

Step 2: 1-Ethanesulfonylmethyl-4-methanesulfonyl-benzene

Following the procedures described in Example 16, but substituting the 1-ethylsulfanylmethyl-4-methanesulfonyl-benzene thioether from Step 1 for Example 15, the 1-ethanesulfonylmethyl-4-methanesulfonyl-benzene compound was isolated as a white solid.

Sulfone 05

2-(4-Methanesulfonyl-phenylmethanesulfonyl)-1-methyl-1H-imidazole

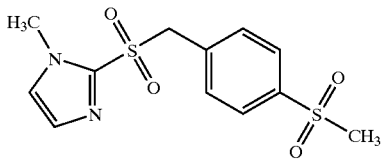

Step 1: 2-(4-Methanesulfonyl-benzylsulfanyl)-1-methyl-1H-imidazole

To a solution of 2-mercapto-N-methylimidazole (570 mg, 4.9 mmol) and 4-methanesulfonylbenzyl chloride (1 g, 4,9 mmol) in DMF (10 mL) at 21° C. was added cesium carbonate (0.8 g, 2.5 mmol). After 18 h, the reaction mixture was diluted with water and ethyl acetate. The organic extracts were washed (H$_2$O), (brine), dried (MgSO$_4$), filtered and concentrated to provide the 2-(4-methanesulfonyl-benzylsulfanyl)-1-methyl-1H-imidazole compound as a white solid.

Step 2: 2-(4-Methanesulfonyl-phenylmethanesulfonyl)-1-methyl-1H-imidazole

Following the procedures described in Example 16, but substituting the 2-(4-methanesulfonyl-benzylsulfanyl)-1-methyl-1H-imidazole thioether from Step 1 for Example 15, the 2-(4-methanesulfonyl-phenylmethanesulfonyl)-1-methyl-1H-imidazole compound was isolated as a white solid.

Sulfone 06

2-(4-Methanesulfonyl-phenylmethanesulfonyl)-thiazole

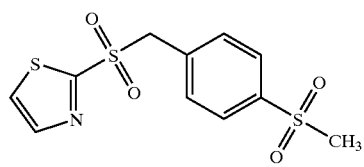

Following the procedures described in Sulfone 04, but substituting 2-mercaptothiazole for ethanethiol, the title compound was obtained as a white solid.

Sulfone 07

2-(4-Methanesulfonylmethyl-phenyl)-propan-2-ol

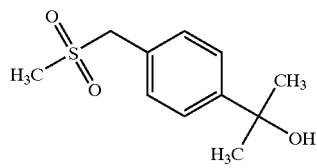

Step 1: 4-Methanesulfonylmethyl-benzoic acid methyl ester

Following the procedures described in Sulfone 01, but substituting 4-carboxymethylbenzyl chloride for 4-methanesulfonylbenzyl chloride, the 4-methanesulfonylmethyl-benzoic acid methyl ester compound was obtained as a white solid.

Step 2: 2-(4-Methanesulfonylmethyl-phenyl)-propan-2-ol

Following the procedures described in Example 29, but substituting the 4-methanesulfonylmethyl-benzoic acid methyl ester from Step 1 for Example 27, the 2-(4-methanesulfonylmethyl-phenyl)-propan-2-ol compound was obtained as a white solid.

Sulfone 08

C-(4-Methanesulfonyl-phenyl)-N,N-dimethyl-methanesulfonamide

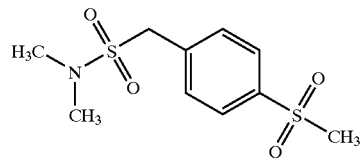

Step 1: (4-Methanesulfonyl-phenyl)-methanethiol

To a solution of potassium acetate (5.86 g, 51 mmol) in THF/DMF (3:1, 400 mL) was added 4-methanesulfonylbenzyl chloride (10 g, 49 mmol). After 3 h at 21° C., the resulting reaction mixture was quenched with LiOH (1M) and stirred again for 2 h. The mixture was diluted with HCl 10% solution and ethyl acetate. The organic extracts were washed (H$_2$O), (brine), dried (MgSO$_4$), filtered and concentrated. Purification by flash chromatography (eluting with CH$_2$Cl$_2$) provided the (4-methanesulfonyl-phenyl)-methanethiol compound.

Step 2: (4-Methanesulfonyl-phenyl)-methanesulfonyl chloride

To a solution of the (4-methanesulfonyl-phenyl)-methanethiol from Step 1 (7.3 g, 36 mmol) in AcOH (75 mL) was added water (25 mL). Then, chlorine was bubbled in the resulting mixture for 2 min. The mixture was diluted with water and filtered to provide the (4-methanesulfonyl-phenyl)-methanesulfonyl chloride.

Step 3: C-(4-Methanesulfonyl-phenyl)-N,N-dimethyl-methanesulfonamide

To a solution of (4-methanesulfonyl-phenyl)-methanesulfonyl chloride from Step 2 (1.0 g, 3.7 mmol) in CH$_2$Cl$_2$ (40 mL) was added dimethylamine (0.42 g, 9.3 mmol) dropwise. After 18 h, the resulting reaction mixture was diluted with a saturated ammonium chloride solution and ethyl acetate. The organic extracts were washed (HCl 10%, NaHCO$_3$, brine), dried (MgSO$_4$), filtered, and concentrated to provided the C-(4-methanesulfonyl-phenyl)-N,N-dimethyl-methanesulfonamide compound.

Sulfone 09

1-(4-Cyclopropanesulfonyl-phenyl)-3-hydroxy-3-methyl-butan-2-one

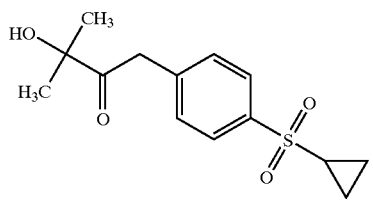

Step 1: 4-bromobenzene disulfide

To a solution of 4-bromothiophenol (16 g, 85 mmol) in CH$_2$Cl$_2$ (85 mL) was added iodine (10.7 g, 42 mmol, in CH$_2$Cl$_2$) and triethylamine (11.8 mL, 85 mmol). After 3 h the resulting reaction mixture was diluted with a sodium bisulfite solution and ethyl acetate. The organic extracts were washed (1N NaOH, brine), dried (MgSO$_4$), filtered and concentrated. The resulting residue was stirred vigorously in hexane/ether for 1 h then filtered to afford the 4-bromobenzene disulfide compound as a white powder.

Step 2: 1-Bromo-4-cyclopropylsulfanyl-benzene

Following the procedures described in Sulfone 03, Step 2 and purification by flash chromatography (eluting with hexane) provided the 1-bromo-4-cyclopropylsulfanyl-benzene compound.

Step 3: 1-(4-Cyclopropylsulfanyl-phenyl)-3-hydroxy-3-methyl-butan-2-one

Following the procedures described in Ketone 01, but substituting the 1-bromo-4-cyclopropylsulfanyl-benzene from Step 2 for 4-bromothioanisole, the 1-(4-cyclopropylsulfanyl-phenyl)-3-hydroxy-3-methyl-butan-2-one compound was obtained.

Step 4: 1-(4-Cyclopropanesulfonyl-phenyl)-3-hydroxy-3-methyl-butan-2-one

Following the procedures described in Ketone 02, but substituting the 1-(4-cyclopropylsulfanyl-phenyl)-3-hydroxy-3-methyl-butan-2-one from Step 3 for Ketone 01, the 1-(4-cyclopropanesulfonyl-phenyl)-3-hydroxy-3-methyl-butan-2-one compound was obtained.

Preparation of Phosphonates

Phosphonate 01

(4-Methanesulfonyl-benzyl)-phosphonic acid dimethyl ester

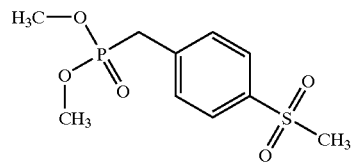

Step 1: (4-Methylsulfanyl-benzyl)-phosphonic acid dimethyl ester

To trimethylphosphite (8.6 g, 70 mmol) at 140° C. was added 4-methylthiobenzyl chloride (10 g, 58 mmol). The resulting mixture was stirred at 140° C. for 18 h, cooled at 21° C. then diluted with HCl 10% and ethyl acetate. The organic extracts were washed (H$_2$O), (brine), dried (MgSO$_4$), filtered, and concentrated. Purification by flash chromatography (eluting with ethyl acetate) provided the (4-methylsulfanyl-benzyl)-phosphonic acid dimethyl ester compound.

Step 2: (4-Methanesulfonyl-benzyl)-phosphonic acid dimethyl ester

Following the procedures described in Example 16, but substituting (4-methylsulfanyl-benzyl)-phosphonic acid dimethyl ester from Step 1 for Example 15, the (4-methanesulfonyl-benzyl)-phosphonic acid dimethyl ester compound was isolated.

Phosphonate 02

[Fluoro-(4-methanesulfonyl-phenyl)-methyl]-phosphonic acid dimethyl ester

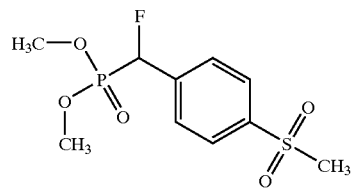

Following the procedures described in Example 37, but substituting Phosphonate 01 for Example 1, using THF as solvent, and purification by flash chromatography (eluting with toluene/acetone, 1:1) afforded the title compound.

Phosphonate 03

2-(4-Methanesulfonyl-benzyl)-5,5-dimethyl-[1,3,2] dioxaphosphinane 2-oxide

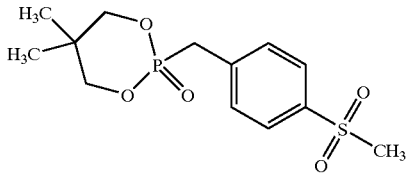

Step 1: (4-Methanesulfonyl-benzyl)-phosphonic acid

To a solution of Phosphonate 01 (5.74 g, 20.6 mmol) in CHCl$_3$ (50 mL) was added TMSBr (27 mL, 206 mmol) dropwise. The resulting reaction mixture was stirred 18 h at 21° C., concentrated under vacuum, and diluted with CHCl$_3$ and EtOH. After 2 h of stirring at 21° C., the mixture was concentrated again under vacuum. The resulting residue was crystallized from CH$_2$Cl$_2$/hexane as a white solid.

Step 2: (4-Methanesulfonyl-benzyl)-phosphonoyl chloride

To a solution of (4-methanesulfonyl-benzyl)-phosphonic acid from Step 1 (5.3 g, 21 mmol) in CH$_2$Cl$_2$ (200 mL) was added oxalyl chloride (4 mL, 45 mmol) dropwise and a few drops of DMF. After 5 days at 21° C., the solvent was evaporated and the residue was used as such in the next step.

Step 3: 2-(4-Methanesulfonyl-benzyl)-5,5-dimethyl-[1,3,2]dioxaphosphinane 2-oxide To a solution of (4-Methanesulfonyl-benzyl)-phosphonoyl chloride from Step 2 (100 mg, 0.35 mmol) in CH$_2$Cl$_2$ (5 mL) was added triethylamine (0.1 mL, 0.7 mmol) and 2,2-dimethyl-1,3-propanediol (48 mg, 0.47 mmol). The resulting reaction mixture was stirred 48 h at 21° C., then diluted with water and ethyl acetate. The organic extracts were washed (H$_2$O), (brine), dried (MgSO$_4$), filtered and concentrated. Purification by crystallization from CH$_2$C$_2$/hexane provided the 2-(4-methanesulfonyl-benzyl)-5,5-dimethyl-[1,3,2]dioxaphosphinane 2-oxide compound as a white solid.

Phosphonate 04

(4-Methanesulfonyl-benzyl)-phosphonic acid bis-(2,2,2-trifluoro-ethyl)ester

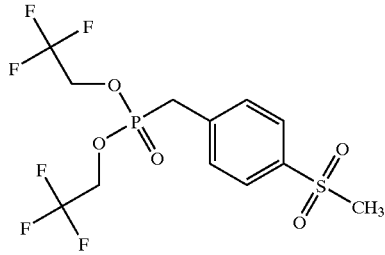

Following the procedures described in Phosphonate 03, but substituting 2,2,2-trifluoroethanol for 2,2-dimethyl-1,3-propanediol, the title compound was obtained.

EXAMPLE 1

4-Hydroxy-1-{3-[6-(1-methanesulfonyl-1-methyl-ethyl)-quinolin-8-yl]-phenyl}-2-(4-methanesulfonyl-phenyl)-4-methyl-pentan-3-one

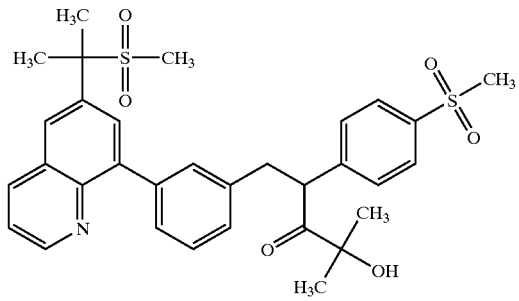

To a solution of Ketone 02 in THF/DMF (4:1, 0.08M) at 0° C. was added potassium tert-butoxide (1M, THF, 1.0 eq) dropwise followed after 10 min by Quinoline 01 (1.0 eq) dissolved in DMF (2M). The resulting reaction mixture was stirred at 21° C. for 3 h and diluted with a saturated ammonium acetate solution and ethyl acetate. The organic extracts were washed (H$_2$O), (brine), dried (MgSO$_4$), filtered, and concentrated. Purification by flash chromatography (eluting with ethyl acetate/dichloromethane, 60:40) provided the title compound as a white foam. The enantiomers can be separated on a chiral column (ChiralPaK AD, hexane/EtOH, 65:35, retention time 12.26 and 13.36 min) to give Example 1A (first to elute, [α]$_D$ 77.3 c=0.94 CH$_2$Cl$_2$) and Example 1B.

$^1$H NMR (400 MHz, acetone-d6): δ 8.93 (dd, 1H), 8.45 (dd, 1H), 8.26 (d, 1H), 8.05 (d, 1H), 7.86 (d, 2H), 7.68 (d, 2H), 7.57 (m, 2H), 7.50 (d, 1H), 7.35 (t, 1H), 7.21 (d, 1H), 5.18 (dd, 1H), 4.46 (s, OH), 3.45 (dd, 1H), 3.08 (dd, 1H), 3.05 (s, 3H), 2.7 (s, 3H), 1.98 (s, 6H), 1.1 (s, 3H), 1.05 (s, 3H).

EXAMPLE 2

1-(4-Fluoro-phenyl)-3-{3-[6-(1-methanesulfonyl-1-methyl-ethyl)-quinolin-8-yl]-phenyl}-2-(4-methanesulfonyl-phenyl)-propan-1-one

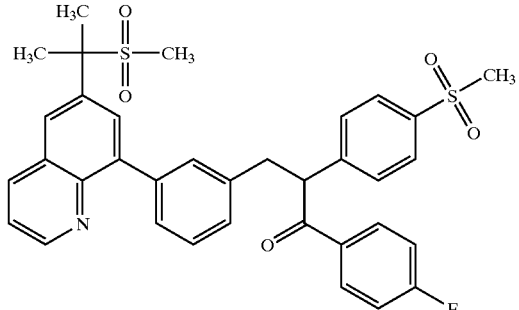

Following the procedures described in Example 1, but substituting Ketone 03 for Ketone 02, the title compound was obtained as a white solid.

$^1$H NMR (400 MHz, acetone-d$_6$): δ 8.88 (dd, 1H), 8.68 (dd, 1H), 8.43 (dd, 1H), 8.25 (d, 1H), 8.19–8.15 (m, 2H), 8.03 (d, 1H), 7.86 (d, 2H), 7.71 (d, 2H), 7.64 (s, 1H), 7.55 (dd, 1H), 7.50 (app d, 1H), 7.30 (t, 1H), 7.24 (app d, 1H), 7.19 (t, 2H), 5.47 (t, 1H), 3.22 (dd, 1H), 3.01 (s, 3H), 2.71 (s, 3H), 1.97 (s, 6H).

EXAMPLE 3

3-{3-[6-(1-Methanesulfonyl-1-methyl-ethyl)quinolin-8-yl]-phenyl}-2-(4-methanesulfonyl-phenyl)-1-p-tolyl-propan-1-one

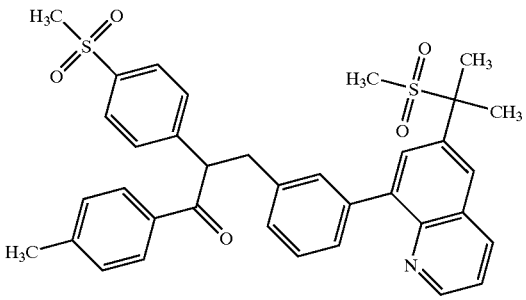

Following the procedures described in Example 1, but substituting Ketone 04 for Ketone 02, the title compound was obtained.

$^1$H NMR (400 MHz, acetone-$d_6$): δ 8.88 (dd, 1H), 8.43 (dd, 1H), 8.24 (d, 1H), 8.02 (d, 1H), 7.98 (d, 2H), 7.85 (d, 2H), 7.71 (d, 2H), 7.64 (s, 1H), 7.55 (dd, 1H), 7.50 (app d, 1H), 7.30 (t, 1H), 7.25 (app d, 3H), 5.45 (t, 1H), 3.68 (dd, 1H), 3.20 (dd, 1H), 3.01 (s, 3H), 2.70 (s, 3H), 2.32 (s, 3H), 1.97 (s, 6H).

EXAMPLE 4

3-{3-[6-(1-Methanesulfonyl-1-methyl-ethyl)-quinolin-8-yl]-phenyl}-2-(4-methanesulfonyl-phenyl)-1-pyridin-2-yl-propan-1-one

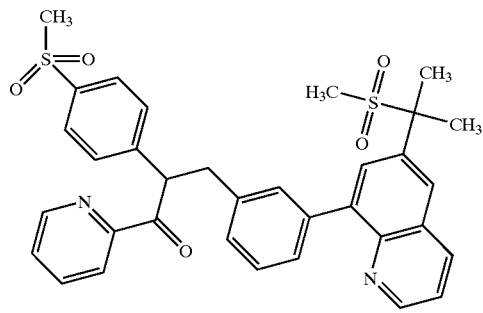

Following the procedures described in Example 1, but substituting Ketone 05 for Ketone 02, the title compound was obtained.

$^1$H NMR (400 MHz, acetone-$d_6$): δ 8.86 (dd, 1H), 8.69 (d, 1H), 8.42 (dd, 1H), 8.24 (d, 1H), 8.02–8.01 (m, 2H), 7.94 (td, 1H), 7.83 (d, 2H), 7.72 (d, 2H), 7.64 (s, 1H), 7.59–7.56 (m, 1H), 7.54 (dd, 1H), 7.50 (app d, 1H), 7.33–7.26 (m, 2H), 6.06 (t, 1H), 3.70 (dd, 1H), 3.27 (dd, 1H), 3.01 (s, 3H), 2.70 (s, 3H), 1.97 (s, 6H).

EXAMPLE 5

3-{3-[6-(1-Methanesulfonyl-1-methyl-ethyl)-quinolin-8-yl]-phenyl}-2-(4-methanesulfonyl-phenyl)-1-pyridin-3-yl-propan-1-one

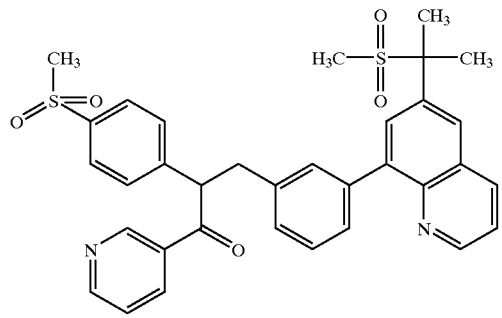

Following the procedures described in Example 1, but substituting Ketone 06 for Ketone 02, the title compound was obtained.

$^1$H NMR (400 MHz, acetone-$d_6$): δ 9.22 (d, 1H), 8.89 (dd, 1H), 8.69 (dd, 1H), 8.43 (dd, 1H), 8.36 (dt, 1H), 8.25 (d, 1H), 8.03 (d, 1H), 7.87 (d, 2H), 7.73 (d, 2H), 7.65 (s, 1H), 7.55 (dd, 1H), 7.49 (app d, 1H), 7.45 (dd, 1H), 7.31 (t, 1H), 7.25 (app d, 1H), 5.52 (t, 1H), 3.70 (dd, 1H), 3.25 (dd, 1H), 3.01 (s, 3H), 2.71 (s, 3H), 1.97 (s, 6H).

EXAMPLE 6

1-{3-[6-(1-Methanesulfonyl-1-methyl-ethyl)-quinolin-8-yl]-phenyl}-2-(4-methanesulfonyl-phenyl)-4,4-dimethyl-pentan-3-one

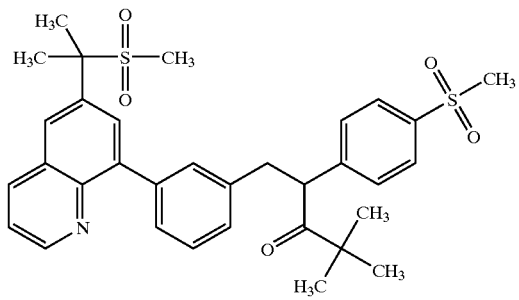

Following the procedures described in Example 1, but substituting Ketone 07 for Ketone 02, the title compound was obtained as white foam.

$^1$H NMR (400 MHz, acetone-d6): δ 8.93 (dd, 1H), 8.44 (dd, 1H), 8.25 (d, 1H), 8.04 (d, 1H), 7.87 (dd, 2H), 7.56 (m, 2H), 7.50 (d, 1H), 7.33 (t, 1H), 7.21 (d, 1H), 7.2 (dd, 2H), 4.89 (dd, 1H), 3.39 (dd, 1H), 3.06 (s, 3H), 3.04 (dd, 1H), 2.71 (s, 3H), 1.98 (s, 6H), 0.95 (s, 9H). 99254-47.

EXAMPLE 7

3-{3-[6-(1-Methanesulfonyl-1-methyl-ethyl)-quinolin-8-yl]-phenyl}-2-(4-methanesulfonyl-phenyl)-propionic acid methyl ester

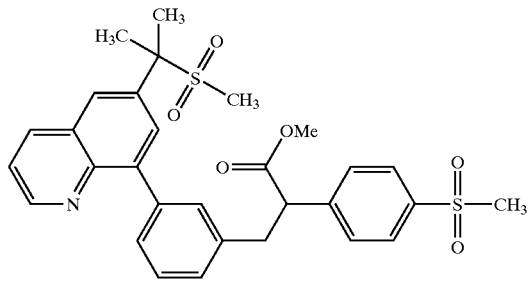

To a solution of Ester 01 (1.26 g, 5.5 mmol) in THF (80 mL) at −78° C. was added LiHMDS (1M, THF, 6.6 mL, 6.6 mmol) dropwise followed, after 30 min, Quinoline 01 (2.1 g, 5.0 mmol) dissolved in DMF (8 mL). The reaction mixture was stirred at −78° C. for 2 h and diluted with a saturated ammonium chloride solution and ethyl acetate. The organic extracts were washed ($H_2O$), (brine), dried ($MgSO_4$), filtered and concentrated. Purification by flash chromatography (eluting with hexane/ethyl acetate, 40:60) provided the title compound as a white foam.

$^1$H NMR (400 MHz, acetone-d6): δ 8.92 (dd, 1H), 8.43 (dd, 1H), 8.25 (d, 1H), 8.06 (d, 1H), 7.99 (d, 2H), 7.9 (d, 2H), 7.57 (m, 3H), 7.34 (t, 1H), 7.24 (d, 1H), 4.24 (t, 1H), 3.62 (s, 3H), 3.54 (dd, 1H), 3.29 (dd, 1H), 3.07 (s, 3H), 1.99 (s, 6H).

EXAMPLE 8

3-{3-[6-(1-Methanesulfonyl-1-methyl-ethyl)quinolin-8-yl]-phenyl}-2-(4-methanesulfonyl-phenyl)-propionic acid

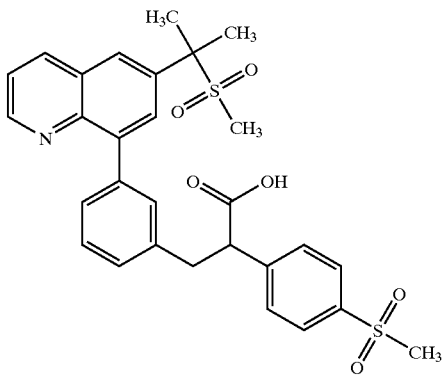

To a solution of Example 7 (130 mg, 0.23 mmol) in THF/MeOH/$H_2O$ (2:2:1, 5 mL) was added LiOH (2M, 0.35 mL, 0.69 mmol). The resulting mixture was stirred at 21° C. 18 h, acidified with HCl 10% and diluted with ethyl acetate. The organic extracts were washed ($H_2O$), (brine), dried ($MgSO_4$), filtered and concentrated. The title compound was obtained as a white powder after sonication in ether/hexane and filtration.

$^1$H NMR (400 MHz, acetone-d6): δ 8.92 (dd, 1H), 8.43 (dd, 1H), 8.25 (d, 1H), 8.06 (d, 1H), 7.9 (d, 2H), 7.70 (d, 2H), 7.62 (s, 1H), 7.54 (m, 2H), 7.34 (t, 1H), 7.26 (d, 1H), 4.22 (dd, 1H), 3.55 (dd, 1H), 3.39 (dd, 1H), 3.07 (s, 3H), 2.71 (s, 3H), 1.98 (s, 6H).

EXAMPLE 9

1-Cyclopropyl-3-{3-[6-(1-methanesulfonyl-1-methyl-ethyl)-quinolin-8-yl]-phenyl}-2-(4-methanesulfonyl-phenyl)-propan-1-one

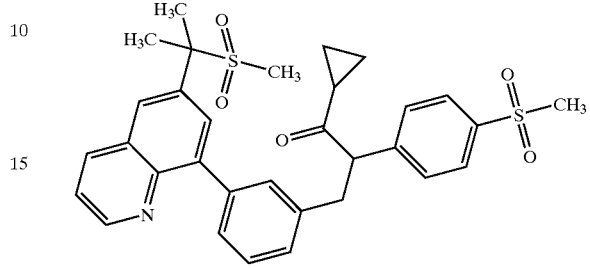

Step 1: 3-{3-[6-(1-Methanesulfonyl-1-methyl-ethyl)-quinolin-8-yl]-phenyl}-2-(4-methanesulfonyl-phenyl)-N-methoxy-N-methyl-propionamide To a solution of N,O-dimethylhydroxylamine (free base, 260 mg, 4.2 mmol) in THF at −78° C. was added MeMgBr (3M, ether, 1.4 mL, 4.2 mmol) dropwise (internal temperature <−65° C.) followed, after 30 min, by Example 7 (600 mg, 1.06 mmol, in THF). The resulting mixture was warmed slowly to 21° C., diluted with ethyl acetate and saturated ammonium chloride solution. The organic extracts were washed ($H_2O$), (brine), dried ($MgSO_4$), filtered, and concentrated. Purification by flash chromatography (eluting with hexane/ethyl acetate, 1:4 to 1:9) provided the 3-{3-[6-(1-methanesulfonyl-1-methyl-ethyl)-quinolin-8-yl]-phenyl}-2-(4-methanesulfonyl-phenyl)-N-methoxy-N-methyl-propionamide compound as a white foam.

Step 2: 1-Cyclopropyl-3-{3-[6-(1-methanesulfonyl-1-methyl-ethyl)-quinolin-8-yl]-phenyl}-2-(4-methanesulfonyl-phenyl)-propan-1-one Anhydrous $CeCl_3$ (266 mg, 1.26 mmol) was heated 2 h at 130° C. under high vacuum, refluxed in THF (10 mL) for 1 h then cooled to 0° C. To the resulting white suspension at 0° C. was added freshly prepared cyclopropylmagnesium bromide (0.6M, THF, 2.11 mL, 1.25 mmol) and the resulting mixture stirred at 0° C. for 1 h then cooled to −78° C. The 3-{3-[6-(1-methanesulfonyl-1-methyl-ethyl)-quinolin-8-yl]-phenyl}-2-(4-methanesulfonyl-phenyl)-N-methoxy-N-methyl-propionamide from Step 1 (in THF, 150 mg, 0.25 mmol) was added and the mixture warmed to 0° C. for 1 h, diluted with ethyl acetate and saturated ammonium chloride solution. The organic extracts were washed ($H_2O$), (brine), dried ($MgSO_4$), filtered and concentrated. Purification by flash chromatography (eluting with hexane/ethyl acetate, 1:4) provided the 1-cyclopropyl-3-{3-[6-(1-methanesulfonyl-1-methyl-ethyl)-quinolin-8-yl]-phenyl}-2-(4-methanesulfonyl-phenyl)-propan-1-one compound as a white foam.

$^1$H NMR (400 MHz, acetone-d6): δ 8.93 (dd, 6H), 8.42 (dd, 1H), 8.25 (d, 1H), 8.06 (d, 1H), 7.95 (d, 2H), 7.63 (d, 2H), 7.54 (m, 3H), 7.31 (t, 1H), 7.20 (d, 1H), 4.61 (t, 1H), 3.56 (dd, 1H), 3.09 (dd, 1H), 3.05 (s, 3H), 2.71 (s, 3H), 2.06 (m, 1H), 1.98 (s, 6H), 0.9–0.7 (m, 4H).

An alternate synthesis of Example 9 is by following the procedures described above in Example 1, but substituting Ketone 08 for Ketone 02.

EXAMPLE 10

5-{3-[6-(1-Methanesulfonyl-1-methyl-ethyl)-quinolin-8-yl]-phenyl}4-(4-methanesulfonyl-phenyl)-2,3-dimethyl-pentane-2,3-diol

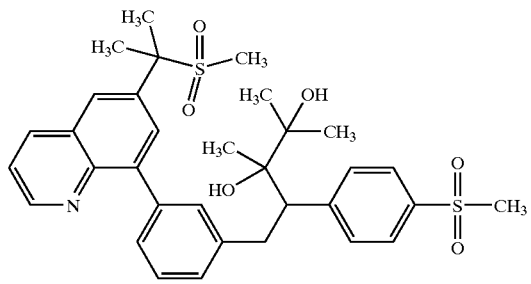

Using Example 01 as the starting material and following the procedures described above in Example 9, Step 2, and substituting methylmagnesium bromide for cyclopropyl magnesium bromide, the title compound was obtained as a white solid (one pair of enantiomer).

$^1$H NMR (400 MHz, acetone-d6): δ 8.89 (dd, 1H), 8.38 (dd, 1H), 8.20 (d, 1H), 7.95 (d, 1H), 7.71 (d, 2H), 7.61 (d, 2H), 7.50 (dd, 1H), 7.47 (s, 1H), 7.39 (d, 1H), 7.16 (t, 1H), 7.08 (d, 1H), 3.74 (m, 2H), 3.63 (s, 1H), 3.29 (s, 1H), 3.19 (m, 1H), 2.93 (s, 3H), 2.70 (s, 3H), 1.95 (s, 6H), 1.41 (s, 6H), 1.32 (s, 3H).

EXAMPLE 11

1-Cyclopropyl-2-fluoro-3-{3-[6-(1-methanesulfonyl-1-methyl-ethyl)-quinolin-8-yl]-phenyl}-2-(4-methanesulfonyl-phenyl)-propan-1-one

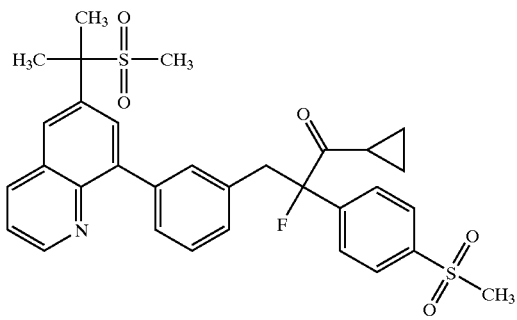

To a solution of Example 9 (1.5 g, 2.62 mmol) in THF/DMF (3:1, 13 mL) at −78° C. was added potassium tert-butoxide (1M THF, 2.9 mL, 2.9 mmol), followed by N-fluorobenzenesulfonimide (1.63 g, 5.2 mmol). The resulting reaction mixture was stirred 2 h at −78° C., then quenched with AcOH (2 drops) and diluted with a saturated ammonium chloride solution and ethyl acetate. The organic extracts were washed (H$_2$O), (brine), dried (MgSO$_4$), filtered and concentrated. Purification by flash chromatography (eluting with toluene/acetone, 80:20) provided the title compound.

$^1$H NMR (400 MH, acetone-d6): δ 8.90 (dd, 1H), 8.40 (dd, 1H), 8.24 (d, 1H), 8.05 (d, 1H), 7.97 (d, 2H), 7.71 (d, 2H), 7.59 (d, 1H), 7.55 (s, 1H), 7.53 (dd, 1H), 7.34 (t, 1H), 7.14 (d, 1H), 3.78 (dd, 1H), 3.52 (dd, 1H), 3.09 (s, 3H), 2.70 (s, 3H), 2.49–2.41 (m, 1H), 1.98 (s, 6H), 0.91–0.85 (m, 4H).

EXAMPLE 12

2-Cyclopropyl-3-fluoro-4-{3-[6-(1-methanesulfonyl-1-methyl-ethyl)-quinolin-8-yl]-phenyl}-3-(4-methanesulfonyl-phenyl)-butan-2-ol

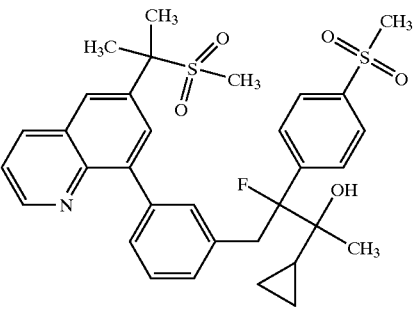

Using Example 11 as starting material and following the procedures described below in Example 29, the title compound was obtained as a white solid (9:1 mixture of diastereoisomers). The enantiomers can be separated on a chiral column (ChiralPaK AD, hexane/EtOH, 1;1, retention time 21 and 29 min) to give Example 12A and Example 12B.

$^1$H NMR (400 MHz, acetone-d6): (major isomer) δ 8.88 (dd, 1H), 8.38 (dd, 1H), 8.20 (d, 1H), 7.91 (d, 1H), 7.83 (d, 2H), 7.78 (d, 2H), 7.51 (dd, 1H), 7.45 (s, 1H), 7.44 (d, 1H), 7.18 (t, 1H), 7.14 (d, 1H), 4.11 (s, OH), 3.83 (s, 1H), 3.77 (dd, 1H), 2.97 (s, 3H), 2.70 (s, 3H), 1.97 (s, 3H), 1.96 (s, 3H), 1.34 (d, 3H), 0.96–0.92 (m, 1H), 0.34–0.22 (m, 3H), 0.14–0.10 (m, 1H). LRMS (CI) 610 (M+H)$^+$.

The other pair of enantiomers can be obtained using Example 14 as the starting material and following procedures described in Example 11 followed with the procedures described above in Example 9, Step 2 (85:15 mixture of diastereoisomers).

$^1$H NMR (400 MHz, acetone-d6): δ 8.88 (dd, 1H), 8.40 (dd, 1H), 8.21 (d, 1H), 7.91 (d, 1H), 7.79 (m, 4H), 7.52 (dd, 1H), 7.43 (m, 2H), 7.15 (m, 2H), 4.1–3.6 (m, 3H), 3.89 (s, 3H), 2.70 (s, 3H), 1.97 (d, 6H), 1.29 (m, 1H), 1.09 (d, 3H), 0.81 (m, 1H), 0.56 (m, 1H), 0.38 (m, 2H).

EXAMPLE 13

3-{3-[6-(1-Methanesulfonyl-1-methyl-ethyl)-quinolin-8-yl]-phenyl}-2-(4-methanesulfonyl-phenyl)-1-phenyl-propan-1-one

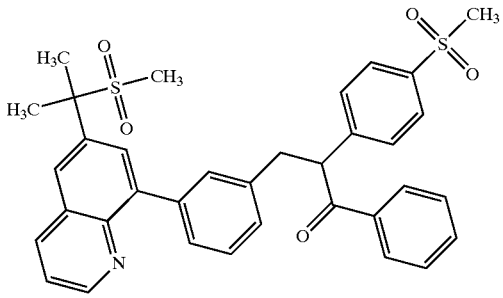

Step 1: 3-{3-[6-(1-Methanesulfonyl-1-methyl-ethyl)-quinolin-8-yl]-phenyl}-2-(4-methylsulfanyl-phenyl)-propionic acid methyl ester To a solution of Ester 04 (4.0 g, 20 mmol) in THF (5 mL) at −78° C. was added KHMDS (0.5M, Tol, 41 mL, 20.5 mmol) dropwise. The resulting reaction mixture was stirred 0.5 h at −78° C. then cannulated into Quinoline O2 (2.95 g, 6.8 mmol) in THF (50 mL) at 21° C. After 15 min, the mixture was diluted with a saturated ammonium chloride solution and ethyl acetate. The organic extracts were washed (H₂O), (brine), dried (MgSO₄), filtered and concentrated. Purification by flash chromatography (eluting with hexane/ethyl acetate, 50:50) provided the 3-{3-[6-(1-methanesulfonyl-1-methyl-ethyl)-quinolin-8-yl]-phenyl}-2-(4-methylsulfanyl-phenyl)-propionic acid methyl ester compound as a white foam.

Step 2: 3-{3-[6-(1-Methanesulfonyl-1-methyl-ethyl)-quinolin-8-yl]-phenyl}-2-(4-methylsulfanyl-phenyl)-propionaldehyde To a solution of 3-{3-[6-(1-methanesulfonyl-1-methyl-ethyl)-quinolin-8-yl]-phenyl}-2-(4-methylsulfanyl-phenyl)-propionic acid methyl ester from Step 1 (1.48 g, 7.5 mmol) in CH₂Cl₂ (80 mL) at −78° C. was added dibal-H (1.6 mL, 7.8 mmol). The resulting reaction mixture was stirred 1 h at −78° C., then quenched with sodium potassium tartrate solution and stirred at 21° C. for 3 h. The organic extracts were washed (H₂O), (brine), dried (MgSO₄), filtered and concentrated to provided the 3-{3-[6-(1-methanesulfonyl-1-methyl-ethyl)-quinolin-8-yl]-phenyl}-2-(4-methylsulfanyl-phenyl)-propionaldehyde compound as a white foam.

Step 3: 3-{3-[6-(1-Methanesulfonyl-1-methyl-ethyl)-quinolin-8-yl]-phenyl}-2-(4-methylsulfanyl-phenyl)-1-phenyl-propan-1-ol To a solution of 3-{3-[6-(1-methanesulfonyl-1-methyl-ethyl)-quinolin-8-yl]-phenyl}-2-(4-methylsulfanyl-phenyl)-propionaldehyde from Step 2 (150 mg, 0.3 mmol) in CH₂Cl₂ (6 mL) at 21° C. was added phenylmagnesium chloride (2M, TBF, 0.45 mL, 0.9 mmol) dropwise. The resulting reaction mixture was stirred 0.5 h at 21° C. then diluted with a saturated ammonium chloride solution and ethyl acetate. The organic extracts were washed (H₂O), (brine), dried (MgSO₄), filtered and concentrated. The crude oil was used as such in the next step.

Step 4: 3-{3-[6-(1-Methanesulfonyl-1-methyl-ethyl)-quinolin-8-yl]-phenyl}-2-(4-methylsulfanyl-phenyl)-1-phenyl-propan-1-one To a solution of the crude oil from Step 3 in CH₂Cl₂ (5 mL) at 21° C. was added Dess-Martin periodinane (255 mg, 0.6 mmol) portionwise. The resulting reaction mixture was stirred 2 h at 21° C., then diluted with a sodium bicarbonate solution and ethyl acetate. The organic extracts were washed (H₂O), (brine), dried (MgSO₄), filtered and concentrated. Purification by flash chromatography (eluting with hexane/ethyl acetate, 50:50) provided the 3-{3-[6-(1-methanesulfonyl-1-methyl-ethyl)-quinolin-8-yl]-phenyl}-2-(4-methylsulfanyl-phenyl)-1-phenyl-propan-1-one compound as a white foam.

Step 5: 3-{3-[6-(1-Methanesulfonyl-1-methyl-ethyl)-quinolin-8-yl]-phenyl}-2-(4-methanesulfonyl-phenyl)-1-phenyl-propan-1-one To a solution of 3-{3-[6-(1-Methanesulfonyl-1-methyl-ethyl)-quinolin-8-yl)-phenyl)-2-(4-methylsulfanyl-phenyl)-1-phenyl-propan-1-one from Step 4 (55 mg, 0.095 mmol) in THF/MeOH/H₂O (2:1:1, 5 mL) at 21° C. was added OXONE® (0.1 g, 0.16 mmol). The resulting reaction mixture was stirred 2 h at 21° C., then diluted with a sodium bicarbonate solution and ethyl acetate. The organic extracts were washed (H₂O), (brine), dried (MgSO₄), filtered and concentrated. The residue was stirred vigorously in hexane/ether for 1 h then filtered to afford the 3-{3-[6-(1-methanesulfonyl-1-methyl-ethyl)-quinolin-8-yl]-phenyl}-2-(4-methanesulfonyl-phenyl)-1-phenyl-propan-1-one compound as a white powder.

¹H NMR (400 MHz, acetone-d6): δ 8.87 (dd, 1H), 8.42 (dd, 1H), 8.24 (d, 1H), 8.08 (d, 2H), 8.03 (d, 1H), 7.85 (d, 2H), 7.71 (d, 2H), 7.65 (s, 1H), 7.56–7.42 (m, 5H), 7.28 (m, 2H), 5.5 (t, 1H), 3.69 (dd, 1H), 3.23 (dd, 1H), 3.00 (s, 3H), 2.70 (s, 3H), 1.97 (s, 6H). 99020-173

EXAMPLE 14

4-{3-[6-(1-Methanesulfonyl-1 methyl-ethyl)-quinolin-8-yl]-phenyl}-3-(4-methanesulfonyl-phenyl)-butan-2-one

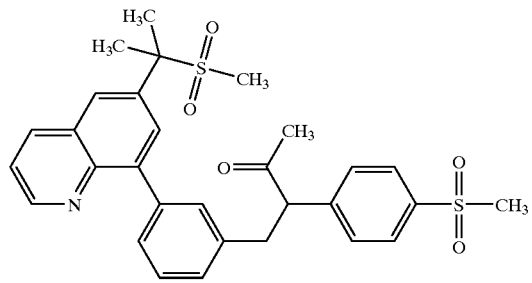

Following the procedures described above in Example 13, but substituting methylmagnesiumbromide for phenylmagnesium bromide in Step 3, the title compound was obtained as a white solid.

¹H NMR (400 MHz, acetone-d6): δ 8.92 (dd, 1H), 8.43 (dd, 1H), 8.25 (d, 1H), 8.03 (d, 1H), 7.95 (d, 2H), 7.62 (d, 2H), 7.60–7.52 (m, 3H), 7.31 (t, 1H), 7.18 (d, 1H), 4.50 (t, 1H), 3.52 (dd, 1H), 3.10 (dd, 1H), 3.05 (s, 3H), 2.83 (s, 3H), 2.11 (s, 3H), 1.98 (s, 6H).

EXAMPLE 15

3-{3-[6-(1-Methanesulfonyl-1-methyl-ethyl)-quinolin-8-yl]-phenyl}-2-(4-methylsulfanyl-phenyl)-propan-1-ol

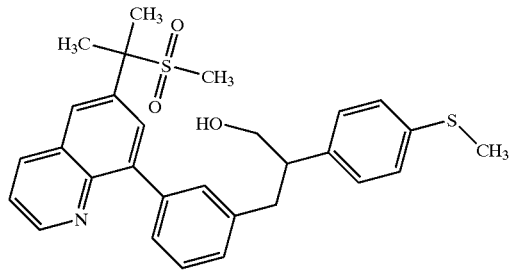

To a solution of the ester from Step 1, Example 13 (1.0 g, 5 mmol) in CH₂Cl₂ (25 mL) at −78° C. was added dibal-H (20.1 mL, 12 mmol). The resulting reaction mixture was warmed slowly to 21° C., then quenched with sodium potassium tartrate solution and stirred at 21° C. for 3 h. The reaction mixture was diluted with ethyl acetate. The organic extracts were washed (H₂O), (brine), dried (MgSO₄), filtered and concentrated. Purification by flash chromatography (eluting with hexane/ethyl acetate, 50:50) provided the title compound as a white foam.

$^1$H NMR (400 MHz, acetone-d6): δ 8.91 (dd, 1H), 8.43 (dd, 1H), 8.24 (d, 1H), 8.01 (d, 1H), 7.56 (dd, 1H), 7.51 (m, 2H), 7.29 (t, 1H), 7.24–7.14 (m, 6H), 3.75 (d, 2H), 3.27 (dd, 1H), 3.14 (m, 1H), 2.96 (dd, 1H), 2.70 (s, 3H), 2.42 (s, 3H), 1.98 (s, 6H).

EXAMPLE 16

3-{3-[6-(1-Methanesulfonyl-1-methyl-ethyl)-quinolin-8-yl]-phenyl}-2-(4-methanesulfonyl-phenyl)-propan-1-ol

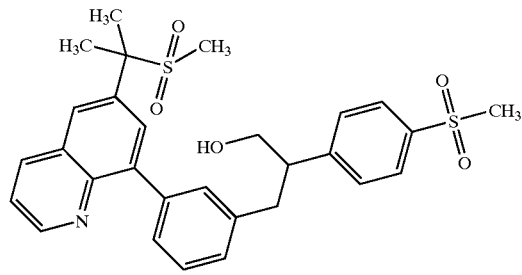

To a solution of Example 15 (350 mg, 0.69 mmol) in THF/MeOH/H$_2$O (2:1:1, 15 mL) at 21° C. was added OXONE® (1.1 g, 1.8 mmol). The resulting reaction mixture was stirred 2 h at 21° C. then diluted with a sodium bicarbonate solution and ethyl acetate. The organic extracts were washed (H$_2$O), (brine), dried (MgSO$_4$), filtered and concentrated to afford the title compound as a pale yellow foam.

$^1$H NMR (400 MHz, acetone-d6): δ 8.91 (dd, 1H), 8.42 (dd, 1H), 8.24 (d, 1H), 8.04 (d, 1H), 7.82 (d, 2H), 7.55 (m, 5H), 7.31 (t, 1H), 7.20 (d, 1H), 3.83 (d, 2H), 3.34 (m, 2H), 3.05 (m, 1H), 3.03 (s, 3H), 2.70 (s, 3H), 1.98 (s, 6H).

EXAMPLE 17

2-Hydroxy-3-{3-[6-(1-methanesulfonyl-1-methyl-ethyl)-quinolin-8-yl]-phenyl}-2-(4-methanesulfonyl-phenyl)-propionic acid ethyl ester

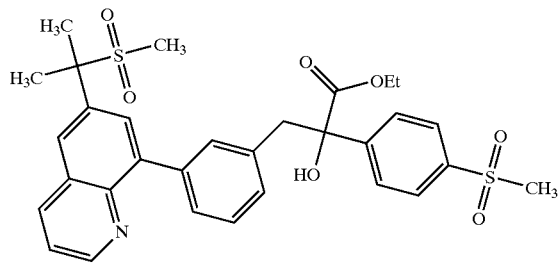

Step 1: 2-Hydroxy-3-{3-(6-(1-methanesulfonyl-1-methyl-ethyl)-quinolin-8-yl]-phenyl}-2-(4-methylsulfanyl-phenyl)-propionic acid ethyl ester To a solution of Ester 02 (220 mg, 0.97 mmol) in THF (6 mL) at –78° C. was added potassium tert-butoxide (1M, THF, 20.1 mL, 2.1 mmol) dropwise. The resulting reaction mixture was warmed to –40° C. for 20 min, then Quinoline 01 (0.25M, THF, 3 mL) was added. The reaction mixture was warmed from 40° C. to –20° C. over a 2 h period, then quenched with a saturated ammonium chloride solution and ethyl acetate. The organic extracts were washed (H$_2$O), (brine), dried (MgSO$_4$), filtered and concentrated. Purification by flash chromatography (eluting with hexane/ethyl acetate, 50:50) provided the 2-hydroxy-3-{3-[6-(1-methanesulfonyl-1-methyl-ethyl)quinolin-8-yl]-phenyl}-2-(4-methylsulfanyl-phenyl)-propionic acid ethyl ester compound as a white foam.

Step 2: 2-Hydroxy-3-{3-[6-(1-methanesulfonyl-1-methyl-ethyl)-quinolin-8-yl]-phenyl}-2-(4-methanesulfonyl-phenyl)-propionic acid ethyl ester Using the 2-hydroxy-3-{3-[6-(1-methanesulfonyl-1-methyl-ethyl)-quinolin-8-yl]-phenyl}-2-(4-methylsulfanyl-phenyl)-propionic acid ethyl ester from Step 1 and following the procedures described in Example 16, and purification by flash chromatography (eluting with hexane/ethyl acetate, 1:4) provided the 2-hydroxy-3-{3-[6-(1-methanesulfonyl-1-methyl-ethyl)-quinolin-8-yl]-phenyl}-2-(4-methanesulfonyl-phenyl)-propionic acid ethyl ester compound as a white foam.

$^1$H NMR (400 MHz, acetone-d6): δ 8.91 (dd, 1H), 8.42 (dd, 1H), 8.25 (d, 1H), 8.07 (d, 1H), 8.02 (d, 2H), 7.93 (d, 2H), 7.65 (s, 1H), 7.56 (m, 2H), 7.33 (m, 2H), 5.07 (s, OH), 4.17 (m, 2H), 3.71 (d, 1H), 3.33 (d, 1H), 3.07 (s, 3H), 2.71 (s, 3H), 1.98 (s, 6H), 1.17 (m, 3H).

EXAMPLE 18

2-(4-Fluoro-phenyl)-4-{3-[6-(1-methanesulfonyl-1-methyl-ethyl)-quinolin-8-yl]-phenyl}-3-(4-methanesulfonyl-phenyl)-butan-2-ol

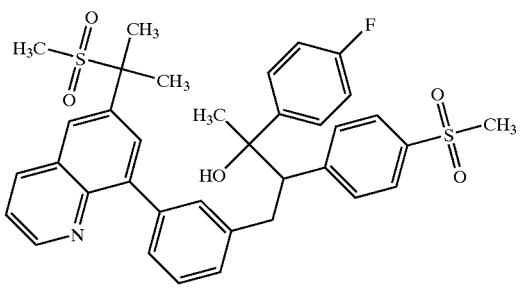

To a solution of Example 02 (101 mg, 0.16 mmol) in THF (2 mL) at 21° C. was added methyl magnesium iodide (3M, Et2O, 0.3 mL, 0.9 mmol) dropwise. The resulting reaction mixture was stirred at 21° C. for 18 h, then diluted with a saturated ammonium chloride solution and ethyl acetate. The organic extracts were washed (H$_2$O), (brine), dried (MgSO$_4$), filtered and concentrated. Purification by flash chromatography (eluting with toluene/acetone, 85:15) provided the title compound as a mixture of diastereoisomers (5:1).

$^1$H NMR (400 MHz, acetone-d6): δ 8.87 (dd, 1H), 8.38 (dd, 1H), 8.20 (d, 1H), 7.93 (d, 1H), 7.76–7.73 (m, 1H), 7.60 (d, 2H), 7.51 (dd, 1H), 7.41–7.33 (m, 5H), 7.17 (d, 1H), 7.12 (t, 1H), 7.07 (d, 1H), 6.93 (t, 1H), 4.50 (s, OH), 3.62 (dd, 1H), 3.54 (dd, 1H), 3.17 (t, 1H), 2.89 (s, 3H), 2.69 (s, 3H), 1.95 (s, 6H), 1.78 (s, 3H). LRMS (CI) 646 (M+H)$^+$.

EXAMPLE 19

1-(4-Fluoro-phenyl)-3-{3-[6-(1-methanesulfonyl-1-methyl-ethyl)-quinolin-8-yl]-phenyl}-2-(4-methanesulfonyl-phenyl)-2-methyl-propan-1-one

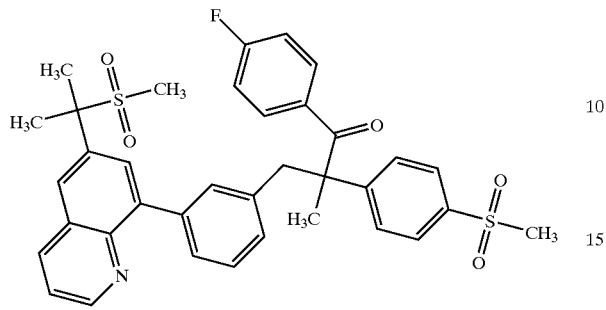

To a solution of Ketone 09 (171 g, 0.56 mmol) in THF (3 mL) at −20° C. was added potassium tert-butoxide (1M, 0.59 mL, 0.59 mmol) dropwise followed, after 15 min, by Quinoline 01 (250 mg, 0.59 mmol) dissolved in DMF (0.4 mL). The resulting reaction mixture was stirred at 21° C. for 3 h and diluted with a saturated ammonium chloride solution and ethyl acetate. The organic extracts were washed ($H_2O$), (brine), dried ($MgSO_4$), filtered and concentrated. Purification by flash chromatography (eluting with toluene/acetone, 85:15) followed by stirring vigorously in hexane/ethyl acetate/ether for 1 h then filtered to afford the title compound as a white powder.

$^1$H NMR (400 Mz, acetone-d6): δ 8.90 (dd, 1H), 8.42 (dd, 1H), 8.23 (d, 1H), 8.02 (d, 1H), 7.85 (d, 2H), 7.64–7.61 (m, 2H), 7.55 (dd, 1H), 7.50 (d, 3H), 7.21 (d, 1H), 7.18 (s, 1H), 7.08–7.04 (m, 2H), 6.69 (d, 1H), 3.54 (d, 1H), 3.46 (d, 1H); 2.84 (s, 3H), 2.71 (s, 3H), 1.97 (s, 6H), 1.77 (s, 3H). LRMS (CI) 644 (M+H)$^+$.

EXAMPLE 20

1-(3-[6-(1-Methanesulfonyl-1-methyl-ethyl)-quinolin-8-yl]-phenyl}-2-(4-methanesulfonyl-phenyl)-2,4,4-trimethyl-pentan-3-one

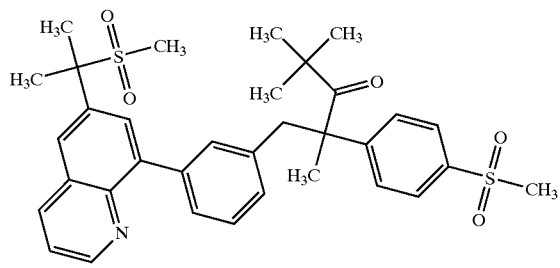

Following the procedures described in Example 19, but substituting Ketone 10 for Ketone 09 and purification by flash chromatography (eluting with dichloromethane/methanol, 99:1), then stirring vigorously the resulting solid in hexane/ethyl acetate/ether for 1 h and then filtration afforded the title compound as a white powder.

$^1$H NMR (400 MHz, acetone-d6): δ 8.91 (dd, 1H), 8.40 (dd, 1H), 8.22 (d, 1H), 8.01 (d, 1H), 7.83 (d, 2H), 7.53 (dd, 1H), 7.46 (dd, 1H), 7.36 (dd, 2H), 7.14 (t, 1H), 7.09 (s, 1H), 6.55 (s, 1H), 3.28 (d, 1H), 3.18 (d, 1H), 2.81 (s, 3H), 2.70 (s, 3H), 1.97 (s, 3H), 1.96 (s, 3H), 1.77 (s, 3H), 1.00 (s, 9H). LRMS (CI) 606 (M+H)$^+$.

EXAMPLE 21

1-{3-[6-(1-Methanesulfonyl-1-methyl-ethyl)-quinolin-8-yl]-phenyl}-2-(4-methanesulfonyl-phenyl)-4,4-dimethyl-pentan-3-ol

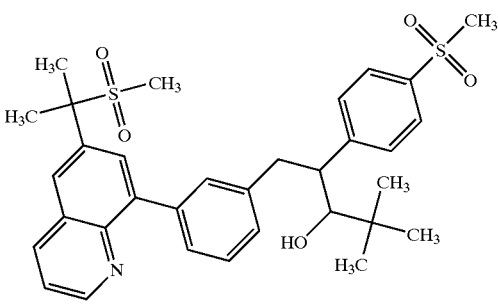

To a solution of Example 06 (75 mg, 0.127 mmol) in MeOH (3 mL) at −78° C. was added sodium borohydride (5 mg, 0.13 mmol). The resulting reaction mixture was warmed to 21° C. then diluted with a saturated ammonium chloride solution and ethyl acetate. The organic extracts were washed ($H_2O$), (brine), dried ($MgSO_4$), filtered and concentrated to provide the title compound as a white foam (one pair of enantiomer).

$^1$H NMR (400 MHz, acetone-d6): δ 8.93 (dd, 1H), 8.45 (dd, 1H), 8.25 (d, 1H), 8.07 (d, 1H), 7.78 (m, 4H), 7.59 (m, 2H), 7.49 (d, 1H), 7.31 (t, 1H), 7.19 (d, 1H), 4.34 (d, OH), 3;66 (m, 1H), 3.45 (m, 1H), 3.29 (dd, 1H), 3.09 (dd, 1H), 3.0 (s, 3H), 2.72 (s, 3H), 1.98 (s, 6H), 0.71 (s, 9H). 99254-62.

EXAMPLE 22

1-(4-Fluoro-phenyl)-3-{3-[6-(1-methanesulfonyl-1-methyl-ethyl)-quinolin-8-yl]-phenyl}-2-(4-methanesulfonyl-phenyl)-propan-1-ol

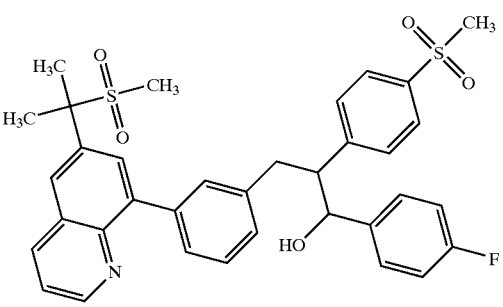

Following the procedures described in Example 21, but substituting Example 02 for Example 06 and purification by flash chromatography (eluting with dichloromethane/methanol, 99:1), then stirring vigorously the resulting residue in hexane/ethyl acetate/ether for 1 h and then filtration afforded the title compound as a white powder (one pair of enantiomer).

$^1$H NMR (400 MHz, acetone-d$_6$): δ 8.90 (dd, 1H), 8.42 (dd, 1H), 8.23 (d, 1H), 8.03 (d, 1H), 7.72 (d, 2H), 7.56–7.53 (m, 2H), 7.49–7.44 (m, 3H), 7.31–7.23 (m, 3H), 7.18 (d, 1H), 7.00–6.95 (m, 2H), 5.11 (t, 1H), 4.65 (d, OH), 3.53–3.50 (m, 1H), 3.27 (dd, 1H), 3.15 (d, 1H), 2.99 (s, 3H), 2.70 (s, 3H), 1.97 (s, 6H).

EXAMPLE 23

2-(4-Fluoro-phenyl)-4-{3-[6-(1-methanesulfonyl-1-methyl-ethyl)-quinolin-8-yl]-phenyl}-3-(4-methanesulfonyl-phenyl)-3-methyl-butan-2-ol

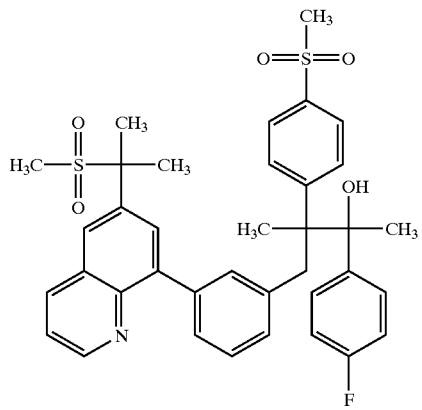

To a solution of Example 19 (93 mg, 0.144 mmol) in CH$_2$Cl$_2$ (4 mL) at −78° C. was added methyl magnesium iodide (3M, Et$_2$O, 0.24 mL, 0.8 mmol) dropwise. The resulting reaction mixture was stirred at 21° C. for 12 h, then diluted with a saturated ammonium chloride solution and ethyl acetate. The organic extracts were washed (H$_2$O), (brine), dried (MgSO$_4$), filtered and concentrated. Purification by flash chromatography (eluting with dichloromethane/methanol, 99:1, 2×), then stirring vigorously the resulting residue in hexane/ethyl acetate/ether for 1 h and then filtration afforded the title compound as a white powder (mixture of diastereoisomers; 1:1).

$^1$H NMR (400 MHz, acetone-d6): δ 8.87–8.80 (m, 2H), 8.41–8.35 (m, 2H), 8.19–8.15 (m, 2H), 7.94 (d, 1H), 7.91 (d, 1H), 7.85–7.78 (m, 4H), 7.70–7.66 (d, 2H), 7.61–7.35 (m, 11H), 7.21–7.08 (m, 4H), 7.05–6.98 (m, 3H), 6.86–6.81 (m, 3H), 4.44 (d, 1H), 4.03 (d, 1H), 3.93 (d, 1H), 3.27 (d, 1H), 2.96 (s, 3H), 2.94 (s, 3H), 2.68 (s, 3H), 2.67 (s, 3H), 1.96–1.94 (m, 12H), 1.80 (s, 3H), 1.50 (s, 6H), 1.39 (s, 3H). LRMS (CI) 660 (M+H)$^+$.

EXAMPLE 24

4-{3-[6-(1-Methanesulfonyl-1-methylethyl)-quinolin-8-yl]-phenyl}-3-(4-methanesulfonyl-phenyl)-2-methyl-butan-2-ol

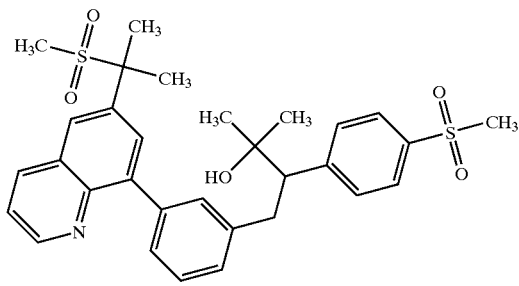

To a solution of Example 07 (230 mg, 0.41 mmol) in TBF/CH$_2$Cl$_2$ (1:1, 6 mL) at 21° C. was added methyl magnesium bromide (3M, Et$_{20}$, 1.0 mL, 3 mmol) dropwise. The resulting reaction mixture was stirred at 21° C. for 0.25 h, then diluted with a saturated ammonium chloride solution and ethyl acetate. The organic extracts were washed (H$_2$O), (brine), dried (MgSO$_4$), filtered and concentrated. Purification by flash chromatography (eluting with ethyl acetate/hexane, 70:30) afforded the title compound as a white foam.

$^1$H NMR (400 MHz, acetone-d6): δ 8.88 (dd, 1H), 8.39 (dd, 1H), 8.21 (d, 1H), 7.94 (d, 1H), 7.77 (d, 2H), 7.61 (d, 2H), 7.52 (dd, 1H), 7.41 (m, 2H), 7.21 (t, 1H), 7.10 (d, 1H), 3.75 (s, OH), 3.52 (m, 3H), 3.26 (m, 1H), 2.98 (s, 3H), 2.70 (s, 3H), 1.96 (s, 6H), 1.5 (s, 3H), 1.17 (s, 3H).

EXAMPLE 25

1,1,1-Trifluoro-4-{3-[6-(1-methanesulfonyl-1-methyl-ethyl)-quinolin-8-yl]-phenyl}-3-(4-methanesulfonyl-phenyl)-butan-2-ol

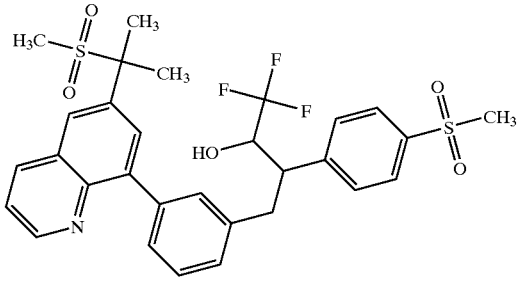

Step 1: 3-{3-[6-(1-Methanesulfonyl-1-methyl-ethyl)-quinolin-8-yl]-phenyl}-2-(4-methanesulfonyl-phenyl)-propionaldehyde Following the procedures described in Example 13, Step 2, but substituting Example 07 for the ester from Step 1, the 3-{3-[6-(1-methanesulfonyl-1-methyl-ethyl)-quinolin-8-yl]-phenyl}-2-(4-methanesulfonyl-phenyl)-propionaldehyde compound was isolated as a white foam.

Step 2: 1,1,1-Trifluoro-4-{3-[6-(1-methanesulfonyl-1-methyl-ethyl)-quinolin-8-yl]-phenyl}-3-(4-methanesulfonyl-phenyl)-butan-2-ol To a solution of 3-{3-[6-(1-methanesulfonyl-1-methyl-ethyl)-quinolin-8-yl]-phenyl}-2-(4-methanesulfonyl-phenyl)-propionaldehyde from Step 1 (413 mg, 0.8 mmol) in THF (10 mL) at −78° C. was added TMSCF$_3$ (0.4 mL, 2.7 mmol) followed by tetrabutylammonium fluoride (1M, THF, 0.12 mL, 120 mmol). The resulting reaction mixture was warmed to 0° C., then quenched with tetrabutylammonium fluoride (1M, THF, 1 mL, 1 mmol). After 1 h, the resulting solution was diluted with a saturated ammonium chloride solution and ethyl acetate. The organic extracts were washed (H$_2$O), (brine), dried (MgSO$_4$), filtered and concentrated. Purification by flash chromatography (eluting with hexane/ethyl acetate, 60:40 to 10:90) and sonication in hexane/ethyl acetate/ether provided the 1,1,1-trifluoro-4-{3-[6-(1-methanesulfonyl-1-methyl-ethyl)-quinolin-8-yl]-phenyl}-3-(4-methanesulfonyl-phenyl)-butan-2-ol compound as a white powder (mixture of diastereoisomers).

$^1$H NMR (400 MHz, acetone-d6, major isomer): δ 8.91 (dd, 1H), 8.43 (dd, 1H), 8.22 (d, 1H), 7.98 (d, 1H), 7.8 (m, 2H), 7.57 (m, 3H), 7.43 (s, 1H), 7.23 (t, 1H), 7.04 (d, 1H), 5.88 (m, OH), 4.5 (m, 1H), 3.6 (m, 2H), 3.2 (m, 1H), 3.04 (s, 3H), 1.97 (s, 6H).

EXAMPLE 26

2-Fluoro-3-{3-[6-(1-methanesulfonyl-1-methyl-ethyl)-quinolin-8-yl]-phenyl}-2-(4-methylsulfanyl-phenyl)-propionic acid ethyl ester

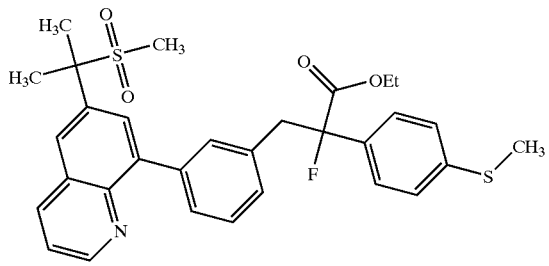

To a solution of Ester 03 (3.4 g, 13 mmol) and Quinoline 01 (4.5 g, 11 mmol) in THF/DMF (2:1, 60 mL) at 0° C. was added potassium tert-butoxide (1M, THF, 13.9 mL, 13.9 mmol) dropwise. After 30 min. at 0° C., the resulting reaction mixture was diluted with a saturated ammonium chloride solution and ethyl acetate. The organic extracts were washed ($H_2O$), (brine), dried ($MgSO_4$), filtered and concentrated. Purification by flash chromatography (eluting with toluene/acetone, 9:1) provided the title compound.

$^1$H NMR (400 MHz, acetone-$d_6$): δ 8.91 (dd, 1H), 8.44 (dd, 1H), 8.26 (d, 1H), 8.05 (d, 1H), 7.63–7.53 (m, 5H), 7.40–7.29 (m, 4H), 4.15 (q, 2H), 3.80 (dd, 1H), 3.53 (dd, 1H), 2.70 (s, 3H), 2.49 (s, 3H), 1.99 (s, 6H), 1.12 (t, 3H).

EXAMPLE 27

2-Fluoro-3-{3-[6-(1-methanesulfonyl-1-methyl-ethyl)-quinolin-8-yl]-phenyl}-2-(4-methanesulfonyl-phenyl)-propionic acid ethyl ester

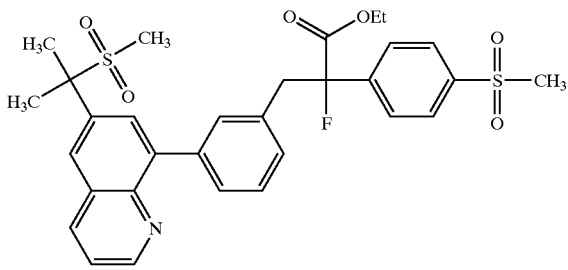

Following the procedures described in Example 16, but substituting Example 26 for Example 15, the title compound was obtained.

$^1$H NMR (400 MHz, acetone-$d_6$): δ 8.92 (dd, 1H), 8.44 (dd, 1H), 8.26 (d, 1H), 8.06 (d, 1H), 8.01 (d, 2H), 7.90 (app d, 2H), 7.64–7.62 (m, 2H), 7.56 (dd, 1H), 7.38 (t, 1H), 7.30 (d, 1H), 4.20 (q, 2H), 3.88 (dd, 1H), 3.60 (dd, 1H), 3.10 (s, 3H), 2.71 (s, 3H), 1.99 (s, 6H), 1.19 (t, 3H).

EXAMPLE 28

2-Fluoro-3-{3-[6-(1-methanesulfonyl-1-methyl-ethyl)-quinolin-8-yl]-phenyl}-2-(4-methanesulfonyl-phenyl)-propan-1-ol

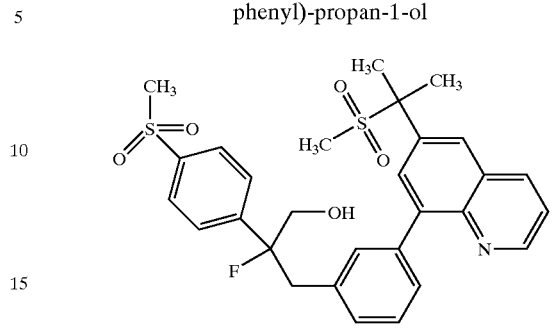

To a solution of Example 27 (1.15 g, 1.95 mmol) in $CH_2Cl_2$ (80 mL) at −78° C. was added dibal-H (0.82 mL, 4.6 mmol). The resulting reaction mixture was stirred 1 h at −78° C., then quenched with sodium potassium tartrate solution and stirred at 21° C. for 3 h. The organic extracts were washed ($H_2O$), (brine), dried ($MgSO_4$), filtered and concentrated. To the residue dissolved in THF/MeOH (2:1, 22 mL) at 21° C. was added $NaBH_4$ (180 mg, 4.9 mmol). After 12 h, the reaction mixture was diluted with a saturated ammonium chloride solution and ethyl acetate. The organic extracts were washed ($H_2O$), (brine), dried ($MgSO_4$), filtered and concentrated to provided the title compound as a white solid.

$^1$H NMR (400 MHz, acetone-$d_6$): δ 8.90 (dd, 1H), 8.43 (dd, 1H), 8.24 (d, 1H), 8.02 (d, 1H), 7.89 (d, 2H), 7.68 (d, 2H), 7.60–7.50 (m, 3H), 7.29 (t, 1H), 7.15 (d, 1H), 4.42 (t, OH), 4.03 (dd, 11), 3.98 (dd, 1H), 3.58 (dd, 1H), 3.44 (dd, 1H), 3.03 (s, 3H), 2.71 (s, 3H), 1.98 (s, 3H), 1.97 (s, 3H).

EXAMPLE 29

3-Fluoro-4-{3-[6-(1-methanesulfonyl-1-methyl-ethyl)-quinolin-8-yl]-phenyl}-3-(4-methanesulfonyl-phenyl)-2-methyl-butan-2-ol

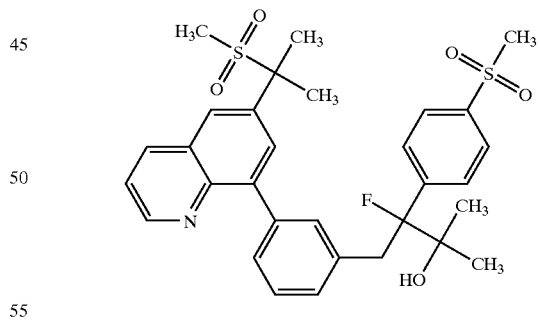

Anhydrous $CeCl_3$ (658 mg, 2.67 mmol) was heated 1 h at 130° C. under high vacuum. It was refluxed in THF (8 mL) for 1 h and then cooled to 0° C. To the resulting white suspension at 0° C., was added methylmagnesium bromide (3M, THF, 0.89 mL, 2.7 mmol). The resulting mixture was stirred at 0° C. for 1 h. Example 27 (267 mg, 0.45 mmol), dissolved in THF (1 mL) was added, and the mixture stirred at 0° C. for 0.5 h, and diluted with ethyl acetate and saturated ammonium chloride solution. The organic extracts were washed ($H_2O$), (brine), dried ($MgSO_4$), filtered and concentrated. Purification by flash chromatography (eluting with toluene/acetone, 9:1) and stirring vigorously in ethyl acetate/ether for 1 h, then filtering afforded the title compound as a white powder. The enantiomers can be separated on a chiral column (ChiralPaK AD, hexane/EtOH, 50:50, retention time 6.82 and 9.27 min) to give Example 29A and Example 29B.

$^1$H NMR (400 Mz, acetone-$d_6$): δ 8.88 (dd, 1H), 8.40 (dd, 1H), 8.21 (d, 1H), 7.91 (d, 1H), 7.82 (d, 2H), 7.75 (app d, 2H), 7.53 (dd, 1H), 7.44 (d, 1H), 7.41 (s, 1H), 7.17 (t, 1H), 7.11 (d, 1H), 4.29 (s, OH), 3.77–3.54 (m, 2H), 2.96 (s, 3H), 2.70 (s, 3H), 1.97 (s, 3H), 1.96 (s, 3H), 1.42 (s, 3H), 1.11 (s, 3H).

EXAMPLE 30

1-{3-[6-(1-Methanesulfonyl-1-methyl-ethyl)-quinolin-8-yl]-phenyl}-2-(4-methanesulfonyl-phenyl)-3-methyl-butane-2,3-diol

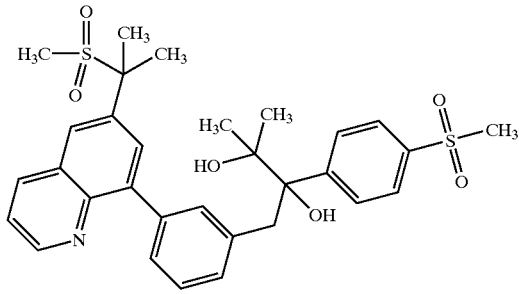

Following the procedures described in Example 29, but substituting Example 17 for Example 27 and purification by flash chromatography (eluting with toluene/acetone, 80:20 afforded the title compound as a white powder.

$^1$H NMR (400 MHz, acetone-d6): δ 8.88 (dd, 1H), 8.40 (dd, 1H), 8.21 (d, 1H), 7.95 (d, 1H), 7.93 (d, 2H), 7.80 (d, 2H), 7.53 (dd, 1H), 7.50 (s, 1H), 7.42 (dt, 1H), 7.18–7.12 (m, 2H), 4.08 (s, OH), 4.06 (s, OH), 3.75 (d, 1H), 3.49 (d, 1H), 2.97 (s, 3H), 2.70 (s, 3H), 1.97 (s, 3H), 1.96 (s, 3H), 1.25 (s, 3H), 1.20 (s, 3H). LRMS (CI) 582 (M+H)$^+$.

EXAMPLE 31

2-Fluoro-3-{3-[6-(1-methanesulfonyl-1-methyl-ethyl)-quinolin-8-yl]-phenyl}-2-(4-methanesulfonyl-phenyl)-propionic acid

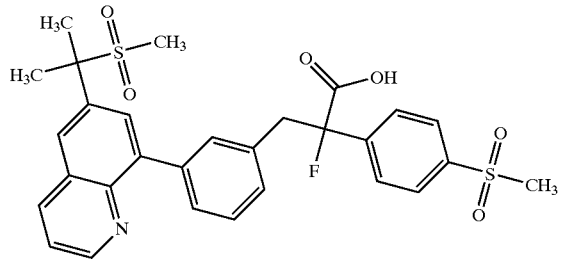

Following the procedures described in Example 08, but substituting Example 27 for Example 07 and using only 1.5 equivalent of LiOH, the title compound was obtained as a white solid.

$^1$H NMR (400 MHz, acetone-$d_6$): δ 8.92 (dd, 1H), 8.44 (dd, 1H), 8.26 (d, 1H), 8.06 (d, 1H), 8.01 (d, 2H), 7.92 (d, 2H), 7.66 (s, 1H), 7.63 (dd, 1H), 7.56 (dd, 1H), 7.37 (t, 1H), 7.32 (d, 1H), 3.90 (dd, 1H), 3.62 (dd, 1H), 3.10 (s, 3H), 2.72 (s, 3H), 1.99 (s, 3H), 1.99 (s, 3H).

EXAMPLE 32

3-Ethyl-2-fluoro-1-{3-[6-(1-methanesulfonyl-1-methyl-ethyl)quinolin-8-yl]-phenyl}-2-(4-methanesulfonyl-phenyl)-pentan-3-ol

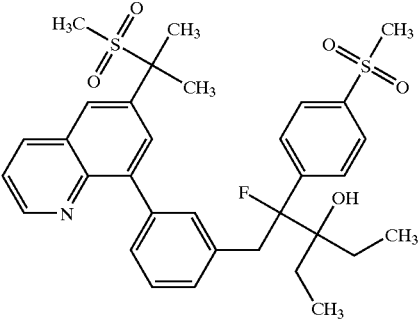

Following the procedures described above in Example 29, but substituting ethylmagnesium bromide for methylmagnesium bromide and purification by flash chromatography (eluting with toluene/acetone, 9:1) afforded the title compound as a white foam.

$^1$H NMR (400 MHz, acetone-d6): δ 8.90 (dd, 1H), 8.41 (dd, 1H), 8.21 (d, 1H), 7.92 (d, 1H), 7.81–7.75 (m, 4H), 7.54 (dd, 1H), 7.43 (d, 1H), 7.35 (s, 1H), 7.16 (t, 1H), 7.05 (d, 1H), 4.07 (s, OH), 3.75–3.59 (m, 2H), 2.93 (s, 3H), 2.71 (s, 3H), 2.01–1.90 (m, 2H), 1.98 (s, 3H), 1.97 (s, 3H), 1.45–1.32 (m, 2H), 1.02 (dt, 3H), 0.82 (dt, 3H). LRMS (CI) 612 (M+H)$^+$.

EXAMPLE 33

1,1-Dicyclopropyl-2-fluoro-3-{3-[6-(1-methanesulfonyl-1-methyl-ethyl)-quinolin-8-yl]-phenyl}-2-(4-methanesulfonyl-phenyl)-propan-1-ol

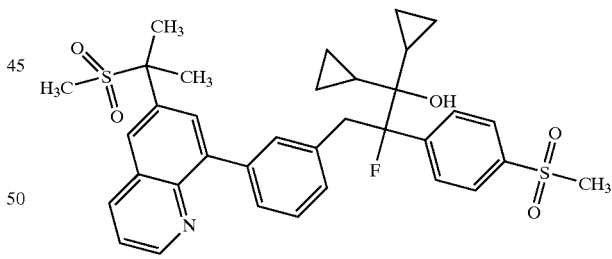

Following the procedures described above in Example 29, but substituting cyclopropyl magnesium bromide for methyl magnesium bromide and purification by flash chromatography (eluting with toluene/acetone, 9:1) afforded the title compound as a white foam. The enantiomers can be separated on a chiral column (ChiralPaK AD, hexane/i-PrOH/EtOH, 3:1:1, retention time 30 and 43 min) to give Example 33A and Example 33B.

$^1$H NMR (400 MHz, acetone-d6): δ 8.89 (dd, 1H), 8.39 (dd, 1H), 8.21 (d, 1H), 7.92 (d, 1H), 7.83 (s, 4H), 7.52 (dd, 1H), 7.47 (s, 1H), 7.44 (dd, 1H), 7.18–7.16 (m, 2H), 3.94 (dd, 1H), 3.87 (dd, 1H), 3.69 (s, OH), 2.97 (s, 3H), 2.71 (s, 3H), 1.98 (s, 3H), 1.97 (s, 3H), 1.12–1.07 (m, 1H), 0.91–0.86 (m, 1H), 0.69–0.64 (m, 1H), 0.53–0.49 (m, 1H), 0.43–0.29 (m, 5H), 0.17–0.12 (m, 1H). LRMS (CI) 636 (M+H)+.

EXAMPLE 34

4-[2-{3-[6-(1-Methanesulfonyl-1-methyl-ethyl)-quinolin-8-yl]-phenyl}-1-(4-methanesulfonyl-phenyl)-ethyl]4,5,5-trimethyl-[1,3]dioxolan-2-one

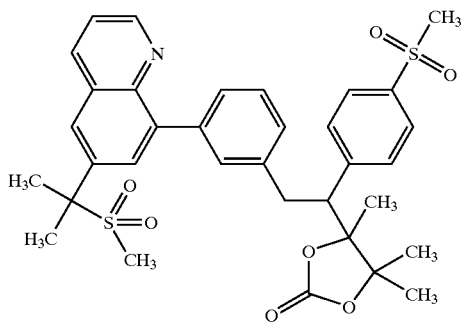

Example 10 (236 mg, 0.39 mmol) and CDI (650 mg, 4 mmol) was heated at 90° C. for 18 h, cooled to 21° C., and then diluted with ethyl acetate and sodium bicarbonate solution. The organic extracts were washed ($H_2O$), (brine), dried ($MgSO_4$), filtered and concentrated. Purification by flash chromatography (eluting with dichloromethane/ethyl acetate, 40:60) provided the title compound as a white solid (245 mg). The enantiomers can be separated on a chiral column (ChiralPaK AD, hexane/i-PrOH, 40:60, retention time 10.7 and 12.6 min) to give Example 34A and Example 34B.

$^1$H NMR (400 MHz, acetone-d6): δ 8.89 (dd, 1H), 8.41 (dd, 1H), 8.21 (d, 1H), 7.95 (d, 1H), 7.86 (d, 2H), 7.78 (d, 2H), 7.59 (s, 1H), 7.54 (dd, 1H), 7.47 (d, 1H), 7.25 (t, 1H), 7.23 (d, 1H), 4.10 (dd, 1H), 3.47 (dd, 1H), 3.16 (dd, 1H), 3.06 (s, 3H), 2.71 (s, 3H), 1.96 (s, 6H), 1.87 (s, 3H), 1.71 (s, 3H), 1.48 (s, 3H).

EXAMPLE 35

5-{3-[6-(1-Methanesulfonyl-1-methyl-ethyl)-quinolin-8-yl]-phenyl}-4-(4-methanesulfonyl-phenyl)-2-methyl-pentane-2,3-diol

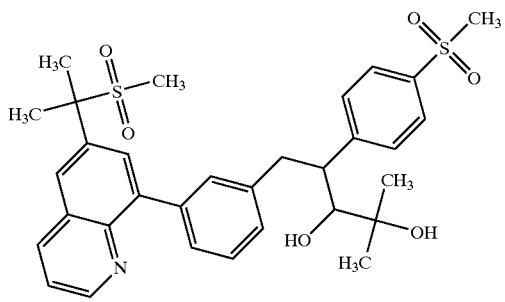

Following the procedures described above in Example 21, but substituting Example 1 for Example 6 and using THF/EtOH as solvent. Purification by flash chromatography (eluting with dichloromethane/ethyl acetate, 40:60) afforded the title compound (one pair of enantiomer).

$^1$H NMR (400 MHz, acetone-d6): δ 8.93 (dd, 1H), 8.43 (dd, 1H), 8.24 (d, 1H), 8.06 (d, 1H), 7.75 (dd, 4H), 7.60 (s, 1H), 7.56 (dd, 1H), 7.50 (d, 1H), 7.31 (t, 1H), 7.20 (d, 1H), 4.12 (d, 1H), 3.81 (m, 1H), 3.50 (m, 1H), 3.36 (dd, 1H), 3.26 (s, 1H), 3.10 (dd, 1H), 2.99 (s, 3H), 2.71 (s, 3H), 1.98 (s, 6H), 1.03 (s, 3H), 0.87 (s, 3H).

EXAMPLE 36

2-Fluoro-4-hydroxy-1-{3-[6-(1-methanesulfonyl-1-methyl-ethyl)quinolin-8-yl]-phenyl}-2-(4-methanesulfonyl-phenyl)$_4$-methyl-pentan-3-one

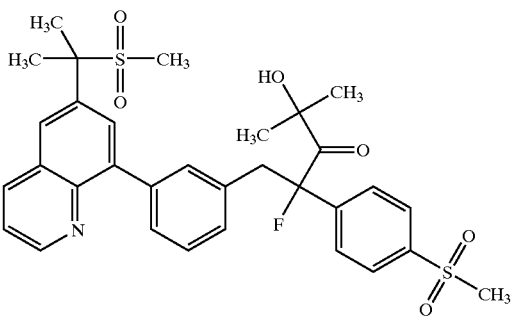

To a solution of Example 1 (200 mg, 0.34 mmol) in THF/DMF (1:1, 10 mL) at 0° C. was added potassium tert-butoxide (1M, THF, 0.34 mL, 0.34 mmol) dropwise. After 15 min, N-fluorobenzene sulfonimide (212 mg, 0.73 mmol) was added and the reaction mixture stirred for 2 h at 21° C. The resulting mixture was diluted with a saturated ammonium chloride solution and ethyl acetate. The organic extracts were washed ($H_2O$), (brine), dried ($MgSO_4$), filtered and concentrated. Purification by flash chromatography (eluting with toluene/acetone, 80:20) provided the title compound.

$^1$H NMR (400 MHz, acetone-d6): δ 8.93 (dd, 1H), 8.45 (dd, 1H), 8.29 (d, 1H), 8.08 (d, 1H), 7.98 (d, 2H), 7.88 (d, 2H), 7.55 (m, 3H), 7.38 (t, 1H), 7.26 (d, 1H), 4.22 (brs, 1H), 3.87 (dd, 1H), 3.42 (dd, 1H), 3.10 (s, 3H), 2.71 (s, 3H), 1.98 (s, 6H), 1.17 (s, 3H), 1.12 (s, 3H).

EXAMPLE 37

4-Hydroxy-1-{3-[6-(1-methanesulfonyl-1-methylethyl)-quinolin-8-yl]-phenyl}-4-methyl-2-(4-methylsulfanyl-phenyl)-pentan-3-one

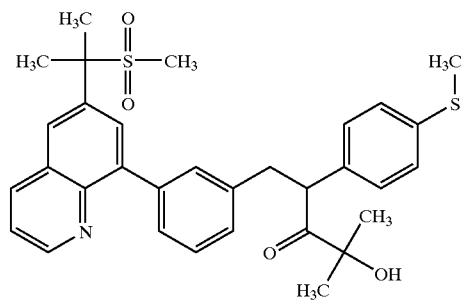

Following the procedures described in Example 1, but substituting Ketone 01 for Ketone 02 and purification by flash chromatography (eluting with ethyl acetate/hexane, 1:1 to 3:2) afforded the title compound as a white foam.

$^1$H NMR (400 Mz, acetone-d6): δ 8.92 (dd, 1H), 8.44 (dd, 1H), 8.25 (d, 1H), 8.03 (d, 1H), 7.56 (dd, 1H), 7.51 (m, 2H), 7.33 (m, 3H), 7.2 (m, 3H), 4.94 (dd, 1H), 4.31 (s, OH), 3.38 (dd, 1H), 3.00 (dd, 1H), 2.7 (s, 3H), 2.44 (s, 3H), 1.98 (s, 6H), 1.07 (s, 3H), 1.03 (s, 3H).

EXAMPLE 38

2-{3-[6-(1-Methanesulfonyl-1-methyl-ethyl)-quinolin-8-yl]-phenyl}-1-(4-methanesulfonyl-phenyl)-ethanone

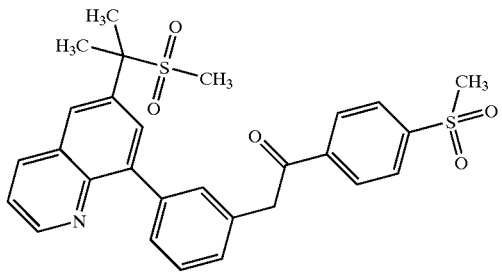

Step 1: (tert-Butyl-dimethyl-silanyloxy)-(4-methylsulfanyl-phenyl)-acetonitrile

To a solution of 4-methylthiobenzaldehyde (8 g, 52.5 mmol) in acetonitrile (260 mL) was added KCN (13.7 g, 210 mmol), ZnI$_2$ (335 mg, 1 mmol) and t-BDMSCl (9.5 g, 63 mmol). After 18 h, the resulting reaction mixture was filtered and the mother liquors concentrated. The resulting residue was left overnight under high vacuum to provided the (tert-butyl-dimethyl-silanyloxy)-(4-methylsulfanyl-phenyl)-acetonitrile compound as a clear oil.

Step 2: 2-(tert-Butyl-dimethyl-silanyloxy)-3-{3-[6-(1-methanesulfonyl-1-methyl-ethyl)-quinolin-8-yl]-phenyl}-2-(4-methylsulfanyl-phenyl)-propionitrile To a solution of (tert-butyl-dimethyl-silanyloxy)-(4-methylsulfanyl-phenyl)-acetonitrile from Step 1 above (1.52 g, 5.2 mmol) in THF (25 mL) at −78° C. was added KHMDS (1M, 5.2 mL, 5.2 mmol) dropwise followed, after 10 min, by Quinoline 01 (1.8 g, 4.3 mmol) in THF (25 mL). The resulting reaction mixture was allowed to warm to −10° C. and diluted with a sodium bicarbonate solution and ethyl acetate. The organic extracts were washed (H$_2$O), (brine), dried (MgSO$_4$), filtered and concentrated.

Step 3: 2-{3-[6-(1-Methanesulfonyl-1-methyl-ethyl)-quinolin-8-yl]-phenyl}-1-(4-methylsulfanyl-phenyl)-ethanone To a solution of crude cyanohydrin from Step 2 above in THF (25 mL) was added tetrabutylammonium fluoride (1M, THF, 6.5 mL, 6.5 mmol) dropwise. The resulting reaction mixture was stirred at 21° C. for 30 min and diluted with a sodium hydroxide solution and ethyl acetate. The organic extracts were washed (1N NaOH 2×), (brine), dried (MgSO$_4$), filtered and concentrated.

Step 4: 2-{3-[6-(1-Methanesulfonyl-1-methyl-ethyl)-quinolin-8-yl]-phenyl}-1-(4-methanesulfonyl-phenyl)-ethanone Following the procedures described above in Example 16, but substituting the 2-{3-[6-(1-methanesulfonyl-1-methyl-ethyl)-quinolin-8-yl]-phenyl}-1-(4-methylsulfanyl-phenyl)-ethanone from step 3 for Example 15, the 2-{3-[6-(1-methanesulfonyl-1-methyl-ethyl)-quinolin-8-yl]-phenyl}-1-(4-methanesulfonyl-phenyl)-ethanone compound was obtained as a foam.

$^1$H NMR (400 MHz, acetone-d$_6$): δ 8.89 (dd, 1H), 8.44 (dd, 1H), 8.35 (d, 2H), 8.26 (d, 1H), 8.10–8.08 (m, 3H), 7.72 (s, 1H), 7.63 (d, 2H), 7.56 (dd, 1H), 7.44 (t, 1H), 7.38 (d, 1H), 4.57 (s, 2H), 3.17 (s, 3H), 2.70 (s, 3H), 1.98 (s, 6H).

EXAMPLE 39

2-{3-[6-(1-Methanesulfonyl-1-methyl-ethyl)-quinolin-8-yl]-phenyl}-1-(4-methanesulfonyl-phenyl)-ethanol

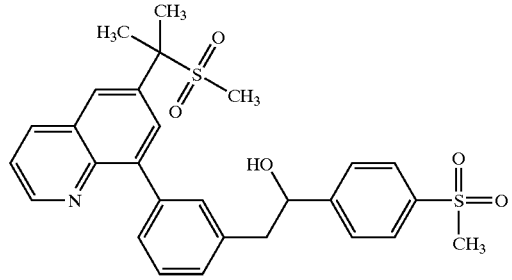

Following the procedures described above in Example 21, but substituting Example 38 for Example 6 and using THF/MeOH as solvent. The resulting residue was stirred vigorously in ethyl acetate/ether for 1 h then filtered to afford the title compound as a white powder.

$^1$H NMR (400 MHz, acetone-d$_6$): δ 8.91 (dd, 1H), 8.44 (dd, 1H), 8.26 (d, 1H), 8.09 (d, 1H), 7.88 (d, 2H), 7.61–7.53 (m, 3H), 7.59 (d, 2H), 7.36 (t, 1H), 7.27 (app d, 1H), 5.62 (app t, 1H), 4.67 (d, OH), 3.11 (d, 2H), 3.06 (s, 3H), 2.72 (s, 3H), 1.98 (s, 6H).

EXAMPLE 40

4-[2-{3-[6-(1-Methanesulfonyl-1-methyl-ethyl)-quinolin-8-yl]-phenyl}-1-(4-methanesulfonyl-phenyl)-ethylsulfanyl]-benzoic acid ethyl ester

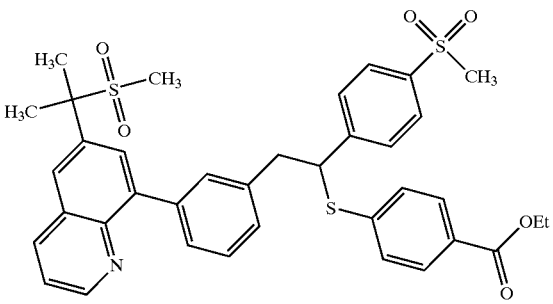

To a solution of Example 39 (283 mg, 0.54 mmol), Ph$_3$P (283 mg, 1.08 mmol) and DEAD (0.17 mL, 1.08 mmol) in THF (3 mL) at 0° C., was slowly added ethyl 4-mercaptobenzoate (200 mg, 1.08 mmol, over 20 min.) in DMF (2 mL). The reaction mixture was stirred at 0° C. 1 h, at 21° C. for 18 h, then diluted with water and ethyl acetate. The organic extracts were washed (H$_2$O), (brine), dried (MgSO$_4$), filtered and concentrated. Purification by flash chromatography (eluting with hexane/ethyl acetate, 1:1) provided the title compound as an oil.

$^1$H NMR (400 MHz, acetone-d$_6$): δ 8.92 (dd, 1H), 8.44 (dd, 1H), 8.25 (d, 1H), 8.05 (d, 1H), 7.85–7.81 (m, 4H), 7.74

(dd, 2H), 7.62 (s, 1H), 7.58–7.55 (m, 2H), 7.45 (dd, 2H), 7.32 (t, 1H), 7.23 (d, 1H), 5.13 (dd, 1H), 4.28 (q, 2H), 3.47–3.38 (m, 2H), 3.01 (s, 3H), 2.72 (s, 3H), 1.98 (s, 6H), 1.31 (t, 3H).

EXAMPLE 41

2-{4-[2-{3-[6-(1-Methanesulfonyl-1-methyl-ethyl)-quinolin-8-yl]-phenyl}-1-(4-methanesulfonyl-phenyl)-ethylsulfanyl]-phenyl}-propan-2-ol

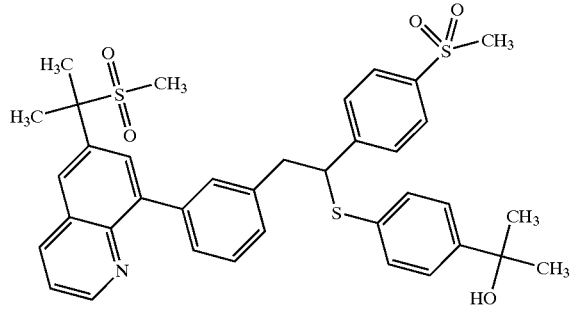

A solution of Example 40 (280 mg, 0.4 mmol) and anhydrous CeCl₃ (150 mg, 0,5 mmol) in THF (5 mL) was stirred at 21° C. for 1 h, then cooled at −78° C. Methylmagnesium bromide (3M, Ether, 0.6 mL, 2.1 mmol) was added and the resulting reaction mixture warmed slowly to 0° C., then diluted with a saturated ammonium chloride solution and ethyl acetate. The organic extracts were washed (H₂O), (brine), dried (MgSO₄), filtered and concentrated. Purification by flash chromatography (eluting with hexane/ethyl acetate, 1:1 to 2:8) provided the title compound as a solid.

¹H NMR (400 MHz, acetone-d₆): δ 8.91 (dd, 1H), 8.44 (dd, 1H), 8.24 (d, 1H), 8.04 (d, 1H), 7.79 (s, 2H), 7.71–7.53 (m, 5H), 7.41 (d, 2H), 7.32–7.28 (m, 3H), 7.19 (d, 1H), 4.88 (dd, 1H), 4.02 (s, OH), 3.45–3.34 (m, 2H), 3.01 (s, 3H), 2.71 (s, 3H), 1.97 (s, 6H), 1.44 (s, 6H).

EXAMPLE 42

2-{4-[2-{3-[6-(1-Methanesulfonyl-1-methyl-ethyl)-quinolin-8-yl]-phenyl}-1-(4-methanesulfonyl-phenyl)-ethanesulfonyl]-phenyl}-propan-2-ol

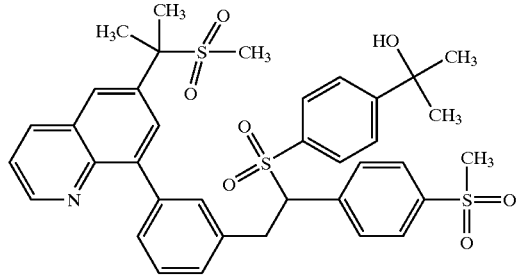

Following the procedures described above in Example 16, but substituting Example 41 for Example 15 and purification by stirring vigorously the resulting solid in hexane/ethyl acetate/ether for 1 h and then filtration afforded the title compound as a white powder.

¹H NMR (400 MHz, acetone-d₆): δ 8.86 (dd, 1H), 8.41 (dd, 1H), 8.22 (d, 1H), 7.93 (d, 1H), 7.79 (d, 2H), 7.71–7.51 (m, 8H), 7.71 (d, 1H), 7.47 (d, 1H), 7.24 (t, 1H), 5.07 (dd, 1H), 4.33 (s, OH), 3.75 (dd, 1H), 3.62 (dd, 1H), 3.05 (s, 3H), 2.70 (s, 3H), 1.95 (s, 6H), 1.50 (s, 3H), 1.50 (s, 3H).

EXAMPLE 43

2-{4-[1-Fluoro-2-{3-[6-(1-methanesulfonyl-1-methyl-ethyl)-quinolin-8-yl]-phenyl}-1-(4-methanesulfonyl-phenyl)-ethanesulfonyl]-phenyl}-propan-2-ol

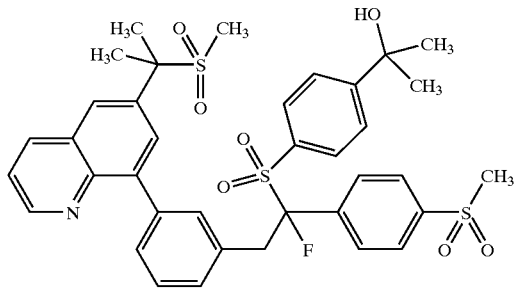

By following the procedures described above in Example 36, but substituting Example 42 for Example 1, the title compound was obtained as a white solid.

¹H NMR (400 MHz, acetone-d₆): δ 8.84 (dd, 1H), 8.41 (dd, 1H), 8.22 (d, 1H), 7.92 (d, 1H), 7.86 (d, 2H), 7.71–7.51 (m, 9H), 7.26 (t, 1H), 7.20 (d, 1H), 4.38 (s, OH), 4.19 (dd, 1H), 3.88 (dd, 1H), 3.07 (s, 3H), 2.69 (s, 3H), 1.96 (s, 3H), 1.94 (s, 3H), 1.51 (s, 3H), 1.50 (s, 3H).

EXAMPLE 44

8-{3-[2-Fluoro-2-methanesulfonyl-2-(4-methanesulfonyl-phenyl)-ethyl]-phenyl}-6-(1-methanesulfonyl-1-methyl-ethyl)-quinoline

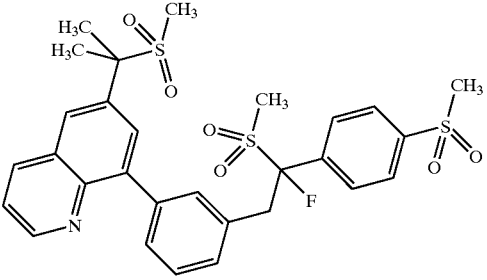

Example 44 was prepared by following the procedures described above in Example 1, but substituting Sulfone 02 for Ketone 02, and using DMF as solvent. Purification by flash chromatography (eluting with ethyl acetate/hexane, 95:5 to 100:0), then stirring vigorously the resulting solid in ether/ethyl acetate for 1 h and filtration afforded the title compound as a white powder. The enantiomers can be separated on a chiral column (ChiralPaK AD, hexane/EtOH/i-PrOH/MeOH, 30:30:30:10, retention time 10.0 and 12.5 min) to give Example 44A and Example 44B.

¹H NMR (400 Mz, ace-d6): δ 8.90 (dd, 1H), 8.42 (dd, 1H), 8.24 (d, 1H), 7.98 (d, 1H), 7.93 (d, 2H), 7.85 (d, 2H), 7.57 (app d, 1H), 7.55 (dd, 1H), 7.50 (app d, 1H), 7.30 (t, 1H), 7.24 (app d, 1H), 5.01 (dd, 1H), 3.87 (dd, 1H), 3.55 (dd, 1H), 3.07 (s, 3H), 2.88 (s, 3H), 2.70 (s, 3H), 1.97 (s, 6H).

EXAMPLE 45

8-{3-[2-Methanesulfonyl-2-(4-methanesulfonyl-phenyl)-ethyl]-phenyl}-6-(1-methanesulfonyl-1-methyl-ethyl)-quinoline

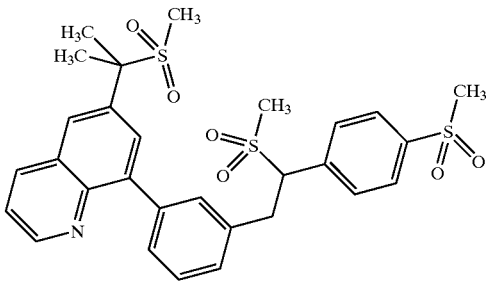

Example 45 was prepared by following the procedures described above in Example 1, but substituting Sulfone 01 for Ketone 02, and using DMF as solvent. Purification by flash chromatography (eluting with ethyl acetate/hexane, 80:20 to 100:0), then stirring vigorously the resulting solid in ethyl acetate/ether for 1 h and filtration afforded the title compound as a white powder.

$^1$H NMR (400 MHz, acetone-$d_6$): δ 8.90 (dd, 1H), 8.43 (dd, 1H), 8.24 (d, 1H), 7.98 (d, 1H), 7.93 (d, 2H), 7.85 (d, 2H), 7.57 (app d, 1H), 7.55 (dd, 1H), 7.50 (d, 1H), 7.30 (t, 1H), 7.24 (d, 1H), 5.01 (dd, 1H), 3.87 (dd, 1H), 3.54 (dd, 1H), 3.07 (s, 3H), 2.88 (s, 3H), 2.70 (s, 3H), 1.97 (s, 6H).

EXAMPLE 46

8-{3-[2-Ethanesulfonyl-2-fluoro-2-(4-methanesulfonyl-phenyl)-ethyl]-phenyl}-6-(1-methanesulfonyl-1-methyl-ethyl)-quinoline

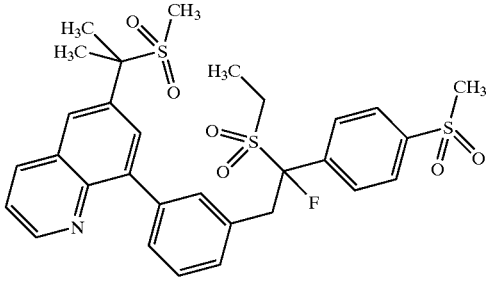

Step 1: 8-{3-[2-Ethanesulfonyl-2-(4-methanesulfonyl-phenyl)-ethyl]-phenyl}-6-(1-methanesulfonyl-1-methyl-ethyl)-quinoline The procedures described above in Example 01 were followed, but Sulfone 04 was substituted for Ketone 02, and THF was used as the solvent. Purification by flash chromatography (eluting with ethyl acetate/hexane, 80:20 to 100:0), then stirring vigorously the resulting solid in ethyl acetate/ether for 1 h and filtration afforded the 8-{3-[2-ethanesulfonyl-2-(4-methanesulfonyl-phenyl)-ethyl]-phenyl}-6-(1-methanesulfonyl-1-methyl-ethyl)-quinoline compound as a white powder.

Step 2: 8-{3-[2-Ethanesulfonyl-2-fluoro-2-(4-methanesulfonyl-phenyl)-ethyl]-phenyl}-6-(1-methanesulfonyl-1-methyl-ethyl)-quinoline Following the procedures described in Example 36, but substituting 8-{3-[2-ethanesulfonyl-2-(4-methanesulfonyl-phenyl)-ethyl]-phenyl}-6-(1-methanesulfonyl-1-methyl-ethyl)-quinoline from Step 1 above for Example 1, the 8-{3-[2-ethanesulfonyl-2-fluoro-2-(4-methanesulfonyl-phenyl)-ethyl]-phenyl}-6-(1-methanesulfonyl-1-methyl-ethyl)-quinoline compound was obtained as a white solid.

$^1$H NMR (400 MHz, ace-$d_6$): δ 8.89 (dd, 1H), 8.42 (dd, 1H), 8.23 (d, 1H), 8.01 (d, 2H), 7.96–7.92 (m, 3H), 7.57–7.53 (m, 3H), 7.29 (t, 1H), 7.21 (app d, 1H), 4.04 (m, 2H), 3.22–3.15 (m, 1H), 3.07 (s, 3H), 3.00–2.91 (m, 1H), 2.70 (s, 3H), 1.97 (s, 3H), 1.96 (s, 3H), 1.26 (t, 3H).

EXAMPLE 47

6-(1-Methanesulfonyl-1-methyl-ethyl)-8-{3-[2-(4-methanesulfonyl-phenyl)-2-(1-methyl-1H-imidazole-2-sulfonyl)-ethyl]-phenyl}-quinoline

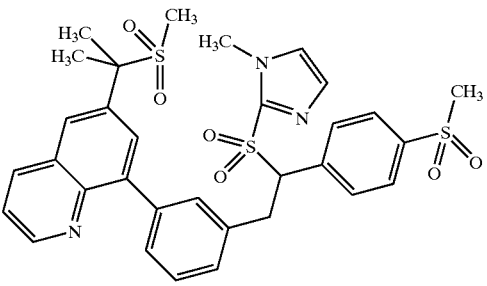

Example 47 was prepared by following the procedures described above in Example 1, but substituting Sulfone 05 for Ketone 02, and using THF as solvent. Purification by flash chromatography (eluting with ethyl acetate), then stirring vigorously the resulting solid in ethyl acetate/ether for 1 h and filtration afforded the title compound as a white powder.

$^1$H NMR (400 MHz, ace-$d_6$): δ 8.91 (dd, 1H), 8.42 (dd, 1H), 8.24 (d, 1H), 7.98 (d, 1H), 7.93 (d, 2H), 7.85 (d, 2H), 7.57 (d, 1H), 7.55 (dd, 1H), 7.50 (d, 1H), 7.30 (t, 1H), 7.24 (d, 1H), 5.01 (dd, 1H), 3.87 (dd, 1H), 3.55 (dd, 1H), 3.07 (s, 3H), 2.88 (s, 3H), 2.70 (s, 3H), 1.97 (s, 6H).

EXAMPLE 48

8-{3-[2-Fluoro-2-(4-methanesulfonyl-phenyl)-2-(1-methyl-1H-imidazole-2-sulfonyl)-ethyl]-phenyl}-6-(1-methanesulfonyl-1-methyl-ethyl)-quinoline

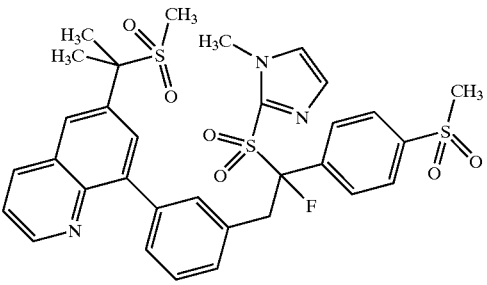

By following the procedures described above in Example 36, but substituting Example 47 for Example 1, the title compound was obtained as a white solid.

$^1$H NMR (400 MHz, ace-d6): δ 8.85 (dd, 1H), 8.41 (dd, 1H), 8.22 (d, 1H), 7.97 (d, 2H), 7.93 (d, 1H), 7.77 (d, 1H), 7.55–7.52 (m, 3H), 7.49 (s, 1H), 7.27 (t, 1H), 7.21 (s, 1H), 7.19 (app d, 1H), 4.23 (d, 1H), 3.95 (dd, 1H), 3.79 (s, 3H), 3.11 (s, 3H), 2.70 (s, 3H), 1.96 (s, 3H), 1.95 (s, 3H).

EXAMPLE 49

8-{3-[2-Fluoro-2-(4-methanesulfonyl-phenyl)-2-(thiazole-2-sulfonyl)-ethyl]-phenyl}-6-(1-methanesulfonyl-1-methyl-ethyl)-quinoline

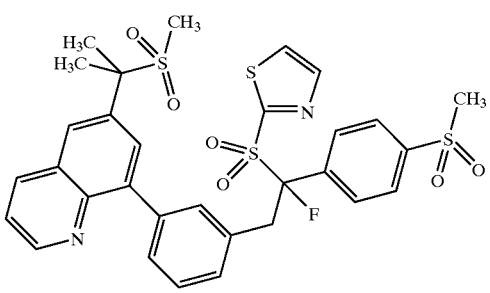

By following the procedures described above in Example 46, but substituting Sulfone 06 for Sulfone 04 in Step 1, the title compound was obtained as a white solid.

$^1$H NMR (400 MHz, ace-d6): δ 8.85 (dd, 1H), 8.41 (dd, 1H), 8.31 (d, 1H), 8.22 (d, 1H), 8.20 (d, 1H), 7.97–7.93 (m, 3H), 7.82 (d, 2H), 7.56–7.52 (m, 3H), 7.28 (t, 1H), 7.21 (app d, 1H), 4.30 (dd, 1H), 4.10 (dd, 1H), 3.09 (s, 3H), 2.70 (s, 3H), 1.96 (s, 3H), 1.95 (s, 3H.

EXAMPLE 50

4-Hydroxy-2-[4-(1-hydroxy-1-methyl-ethyl)-phenyl]-1-{3-[6-(1-methanesulfonyl-1-methyl-ethyl)-quinolin-8-yl]-phenyl}4-methyl-pentan-3-one

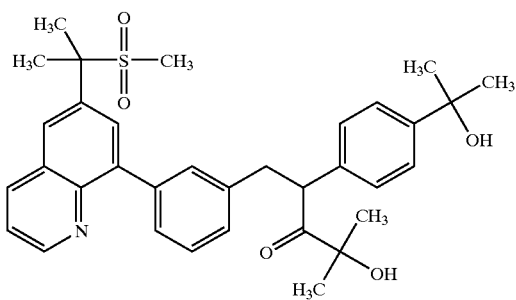

By following the procedures described above in Example 1, but substituting Ketone 11 for Ketone 02, the title compound was obtained as a white foam.

$^1$H NMR (400 MHz, acetone-d6): δ 8.93 (dd, 1H), 8.44 (dd, 1H), 8.26 (d, 1H), 8.07 (d, 1H), 7.58 (m, 2H), 7.49 (d, 1H), 7.45 (d, 2H), 7.35 (m, 3H), 7.22 (d, 1H), 4.97 (dd, 1H), 4.27 (s, OH), 3.94 (s, OH), 3.38 (dd, 1H), 2.99 (dd, 1H), 2.71 (s, 3H), 1.99 (s, 6H), 1.46 (s, 6H), 1.04 (s, 3H), 1.00 (s, 3H).

EXAMPLE 51

4-[4-(1-Hydroxy-1-methyl-ethyl)-phenyl]-5-{3-[6-(1-methanesulfonyl-1-methyl-ethyl)-quinolin-8-yl]-phenyl}-2-methyl-pentane-2,3-diol

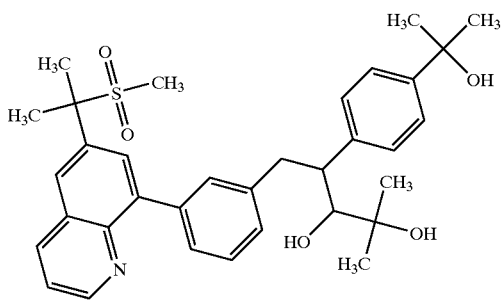

By following the procedures described above in Example 21, but substituting Example 50 for Example 6 and using EtOH as solvent, the title compound was obtained as a white foam.

$^1$H NMR (400 MHz, acetone-d6): δ 8.93 (dd, 1H), 8.43 (dd, 1H), 8.24 (d, 1H), 8.09 (d, 1H), 7.65 (s, 1H), 7.56 (dd, 1H), 7.52 (d, 1H), 7.45–7.32 (m, 4H), 7.32 (t, 1H), 7.23 (d, 1H), 3.86 (s, OH), 3.71 (m, 2H), 3.30 (m, 2H), 3.01 (m, 2H), 2.71 (s, 3H), 1.99 (s, 6H), 1.45 (s, 6H), 1.05 (s, 3H), 0.78 (s, 3H).

EXAMPLE 52

2-[4-(1-Methanesulfonyl-2-{3-[6-(1-methanesulfonyl-1-methyl-ethyl)-quinolin-8-yl]-phenyl}-ethyl)-phenyl]-propan-2-ol

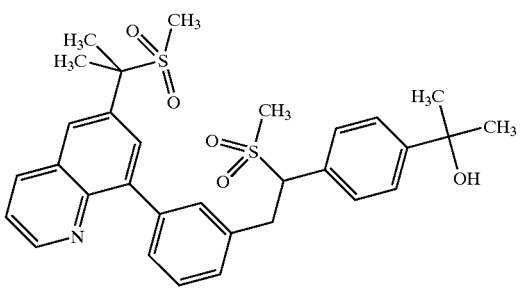

By following the procedures described above in Example 1, but substituting Sulfone 07 for Ketone 02, the title compound was obtained as a white foam.

$^1$H NMR (400 MHz, acetone-d6): δ 8.90 (dd, 2H), 8.42 (dd, 2H), 8.24 (d, 1H), 8.00 (d, 1H), 7.59 (s, 1H), 7.55 (dd, 1H), 7.51 (m, 5H), 7.29 (t, 1H), 7.21 (d, 1H), 4.75 (dd, 1H), 3.99 (s, OH), 3.81 (dd,), 3.49 (dd, 1H), 2.74 (s, 3H), 2.7 (s, 3H), 1.97 (s, 6H), 1.44 (s, 6H).

EXAMPLE 53

[2-{3-[6-(1-Methanesulfonyl-1-methyl-ethyl)-quinolin-8-yl]-phenyl}-1-(4-methanesulfonyl-phenyl)-ethyl]-phosphonic acid dimethyl ester

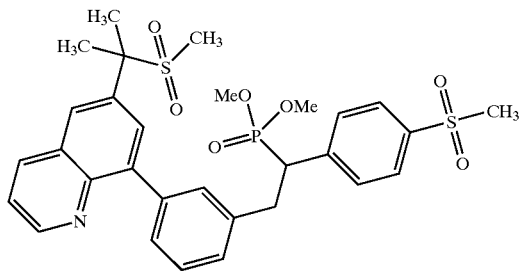

By following the procedures described above in Example 1, but substituting Phosphonate 01 for Ketone 02 and purification by flash chromatography (eluting with toluene/acetone, 50:50), the title compound was obtained as a white foam.

$^1$H NMR (400 MHz, acetone-d6): δ 8.89 (dd, 1H), 8.40 (dd, 1H), 8.23 (d, 1H), 8.01 (d, 1H), 7.84 (d, 2H), 7.71 (d, 2H), 7.50 (m, 3H), 7.26 (s, 1H), 7.19 (d, 1H), 3.90 (m, 1H), 3.71 (d, 3H), 3.57 (d, 3H), 3.55 (m, 1H), 3.40 (m, 1H), 3.02 (s, 3H), 2.70 (s, 3H), 1.98 (s, 6H).

EXAMPLE 54

8-{3-[2-(5,5-Dimethyl-2-oxo-2λ$^5$-[1,3,2]dioxaphosphinan-2-yl)-2-(4-methanesulfonyl-phenyl)-ethyl]-phenyl}-6-(1-methanesulfonyl-1-methyl-ethyl)-quinoline

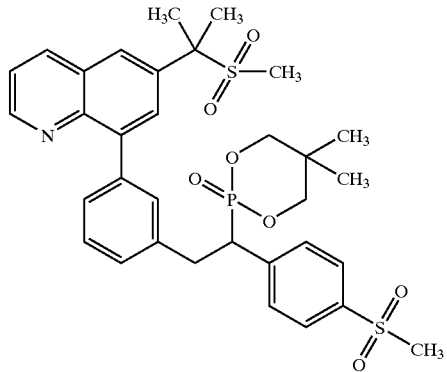

By following the procedures described above in Example 1, but substituting Phosphonate 03 for Ketone 02 and purification by flash chromatography (eluting with toluene/acetone, 60:40), the title compound was obtained as a white foam.

$^1$H NMR (400 MHz, acetone-d6): δ 8.90 (dd, 1H), 8.42 (dd, 1H), 8.24 (d, 1H), 8.00 (d, 1H), 7.84 (d, 2H), 7.73 (d, 2H), 7.53 (m, 3H), 7.27 (t, 1H), 7.18 (d, 1H), 4.20 (m, 3H), 4.03 (m, 1H), 3.92 (m, 1H), 3.57 (m, 1H), 3.40 (m, 1H), 3.06 (s, 3H), 2.72 (s, 3H), 1.97 (s, 6H), 1.13 (s, 3H), 0.91 (s, 3H).

EXAMPLE 55

[1-Fluoro-2-{3-[6-(1-methanesulfonyl-1-methyl-ethyl)-quinolin-8-yl]-phenyl}-1-(4-methanesulfonyl-phenyl)-ethyl]-phosphonic acid dimethyl ester

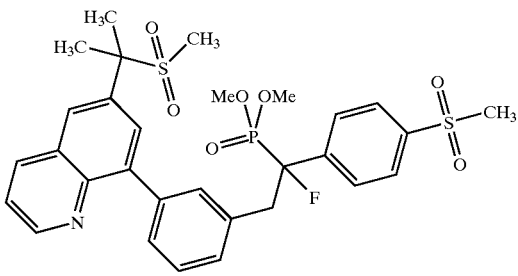

By following the procedures described above in Example 1, but substituting Phosphonate 02 for Ketone 02 and purification by flash chromatography (eluting with toluene/acetone, 60:40), the title compound was obtained as a white foam.54 corrected $^1$H NMR (400 MHz, acetone-d6): δ 8.88 (dd, 1H), 8.41 (dd, 1H), 8.22 (d, 1H), 7.96 (d, 1H), 7.92 (d, 2H), 7.78 (d, 2H), 7.53 (m, 2H), 7.49 (s, 1H), 7.28 (t, 1H), 7.14 (s, 1H), 3.84 (d, 3H), 3.83 (m, 2H), 3.58 (d, 3H), 3.02 (s, 3H), 2.70 (s, 3H), 1.97 (s, 3H), 1.96 (s, 3H).

EXAMPLE 56

8-{3-[2-(5,5-Dimethyl-2-oxo-2λ$^5$-[1,3,2]dioxaphosphinan-2-yl)-2-fluoro-2-(4-methanesulfonyl-phenyl)-ethyl]-phenyl}-6-(1-methanesulfonyl-1-methyl-ethyl)-quinoline

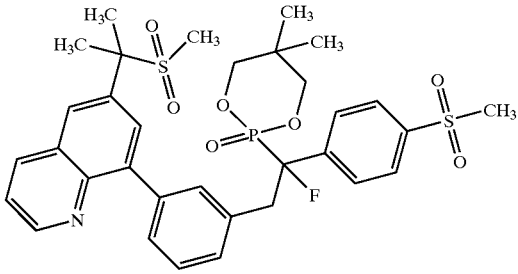

By following the procedures described above in Example 36, but substituting Example 54 for Example 1 and purification by flash chromatography (eluting with toluene/acetone, 75:25), the title compound was obtained as a white foam.

$^1$H NMR (400MHz, acetone-d6): δ 8.90 (dd, 1H), 8.41 (dd, 1H), 8.22 (d, 1H), 7.98 (d, 1H), 7.93 (d, 2H), 7.80 (d, 2H), 7.53 (m, 2H), 7.48 (s, 1H), 7.26 (t, 1H), 7.14 (d, 1H), 4.53 (dd, 1H), 4.38 (dd, 1H), 4.14 (m, 1H), 3.96 (m, 1H), 3.89 (m, 1H), 3.72 (m, 1H), 3.02 (s, 3H), 2.70 (s, 3H), 1.97 (s, 6H), 1.25 (s, 3H), 0.93 (s, 3H).

EXAMPLE 57

8-{3-[2-[Bis-(2,2,2-trifluoro-ethyl)-phosphinoyl]-2-fluoro-2-(4-methanesulfonyl-phenyl)-ethyl]-phenyl}-6-(1-methanesulfonyl-1-methyl-ethyl)-quinoline

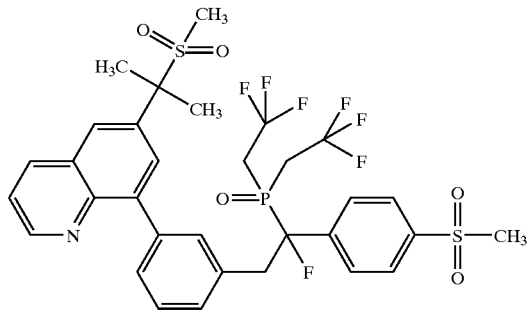

Following the procedures described above in Example 46, but substituting Phosphonate 04 for Sulfone 04 and purification by flash chromatography (eluting with toluene/acetone, 70:30), afforded the title compound as a white foam.

$^1$H NMR (400 MHz, acetone-d6): δ 8.90 (dd, 1H), 8.45 (m, 1H), 8.29 (m, 1H), 8.25 (d, 1H), 8.10 (d, 1H), 7.95 (d, 2H), 7.85 (d, 1H), 7.59 (m, 3H), 7.33 (t, 1H), 7.27 (d, 1H), 4.78 (m, 1H), 4.59 (m, 2H), 4.39 (m, 1H), 3.85 (m, 2H), 3.05 (s, 3H), 2.71 (s, 3H), 1.98 (s, 6H).

EXAMPLE 58

2-{3-[6-(1-Methanesulfonyl-1-methyl-ethyl)-quinolin-8-yl]-phenyl}-1-(4-methanesulfonyl-phenyl)-ethanesulfonic acid dimethylamide

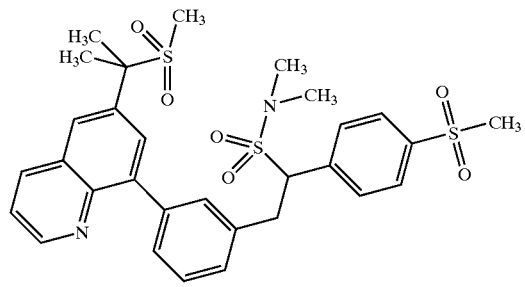

By following the procedures described above in Example 1, but substituting Sulfone 08 for Ketone 02, the title compound was obtained as a white foam.

$^1$H NMR (400 MHz, acetone-d6): δ 8.88 (dd, 1H), 8.39 (dd, 1H), 8.22 (d, 1H), 7.97 (d, 1H), 7.93 (d, 2H), 7.86 (d, 2H), 7.55–7.50 (m, 3H), 7.29–7.19 (m, 2H), 5.03 (dd, 1H), 3.75 (dd, 1H), 3.57 (dd, 1H), 3.05 (s, 3H), 2.70 (s, 3H), 2.67 (s, 6H), 1.96 (s, 6H).

EXAMPLE 59

1-Fluoro-2-{3-[6-(1-methanesulfonyl-1-methyl-ethyl)-quinolin-8-yl]-phenyl}-1-(4-methanesulfonyl-phenyl)-ethanesulfonic acid dimethylamide

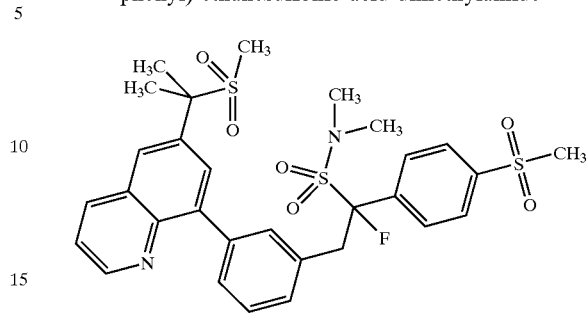

By following the procedures described above in Example 36, but substituting Example 58 for Example 1, the title compound was obtained as a white solid.

$^1$H NMR (400 MHz, acetone-d$_6$): δ 8.98 (d, 11H), 8.88 (dd, 1H), 8.18 (dd, 1H), 7.90 (d, 2H), 7.81 (d, 3H), 7.48 (d, 1H), 7.41 (dd, 1H), 7.39 (s, 1H), 7.25 (t, 1H), 7.07 (d, 1H), 3.96–3.80 (m, 2H), 2.95 (s, 3H), 2.68 (br s, 6H), 2.60 (s, 3H), 1.944 (s, 3H), 1.936 (s, 3H).

EXAMPLE 60

8-{3-[1-(4-Chloro-phenyl)-2-pyridin-4-yl-ethyl]-phenyl}-6-isopropyl-quinoline

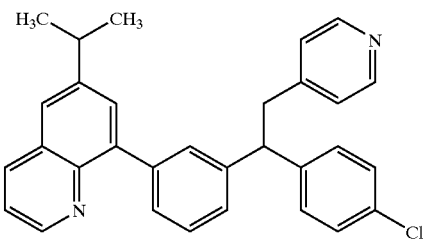

Step 1: (4-Chloro-phenyl)-[3-(6-isopropyl-quinolin-8-yl)-phenyl]-methanol

To a solution of Quinoline 04 (1.0 g, 3.6 mmol) in CH$_2$Cl$_2$ (5 mL) at −10° C. was added 4-chlorophenylmagnesium bromide (0.7M, THF, 5 mL, 7 mmol) dropwise. After 1 h, a saturated ammonium chloride solution was added and the reaction mixture extracted with CH$_2$Cl$_2$ (3×). The organic extracts were washed (H$_2$O, brine), dried (MgSO$_4$), filtered and concentrated. Purification by flash chromatography (eluting with hexane/ethyl acetate, 70:30) provided the (4-chloro-phenyl)-[3-(6-isopropyl-quinolin-8-yl)-phenyl]-methanol compound as a white solid.

Step 2: 8-{3-[Chloro-(4-chloro-phenyl)-methyl]-phenyl}-6-isopropyl-quinoline

To a solution of (4-chloro-phenyl)-[3-(6-isopropyl-quinolin-8-yl)-phenyl]-methanol from Step 1 (1.0 g, 2.58 mmol) in benzene (7 mL) at 0° C. was added SOCl$_2$ (0.375 mL, 5.2 mmol) dropwise. After 45 min. at 0–10° C., the resulting reaction mixture was filtered through silica gel and celite and then concentrated.

Step 3: 3-(4-Chloro-phenyl)-3-[3-(6-isopropyl-quinolin-8-yl)-phenyl]-2-pyridin-4-yl-propionic acid ethyl ester To a solution of ethyl 4-pyridinylacetate (1.28 g, 7.74 mmol) in THF/HMPA (3:1, 5 mL) at −10° C. was added NaHMDS (1M, 7.8 mL, 7.8 mmol) dropwise. After 60 min., the crude chloride from Step 2 above was added and the resulting reaction mixture was stirred for 18 h at 21° C., and then diluted with a saturated ammonium chloride solution and ethyl acetate. The organic extracts were washed (H$_2$O, brine), dried (MgSO$_4$), filtered and concentrated.

Step 4: 8-{3-[1-(4-Chloro-phenyl)-2-pyridin-4-yl-ethyl]-phenyl}-6-isopropyl-quinoline To a solution of the crude ester from Step 3 above in THF/EtOH (10 mL) was added NaOH (2N, 2 mL). The resulting reaction mixture was stirred 18 h at 100° C. then neutralized with HCl 6N to pH 7 and diluted with ethyl acetate. The organic extracts were washed (H$_2$O, brine), dried (MgSO$_4$), filtered and concentrated. Purification by flash chromatography (eluting with hexane/ethyl acetate, 1:1) provided the 8-{3-[1-(4-chloro-phenyl)-2-pyridin-4-yl-ethyl]-phenyl}-6-isopropyl-quinoline compound.

$^1$H NMR (500 MHz, acetone-d6): δ 8.81 (dd, 1H), 8.36 (d, 2H), 8.30 (dd, 1H), 7.76 (d, 2H), 7.6 (s, 1H), 7.51 (d, 1H), 7.46 (m, 3H), 7.33 (m, 4H), 7.22 (d, 2H), 4.53 (t, 1H), 3.52 (m, 2H), 3.15 (m, 1H), 1.39 (s, 6H).

EXAMPLE 61

8-{3-[1-(4-Chloro-phenyl)-2-(1-oxy-pyridin-4-yl)-ethyl]-phenyl}-6-isopropyl-quinoline

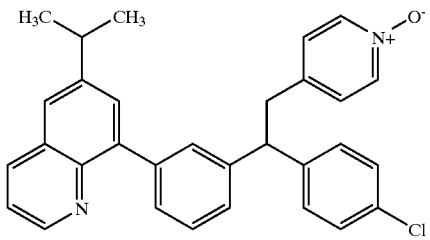

To a solution of Example 60 (100 mg, 0.22 mmol) in CH$_2$Cl$_2$/MeOH (1:1, 6 mL) was added MMPP (320 mg, 0.65 mmol). After 18 h, the resulting reaction mixture was diluted with a sodium bicarbonate solution and ethyl acetate. The organic extracts were washed (H$_2$O, brine), dried (MgSO$_4$), filtered and concentrated. Purification by flash chromatography (eluting with ethanol/ethyl acetate, 10:90 to 25:75) provided the title compound.

$^1$H NMR (500 MHz, acetone-d6): δ 8.83 (dd, 1H), 8.30 (dd, 1H), 7.95 (d, 2H), 7.76 (d, 2H), 7.63 (s, 1H), 7.48 (m, 4H), 7.35 (m, 4H), 7.22 (d, 2H), 4.49 (t, 1H), 3.52 (m, 2H), 3.18 (m, 1H), 1.39 (s, 6H).

EXAMPLE 62

8-{3-[1-(4-Chloro-phenyl)-2-pyridin-4-yl-ethyl]-phenyl}-quinoline

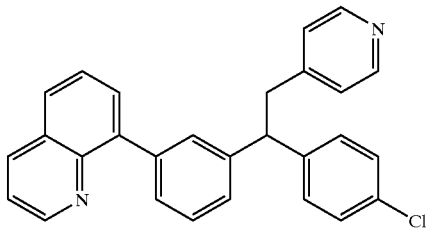

Step 1: 4-[2-(3-Bromo-phenyl)-2-(4-chloro-phenyl)-ethyl]-pyridine

Following the procedures described above in Example 60, but substituting 3-bromobenzaldehyde for Quinoline 04 and purification by flash chromatography (eluting with hexane/ethyl acetate, 4:1) afforded the 4-[2-(3-bromo-phenyl)-2-(4-chloro-phenyl)-ethyl]-pyridine compound.

Step 2: 8-{3-[1-(4-Chloro-phenyl)-2-pyridin-4-yl-ethyl]-phenyl}-quinoline

A solution of 4-[2-(3-bromo-phenyl)-2-(4-chloro-phenyl)-ethyl]-pyridine from Step 1 above (400 mg, 1.07 mmol), diboron pinacol ester (300 mg, 1.18 mmol), KOAc (315 mg, 3.2 mmol) and PdCl$_2$(dppf) (26 mg, 0.032 mmol) in DMF (20 mL) was heated at 80° C. under N$_2$ for 5 h. The resulting reaction mixture was cooled to 21° C., 8-bromoquinoline (290 mg, 1.4 mmol), Na$_2$CO$_3$ (2M, 1.61 mL, 3.2 mmol) and PdCl$_2$(dppf) (26 mg, 0.032 mmol) was then added. The reaction mixture was stirred 18 h at 80° C., then diluted with a saturated ammonium chloride solution and ethyl acetate. The organic extracts were washed (H$_2$O, brine), dried (MgSO$_4$), filtered and concentrated. Purification by flash chromatography (eluting with hexane/ethyl acetate, 50:50 to 25:75) provided the 8-{3-[1-(4-chloro-phenyl)-2-pyridin-4-yl-ethyl]-phenyl}-quinoline compound (319 mg).

$^1$H NMR (500 MHz, acetone-d6): δ 8.88 (dd, 1H), 8.37 (d, 1H), 8.36 (d, 2H), 7.95 (dd, 1H), 7.76 (s, 1H), 7.71 (dd, 1H), 7.64 (t, 1H), 7.52 (m, 2H), 7.48 (d, 2H), 7.37 (d, 2H), 7.28 (d, 2H), 7.21 (d, 2H), 4.51 (t, 1H), 3.52 (m, 2H).

EXAMPLE 63

8-{3-[1-(4-Chloro-phenyl)-2-(1-oxy-pyridin-4-yl)-ethyl]-phenyl}-quinoline

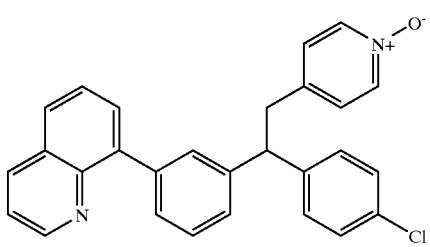

Following the procedures described above in Example 61, but substituting Example 62 for Example 60, the title compound was obtained.

$^{1}$H NMR (500 Mz, acetone-d6): δ 8.90 (dd, 1H), 8.38 (dd, 1H), 7.94 (m, 3H), 7.72 (t, 2H), 7.65 (t, 1H), 7.52 (m, 2H), 7.48 (d, 2H), 7.32 (m, 4H), 7.21 (d, 2H), 4.48 (t, 1H), 3.50 (m, 2H).

EXAMPLE 64

6-Isopropyl-8-[3-(2-pyridin-4-yl-ethyl)-phenyl]-quinoline

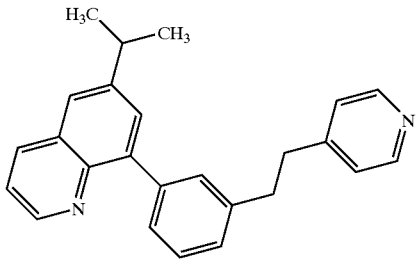

Using 3-bromobenzyl chloride as the starting material, and following the procedures described above in Example 60, Steps 3 and 4, followed by procedures described in Example 62, Step 2, the title compound was obtained.

$^{1}$H NMR (300 MHz, acetone-d6): δ 8.80 (dd, 1H), 8.44 (dd, 2H), 8.29 (dd, 1H), 7.76 (d, 1H), 7.63 (d, 1H), 7.52 (s, 2H), 7.46 (q, 1H), 7.25 (t, 1H), 7.25 (d, 3H), 3.16 (m, 1H), 3.01 (s, 4H), 1.38 (d, 6H).

EXAMPLE 65

6-Isopropyl-8-{3-[2-(1-oxy-pyridin-4-yl)-ethyl)-phenyl}-quinoline

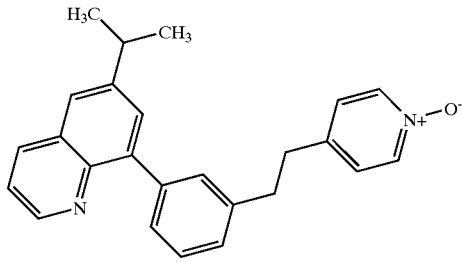

Following the procedures described in Example 61, but substituting Example 64 for Example 60, the title compound was obtained.

$^{1}$H NMR (500 MHz, acetone-d6): δ 8.82 (dd, 1H), 8.30 (dd, 1H), 8.01 (d, 2H), 7.76 (d, 1H), 7.65 (d, 1H), 7.52 (s&dd, 2H), 7.48 (q, 1H), 7.36 (t, 1H), 7.24 (d, 3H), 3.17 (m, 1H), 3.01 (s, 4H), 1.36 (s, 6H).

EXAMPLE 66

3-[3-(6-Isopropyl-quinolin-8-yl)-phenyl]-2-pyridin-4-yl-propionic acid ethyl ester

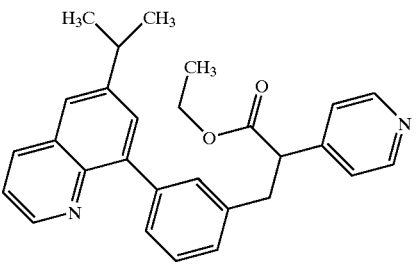

Using 3-bromobenzyl chloride as the starting material, and following the procedures described in Example 60, Step 3, followed by procedures described in Example 62, Step 2, the title compound was obtained as an oil.

$^{1}$H NMR (500 MHz, acetone-d6): δ 8.82 (s, 1H), 8.52 (d, 2H), 8.28 (dd, 1H), 7.78 (d, 1H), 7.58 (d, 2H), 7.49 (t, 2H), 7.38 (m, 3H), 7.21 (d, 1H), 4.05 (q, 1H), 3.48 (q, 2H), 3.1 (q, 2H), 1.38 (d, 6H), 1.1 (t, 3H).

EXAMPLE 67

3-[3-(6-Isopropyl-quinolin-8-yl)-phenyl]-2-pyridin-4-yl-propan-1-ol

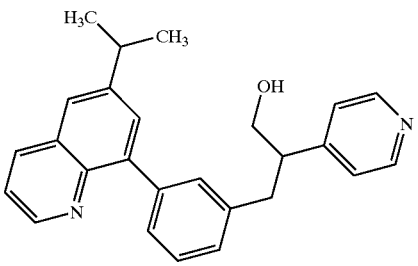

To a solution of Example 66 (15 mg, 0.035 mmol) in THF (mL) at 0° C. was added LiAlH$_4$ (1M, THF, 0.35 mL, 0.35 mmol) dropwise. The resulting reaction mixture was stirred 1 h at 0° C., 1 h at 21° C., and then quenched with water and neutralized using 1N HCl. The organic extracts were washed (H$_2$O, brine), dried (MgSO$_4$), filtered and concentrated. Purification by flash chromatography (eluting with ethanol/ethyl acetate, 1:9) provided the title compound.

$^{1}$H NMR (400 MHz, acetone-d6): δ 8.78 (dd, 1H), 8.33 (dd, 1H), 7.76 (d, 1H), 7.49 (q, 1H), 7.45 (d, 1H), 7.42 (d, 1H), 7.29 (t, 4H), 7.13 (d, 1H), 4.78 (t, 1H), 3.6 (m, 2H), 3.16 (m, 3H), 2.92 (q, 1H), 1.31 (s, 6H).

EXAMPLE 68

4-[3-(6-Isopropyl-quinolin-8-yl)-phenyl]-2-methyl-3-pyrdin-4-yl-butan-2-ol

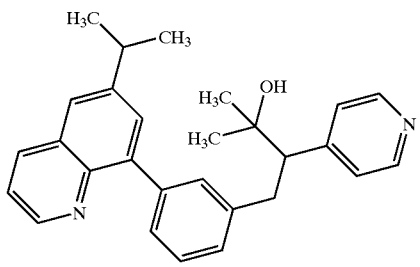

To a solution of Example 66 (750 mg, 1.77 mmol) in THF (40 mL) at 0° C. was added methylmagnesium iodide (3M, THF, 12 mL, 35 mmol) dropwise. The reaction mixture was stirred 3 h at 0° C., then quenched with a saturated ammonium chloride solution. The organic extracts were washed ($H_2O$, brine), dried ($MgSO_4$), filtered and concentrated. Purification by flash chromatography (eluting with hexane/ethyl acetate, 1:1) provided the title compound.

$^1$H NMR (400 MHz, acetone-d6): δ 8.77 (dd, 1H), 8.39 (dd, 2H), 8.27 (dd, 1H), 7.71 (d, 1H), 7.45 (q, 1H), 7.41 (d, 2H), 7.30 (d, 3H), 7.18 (t, 1H), 7.08 (d, 1H), 3.73 (s, 1H), 3.51 (dd, 1H), 3.16 (m, 2H), 3.03 (dd, 1H), 1.36 (d, 6H), 1.28 (s, 3H), 1.19 (s, 3H).

EXAMPLE 69

4-[3-(6-Isopropyl-quinolin-8-yl)-phenyl]-2-methyl-3-(1-oxy-pyridin-4-yl)-butan-2-ol

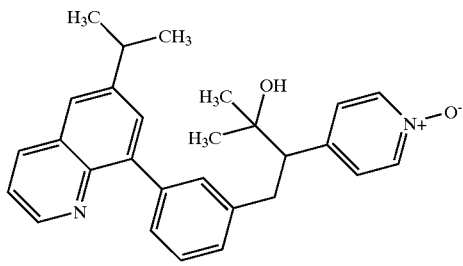

Following the procedures described in Example 61, but substituting Example 68 for Example 60, the title compound was obtained.

$^1$H NMR (400 MHz, acetone-d6): δ 8.82 (dd, 1H), 8.27 (dd, 1H), 7.96 (d, 2H), 7.73 (dd, 1H), 7.51 (d, 1H), 7.44 (q, 1H), 7.38 (m, 2H), 7.31 (d, 2H), 7.22 (t, 1H), 7.09 (d, 1H), 3.84 (s, 1H), 3.48 (d, 1H), 3.15 (m, 3H), 1.36 (t, 9H), 1.18 (s, 3H).

EXAMPLE 70

3-(3-(6-Isopropyl-quinolin-8-yl)-phenyl]-2-pyridin-4-yl-butyric acid ethyl ester

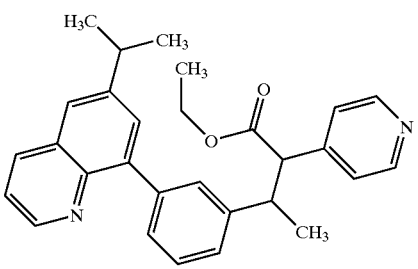

Following the procedures described in Example 60, Steps 1–3, but substituting methylmagnesium iodide for 4-chlorophenylmagnesium bromide, the title compound was obtained as a mixture of diastereoisomer.

$^1$H NMR (500 MHz, acetone-$d_6$): δ 8.83 (dd, 1H), 8.36 (dd, 2H), 8.26 (dd, 1H), 7.72 (d, 1H), 7.42 (m, 4H), 7.31 (dd, 2H), 7.22 (t, 1H), 7.13 (d, 1H), 4.21 (m, 3H), 3.95 (d, 1H), 3.58 (m, 1H), 3.12 (m, 1H), 1.48 (d, 3H), 1.36 (d, 6H), 1.18 (t, 2H).

EXAMPLE 71

4-[3-(6-Isopropyl-quinolin-8-yl)-phenyl]-2-methyl-3-pyridin-4-yl-pentan-2-ol

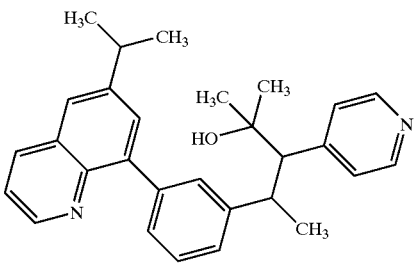

Following the procedures described in Example 68, but substituting Example 70 for Example 66, the title compound was obtained as a mixture of diastereoisomers.

$^1$H NMR (400 MHz, acetone-d6): δ 8.83 (dd, 1H), 8.34 (dd, 2H), 8.27 (dd, 1H), 7.79 (d, 1H), 7.49 (m, 2H), 7.42 (d, 1H), 7.38 (dd, 2H), 7.28 (dd, 2H), 7.18 (d, 1H), 4.39 (s, 1H), 3.58 (m, 1H), 3.12 (m, 1H), 2.88 (d, 1H), 1.35 (d, 6H), 1.21 (s, 3H), 1.05 (d, 3H), 0.9 (s, 3H).

EXAMPLE 72

4-(4-Chloro-phenyl)4-[3-(6-isopropyl-quinolin-8-yl)-phenyl]-2-methyl-3-pyridin-4-yl-butan-2-ol

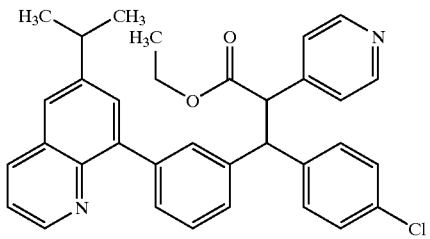

Following the procedures described in Example 60, Steps 1–3, the title compound was obtained as a mixture of diastereoisomers.

Isomer A: $^1$H NMR (400 MHz, acetone-d6): δ 8.81 (dd, 1H), 8.48 (d, 2H), 8.31 (dd, 1H), 7.92 (s, 1H), 7.78 (s, 1H), 7.68 (s, 1H), 7.58 (d, 1H), 7.52 (d, 1H), 7.48 (q, 1H), 7.41 (m, 6H), 7.18 (d, 1H), 4.92 (d, 1H), 4.81 (d, 1H), 4.02 (m, 2H), 3.12 (m, 1H), 1.39 (d, 6H), 0.92 (t, 3H).

Isomer B: $^1$H NMR (500 MHz, acetone-d$_6$): δ 8.81 (dd, 1H), 8.48 (d, 1H), 8.42 (dd, 1H), 8.31 (m, 2H), 7.72 (d, 1H), 7.68 (d, 1H), 7.62 (d, 1H), 7.52 (d, 2H), 7.43 (m, 3H), 7.35 (d, 2H), 7.21 (t, 1H), 7.15 (d, 1H), 4.95 (d, 1H), 4.78 (d, 1H), 3.98 (m, 2H), 3.11 (m, 1H), 1.37 (d, 6H), 0.95 (t, 3H).

EXAMPLE 73

4-(4-Chloro-phenyl)-4-[3-(6-isopropyl-quinolin-8-yl)-phenyl]-2-methyl-3-pyridin-4-yl-butan-2-ol

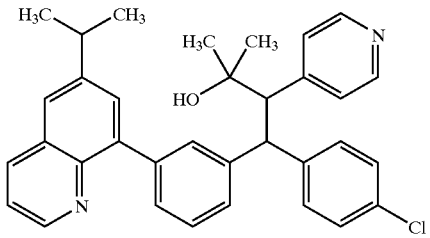

Following the procedures described in Example 68, but substituting Example 72 for Example 66, the title compound was obtained as a mixture of diastereoisomer.

$^1$H NMR (400 MHz, acetone-d6): δ 8.81 (dd, 1H), 8.48 (d, 2H), 8.31 (dd, 1H), 7.92 (s, 1H), 7.78 (s, 1H), 7.68 (s, 1H), 7.58 (d, 1H), 7.52 (d, 1H), 7.48 (q, 1H), 7.41 (m, 6H), 7.18 (d, 1H), 5.0 (d, 1H), 4.02 (d, 1H), 3.15 (m, 1H), 1.38 (m 9H), 1.1 (t, 3H).

EXAMPLE 74

2-Pyridin-4-yl-3-[3-(6-pyridin-4-ylmethyl-quinolin-8-yl)-phenyl]-propionic acid ethyl ester

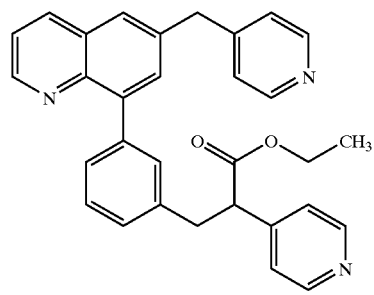

Using procedures described in Example 60, Step 3, but using 3-bromobenzyl chloride as the starting material, followed by the procedures described in Example 62, Step 2, but substituting 8-bromo 6-[(4-pyridinyl)methyl]quinoline for 8-bromoquinoline, the title compound was obtained as a oil.

$^1$H NMR (500 MHz, acetone-d6): δ 8.82 (dd, 1H), 8.46 (q, 4H), 8.30 (dd, 1H), 7.81 (s, 1H), 7.50 (s, 1H), 7.48 (m, 2H), 7.44 (s, 1H), 7.34 (m, 5H), 7.22 (d, 1H), 4.25 (s, 2H), 4.05 (m, 3H), 3.44 (dd, 1H), 3.13 (dd, 1H), 1.07 (t, 3H).

EXAMPLE 75

2-Methyl-3-pyridin-4-yl-4-[3-(6-pyridin-4-ylmethyl-quinolin-8-yl)-phenyl]-butan-2-ol

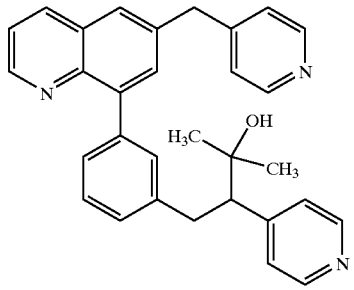

Following the procedures described in Example 68, but substituting Example 74 for Example 66, the title compound was obtained.

$^1$H NMR (400 MHz, acetone-d6): δ 8.81 (dd, 1H), 8.48 (dd, 2H), 8.36 (dd, 2H), 8.27 (dd, 1H), 7.76 (d, 1H), 7.48 (q, 1H), 7.34 (m, 5H), 7.28 (d, 2H), 7.18 (t, 1H), 7.05 (d, 1H), 4.23 (s, 2H), 3.48 (dd, 1H), 3.11 (m, 2H), 1.32 (s, 3H), 1.14 (s, 3H).

EXAMPLE 76

8-{3-[1-(4-Chloro-phenyl)-2-pyridin-4-yl-ethyl]-phenyl}-6-pyridin-4-ylmethyl-quinoline

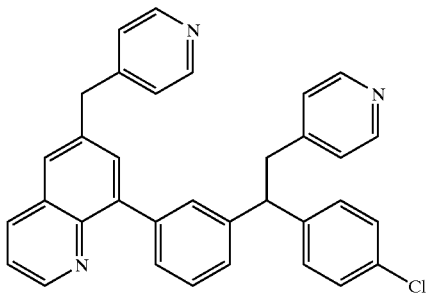

Following the procedures described in Example 62, but substituting 8-bromo-6-pyridin-4-ylmethyl-quinoline for 8-bromoquinoline and purification by flash chromatography (eluting with ethyl acetate/EtOH, 10:0 to 9:1) afforded the title compound.

$^1$H NMR (500 MHz, acetone-d6): δ 8.84 (dd, 1H), 8.48 (dd, 2H), 8.35 (dd, 2H), 8.29 (dd, 1H), 7.81 (d, 1H), 7.68 (s, 1H), 7.51 (d, 1H), 7.45 (m, 2H), 7.40 (d, 2H), 7.32 (dd, 4H), 7.27 (d, 2H), 7.20 (dd, 2H), 4.50 (t, 1H), 4.24 (s, 2H), 3.47 (m, 2H).

EXAMPLE 77

3-[3-(6-Isopropyl-quinolin-8-yl)-phenyl]-2-pyridin-4-yl-propionitrile

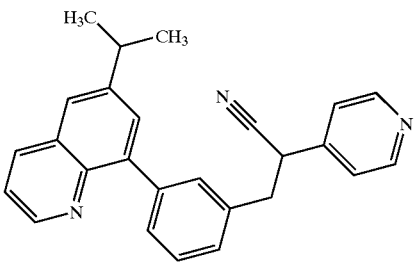

Step 1: 3-(3-Bromo-phenyl)-2-pyridin-4-yl-propionitrile

The procedures described in Example 60, Step 3, were followed but substituting 4-pyridinylacetonitrile for ethyl 4-pyridinylacetate and using 3-bromobenzyl chloride as the starting material.

Step 2: 3-[3-(6-Isopropyl-quinolin-8-yl)-phenyl]-2-pyridin-4-yl-propionitrile Following the procedures described in Example 62, Step 2, but substituting 8-bromo-6-isopropylquinoline for 8-bromoquinoline and purification by flash chromatography (eluting with ethylacetate/hexane, 75:25) afforded the 3-[3-(6-isopropyl-quinolin-8-yl)-phenyl]-2-pyridin-4-yl-propionitrile compound.

$^1$H NMR (500 MHz, acetone-d6): δ 8.81 (dd, 1H), 8.60 (dd, 2H), 8.30 (dd, 1H), 7.76 (d, 1H), 7.65 (d, 1H), 7.60 (d, 1H); 7.54 (s, 1H), 7.47 (q, 1H), 7.43 (dd, 2H), 7.39 (t, 1H), 7.29 (d, 1H), 4.56 (t, 1H), 3.36 (d, 2H), 3.16 (m, 1H), 1.37 (s, 6H).

EXAMPLE 78

3-[3-(6-Isopropyl-quinolin-8-yl)-phenyl]-2-(4-methanesulfonyl-phenyl)-propionitrile

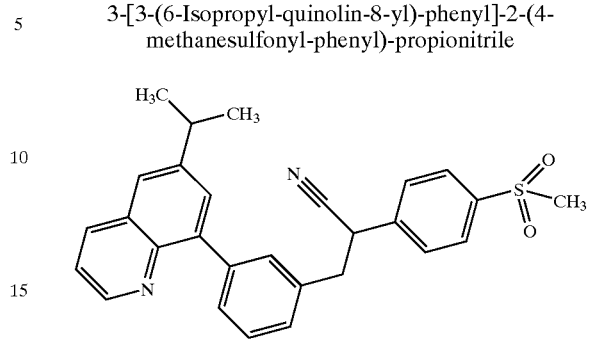

Step 1: (4-Methanesulfonyl-phenyl)-acetonitrile

To a solution of 4-methanesulfonylbenzyl chloride (10 g, 49 mmol) in DMF (100 mL) was added HMPA (9.35 mL, 54 mmol) and KCN (3.5 g, 54 mmol). The resulting reaction mixture was stirred 18 h at 80° C., then diluted with water and ethyl acetate. The organic extracts were washed (NaHCO$_3$, brine), dried (MgSO$_4$), filtered and concentrated. Purification by flash chromatography (eluting with hexane/ethyl acetate, 1:1 to 25:75) provided the (4-methanesulfonyl-phenyl)-acetonitrile compound.

Step 2: 3-[3-(6-Isopropylquinolin-8-yl)-phenyl]-2-[4-(methylsulfonyl)-phenyl]-prop-2-enenitrile A solution of Quinoline 04 (5 g, 18 mmol), 4-methanesulfonylacetonitrile (3.5 g, 18 mmol) from Step 1 and piperidine (0.1 mL) in toluene (5 mL) was heated at 130° C. After 6 h, the mixture was cooled to 21° C. and purified by flash chromatography (eluting with ethylacetate/hexane, 1:1 to 75:25) to afforded the title compound.

Step 3: 3-[3-(6-Isopropyl-quinolin-8-yl)-phenyl]-2-(4-methanesulfonyl-phenyl)-propionitrile A solution of the nitrile from Step 2 (400 mg, 0.88 mmol) in THF/EtOH (1:1, 10 mL) containing Pd/C (10%, 40 mg) was stirred under H$_2$ (1 atm) for 3 days. Filtration on celite, evaporation, stirring vigorously in ether for 1 h then filtration afforded the 3-[3-(6-Isopropyl-quinolin-8-yl)-phenyl]-2-(4-methanesulfonyl-phenyl)-propionitrile compound as a white powder.

$^1$H NMR (500 MHz, acetone-d$_6$): δ 8.81 (dd, 1H), 8.31 (dd, 1H), 7.97 (d, 2H), 7.78 (s, 1H), 7.76 (d, 2H), 7.68 (s, 1H), 7.64 (d, 2H), 7.46 (q, 1H), 7.40 (t, 1H), 7.29 (d, 1H), 4.68 (t, 1H), 3.42 (dd, 2H), 3.15 (m, 1H), 3.08 (s, 3H), 1.38 (s, 6H).

EXAMPLE 79

6-Isopropyl-8-{3-[2-(4-methanesulfonyl-phenyl)-2-(1H-tetrazol-5-yl)-ethyl]-phenyl}-quinoline

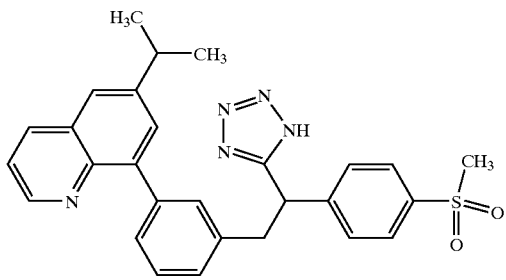

A solution of Example 78 (160 mg, 0.35 mmol), tri-n-butyltin chloride (0.478 mL, 1.76 mmol) and sodium azide (115 mg, 1.76 mmol) in xylene (5 mL) was heated at 150° C. for 18 h. Cooling to 21° C., then purification by flash chromatography (eluting with $CH_2Cl_2$/MeOH, $NH_4OH$, 50:5:1) followed by stirring vigorously in ether for 1 h, then filtered, afforded the title compound as a white powder.

$^1$H NMR (500 MH, acetone-$d_6$): δ 8.88 (d, 1H), 8.42 (d, 1H), 7.91 (d, 2H), 7.83 (s, 1H), 7.81 (d, 2H), 7.64 (dd, 2H), 7.56 (q, 1H), 7.49 (d, 1H), 7.29 (t, 1H), 7.12 (d, 1H), 5.13 (q, 1H), 3.68 (q, 1H), 3.54 (q, 1H), 3.21 (m, 1H), 3.06 (s, 3H), 1.38 (d, 6H).

EXAMPLE 80

3-{3-[6-(Cyano-dimethyl-methyl)-quinolin-8-yl]-phenyl}-N-isopropyl-2-(4-methanesulfonyl-phenyl)-propionamide

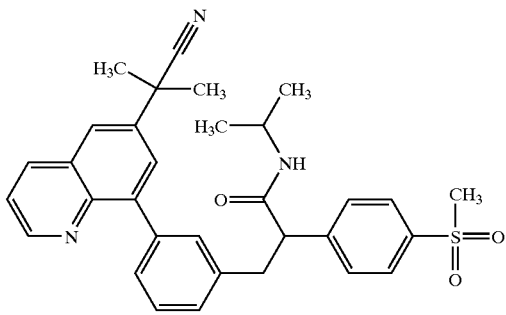

Step 1: (E)-3-(3-Bromophenyl)-2-[4-(methylsulfonyl)phenyl]-2-propenoic acid

To a solution of 3-bromobenzaldehyde (12.9 g, 70 mmol) in toluene (100 mL) was added 4-(methylsulfonyl) phenylacetic acid (15 g, 70 mmol) and piperidine (2 mL). After overnight refluxing, the mixture was cooled down to r.t. To the slurry thus formed, toluene was added (10 mL). Filtration gave the (E)-3-(3-bromophenyl)-2-[4-(methylsulfonyl)phenyl]-2-propenoic acid as a white solid.

Step 2: (E)-N-Isopropyl-3-(3-bromophenyl)-2-[4-(methylsulfonyl)phenyl]-2-propenamide To a solution of (E)-3-(3-bromophenyl)-2-[4-(methylsulfonyl)phenyl]-2-propenoic acid from Step 1 (24.9 g, 65 mmol) in toluene (250 mL) was added thionyl chloride (14.3 mL, 196 mmol) and triethylamine (34 mL, 245 mmol). After stirring at 21° C. for 0.5 h., isopropyl amine (28 mL, 327 mmol) was added. After a further 2 h at r.t., the mixture was cooled to 0° C. and was neutralised with saturated $NH_4Cl$ solution, then extracted with EtOAc. The organic extracts were washed ($H_2O$, brine), dried ($MgSO_4$), filtered and concentrated. Purification by flash chromatography (Hex:EtOAc, 1:1 to pure EtOAc) yielded the (E)-N-isopropyl-3-(3-bromophenyl)-2-[4-(methylsulfonyl) phenyl]-2-propenamide compound.

Step 3: 3-{3-[6-(Cyano-dimethyl-methyl)-quinolin-8-yl]-phenyl}-N-isopropyl-2-(4-methanesulfonyl-phenyl)-acrylamide Following the procedures described above in Example 62, Step 2, but substituting Quinoline 08 for 8-bromoquinoline and purification by flash chromatography (eluting with ethylacete/hexane, 75:25) afforded the 3-{3-[6-(Cyano-dimethyl-methyl)-quinolin-8-yl]-phenyl}-N-isopropyl-2-(4-methanesulfonyl-phenyl)-acrylamide compound.

Step 4: 3-{3-[6-(Cyano-dimethyl-methyl)-quinolin-8-yl]-phenyl}-N-isopropyl-2-(4-methanesulfonyl-phenyl)-propionamide A solution of 3-{3-[6-(cyano-dimethyl-methyl)-quinolin-8-yl]-phenyl}-N-isopropyl-2-(4-methanesulfonyl-phenyl)-acrylamide from Step 3 (20 mg, 0.038 mmol) in THF (1 mL) containing Pd/C (10%, 9 mg) was stirred under $H_2$ (50 psi) for 18 h. Filtration on celite, evaporation, and purification on HPLC (u-porasil ethyl acetate/hexane, 70:30 to 100:0, over 30 min.) afforded the 3-{3-[6-(cyano-dimethyl-methyl)-quinolin-8-yl]-phenyl}-N-isopropyl-2-(4-methanesulfonyl-phenyl)-propionamide compound as a foam.

Example 80 can also be prepared according to the procedure described in Example 1 but using Quinoline 09 and Ester 05 as the starting material. After flash chromatography (hexane/EtOAc 50:50), the residue was stirred vigorously in ether for 1 h then filtered to afford the 3-{(3-[6-(cyano-dimethyl-methyl)-quinolin-8-yl]-phenyl}-N-isopropyl-2-(4-methanesulfonyl-phenyl)-propionamide compound as a white powder.

$^1$H NMR (500 MHz, acetone-$d_6$): δ 8.92 (dd, 1H), 8.46 (d, 1H), 8.11 (d, 1H), 7.86 (d, 3H), 7.72 (d, 2H), 7.65 (s, 1H), 7.58 (q, 1H), 7.51 (d, 1H), 7.35 (t, 1H), 7.28 (d, 1H), 7.12 (d, 1H), 3.96 (t, 1H), 3.85 (m, 1H), 3.51 (t, 1H), 3.07 (m, 4H), 1.85 (s, 6H), 0.93 (d, 3H), 0.88 (d, 3H).

EXAMPLE 81

6-(1-Methanesulfonyl-1-methyl-ethyl)-8-{3-[2-(4-methanesulfonyl-phenyl)-2-(3-methyl-[1,2,4]oxadiazol-5-yl)-ethyl]-phenyl}-quinoline

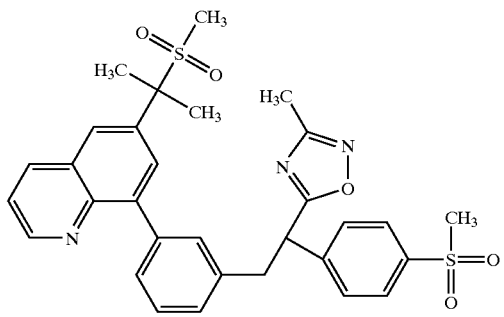

Example 81 was prepared according to the procedure described above in Example 1 but using Quinoline 01 and Ester 06 as the starting material and the reaction performed from −78° C. to 21° C. Flash chromatography (hexane/EtOAc 50:50 to 10:90) afforded the title compound.

$^1$H NMR (500 MHz, acetone-d$_6$): δ 8.91 (dd, 1H), 8.43 (dd, 1H), 8.24 (d, 1H), 8.01 (d, 1H), 7.90 (d, 2H), 7.74 (d, 2H), 7.60 (s, 1H), 7.54 (m, 2H), 7.33 (t, 1H), 7.25 (d, 1H), 4.97 (t, 1H), 3.73 (q, 1H), 3.48 (q, 1H), 3.06 (s, 3H), 2.70 (s, 3H), 2.31 (s, 3H), 1.96 (d, 6H).

EXAMPLE 82

3-[3-(6-Isopropyl-quinolin-8-yl)-phenyl]-2-(4-methanesulfonyl-phenyl)-propionic acid methyl ester

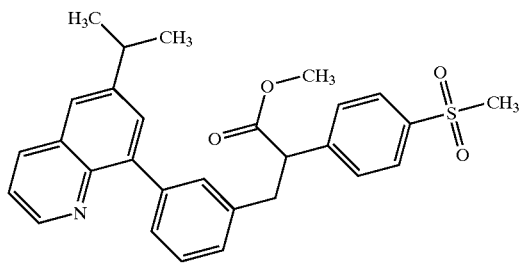

Step 1: 3-[3-(6-Isopropyl-quinolin-8-yl)-phenyl]-2-(4-methylsulfanyl-phenyl)-propionic acid methyl ester Following the procedures described in Example 13, Step 1, but substituting Quinoline 06 for Quinoline 01, the 3-[3-(6-isopropyl-quinolin-8-yl)-phenyl]-2-(4-methylsulfanyl-phenyl)-propionic acid methyl ester compound was obtained as a white foam.

Step 2: 3-[3-(6-Isopropyl-quinolin-8-yl)-phenyl]-2-(4-methanesulfonyl-phenyl)-propionic acid methyl ester A solution of 3-[3-(6-isopropyl-quinolin-8-yl)-phenyl]-2-(4-methylsulfanyl-phenyl)-propionic acid methyl ester from Step 1 (1.05 g, 2.3 mmol), NMO (655 mg, 4.85 mmol) and OsO$_4$ (4%, H$_2$O, 1 mL, 0.16 mmol) in THF (20 mL) was stirred 18 h at 21° C. The resulting reaction mixture was diluted with a sodium metabisulfite solution and ethyl acetate. The organic extracts were washed (H$_2$O, brine), dried (MgSO$_4$), filtered and concentrated. Purification by flash chromatography (eluting with hexane/ethyl acetate, 80:20) provided the 3-[3-(6-isopropyl-quinolin-8-yl)-phenyl]-2-(4-methanesulfonyl-phenyl)-propionic acid methyl ester compound.

$^1$H NMR (400 MHz, acetone-d6): δ 8.81 (dd, 1H), 8.29 (dd, 1H), 7.89 (dd, 2H), 7.76 (d, 1H), 7.67 (d, 2H), 7.63 (d, 1H), 7.56–7.53 (m, 2H), 7.46 (dd, 1H), 7.32 (t, 1H), 7.21 (d, 1H), 4.23 (t, 1H), 3.61 (s, 3H), 3.54 (dd, 1H), 3.19–3.13 (m, 2H), 3.06 (s, 3H), 1.37 (s, 3H), 1.36 (s, 3H). LRMS (CI) 488 (M+H)$^+$.

EXAMPLE 83

3-[3-(6-Isopropyl-quinolin-8-yl)-phenyl]-2-(4-methanesulfonyl-phenyl)-propionic acid

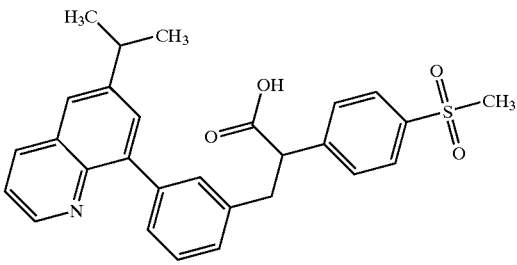

Following the procedures described in Example 8, but substituting Example 82 for Example 7, the title compound was obtained as a white solid.

$^1$H NMR (400 MHz, acetone-d6): δ 8.81 (dd, 1H), 8.29 (dd, 1H), 7.98 (d, 2H), 7.76 (s, 1H), 7.70 (d, 2H), 7.64 (dd, 1H), 7.59 (s, 1H), 7.54 (d, 1H), 7.47 (dd, 1H), 7.32 (t, 1H), 7.24 (d, 1H), 4.22 (t, 1H), 3.53 (dd, 1H), 3.20–3.13 (m, 2H), 3.07 (s, 3H), 1.38 (s, 3H), 1.36 (s, 3H). LRMS (CI) 474 (M+H)$^+$ 430 (M+H−COOH)$^+$.

EXAMPLE 84

6-Isopropyl-8-{3-[2-(4-methanesulfonyl-phenyl)-2-(3-methyl-[1,2,4]oxadiazol-5-yl)-ethyl]-phenyl}-quinoline

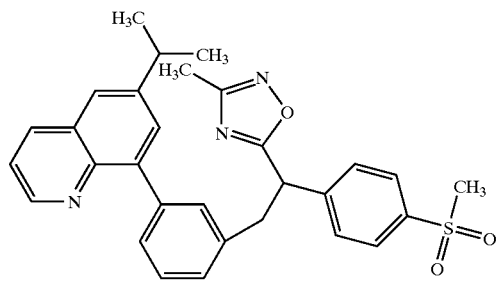

To a solution of Example 83 (177 mg, 0.37 mmol) in diglyme (3 mL) was added EDCI (93 mg, 0.48 mmol) and, after 10 min, N-hydroxyacetamidine (41 mg, 0.55 mmol). The resulting reaction mixture was stirred 3 h at 110° C., then diluted with a saturated sodium bicarbonate solution and ethyl acetate. The organic extracts were washed (H$_2$O, brine), dried (MgSO$_4$), filtered and concentrated. Purification by flash chromatography (eluting with hexane/ethyl acetate, 80:20 to 100:0) provided the title compound.

$^1$H NMR (400 MHz, acetone-d6): δ 8.81 (dd, 1H), 8.30 (dd, 1H), 7.91 (dd, 2H), 7.77–7.74 (m, 3H), 7.59 (d, 1H), 7.56–7.53 (m, 2H), 7.47 (dd, 1H), 7.31 (t, 1H), 7.22 (d, 1H), 4.97 (t, 1H), 4.74 (dd, 1H), 3.48 (dd, 1H), 3.16 (q, 1H), 3.06 (s, 3H), 2.32 (s, 3H), 1.38 (s, 3H), 1.37 (s, 3H). LRMS (CI) 512 (M+H)$^+$.

EXAMPLE 85

3-(2-Cyano-phenyl)-2-[3-(6-isopropyl-quinolin-8-yl)-phenyl]-propionic acid methyl ester

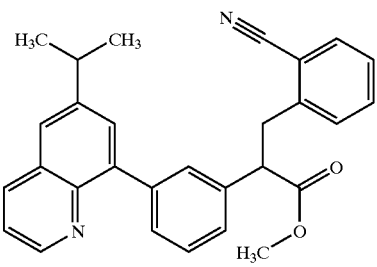

To a solution of Quinoline 05 (100 mg, 0.31 mmol) in THF/DMF (1:1, 3 mL) at −78° C. was added potassium tert-butoxide (1M, 0.31 mL, 0.31 mmol) dropwise. The resulting reaction mixture was stirred 5 min., then cannulated into a solution of 2-cyanobenzylbromide (123 mg, 0.63 mmol) in THF (1 mL) at 21° C. After 3 h, the reaction mixture was diluted with a saturated ammonium chloride solution and ethyl acetate. The organic extracts were washed ($H_2O$, brine), dried ($MgSO_4$), filtered and concentrated. Purification by flash chromatography (eluting with hexane/ethyl acetate, 80:20 to 20:80) provided the title compound.

$^1$H NMR (300 MHz, acetone-d6): δ 8.81 (dd, 1H), 8.28 (dd, 1H), 7.50 (s, 11H), 4.19 (t, 1H), 3.65 (dd, 1H), 3.61 (s, 3H), 3.39 (dd, 1H), 3.15 (m, 1H), 1.37 (d, 6H).

EXAMPLE 86

3-(3-Cyano-phenyl)-2-[3-(6-isopropyl-quinolin-8-yl)-phenyl]-propionic acid methyl ester

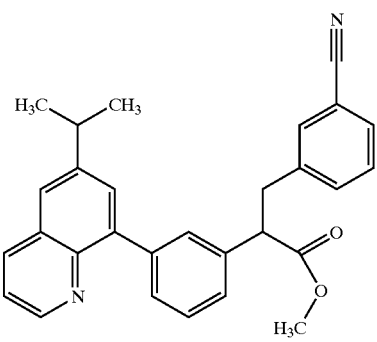

Following the procedures described above in Example 85, but substituting 3-cyanobenzylbromide for 2-cyanobenzylbromide, the title compound was obtained.

$^1$H NMR (300 MHz, acetone-d6): δ 8.83 (dd, 1H), 8.29 (dd, 1H), 7.76 (d, 1H), 7.68 (s, 2H), 7.65–7.30 (m, 8H), 4.10 (t, 1H), 3.60 (s, 3H), 3.49 (dd, 1H), 3.20 (dd, 1H), 3.15 (m, 1H), 1.39 (d, 6H).

EXAMPLE 87

3-(4-Cyano-phenyl)-2-[3-(6-isopropyl-quinolin-8-yl)-phenyl]-propionic acid methyl ester

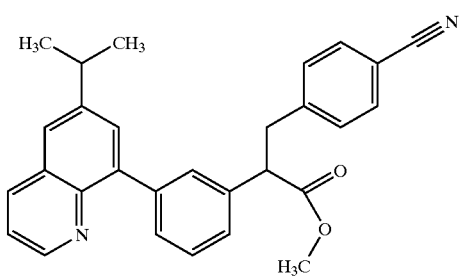

Following the procedures described above in Example 85, but substituting 4-cyanobenzylbromide for 2-cyanobenzylbromide, the title compound was obtained.

$^1$H NMR (300 MHz, acetone-d6): δ 8.82 (dd, 1H), 8.30 (dd, 1H), 7.80 (d, 1H), 7.70–7.30 (m, 10H), 4.10 (t, 1H), 3.61 (s, 3H), 3.52 (dd, 1H), 3.25 (dd, 1H), 3.18 (m, 1H), 1.38 (d, 6H).

EXAMPLE 88

3-(2-Chloro-4-fluoro-phenyl)-2-[3-(6-isopropyl-quinolin-8-yl)-phenyl]-propionic acid methyl ester

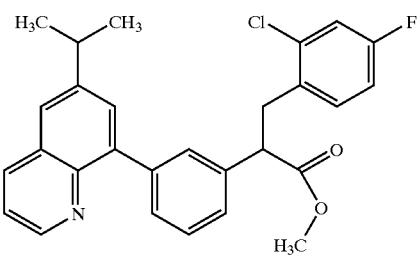

Following the procedures described above in Example 85, but substituting 2-chloro-4-fluorobenzyl bromide for 2-cyanobenzylbromide, the title compound was obtained.

$^1$H NMR (300 MHz, acetone-d6): δ 8.83 (dd, 1H), 8.28 (dd, 1H), 7.77–7.30 (m, 9H), 6.98 (dt, 1H), 4.13 (t, 1H), 3.61 (s, 3H), 3.53 (dd, 1H), 3.25 (dd, 1H), 3.17 (m, 1H), 1.38 (d, 6H).

EXAMPLE 89

2-[3-(6-isopropylquinolin-8-yl)-phenyl]-3-[4-(1,2,3-thiadiazol-5-yl)-phenyl]-propionic acid methyl ester

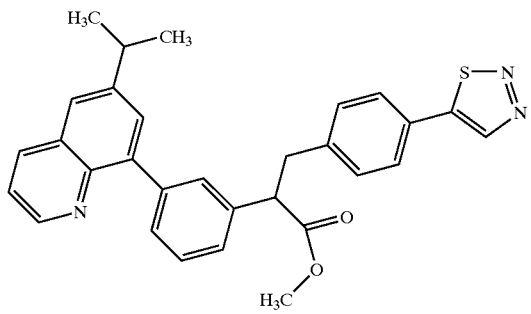

Following the procedures described above in Example 85, but substituting 4-(4-bromomethylphenyl)-[1,2,3]thiadiazole for 2-cyanobenzylbromide, the title compound was obtained.

$^1$H NMR (400 MHz, acetone-d6): δ 9.29 (s, 1H), 8.82 (dd, 1H), 8.30 (dd, 1H), 8.06 (d, 2H), 7.76 (d, 1H), 7.65–7.59 (m, 3H), 7.49–7.23 (m, 5H), 4.11 (t, 1H), 3.61 (s, 3H), 3.52 (dd, 1H), 3.22 (dd, 1H), 3.09 (m, 1H), 1.31 (d, 6H).

EXAMPLE 90

2-[3-(6-Isopropyl-quinolin-8-yl)-phenyl]-3-pyridin-4-yl-propionic acid methyl ester

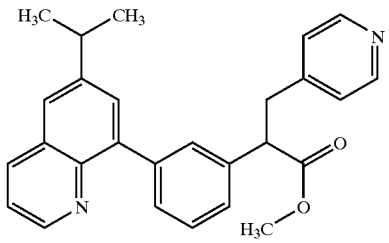

Following the procedures described above in Example 85, but substituting 4-picolyl chloride for 2-cyanobenzylbromide, the title compound was obtained.

$^1$H NMR (300 MHz, acetone-d6): δ 8.82 (dd, 1H), 8.45 (d, 2H), 8.30 (dd, 1H), 7.80 (d, 1H), 7.70–7.35 (m, 6H), 7.25 (d, 2H), 4.15 (t, 1H), 3.60 (s, 3H), 3.46 (dd, 1H), 3.18 (m, 2H), 1.39 (d, 6H).

EXAMPLE 91

2-[3-(6-Isopropyl-quinolin-8-yl)-phenyl]-3-phenyl-propionic acid methyl ester

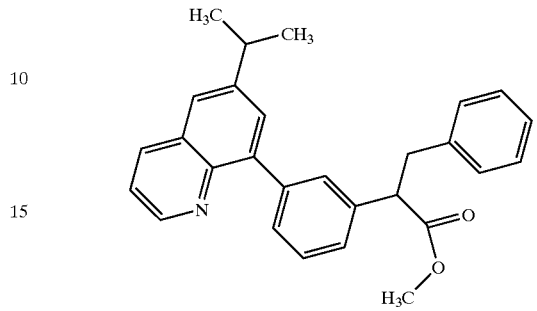

Following the procedures described above in Example 85, but substituting benzyl chloride for 2-cyanobenzylbromide, the title compound was obtained.

$^1$H NMR (300 MHz, acetone-d6): δ 8.81 (dd, 1H), 8.30 (dd, 1H), 7.77 (d, 1H), 7.70–7.10 (m, 11H), 4.05 (t, 1H), 3.60 (s, 3H), 3.45 (dd, 1H), 3.18 (m, 1H), 3.12 (dd, 1H), 1.40 (d, 6H).

EXAMPLE 92

2-[3-(6-Isopropyl-quinolin-8-yl)-phenyl]-3-(4-methanesulfonyl-phenyl)-propionic acid methyl ester

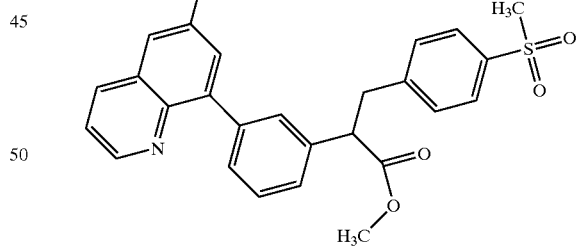

Following the procedures described above in Example 85, but substituting 4-methanesulfonylbenzyl chloride for 2-cyanobenzylbromide, the title compound was obtained.

$^1$H NMR (400 MHz, acetone-d6): □8.85 (dd, 1H), 8.32 (dd, 1H), 7.81 (m, 3H), 7.72 (s, 1H), 7.69 (s, 1H), 7.61 (d, 1H), 7.56 (d, 2H), 7.49 (dd, 1H), 7.40 (t, 1H), 7.34 (d, 1H), 4.12 (t, 1H), 3.60 (s, 3H), 3.55 (dd, 1H), 3.38 (dd, 1H), 3.29 (m, 1H), 3.05 (s, 3H), 1.38 (d, 6H).

EXAMPLE 93

2-[3-(6-Isopropyl-quinolin-8-yl)-phenyl]-3-(4-methanesulfonyl-phenyl)-propionic acid

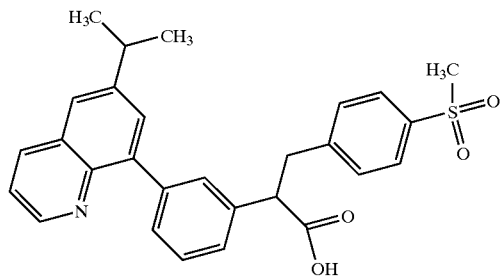

Following the procedures described above in Example 8, but substituting Example 92 for Example 7, the title compound was obtained.

$^1$H NMR (400 MHz, acetone-d6): δ 8.85 (dd, 1H), 8.31 (dd, 1H), 7.82 (d, 2H), 7.78 (d, 2H), 7.68 (s, 1H), 7.60 (m, 3H), 7.48 (dd, 1H), 7.40 (m, 2H), 4.10 (t, 1H), 3.55 (dd, 1H), 3.25 (dd, 1H), 3.18 (m, 1H), 3.05 (s, 3H), 1.38 (s, 6H).

EXAMPLE 94

3-[3-(6-Isopropyl-quinolin-8-yl)-phenyl]4-(4-methanesulfonyl-phenyl)-2-methyl-butan-2-ol

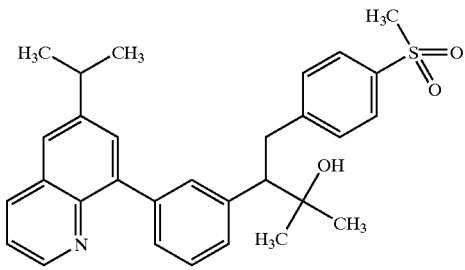

To a solution of Example 92 (100 mg, 0.2 mmol) in CH$_2$Cl$_2$ (2 mL) at −78° C. was added methylmagnesium chloride (3M, THF, 0.2 mL, 0.6 mmol) dropwise. The resulting reaction mixture was stirred 1 h at 21° C., then quenched with a saturated ammonium chloride solution. The organic extracts were washed (H$_2$O, brine), dried (MgSO$_4$), filtered and concentrated. Purification by flash chromatography (eluting with hexane/ethyl acetate, 7:3) provided the title compound.

$^1$H NMR (300 MHz, acetone-d6): δ 8.85 (dd, 1H), 8.30 (dd, 1H), 7.80–7.65 (m, 5H), 7.55–7.45 (m, 4H), 7.35–7.20 (m, 2H), 3.70 (brs, 1H), 3.60 (dd, 1H), 3.30 (t, 1H), 3.15 (dd, 1H), 3.12 (m, 1H), 3.00 (s, 3H), 1.38 (d, 6H), 1.30 (s, 3H), 1.25 (s, 3H).

EXAMPLE 95

N-Isopropyl-2-[3-(6-isopropyl-quinolin-8-yl)-phenyl]-3-(4-methanesulfonyl-phenyl)-propionamide

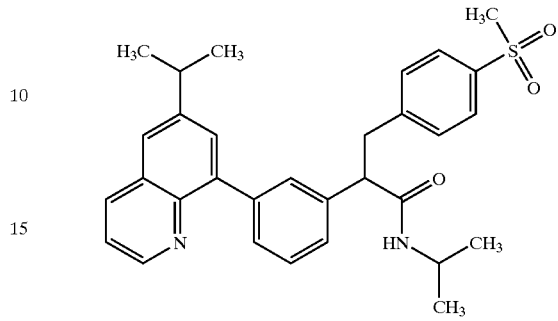

To a solution of Example 93 (100 mg, 0.21 mmol) in CH$_2$Cl$_2$ (2 mL) was added DMAP (26 mg, 0.21 mmol), EDCI (45 mg, 0.23 mmol), then isopropyl amine (1 mL, 12 mmol). The resulting reaction mixture was stirred 18 h at 21° C., then diluted with a sodium bicarbonate solution and ethyl acetate. The organic extracts were washed (H$_2$O, brine), dried (MgSO$_4$), filtered and concentrated. Purification by flash chromatography (eluting with hexane/ethyl acetate, 80:20 to 20:80) provided the title compound.

$^1$H NMR (300 MHz, acetone-d6): δ 8.82 (dd, 1H), 8.35 (dd, 1H), 7.95 (m, 1H), 7.85–7.75 (m, 4H), 7.65–7.52 (m, 3H), 7.50 (dd, 1H), 7.45–7.35 (m, 2H), 7.10 (brd, 1H), 3.88 (m, 2H), 3.59 (dd, 1H), 3.15 (m, 2H), 3.09 (s, 3H), 1.38 (d, 6H), 0.99 (d, 3H), 0.96 (d, 3H).

EXAMPLE 96

6-Isopropyl-8-{3-[2-(4-methanesulfonyl-phenyl)-1-(3-methyl-[1,2,4]oxadiazol-5-yl)-ethyl]-phenyl}-quinoline

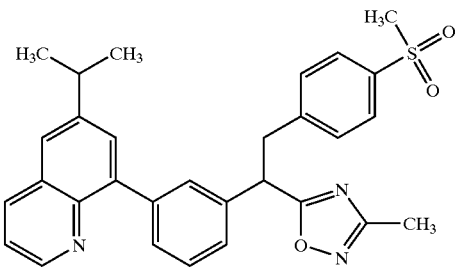

Following the procedures described above in Example 84, but substituting Example 93 for Example 83, the title compound was obtained.

$^1$H NMR (300 MHz, acetone-d6): δ 8.82 (dd, 1H), 8.30 (dd, 1H), 7.80 (m, 4H), 7.70–7.58 (m, 4H), 7.50 (dd, 1H), 7.40 (m, 2H), 4.85 (t, 1H), 3.78 (dd, 1H), 3.60 (dd, 1H), 3.28 (m, 1H), 3.05 (s, 3H), 2.30 (s, 3H), 1.40 (d, 6H).

EXAMPLE 97

2-[3-(6-Isopropyl-quinolin-8-yl)-phenyl]-3-(4-methanesulfonyl-phenyl)-propionitrile

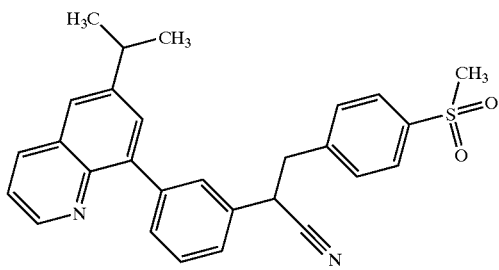

Following the procedures described above in Example 85, but substituting Quinoline 07 for Quinoline 05 and substituting 4-methanesulfonylbenzyl chloride for 2-cyanobenzylbromide, the title compound was obtained.

$^1$H NMR (300 MHz, acetone-d6): δ 8.85 (dd, 1H), 8.30 (dd, 1H), 7.90 (d, 2H), 7.80 (m, 2H), 7.70 (m, 2H), 7.60 (d, 2H), 7.45 (m, 3H), 4.57 (t, 1H), 3.45 (d, 2H), 3.19 (m, 1H), 3.09 (s, 3H), 1.40 (d, 6H).

EXAMPLE 98

2-[3-(6-Isopropyl-quinolin-8-yl)-phenyl]-3-pyridin-3-yl-propionic acid methyl ester

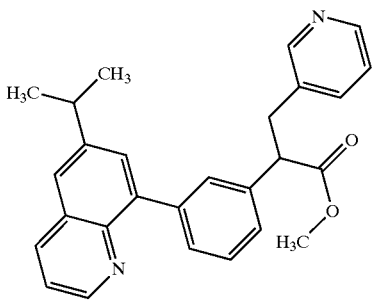

Following the procedures described above in Example 85, but substituting 3-picolyl chloride for 2-cyanobenzylbromide, the title compound was obtained.

$^1$H NMR (400 MHz, acetone-d6): δ 8.82 (dd, 1H), 8.48 (d, 1H), 8.38 (dd, 1H), 8.29 (dd, 1H), 7.77 (d, 1H), 7.68 (t, 1H), 7.64 (m, 3H), 7.47 (dd, 1H), 7.41 (t, 1H), 7.34 (d, 1H), 7.22 (dd, 1H), 4.06 (t, 1H), 3.59 (s, 3H), 3.42 (dd, 1H), 3.16 (m, 2H), 1.37 (d, 6H).

EXAMPLE 99

2-[3-(6-Isopropyl-quinolin-8-yl)-phenyl]-3-(4-methanesulfonyl-phenyl)-2-methyl-propionic acid methyl ester

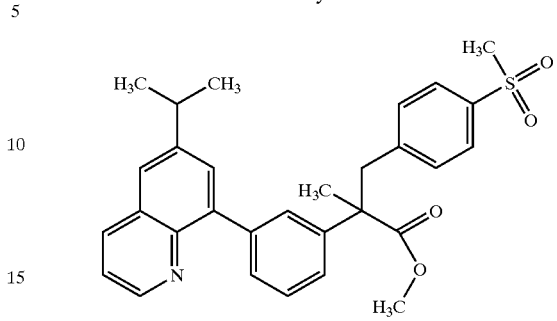

To a solution of Example 92 (90 mg, 0.185 mmol) in THF/DMF (1:1, 2 mL) at −78° C. was added potassium tert-butoxide (1M, 0.19 mL, 0.19 mmol) dropwise followed by MeI (0,014 mL, 0.22 mmol) after 15 min. The resulting reaction mixture was stirred 18 h at 21° C., then diluted with a saturated ammonium chloride solution and ethyl acetate. The organic extracts were washed (H$_2$O, brine), dried (MgSO$_4$), filtered and concentrated. Purification by flash chromatography (eluting with hexane/ethyl acetate, 50:50) provided the title compound.

$^1$H NMR (300 MHz, acetone-d6): δ 8.84 (dd, 1H), 8.30 (dd, 1H), 7.80–7.70 (m, 5H), 7.62 (d, 1H), 7.49 (dd, 1H), 7.40 (m, 3H), 7.30 (d, 1H), 3.70 (s, 3H), 3.52 (dd, 2H), 3.20 (m, 1H), 3.03 (s, 3H), 1.55 (s, 3H), 1.40 (d, 6H).

EXAMPLE 100

2-{3-[6-(1-Methanesulfonyl-1-methyl-ethyl)-quinolin-8-yl]-phenyl}-1-(4-methanesulfonyl-phenyl)-cyclopropanecarboxylic acid

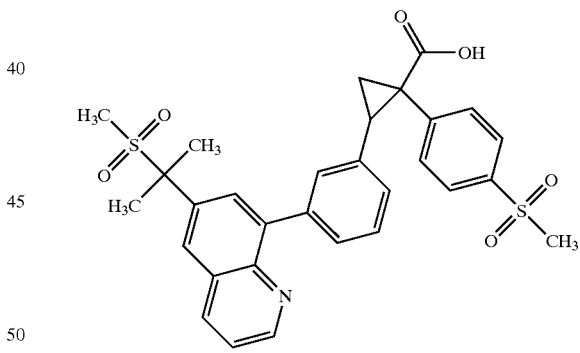

Step 1: 3-{3-[6-(1-Methanesulfonyl-1-methyl-ethyl)-quinolin-8-yl]-phenyl}-2-(4-methanesulfonyl-phenyl)-acrylic acid Following the procedures described above in Example 80, Step 1, but substituting Quinoline 03 for 3-bromobenzaldehyde, the 3-{3-[6-(1-methanesulfonyl-1-methyl-ethyl)-quinolin-8-yl]-phenyl}-2-(4-methanesulfonyl-phenyl)-acrylic acid compound was obtained as a white solid.

Step 2: 3-{3-[6-(1-Methanesulfonyl-1-methyl-ethyl)-quinolin-8-yl]-phenyl}-2-(4-methanesulfonyl-phenyl)-acrylic acid methyl ester Following the procedures described above in Ester 01, the 3-{3-[6-(1-methanesulfonyl-1-methyl-ethyl)-quinolin-8- yl]-phenyl}-2-(4-methanesulfonyl-phenyl)-acrylic acid methyl ester compound was obtained as a white solid.

Step 3: 2-{3-[6-(1-Methanesulfonyl-1-methyl-ethyl)-quinolin-8-yl]-phenyl}-1-(4-methanesulfonyl-phenyl)-cyclopropanecarboxylic acid methyl ester To a suspension of trimethylsulfoxonium iodide (400 mg, 1.83 mmol) in DMSO (25 mL) at 0° C. was added NaH (60%, 73 mg, 1.83 mmol). After 30 min., 3-{3-[6-(1-methanesulfonyl-1-methyl-ethyl)-quinolin-8-yl]-phenyl}-2-(4-methanesulfonyl-phenyl)-acrylic acid methyl ester from Step 2 (688 mg, 1.22 mmol) was added and the resulting reaction mixture stirred for 18 h at 21° C., then diluted with water and ethyl acetate. The organic extracts were washed ($H_2O$, brine), dried ($MgSO_4$), filtered and concentrated. Purification by flash chromatography (eluting with toluene/acetone, 80:20) provided the 2-{3-[6-(1-methanesulfonyl-1-methyl-ethyl)-quinolin-8-yl]-phenyl}-1-(4-methanesulfonyl-phenyl)-cyclopropanecarboxylic acid methyl ester compound.

Step 4: 2-{3-[6-(1-Methanesulfonyl-1-methyl-ethyl)-quinolin-8-yl]-phenyl}-1-(4-methanesulfonyl-phenyl)-cyclopropanecarboxylic acid Following the procedures described above in Example 08, the 2-{3-[6-(1-methanesulfonyl-1-methyl-ethyl)quinolin-8-yl]-phenyl}-1-(4-methanesulfonyl-phenyl)-cyclopropanecarboxylic acid compound was obtained as a white solid.

$^1$H NMR (400 MHz, acetone-d6): δ 8.91 (dd, 1H), 8.44 (dd, 1H), 8.26 (d, 1H), 8.13 (d, 1H), 7.92 (d, 2H), 7.85 (d, 2H), 7.80 (s, 1H), 7.66 (d, 1H), 7.55 (dd, 1H), 7.52 (d, 1H), 7.45 (m, 1H), 3.12 (s, 3H), 3.06 (t, 1H), 2.73 (s, 3H), 2.42 (dd, 1H), 1.98 (s, 6H), 1.74 (dd, 1H).

EXAMPLE 101

[2-{3-[6-(1-Methanesulfonyl-1-methyl-ethyl)-quinolin-8-yl]-phenyl}-1-(4-methanesulfonyl-phenyl)-cyclopropyl]-methanol

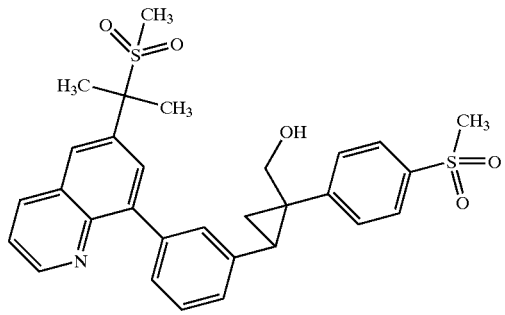

Using the compound from Example 100, Step 3 as the starting material and following the procedures described above in Example 15 and purification by flash chromatography (eluting with $CH_2Cl_2$/ethyl acetate, 60:40) provided the title compound.

$^1$H NMR (300 MHz, acetone-d6): δ 8.86 (dd, 1H), 8.45 (dd, 1H), 8.28 (d, 1H), 8.20 (d, 1H), 7.91 (brs, 1H), 7.87 (d, 2H), 7.80 (d, 2H), 7.55 (m, 2H), 7.48 (m, 2H), 3.95 (dd, 1H), 3.75 (dd, 1H), 3.55 (dd, 1H), 3.09 (s, 3H), 2.75 (m, 1H), 2.71 (s, 3H), 2.00 (s, 3H), 1.99 (s, 3H), 1.58 (dd, 1H), 1.46 (dd, 1H).

EXAMPLE 102

2-[2-{3-[6-(1-Methanesulfonyl-1-methyl-ethyl)-quinolin-8-yl]-phenyl}-1-(4-methanesulfonyl-phenyl)-cyclopropyl]-propan-2-ol

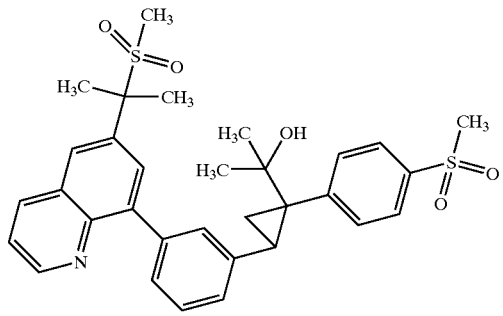

Using the compound from Example 100, Step 3 as the starting material and following the procedures described above in Example 29 and purification by flash chromatography (eluting with $CH_2Cl_2$/ethyl acetate, 60:40) provided the title compound.

$^1$H NMR (300 MHz, acetone-d6): δ 8.90 (dd, 1H), 8.45 (dd, 1H), 8.28 (d, 1H), 8.19 (d, 1H), 7.99 (s, 1H), 7.87 (s, 4H), 7.56 (m, 3H), 7.47 (t, 1H), 3.10 (s, 3H), 2.72 (s, 3H), 2.55 (t, 1H), 2.04 (m, 1H), 2.00 (s, 3H), 1.99 (s, 3H), 1.32 (dd, 1H), 1.17 (s, 3H), 1.06 (s, 3H).

EXAMPLE 103

8-{4-Fluoro-3-[2-(4-methanesulfonyl-phenyl)ethyl]-phenyl}-6-isopropyl-quinoline

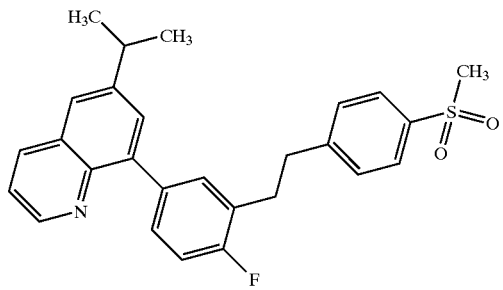

Step 1: 4-Fluoro-3-hydroxymethyl-benzene-boronic acid

To a solution of 4-bromo-2-fluoro-benzyl alcohol (10 g, 49 mmol) in TBF (500 mL) at −78° C. was added BuLi (2.5M, 43 mL, 107 mmol) dropwise keeping the internal temperature below −73° C. After 25 min., trimethylborate (25 mL, 107 mmol) was added and the resulting reaction mixture stirred for 15 h at −78° C., 1 h at 21° C., then diluted with HCl 10% and ethyl acetate. The organic extracts were washed ($H_2O$, brine), dried ($MgSO_4$), filtered and concentrated. The residue was solidified from hexane/ethyl acetate with water (5 drops) to afford the 4-fluoro-3-hydroxymethyl-benzene-boronic acid compound as a white solid.

Step 2: [2-Fluoro-5-(6-isopropyl-quinolin-8-yl)-phenyl]-methanol

Following the procedures described above in Quinoline 01, Step 3, and purification by flash chromatography (eluting with hexane/ethyl acetate, 70:30) provided the [2-fluoro-5-(6-isopropyl-quinolin-8-yl)-phenyl]-methanol compound.

Step 3: 2-Fluoro-5-(6-isopropyl-quinolin-8-yl)-benzaldehyde

A solution of [2-fluoro-5-(6-isopropyl-quinolin-8-yl)-phenyl]-methanol from Step 2 (2.23 g, 7.55 mmol) and MnO₂ (13 g, 150 mmol) in CH₂Cl₂ (70 mL) was stirred at 21° C. for 18 h. The mixture was filtered through a pad of celite and concentrated. Purification by flash chromatography (eluting with hexane/ethyl acetate, 70:30) provided the 2-fluoro-5-(6-isopropylquinolin-8-yl)-benzaldehyde compound.

Step 4: 8-{4-Fluoro-3-[2-(4-methanesulfonyl-phenyl)-vinyl]-phenyl}-6-isopropyl-quinoline A solution of 4-methanesulfonylbenzyl chloride (10 g, 49 mmol) and triphenylphosphine (12.8 g, 49 mmol) in acetonitrile (100 mL) was stirred for 18 h at reflux. The resulting reaction mixture was cooled to 21° C. and the phosphorus salt crystallised from CH₃CN/ether. To a suspension of the salt (875 mg, 1.87 mmol) in THF (15 mL) at 0° C. was added potassium tert-butoxide (1M, THF, 1.87 mL, 1.87 mmol) dropwise and the resulting mixture stirred 30 min at 0° C. The mixture was cooled to −78° C. and the 2-fluoro-5-(6-isopropyl-quinolin-8-yl)-benzaldehyde from Step 3 (0.5 g, 1.7 mmol, in THF) was added. After 90 min. at 21° C., the reaction mixture was diluted with HCl 10% and ethyl acetate. The organic extracts were washed (H₂O, brine), dried (MgSO₄), filtered and concentrated. Purification by flash chromatography (eluting with hexane/ethyl acetate, 60:40) provided the 8-{4-fluoro-3-[2-(4-methanesulfonyl-phenyl)-vinyl]-phenyl}-6-isopropyl-quinoline compound as a mixture of isomer (3:1).

Step 5: 8-{4-Fluoro-3-[2-(4-methanesulfonyl-phenyl)-ethyl]-phenyl}-6-isopropyl-quinoline A solution of 8-{4-fluoro-3-[2-(4-methanesulfonyl-phenyl)-vinyl]-phenyl}-6-isopropyl-quinoline from Step 4 (200 mg, 0.45 mmol) and polymer supported phenylsulfonyl hydrazide (1.0 g) in toluene (10 mL) was heated at 100° C. for 18 h. The resulting mixture was cooled at 21° C., filtered and the solvent evaporated. Purification by flash chromatography (eluting with hexane/ethyl acetate, 70:30 to 40:60) provided the 8-{4-fluoro-3-[2-(4-methanesulfonyl-phenyl)-ethyl]-phenyl}-6-isopropyl-quinoline compound.

¹H NMR (300 MHz, acetone-d6): δ 8.82 (dd, 1H), 8.30 (dd, 1H), 7.87 (d, 2H), 7.78 (dd, 1H), 7.70–7.59 (m, 3H), 7.55 (d, 2H), 7.45 (dd, 1H), 7.17 (dd, 1H), 3.15 (m, 1H), 3.10 (brs, 4H), 3.05 (s, 3H), 1.40 (d, 6H).

EXAMPLE 104

8-{2-Fluoro-5-[2-(4-methanesulfonyl-phenyl)-ethyl]-phenyl}-6-isopropyl-quinoline

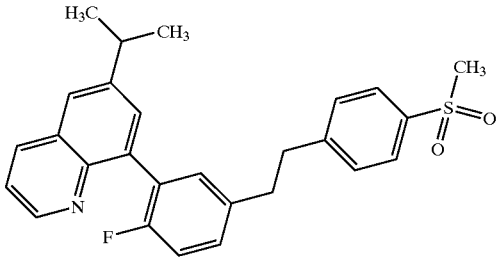

Following the procedures described above in Example 103, but substituting 3-bromo-4-fluorobenzyl alcohol for 4-bromo-2-fluoro-benzyl alcohol, the title compound was obtained.

¹H NMR (300 MHz, acetone-d6): δ 8.78 (dd, 1H), 8.30 (dd, 1H), 7.83 (d, 2H), 7.81 (d, 1H), 7.63 (d, 1H), 7.51 (d, 2H), 7.45 (dd, 1H), 7.32 (m, 2H), 7.10 (dd, 1H), 3.15 (m, 1H), 3.10 (m, 4H), 3.04 (s, 3H), 1.37 (d, 6H).

EXAMPLE 105

8-{3-[2-Cyclopropanesulfonyl-2-fluoro-2-(4-methanesulfonyl-phenyl)-ethyl]-phenyl}-6-(1-methanesulfonyl-1-methyl-ethyl)-quinoline

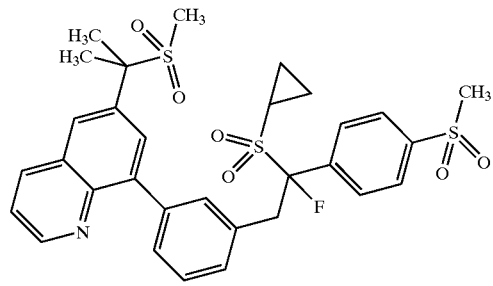

Following the procedures described above in Example 1, but substituting Sulfone 03 for Ketone 02 and then using the procedures described in Example 37 (2 steps in a one pot reaction) followed by purification by flash chromatography (eluting with ethyl acetate/hexane) afforded the title compound as a pale beige powder. The enantiomers can be separated on a chiral column (ChiralPaK AD, hexane/EtOH/i-PrOH/MeOH, 30:30:30:10, retention time 8.1 and 10.2 min) to give Examples 105A and Example 105B.

¹H NMR (400 MHz, ace-d6): δ 8.88 (dd, 1H), 8.42 (dd, 1H), 8.23 (d, 1H), 8.01–7.94 (m, 5H), 7.57–7.53 (s, 3H), 7.30 (t, 1H), 7.24 (d, 1H), 4.05–3.97 (m, 2H), 3.08 (s, 3H), 2.70 (s, 3H), 2.49–2.43 (m, 1H), 1.97 (s, 3H), 1.96 (s, 3H), 1.18–1.08 (m, 2H), 1.00–0.93 (m, 1H), 0.84–0.77 (m, 1H).

EXAMPLE 106

2-(4-Cyclopropanesulfonyl-phenyl)-4-hydroxy-1-{3-[6-(1-methanesulfonyl-1-methyl-ethyl)-quinolin-8-yl]-phenyl}-4-methyl-pentan-3-one

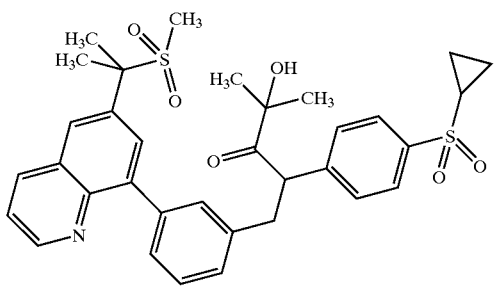

Example 106 was prepared by following the procedures described above in Example 1, but substituting Sulfone 09 for Ketone 02. Purification by flash chromatography (eluting with ethyl acetate/hexane, 1:1 to 8:2) afforded the title compound.

$^1$H NMR (400 MHz, ace-d6): δ 8.93 (dd, 1H), 8.44 (dd, 1H), 8.26 (d, 1H), 8.05 (d, 1H), 7.83 (d, 2H), 7.67 (d, 2H), 7.58–7.54 (m, 2H), 7.51 (app d, 1H), 7.33 (t, 1H), 7.22 (app d, 1H), 5.18 (d, 1H), 4.48 (s, 1H), 3.45 (dd, 1H), 3.07 (dd, 1H), 2.71 (s, 3H), 2.60 (m, 1H), 1.95 (s, 6H), 1.14 (dd, 2H), 1.10 (s, 3H), 1.05 (s, 3H), 1.00 (m, 2H).

EXAMPLE 107

4-Ethyl-4-hydroxy-1-{3-[6-(1-methanesulfonyl-1-methyl-ethyl)-quinolin-8-yl]-phenyl}-2-(4-methanesulfonyl-phenyl)-hexan-3-one

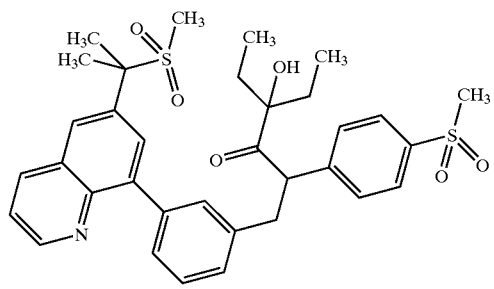

Example 107 was prepared by following the procedures described above in Example 1, but substituting Ketone 12 for Ketone 02. Purification by flash chromatography (eluting with ethyl acetate/hexane, 3:2) afforded the title compound as a white foam.

$^1$H NMR (400 MHz, acetone-d6): δ 9.93 (dd, 1H), 8.44 (dd, 1H), 8.25 (d, 1H), 8.03 (d, 1H), 7.85 (m, 2H), 7.67 (m, 2H), 7.57 (m, 2H), 7.48 (dd, 1H), 7.32 (t, 1H), 7.20 (dd, 1H), 5.13 (t, 1H), 4.15 (s, OH), 3.42 (dd, 1H), 3.09 (dd, 1H), 3.03 (s, 3H), 2.72 (s, 3H), 1.98 (s, 6H), 1.6–1.4 (m, 4H), 0.49 (t, 6H).

EXAMPLE 108

8-{3-[2,2-Bis-(4-chloro-phenyl)-cyclopropyl]-phenyl}-6-isopropyl-quinoline

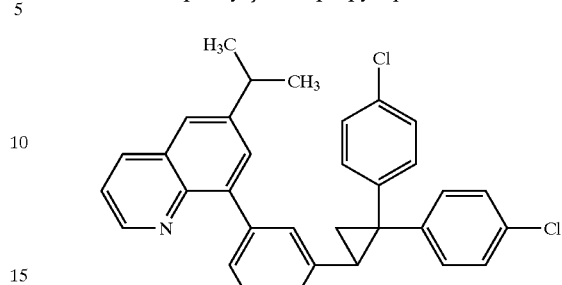

Step 1: [Bis-(4-chloro-phenyl)-methylene]-hydrazine

A solution of bis-(4-chloro-phenyl)-methanone (5.0 g, 19.9 mmol) and hydrazine monohydrate (5 mL, 103 mmol) in ethanol (25 mL) was heated to reflux 18 h, cooled to 21° C., and filtered to afforded the [bis-(4-chloro-phenyl)-methylene]-hydrazine compound as a yellow solid.

Step 2: Diazo bis-(4-chloro-phenyl)-methane

To a solution of [bis-(4-chloro-phenyl)-methylene]-hydrazine from Step 1 (2.0 g, 7.5 mmol) in CHCl$_3$ (20 mL) was added MnO$_2$ (5.0 g, 57 mmol). The resulting reaction mixture was stirred 1 h at 21° C., then filtered on a bed of MgSO$_4$ and the filtrate concentrated to provided the diazo bis-(4-chloro-phenyl)-methane compound as a purple solid.

Step 3: 6-Isopropyl-8-(3-vinyl-phenyl)-quinoline

To a solution of methyl triphenylphosphonium bromide (5.2 g, 14.6 mmol) in THF (20 mL) at 0° C. was added potassium tert-butoxide (1M, THF, 14.5 mL, 14.5 mmol) followed, after 15 min, by Quinoline 04 (3.33 g, 12.1 mmol) in THF (5 mL). The resulting reaction mixture was stirred 2 h at 0° C., then diluted with a saturated ammonium chloride solution and ethyl acetate. The organic extracts were washed (H$_2$O, brine), dried (MgSO$_4$), filtered and concentrated. Purification by flash chromatography (eluting with hexane/ethyl acetate, 90:10) provided the 6-isopropyl-8-(3-vinyl-phenyl)-quinoline compound.

Step 4: 8-{3-[2,2-Bis-(4-chloro-phenyl)-cyclopropyl]-phenyl}-6-isopropyl-quinoline A solution of the 6-isopropyl-8-(3-vinyl-phenyl)-quinoline from Step 3 (230 mg, 0.84 mmol) and the diazo bis-(4-chloro-phenyl)-methane from Step 2 (530 mg, 2.0 mmol) in benzene (10 mL) was heated to reflux for 18 h, cooled to 21° C., and purified by flash chromatography (eluting with hexane/ethyl acetate, 90:10) to provide the 8-{3-[2,2-bis-(4-chloro-phenyl)-cyclopropyl]-phenyl}-6-isopropyl-quinoline compound as a yellow foam.

$^1$H NMR (400 MHz, acetone-d$_6$): δ 8.79 (dd, 1H), 8.28 (dd, 1H), 7.73 (d, 1H), 7.47–7.39 (m, 4H), 7.33–7.21 (m, 8H), 7.14 (m, 2H), 3.13 (m, 1H), 3.03 (dd, 1H), 2.18 (dd, 1H), 1.80 (dd, 1H), 1.36 (d, 6H).

EXAMPLE 109

8-{3-[2,2-Bis-(4-methanesulfonyl-phenyl)-cyclopropyl]-phenyl}-6-isopropyl-quinoline

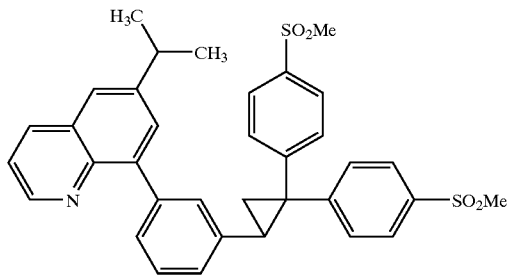

Step 1: Bis-(4-methylsulfanyl-phenyl)-methanol

To a solution of 4-bromothioanisole (1.06 g, 5.2 mmol) in THF (20 mL) at −78° C. was added BuLi (2.3M, hexane, 2.2 mL, 5 mmol) dropwise. After 30 min at −78° C., 4-methylthiobenzaldehyde (685 mg, 4.5 mmol) was added. After 20 min., the resulting reaction mixture was diluted with a saturated ammonium chloride solution and ethyl acetate. The organic extracts were washed ($H_2O$, brine), dried ($MgSO_4$), filtered and concentrated. Purification by flash chromatography (eluting with hexane/ethyl acetate, 80:20) provided the bis-(4-methylsulfanyl-phenyl)-methanol compound.

Step 2: Bis-(4-methylsulfanyl-phenyl)-methanone

A solution of bis-(4-methylsulfanyl-phenyl)-methanol from Step 1 (1.0 g, 3.6 mmol) and $MnO_2$ (3 g, 35 mmol) in $CH_2Cl_2$ (30 mL) was stirred at 21° C. for 18 h. The resulting mixture was filtered through a pad of celite and concentrated. Purification by flash chromatography (eluting with hexane/ethyl acetate, 85:15) provided the bis-(4-methylsulfanyl-phenyl)-methanone compound.

Step 3: Bis-(4-methanesulfonyl-phenyl)-methanone

A solution of bis-(4-methylsulfanyl-phenyl)-methanone from Step 2 (0.9 g, 3.2 mmol), NMO (2.2 g, 19 mmol) and $OsO_4$ (4%, $H_2O$, 1 mL, 0.16 mmol) in acetone (20 mL) was stirred 18 h at 21° C. The resulting reaction mixture was diluted with a sodium metabisulfite solution and ethyl acetate. The organic extracts were washed ($H_2O$, brine), dried ($MgSO_4$), filtered and concentrated. Purification by flash chromatography (eluting with hexane/ethyl acetate, 70:30) provided the bis-(4-methanesulfonyl-phenyl)-methanone compound.

Step 4: 8-{3-[2,2-Bis-(4-methanesulfonyl-phenyl)-cyclopropyl]-phenyl}-6-isopropyl-quinoline The procedures described above in Example 108 were followed, but substituting bis-(4-methanesulfonyl-phenyl)-methanone from Step 3 instead of bis-(4-chloro-phenyl)-methanone. Purification by flash chromatography (eluting with ethyl acetate/hexane, 3:7) afforded the 8-{3-[2,2-bis-(4-methanesulfonyl-phenyl)-cyclopropyl]-phenyl}-6-isopropyl-quinoline compound as a white solid.

$^1$H NMR (400 MHz, acetone-$d_6$): δ 8.81 (dd, 1H), 8.29 (dd, 1H), 7.88 (d, 2H), 7.76–7.70 (m, 5H), 7.58 (d, 2H), 7.48–7.40 (m, 4H), 7.21 (t, 1H), 7.05 (d, 1H), 3.23 (dd, 1H), 3.14 (m, 1H), 3.09 (s, 3H), 2.93 (s, 3H), 2.4 (dd, 1H), 1.97 (dd, 1H), 1.35 (d, 6H).

EXAMPLES 110 and 111

3-[3-(6-Isopropyl-quinolin-8-yl)-phenyl]-2-pyridin-4-yl-oxirane-2-carbonitrile and 3-[3-(6-Isopropyl-quinolin-8-yl)-phenyl]-2-(1-oxy-pyridin-4-yl)-oxirane-2-carbonitrile

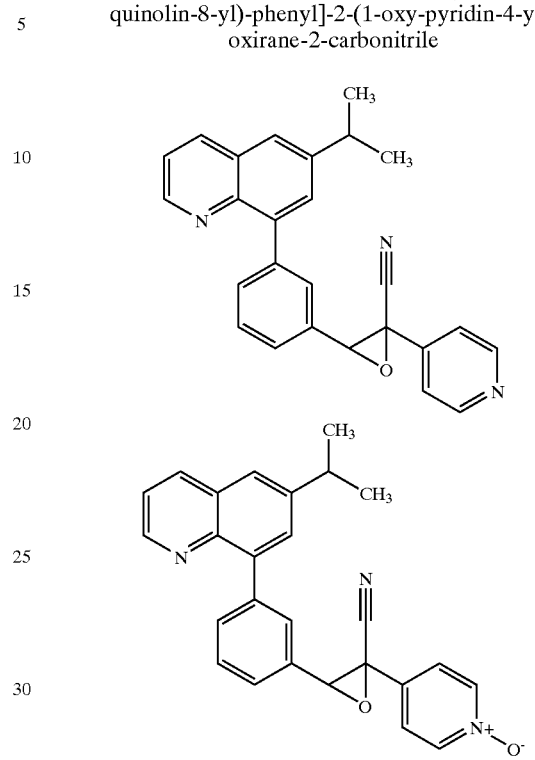

Step 1: 3-[3-(6-Isopropyl-quinolin-8-yl)-phenyl]-2-pyridin-4-yl-acrylonitrile Following the procedures described above in Example 78, Step 2, but substituting 4-methanesulfonylacetonitrile for 4-pyridinylacetonitrile, and purification by flash chromatography (eluting with ethyl acetate/hexane, 3:7) afforded the 3-[3-(6-isopropyl-quinolin-8-yl)-phenyl]-2-pyridin-4-yl-acrylonitrile compound.

Step 2: 3-[3-(6-Isopropyl-quinolin-8-yl)-phenyl]-2-pyridin-4-yl-oxirane-2-carbonitrile To a solution of 3-[3-(6-isopropyl-quinolin-8-yl)-phenyl]-2-pyridin-4-yl-acrylonitrile from Step 1 (75 mg, 0.3 mmol) in $CH_2Cl_2$/MeOH (1:1, 2 mL) was added MMPP (148 mg, 0.3 mmol). The resulting reaction mixture was stirred 18 h at 21° C., then diluted with a sodium bicarbonate solution and ethyl acetate. The organic extracts were washed ($H_2O$, brine), dried ($MgSO_4$), filtered and concentrated. Purification by flash chromatography (eluting with EtOH/ethyl acetate, 10:90) provided the title compounds.

3-[3-(6-Isopropyl-quinolin-8-yl)-phenyl]-2-pyridin-4-yl-oxirane-2-carbonitrile: $^1$H NMR (500 MHz, acetone-$d_6$): δ 8.83 (dd, 1H), 8.74 (m, 2H), 8.32 (dd, 1H), 7.95 (d, 1H), 7.90 (m, 1H), 7.81 (d, 1H), 7.79 (d, 1H), 7.61 (m, 2H), 7.56 (dd, 2H), 7.49 (dd, 1H), 4.7 (s, 1H), 3.18 (m, 1H), 1.38 (d, 3H), 1.37 (d, 3H).

3-[3-(6-Isopropyl-quinolin-8-yl)-phenyl]-2-(1-oxy-pyridin-4-yl)-oxirane-2-carbonitrile: $^1$H NMR (500 MHz, acetone-$d_6$): δ 8.83 (dd, 1H), 8.33 (dd, 1H), 8.27 (m, 2H), 7.92 (s, 1H), 7.90 (m, 1H), 7.81 (d, 1H), 7.78 (d, 1H), 7.61–7.56 (m, 4H), 7.50 (dd, 1H), 4.8 (s, 1H), 3.18 (m, 1H), 1.39 (d, 3H), 1.37 (d, 3H).

EXAMPLES 112 and 113

3-[3-(6-Isopropyl-quinolin-8-yl)-phenyl]-2-pyridin-2-yl-oxirane-2-carboxylic acid ethyl ester and 3-[3-(6-Isopropyl-quinolin-8-yl)-phenyl]-2-(1-oxy-pyridin-2-yl)-oxirane-2-carboxylic acid ethyl ester

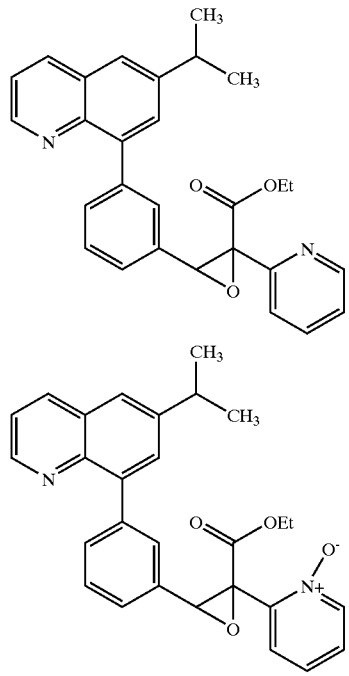

Following the procedures described in Example 110, but substituting 4-pyridinylacetonitrile for ethyl 2-pyridinylacetate, and purification by flash chromatography (eluting with EtOH/ethyl acetate, 10:90) provided the title compounds.

3-[3-(6-Isopropyl-quinolin-8-yl)-phenyl]-2-pyridin-2-yl-oxirane-2-carboxylic acid ethyl ester: $^1$H NMR (500 MHz, acetone-$d_6$): δ 8.80 (dd, 1H), 8.29 (dd, 1H), 8.05 (d, 1H), 7.76 (d, 1H), 7.61 (m, 1H), 7.57 (s, 1H), 7.53 (dd, 1H), 7.50 (d, 1H), 7.46 (dd, 1H), 7.35–7.27 (m, 5H), 5.11 (s, 1H), 4.20 (m, 2H), 3.16 (m, 1H), 1.37 (d, 6H), 1.20 (t, 3H).

3-[3-(6-Isopropyl-quinolin-8-yl)-phenyl]-2-(1-oxy-pyridin-2-yl)-oxirane-2-carboxylic acid ethyl ester: $^1$H NMR (500 MHz, acetone-$d_6$): δ 8.83 (dd, 1H), 8.59 (d, 1H), 8.31 (dd, 1H), 7.89 (m, 1H), 7.87 (m, 2H), 7.75 (m, 2H), 7.48 (m, 3H), 7.42 (m, 1H), 4.9 (s, 1H), 4.05 (m, 2H), 3.18 (m, 1H), 1.39 (d, 3H), 1.37 (d, 3H), 0.89 (t, 3H).

Other variations or modifications, which will be obvious to those skilled in the art, are within the scope and teachings of this invention. This invention is not to be limited except as set forth in the following claims.

What is claimed is:
1. A compound represented by (I):

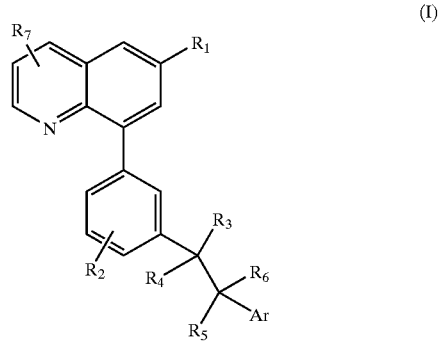

or a pharmaceutically acceptable salt thereof, wherein
Ar is phenyl, pyridinone, pyridyl, or pyridyl N-oxide, optionally substituted with 1–5 independent —$C_{1-6}$alkyl, —OH, —CN, halogen, —$CF_3$, —($C_{0-6}$alkyl)-$SO_n$—($C_{1-6}$alkyl), —($C_{0-6}$alkyl)-$SO_n$—NH—($C_{1-6}$alkyl) or 5-membered heteroaryl ring containing 1–4 heteroatoms independently selected from O, S or N, wherein the 5-membered-ring is optionally substituted with $C_{1-6}$alkyl, and the alkyl group- is optionally substituted with 1–3 independent —OH, —CN, halogen, or —$CF_3$;
$R_1$ is hydrogen, halogen; or a —$C_{1-6}$alkyl, -cyclo$C_{3-6}$alkyl, —$C_{1-6}$alkenyl, —$C_{0-4}$alkyl-C(O)—$C_{0-4}$alkyl, —$C_{1-6}$alkoxy, aryl, heteroaryl, —CN, -heterocyclo$C_{3-6}$alkyl, -amino, —$C_{1-6}$alkylamino, —($C_{1-6}$alkyl)($C_{1-6}$alkyl)amino, —$C_{1-6}$alkyl(oxy)$C_{1-6}$alkyl, —C(O)NH(aryl), —C(O)NH(heteroaryl), —$SO_n$NH(aryl), —$SO_n$NH(heteroaryl), —$SO_n$NH($C_{1-6}$alkyl), —C(O)N($C_{0-6}$alkyl)($C_{0-6}$alkyl), —NH—$SO_n$—($C_{1-6}$alkyl), -carbamoyl, —($C_{1-6}$alkyl-O—C(CN)-dialkylamino, or —$C_{0-6}$alkyl)$SO_n$—$C_{1-6}$alkyl) group, wherein any of the groups is optionally substituted with 1–5 substituents; wherein each substituent is independently a halogen, —OH, —CN, —$C_1$-$C_6$alkyl, —C(O)(heterocyclo$C_{3-6}$alkyl), —C(O)—O—($C_{0-6}$alkyl), —C(O)—O-aryl, alkoxy, cycloalkyloxy, acyl, acyloxy, -cyclo$C_{3-6}$alkyl, heterocyclo$C_{3-6}$alkyl, aryl, heteroaryl, pyridyl N-oxide, carbonyl, carbamoyl, or —$SO_n$—($C_{1-6}$ alkyl);
$R_2$, $R_3$, $R_6$, and $R_7$ are each independently hydrogen, halogen, hydroxyl, —$C_{1-6}$alkyl, or —$C_{1-6}$alkoxy, wherein the alkyl and alkoxy are optionally substituted with 1–3 independently halogen or OH;
$R_4$ is hydrogen, halogen, —CN, phenyl, oxadiazolyl, or —C(O)—O—$C_{0-6}$alkyl, wherein the phenyl, oxadiazolyl, or —C(O)—O—$C_{0-6}$alkyl is optionally substituted with 1–3 independent halogen, CN, CF3, —$SO_n$—$C_{1-6}$alkyl, or $C_{1-6}$alkyl substituents, and the alkyl group is optionally substituted with OH
R5 is hydrogen, hydroxyl, —CN; or a —$C_{1-6}$alkyl, —C(O)$C_{1-6}$alkyl, —C(O)-aryl, —C(O)-pyridyl, —C(O)—O—$C_{0-6}$alkyl, —C(O)—$C_{3-7}$cycloalkyl, —$C_{1-6}$alkyl-$C_{3-7}$cycloalkyl, —$C_{1-6}$alkyl($C_{3-7}$cycloalkyl)$_2$, —$C_{1-6}$alkyl-aryl, —C(O)—N($C_{0-6}$alkyl)$_2$, —$SO_n$aryl, —$SO_n$—$C_{1-6}$alkyl, —$SO_n$—$C_{3-7}$cycloalkyl, —$SO_n$—N($C_{0-6}$alkyl)$_2$, —P(O)($C_{1-6}$alkyl)$_2$, —P(O)($C_{1-6}$alkoxy)$_2$, phenyl, pyridyl, —$SO_n$imidazolyl, —$SO_n$thiazolyl, 5-membered heteroaryl ring containing 1–4 heteroatoms independently selected from O, S or N or oxoisoxaphosphinanyl group, any of which group optionally substituted with 1–6 independent halogen, hydroxyl, —CN, —CF$_3$, —C$_{1-6}$alkyl, —SO$_n$—C$_{1-6}$alkyl, —C(O)—O—C$_{0-6}$alkyl, or hydroxyC$_{1-6}$alkyl substituents;

or R$_5$ and R$_6$ form =O;

or R$_6$ and R$_3$ form —CH$_2$— or —O—; and n is 0, 1, or 2.

2. The compound according to claim 1, or a pharmaceutically acceptable salt thereof, wherein Ar is phenyl optionally substituted with 1–5 independent —C$_{1-6}$alkyl, —OH, —CN, halogen, —CF$_3$, —(C$_{0-6}$alkyl)-SO$_n$—(C$_{1-6}$alkyl), —(C$_{0-6}$alkyl)-SO$_n$—NH—(C$_{1-6}$alkyl) or 5-membered heteroaryl ring containing 1–4 heteroatoms independently selected from O, S or N, wherein the 5-membered-ring is optionally substituted with C$_{1-6}$alkyl, and the alkyl group- is optionally substituted with 1–3 independent —OH, —CN, halogen, or —CF$_3$.

3. The compound according to claim 2, or a pharmaceutically acceptable salt thereof, wherein R$_4$ is hydrogen, halogen, —CN, or —C(O)—O—C$_{0-6}$alkyl, wherein the —C(O)—O—C$_{0-6}$alkyl is optionally substituted with 1–3 independent halogen or C$_{1-4}$alkyl substituents.

4. The compound according to claim 2, or a pharmaceutically acceptable salt thereof, wherein R$_4$ is oxadiazolyl optionally substituted with 1–3 independent halogen or C$_{1-4}$alkyl substituents.

5. The compound according to claim 2, or a pharmaceutically acceptable salt thereof, wherein R$_6$ and R$_3$ form —CH$_2$—.

6. The compound according to claim 1, or a pharmaceutically acceptable salt thereof, wherein Ar is pyridyl or pyridyl N-oxide.

7. The compound according to claim 6, or a pharmaceutically acceptable salt thereof, wherein R$_4$ is phenyl optionally substituted with 1–3 independent halogen or C$_{1-4}$alkyl substituents.

8. The compound according to claim 6, or a pharmaceutically acceptable salt thereof, wherein R$_4$ is hydrogen, halogen, —CN, or —C(O)—O—C$_{0-6}$alkyl, wherein the —C(O)—O—C$_{0-6}$alkyl is optionally substituted with 1–3 independent halogen or C$_{1-4}$alkyl substituents.

9. The compound according to claim 6, or a pharmaceutically acceptable salt thereof, wherein R$_6$ and R$_3$ form —O—.

10. The compound according to claim 1, represented by

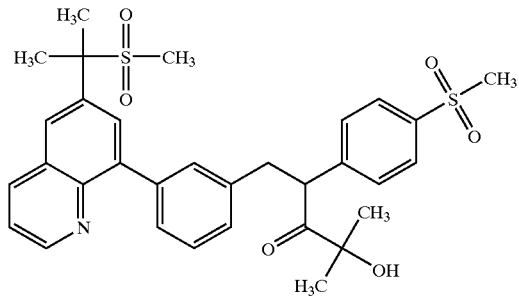

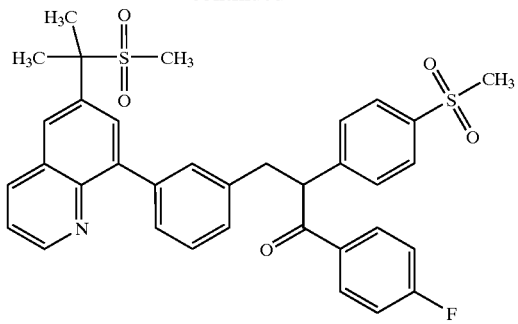

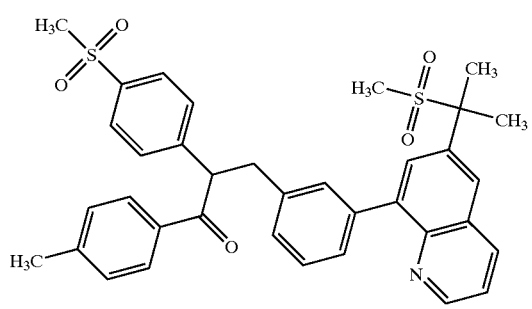

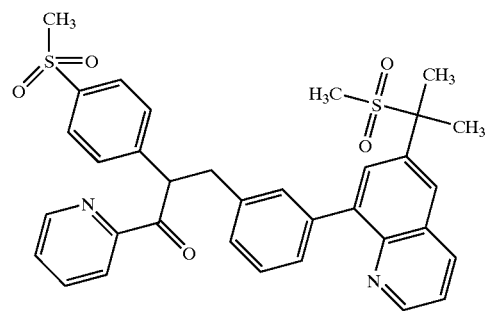

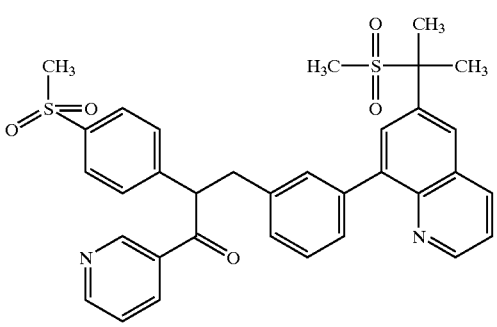

125
-continued
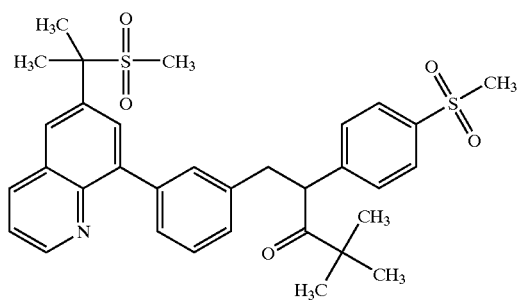
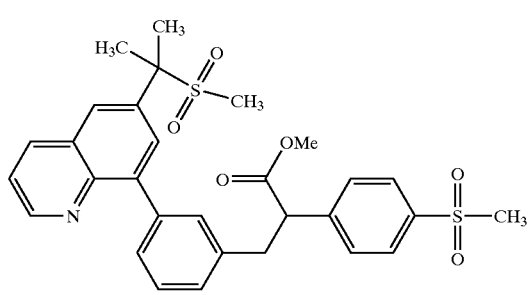
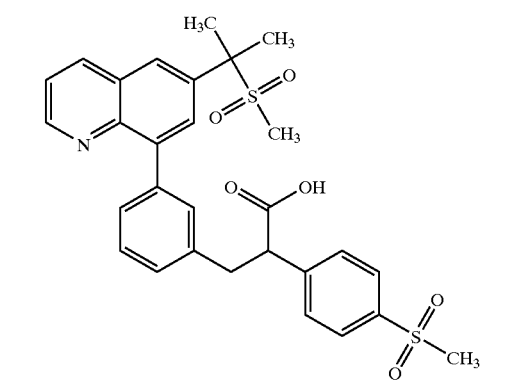
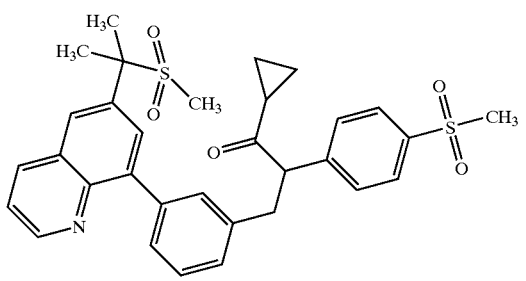
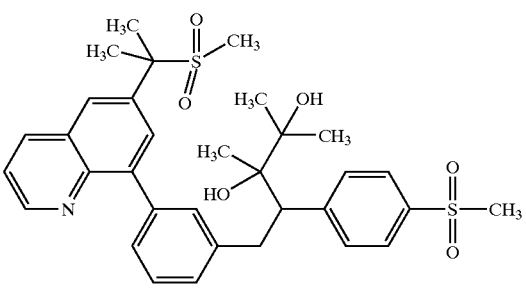
126
-continued
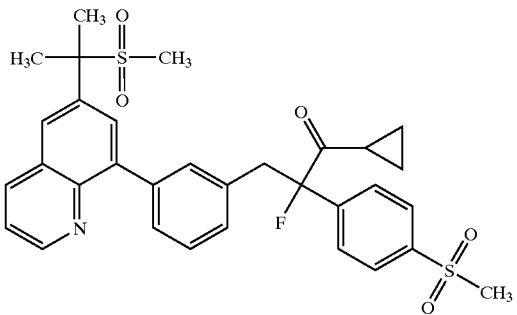
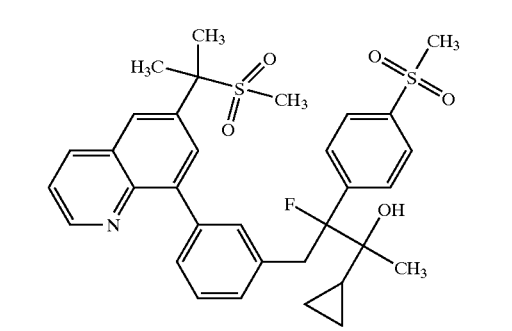
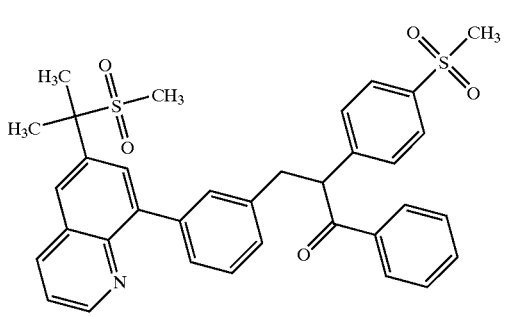
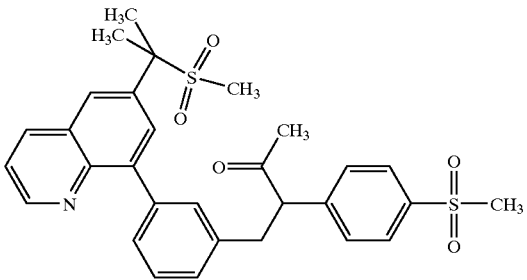
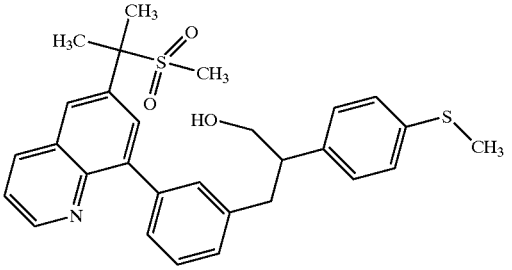

127
-continued
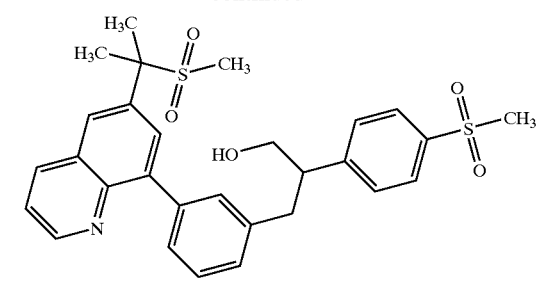
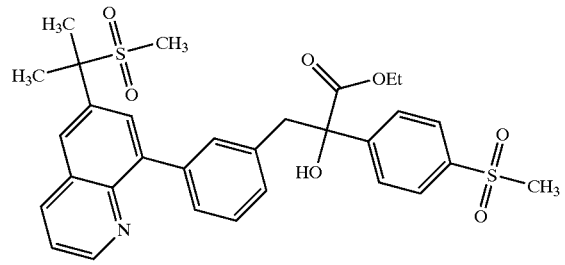
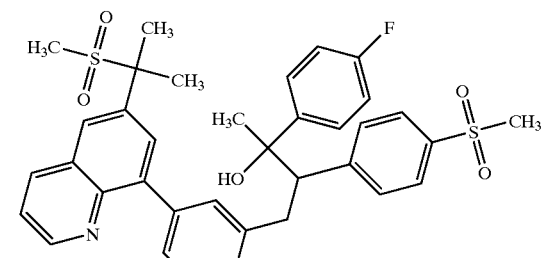
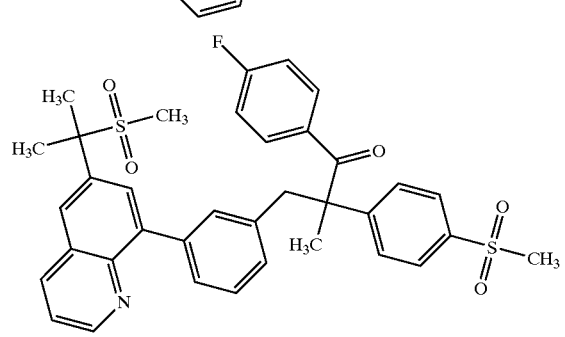
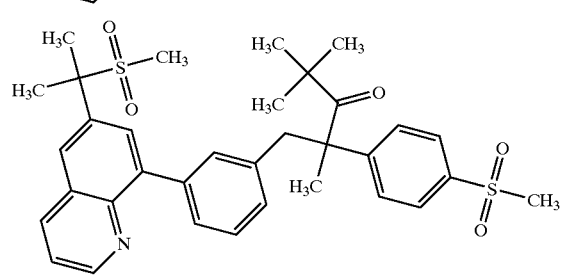
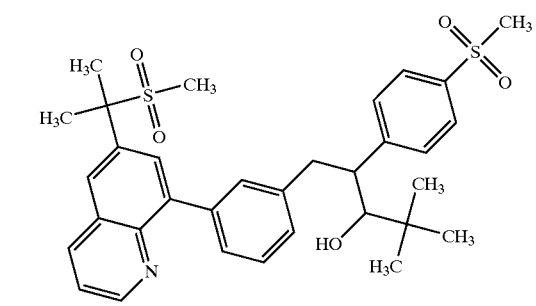
128
-continued
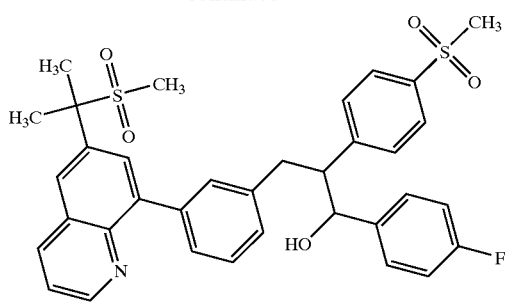
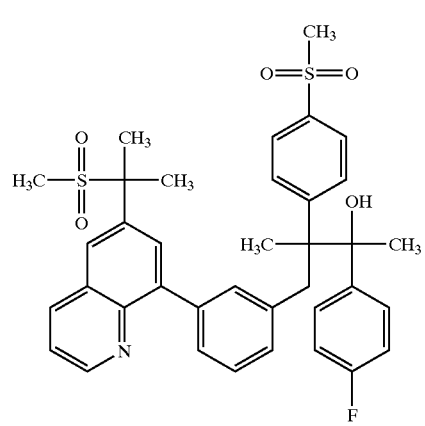
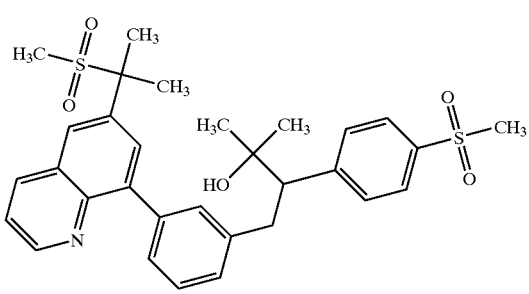
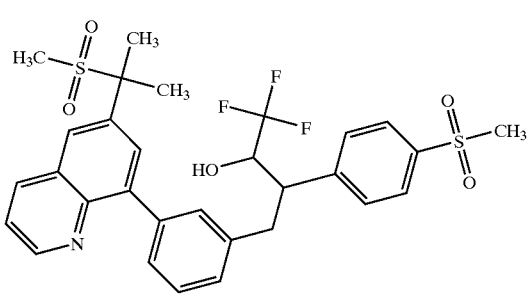
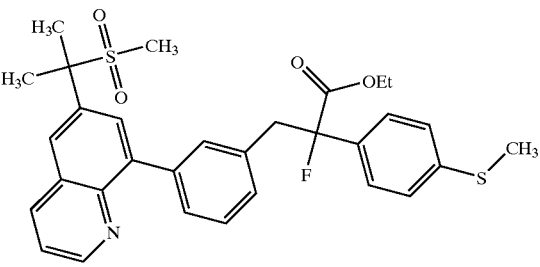

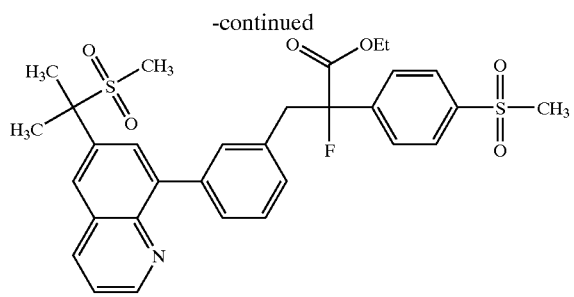
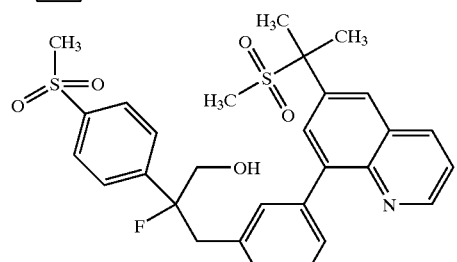
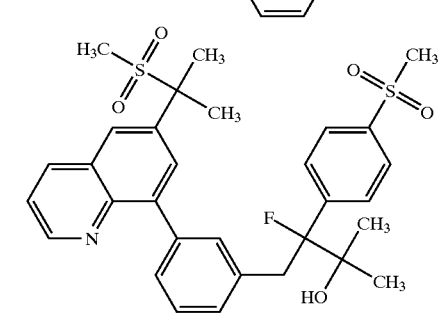
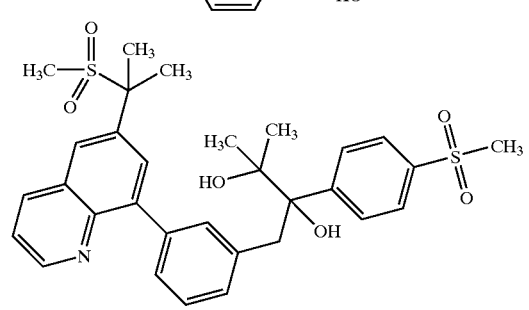
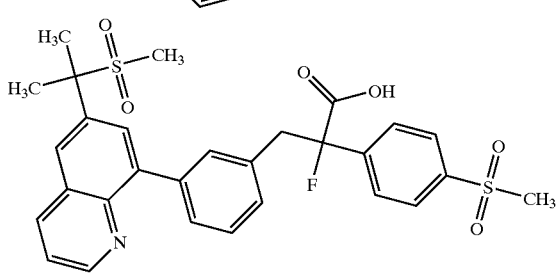
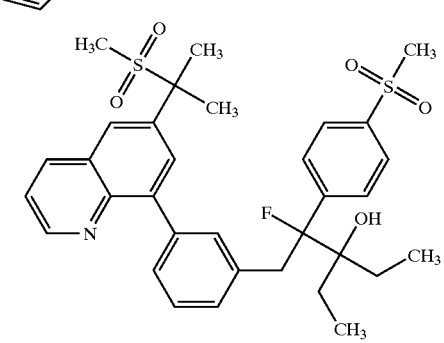
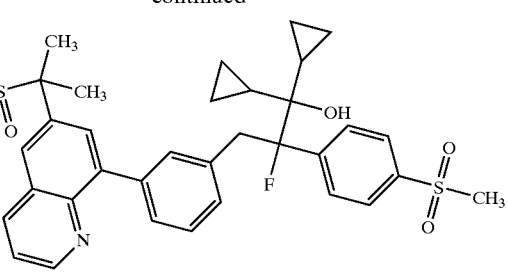
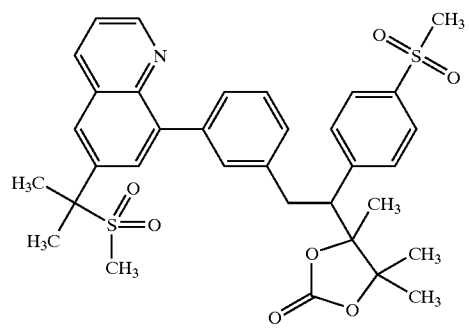
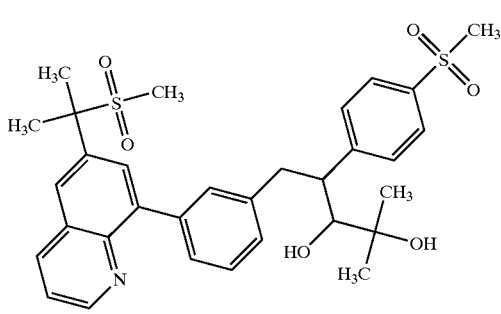
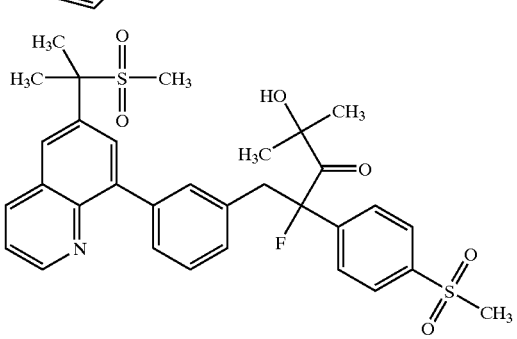
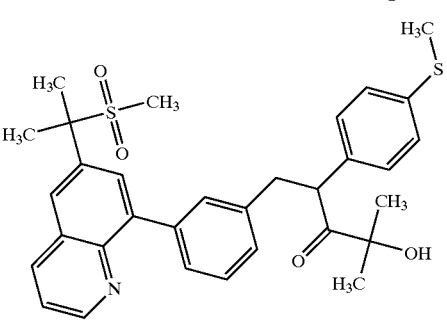

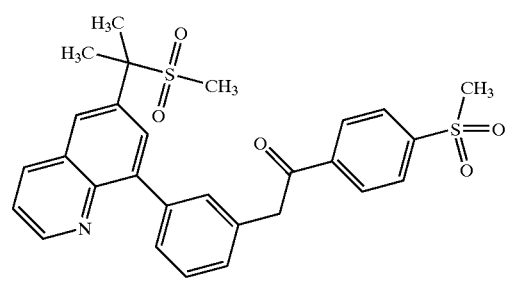
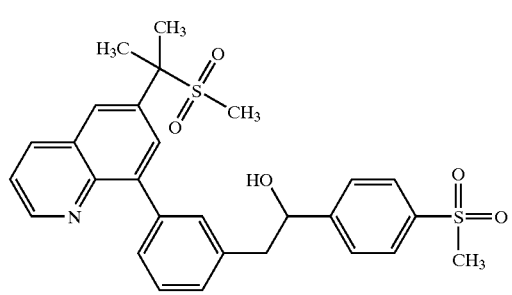
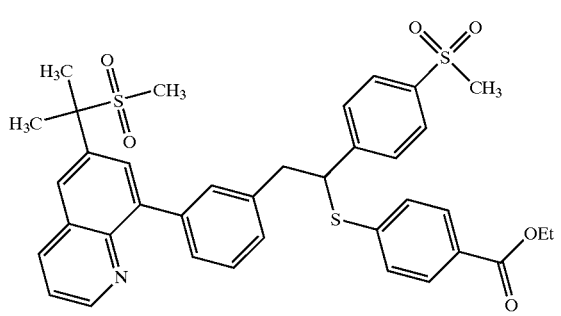
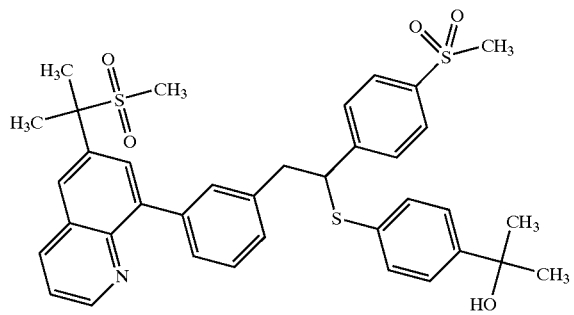
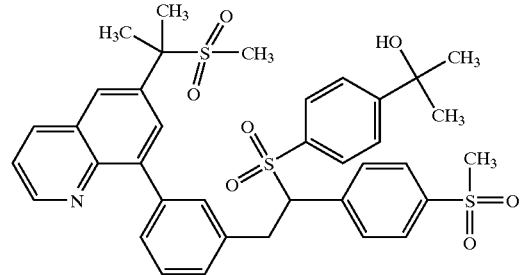
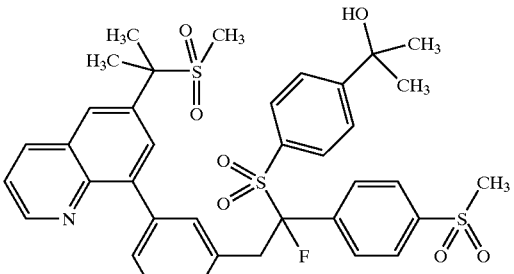
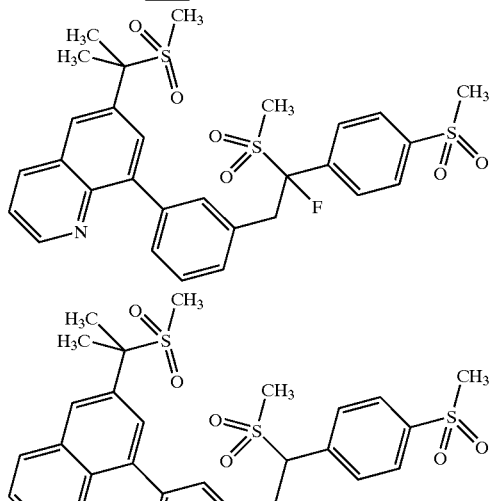
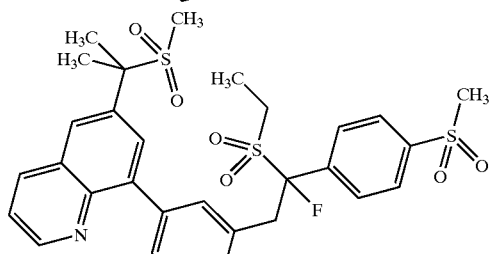
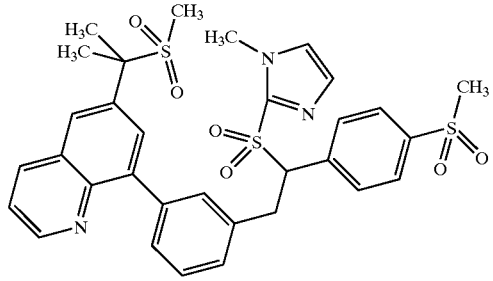
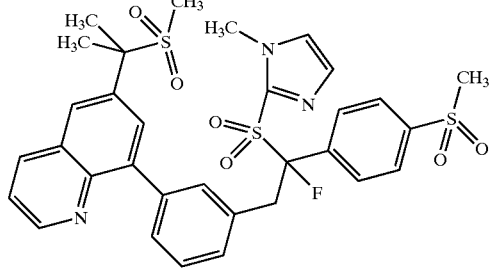

133
-continued
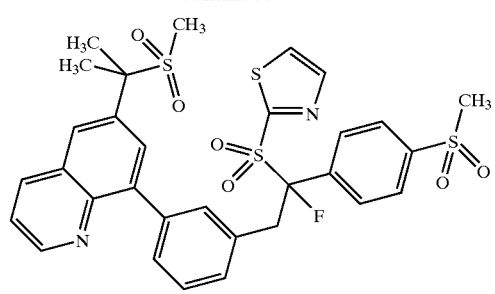
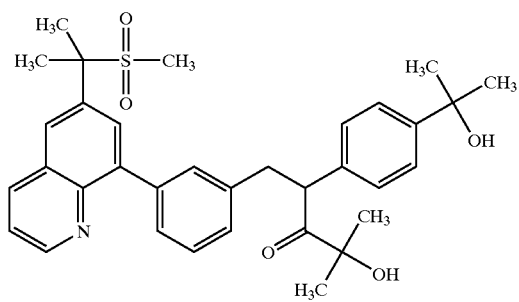
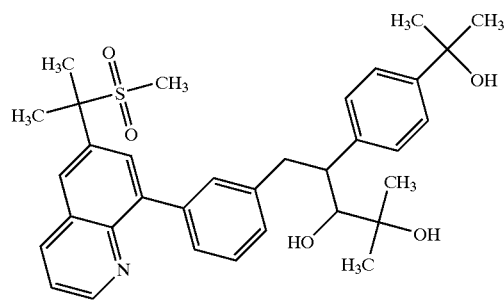
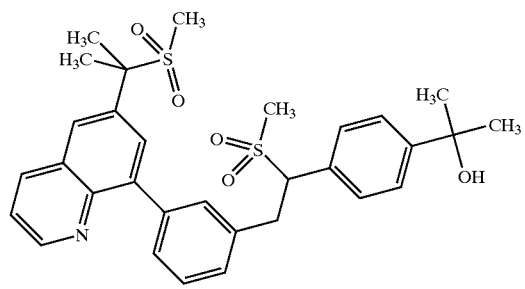
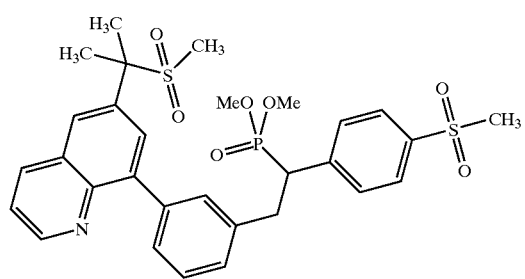
134
-continued
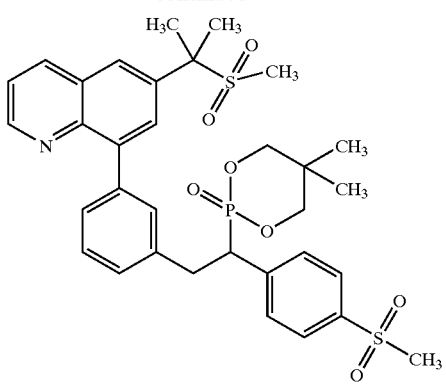
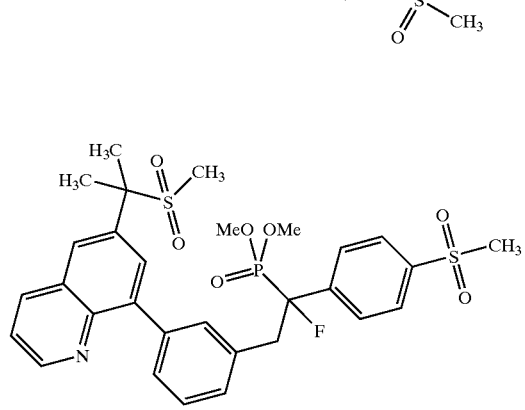
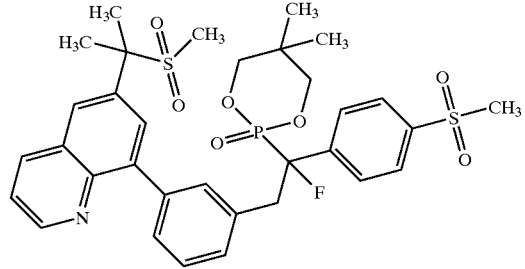
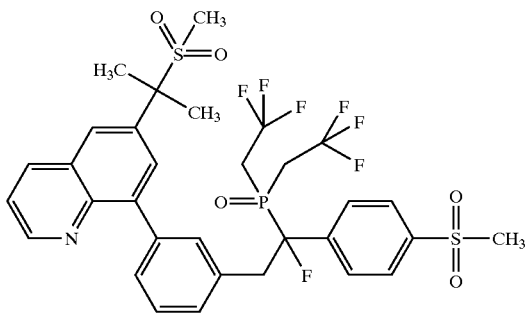
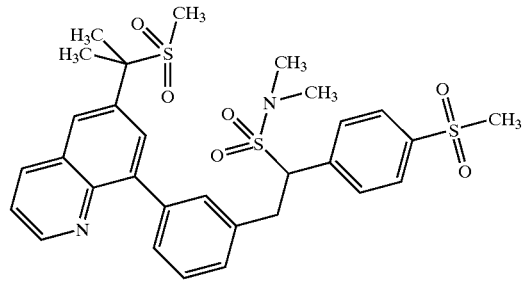

135
-continued
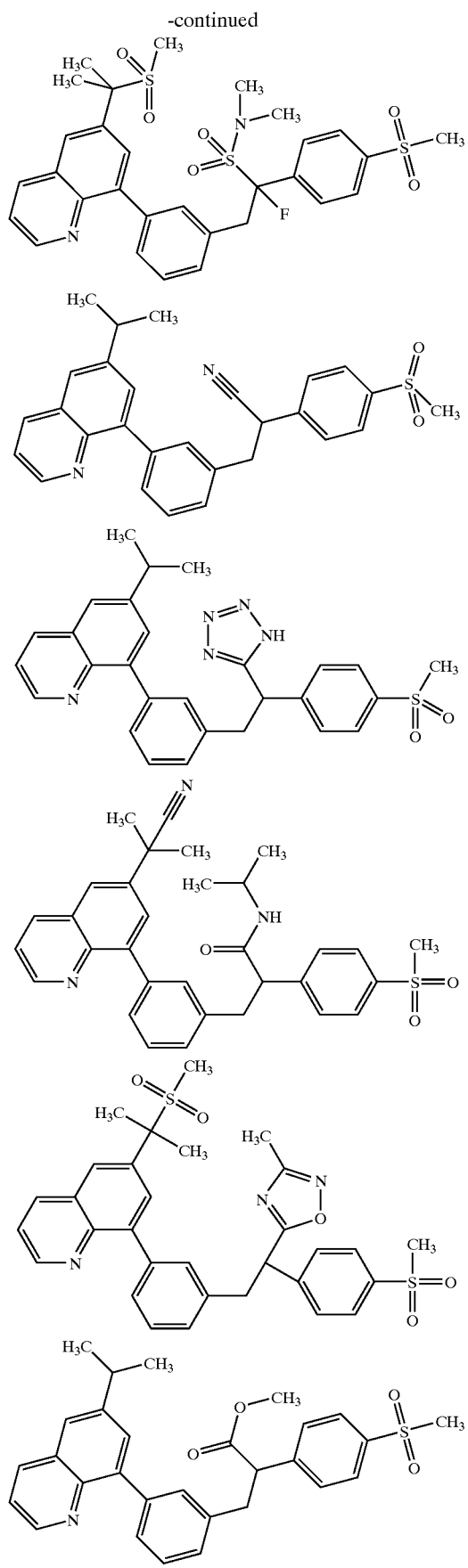
136
-continued
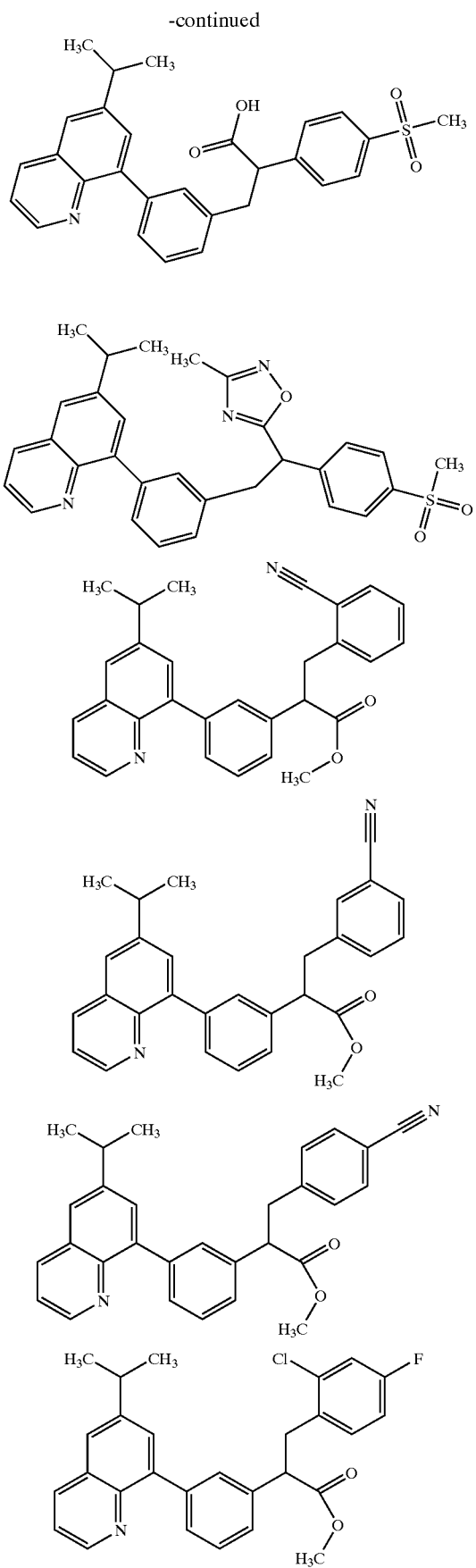

137
-continued
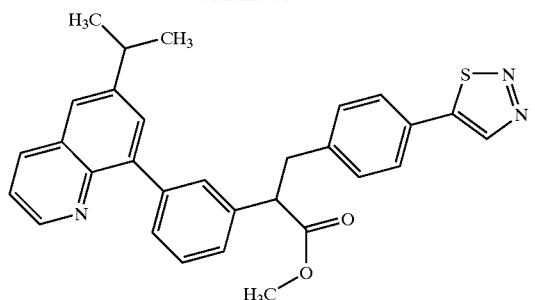
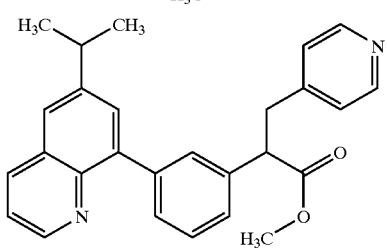
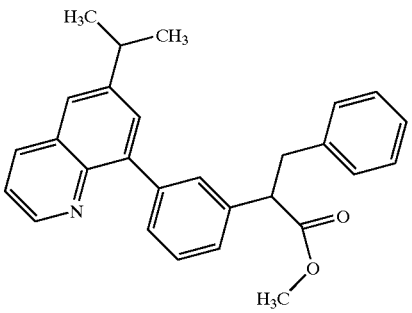
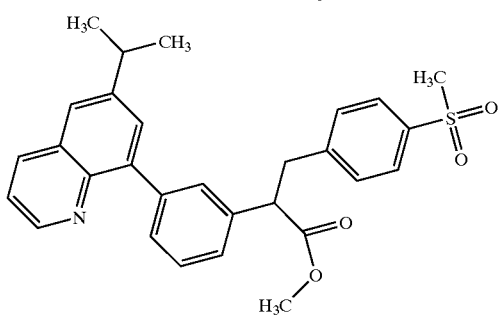
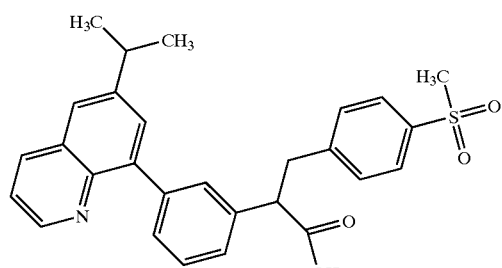
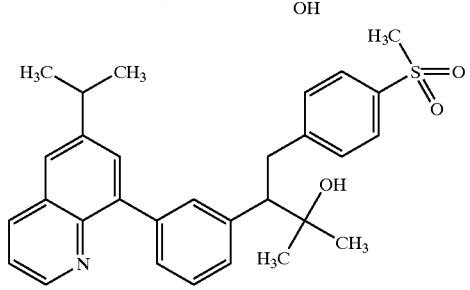
138
-continued
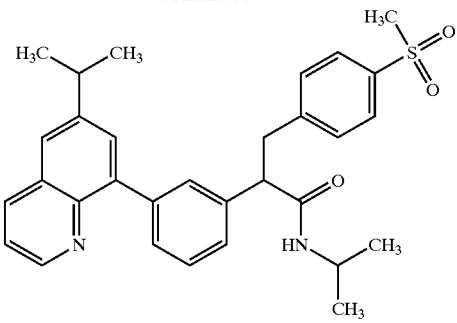
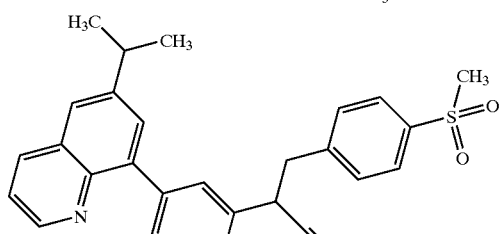
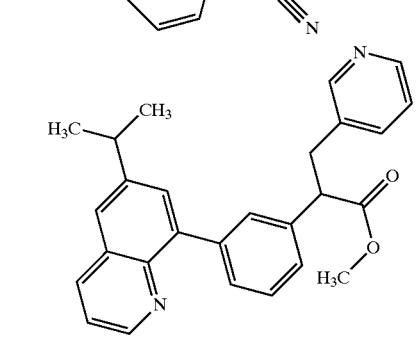
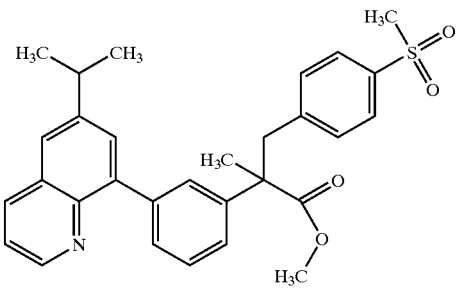
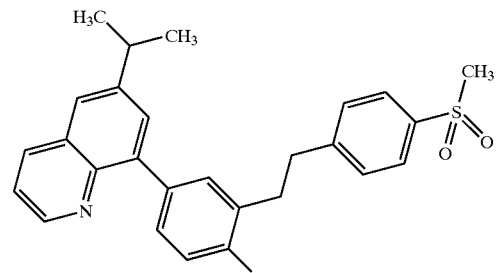
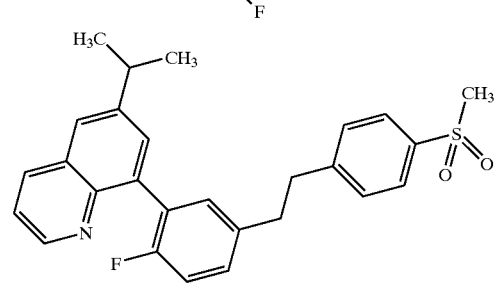

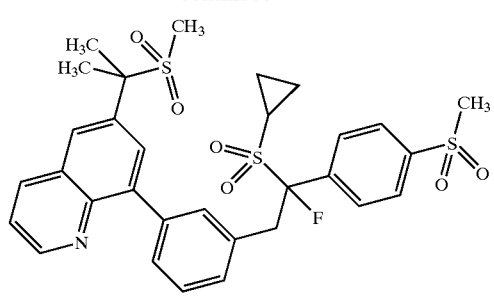
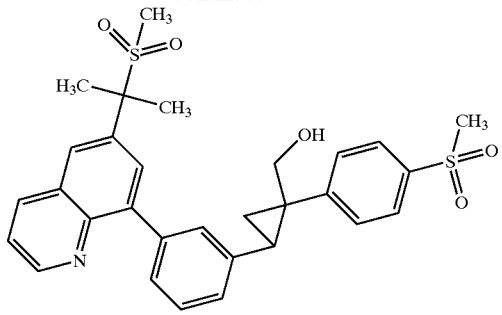
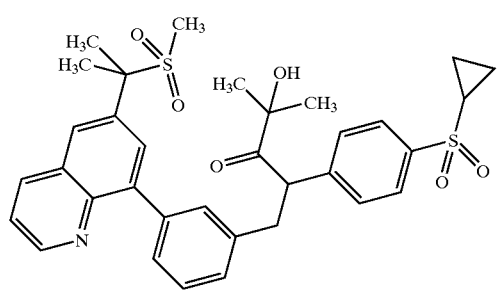
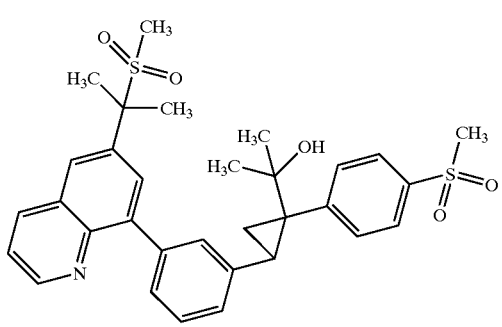
or a pharmaceutically acceptable salt thereof.
11. The compound according to claim 1 represented by
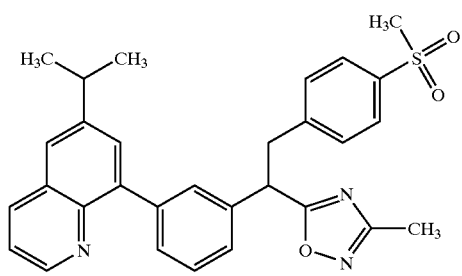
or a pharmaceutically acceptable salt thereof.
12. The compound according to claim 1 represented by
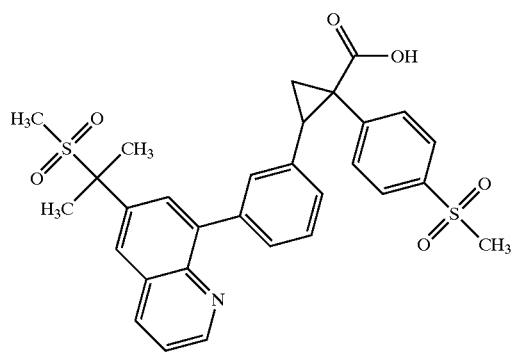
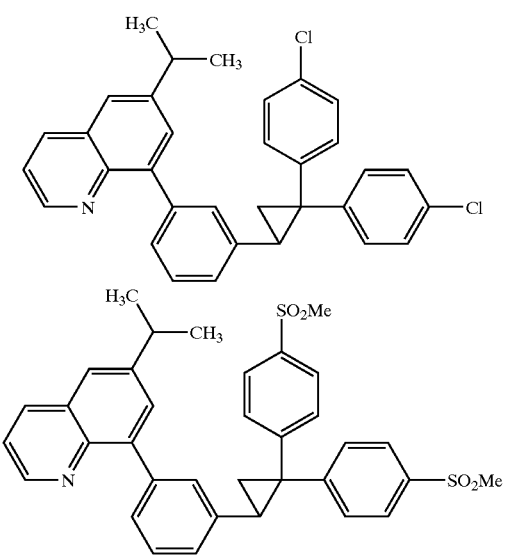
or a pharmaceutically acceptable salt thereof.
13. The compound according to claim 1 represented by
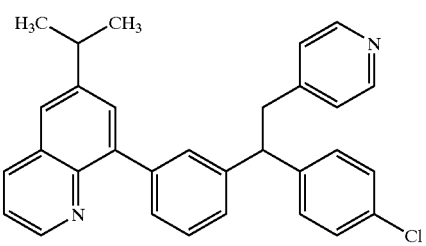

141
-continued
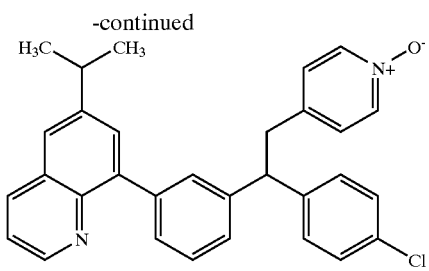
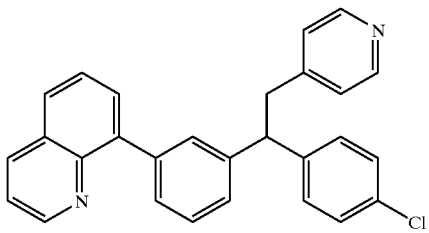
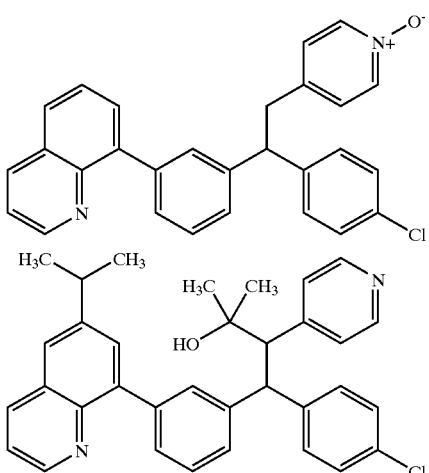
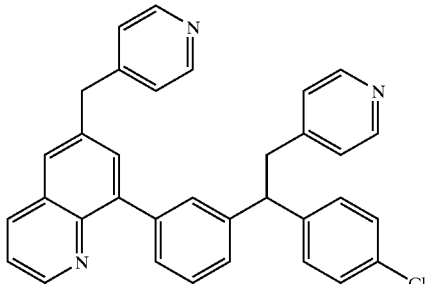
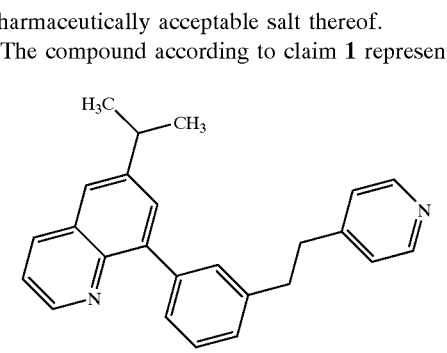
or a pharmaceutically acceptable salt thereof.
14. The compound according to claim 1 represented by
142
-continued
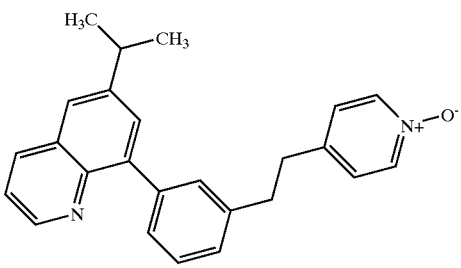
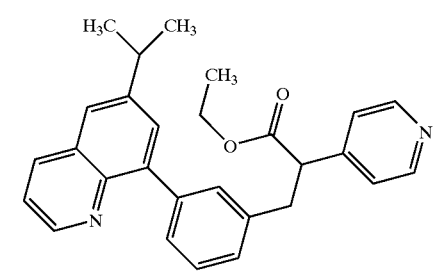
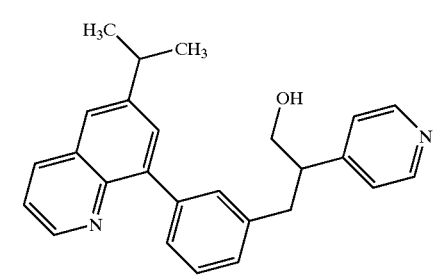
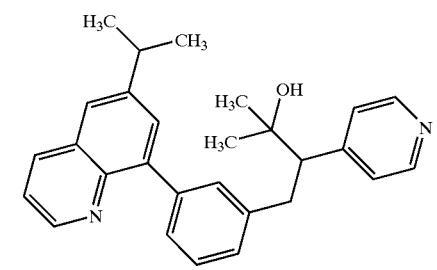
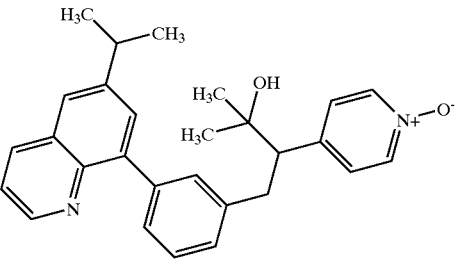
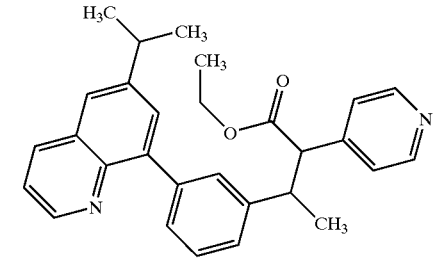

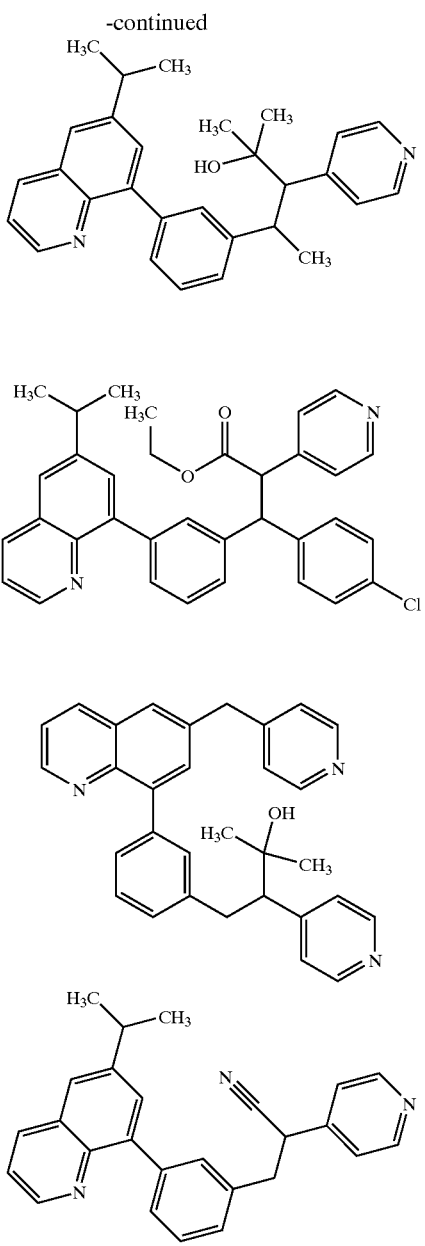

or a pharmaceutically acceptable salt thereof.

15. The compound according to claim 1 represented by

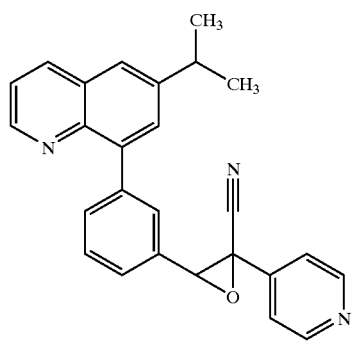

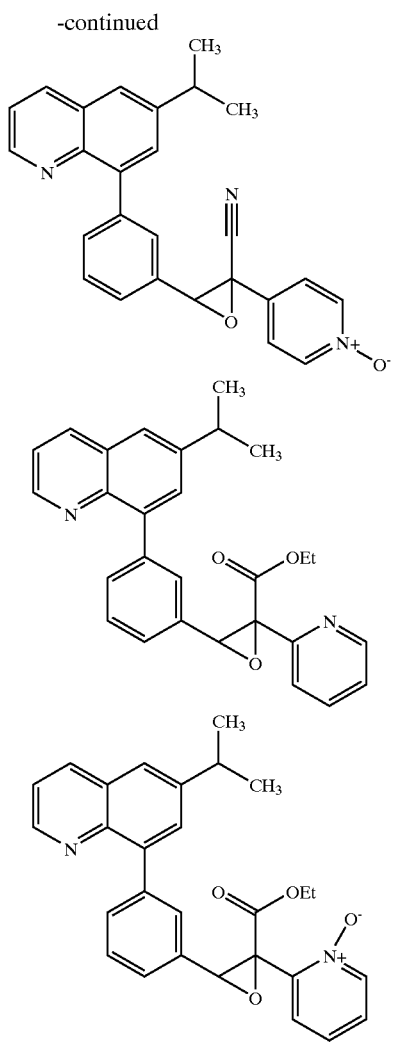

or a pharmaceutically acceptable salt thereof.

16. A pharmaceutical composition comprising a therapeutically effective amount of the compound according to claim 1 or a pharmaceutically acceptable salt thereof; and a pharmaceutically acceptable carrier.

17. A method of inhibiting PDE-4 in a mammal comprising administering to the mammal a therapeutically effective amount of a compound according to claim 1 or a pharmaceutically acceptable salt thereof.

18. The method of claim 17 wherein the mammal has a condition selected from asthma, chronic bronchitis, or chronic obstructive pulmonary disease.

19. The method of claim 17 wherein the mammal has a condition selected from laminitis in horses, or colic in horses.

20. The method of claim 17 wherein the mammal has a condition selected from endotoxic shock, septic shock, ulcerative colitis, bacterial or fungal induced sepsis, viral induced sepsis, bacterial or fungal induced septic shock, or viral induced septic shock.

21. The method of claim 17 wherein the mammal has a condition selected from Crohn's disease, reperfusion injury of the myocardium and brain, inflammatory arthritis, chronic glomerulonephritis, urticaria, rheumatoid arthritis, transplant rejection, graft versus host disease, inflammation-mediated chronic tissue degeneration, cytokine-mediated chronic tissue degeneration, osteoarthritis, or muscle wasting.

22. The method of claim 17 wherein the mammal has a condition selected from adult respiratory distress syndrome, chronic obstructive pulmonary disease in animals, diabetes insipidus, allergic rhinitis, allergic conjunctivitis, vernal conjunctivitis, arterial restenosis, ortherosclerosis, atherosclerosis, neurogenic inflammation, pain, cough, ankylosing spondylitis, hypersecretion of gastric acid, cancer, cachexia, depression, memory impairment, tumour growth, or cancerous invasion of normal tissues.

23. The method of claim 17 wherein the mammal has a condition selected from monopolar depression, acute and chronic neurodegenerative disorders with inflammatory components, Parkinson disease, Alzheimer's disease, spinal cord trauma, head injury, or multiple sclerosis.

* * * * *